(12) United States Patent
Bansal

(10) Patent No.: US 11,981,727 B2
(45) Date of Patent: May 14, 2024

(54) MONOSPECIFIC AND BISPECIFIC ANTIBODIES AND ANTIGEN BINDING FRAGMENTS THEREOF

(71) Applicant: NOVELMED THERAPEUTICS, INC, Cleveland, OH (US)

(72) Inventor: Rekha Bansal, Solon, OH (US)

(73) Assignee: NOVELMED THERAPEUTICS, INC, Cleveland, OH (US)

( * ) Notice: Subject to any disclaimer, the term of this patent is extended or adjusted under 35 U.S.C. 154(b) by 0 days.

(21) Appl. No.: 17/462,795

(22) Filed: Aug. 31, 2021

(65) Prior Publication Data

US 2023/0073274 A1 Mar. 9, 2023

(51) Int. Cl.
*C07K 16/18* (2006.01)
*C07K 16/22* (2006.01)
*C07K 16/24* (2006.01)

(52) U.S. Cl.
CPC .............. *C07K 16/18* (2013.01); *C07K 16/22* (2013.01); *C07K 16/241* (2013.01); *C07K 2317/24* (2013.01); *C07K 2317/31* (2013.01); *C07K 2317/52* (2013.01); *C07K 2317/522* (2013.01); *C07K 2317/55* (2013.01); *C07K 2317/565* (2013.01); *C07K 2317/569* (2013.01); *C07K 2317/622* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | |
|---|---|---|
| 6,333,034 B1 | 12/2001 | Gupta-Bansal et al. |
| 7,959,919 B2 | 6/2011 | Bansal |
| 8,192,742 B2 | 6/2012 | Bansal |
| 8,435,512 B2 | 5/2013 | Bansal |
| 8,664,362 B2 | 3/2014 | Bansal |
| 8,981,060 B2 | 3/2015 | Bansal |
| 9,023,831 B2 | 5/2015 | Bansal |
| 9,243,060 B2 | 1/2016 | Bansal |
| 9,243,070 B2 | 1/2016 | Bansal |
| 9,676,842 B2 | 6/2017 | Bansal |
| 9,745,367 B2 | 8/2017 | Bansal |
| 9,926,366 B2 | 3/2018 | Bansal |
| 9,988,441 B2 | 6/2018 | Bansal |
| 10,131,706 B2 | 11/2018 | Bansal |
| 10,183,989 B2 | 1/2019 | Bansal |
| 10,696,740 B2 | 6/2020 | Bansal |
| 10,711,056 B2 | 7/2020 | Bansal |
| 10,858,420 B2 | 12/2020 | Bansal |
| 2019/0352381 A1 | 11/2019 | Sheridan et al. |

OTHER PUBLICATIONS

Pauly, Diana, et al., "A Novel Antibody against Human Properdin Inhibits the Alternative Complement System and Specifically Detects Properdin from Blood Samples", PLOS One, May 2014, vol. 9, ssue 5 pp. 1-13.
Gupta-Bansal, Rekha, et al., "Inhibition of complement alternative pathway function with anti-properdin monoclonal antibodies" Molecular Immunity 37 (2000) 191-201.

*Primary Examiner* — Marianne P Allen
(74) *Attorney, Agent, or Firm* — TAROLLI, SUNDHEIM, COVELL & TUMMINO L.L.P.

(57) ABSTRACT

Isolated monospecific and bispecific anti-properdin antibodies or antigen binding fragments thereof for use in treating complement mediated disorders.

8 Claims, 51 Drawing Sheets

Specification includes a Sequence Listing.

NM5072 & Presta 9401 Variable Sequences and Antibody Structure

| Monospecific Ab | NM5072 V$_H$ Regions |
|---|---|
| NM5072 fAb<br>Presta9401 fAb<br><br>V$_H$ V$_H$<br>V$_L$ CH1 V$_L$<br>C$_L$ C$_L$<br>CH2<br>CH3<br><br>Hinge regions<br>Disulfide bonds | SEQ ID NO: 204<br>EVQLVQSGAEVKKPGASVKVSCKAS<u>GYIFTX$_1$YPIHW</u><br>VRQAPGQGLEWMG<u>FIX$_1$PGGGX$_2$DEX$_3$X$_4$X$_5$X$_6$X$_7$X$_8$X$_9$</u><br>RVTMTADTSTSTAYMELSSLRSEDTAVYYCAR<u>RGGGY</u><br><u>YLDY</u>WGQGTTVTVSS |
| | Presta Humanized Mouse 9401 V$_H$ Regions |
| | SEQ ID NO: 205<br>QVQLVQSGAEVKKPGASVKVSCKAS<u>GYIFTX$_1$YPIHW</u><br>VRQAPGQGLEWMG<u>FIX$_1$PGGGX$_2$DEX$_3$X$_4$X$_5$X$_6$X$_7$X$_8$X$_9$</u><br>RVTMTRDTSTSTVYMELSSLRSEDTAVYYCAR<u>RGGGY</u><br><u>YLDY</u>WGQGTTVTVSS |
| | NM5072 V$_L$ Regions |
| | SEQ ID NO: 209<br>DIQMTQSPSSLSASVGDRVTITC<u>RASQDISFFLN</u>WYQ<br>QKPGKAPKLLIY<u>X$_1$X$_2$SX$_3$YHS</u>GVPSRFSGSGSGTDFTLTI<br>SSLQPEDFATYYC<u>QHGX$_1$TLPX$_2$T</u>FGQGTKLEIK |
| | Presta Humanized Mouse 9401 V$_L$ Regions |
| | SEQ ID NO: 210<br>DIQMTQSPSSLSASVGDRVTITC<u>RASQDISFFLN</u>WYQ<br>QKPGKAPKLLIY<u>X$_1$X$_2$SX$_3$YHS</u>GVPSRFSGSGSGTDFTLTI<br>SSLQPEDFATYYC<u>QHGX$_1$TLPX$_2$T</u>FGQGTKLEIK |

Fig. 1

Variable and Constant Chain Linkers

| SEQ ID NO: 140 | GGGGS |
| --- | --- |
| SEQ ID NO: 141 | GGGSG |
| SEQ ID NO: 142 | SGGG |
| SEQ ID NO: 143 | GGGGSGGGGSGGGGS |
| SEQ ID NO: 144 | GGGGDGGGGDGGGG |
| SEQ ID NO: 145 | GGGGEGGGGEGGGG |
| SEQ ID NO: 146 | GGGD |
| SEQ ID NO: 147 | GGGE |
| SEQ ID NO: 148 | GGGGA |
| SEQ ID NO: 149 | GGGGAGGGGAGGGGS |

Fig. 4

Camelid Anti-P & Anti-Alb Variable Sequences and Antibody Structure

| Bispecific Ab | Camelid Anti-P |
| --- | --- |
| Anti-ALB, Camelid V$_{HH}$, Linker, CH2, CH3, Disulfide bonds | SEQ ID NO: 240<br>EVQLLESGGGLVQPGGSLRLSCAASGRISSHHMAWFRQAPGKERELVSEISRX$_1$GTTX$_1$YAX$_2$SX$_1$X$_3$GRFTISRDNSKNTLYLQMNSLKPEDTAVYYCNALQYEX$_3$HGGAX$_2$YWGQGTLVTVSS |
| | Camelid Anti-P |
| | SEQ ID NO: 244<br>QVQLAESGGGLVQAGDSLKLSCTASGRIFEX$_1$X$_2$MMAWYRQAPGKDRELVAEISRX$_1$GTTTYAX$_2$SX$_1$X$_3$GRFTISRDSAKNTVTLQMNSLKSEDTAVYYCNALQYEX$_3$HGGAX$_2$YWGQGTQVTVSG |
| | ALXN Anti-ALB |
| | SEQ ID NO: 108<br>EVQLVESGGGLVKPGGSLRLSCAASGRPVSNYAAAW FRQAPGKEREFVSAINWQKTATYADSVKGRFTISRDNAKNSLYLQMNSLRAEDTAVYYCAAYFRVVAPKTQYDYDYWGQGTLVTVSS |
| | Ablynx Anti-ALB |
| | SEQ ID NO: 119<br>EVQLLESGGGLVQPGGSLRLSCAASGFTFRSFGMSWVRQAPGKGPEWVSSISGSGSDTLYADSVKGRFTISRDNSKNTLYLQMNSLRPEDTAVYYCTIGGSLSRSSQGTLVTVSS |

Fig. 5

Single Chain mAb Sequences

| mAb | Anti-Albumin | Camelid Anti-P |
|---|---|---|
| Single Chain (NMT1001) | SEQ ID NO: 108<br>EVQLVESGGGLVKPGGSLRLSCAASGRPVS NYAAAWFRQAPGKEREFVSAINWQKTATYAD SYKGRFTISRDNAKNSLYLQMNSLRAEDTAV YYCAAYFRYYAPKTQYDYDYWGQGTLVTVSS<br><br>GGGGSGGGGSGGGGS (linker) | EVQLVESGGGLVQPGGSLRLSCAASGRISSIHRM AWVRQAPGKQRELVSEISRVGTTYYAISVKG RFTISRDNSKNTLYLQMNSLRAEDTAVYYCNA LQYEKHGGADYWGQGTLVTVSS |
| Single Chain (NMT1002) | EVQLVESGGGLVQPGGSLRLSCAASGFTFRSFG MSWVRQAPGKEPEWVSSISGSSSDTLYADSVK GRFTISRDNAKTTLYLQMNSLKPEDTAVYYCTI GSSLSRSSQGTQVTVSS<br><br>GGGGSGGGGSGGGGS (linker) | EVQLVESGGGLVQPGGSLRLSCAASGRISSIHRM AWVRQAPGKQRELVSEISRVGTTYYAISVKG RFTISRDNSKNTLYLQMNSLRAEDTAVYYCNA LQYEKHGGADYWGQGTLVTVSS |
| |  linker | |

Fig. 6

NMT15 (Fab)2 Monospecific Anti-Properdin Antibody

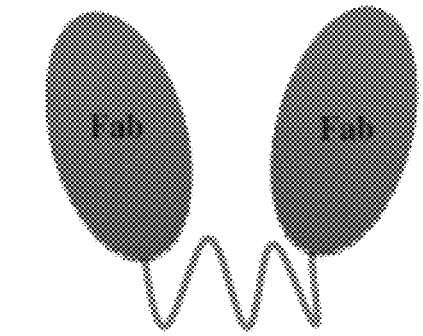

| | |
|---|---|
| | NMT15 Anti-Properdin V_H |
| | QVQLVQSAPEVAKPGTSVKMSCKASGYIFTNYPIH WVKQAPGQGLEWIGFIDPGGGYDIEPIERFRDRAT LTADKSTSTAYMELSSLRSEDTAIYYCARRGGGYY LDYWGQGTLVTVSSASTK |
| | Genscript Fc – CH1 Only |
| | GPSVFPLAPSSKSTSGGTAALGCLVKDYFPEPVTVS WNSGALTSGVHTFPAVLQSSGLYSLSSVVTVPSSSL GTQTYICNVNHKPSNTKVDKKVEPKSCD |
| | NMT15 Anti-Properdin V_L |
| | DIQMTQSPSSLSASLGDRVTITCRASQDISFTLNWY QQKPDGTVKLLIYYTSRYHSGVPSRFSGSGSGTDF TLTISSLQPEDFATYFCQHGNTLPWTFGQGTKLEIK RTVAAP |
| | Fc - CL |
| | SVFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC |
| | (G4S)3 Linker |
| | GGGGSGGGGSGGGGS |

Fig. 7

Anti-Alb Fab mAb

| mAb | Anti-Albumin | Heavy Chain |
|---|---|---|
| Alb-Fab (NMT1004) | EVQLVESGGGLVKPGGSLRLSCAASGRPVS NYAAAWFRQAPGKEREFVSAINWQKTATYAD SVKGRFTISRDNAKNSLYLQMNSLRAEDTAV YYCAANFRYVAPKTDYDYDYWGQGTLVTVSS GGGGSGGGGSGGGGS (linker) | QVQLVQSAPEVAKPGTSVKMSCKASGYIFTNY PIHWVKQAPGQGLEWIGHIDPGGGYDEPDERF RDRATLTADKSTSTAYMELSSLRSEDTAIYYC ARRGGGYYLDYWGQGTLVTVSSASTK |
| | | Light Chain |
| | | DIQMTQSPSSLSASLGDRVTITCRASQDISTFLN WYQQKPDGTVKLLIYYTSRYHSGVPSRFSGSG SGTDFTLTISSLQPEDFATYFCQHGNTLPWTFG QGTKLEIKRTVAAP |
| Alb-Fab (NMT1005) | EVQLVESGGGLVQPGGSLRLSCAASGFTFSSFG MSWVRQAPGKEPEWVSSISGSGSDTLYADSYK GRFTISRDNAKTTLYLQMNSLKPEDTAVYYCTI GGSLSESSQGTQVTVSS GGGGSGGGGSGGGGS (linker) | QVQLVQSAPEVAKPGTSVKMSCKASGYIFTNY PIHWVKQAPGQGLEWIGHIDPGGGYDEPDERF RDRATLTADKSTSTAYMELSSLRSEDTAIYYC ARRGGGYYLDYWGQGTLVTVSSASTK |
| | | Light Chain |
| | | DIQMTQSPSSLSASLGDRVTITCRASQDISTFLN WYQQKPDGTVKLLIYYTSRYHSGVPSRFSGSG SGTDFTLTISSLQPEDFATYFCQHGNTLPWTFG QGTKLEIKRTVAAP |

Fig. 8

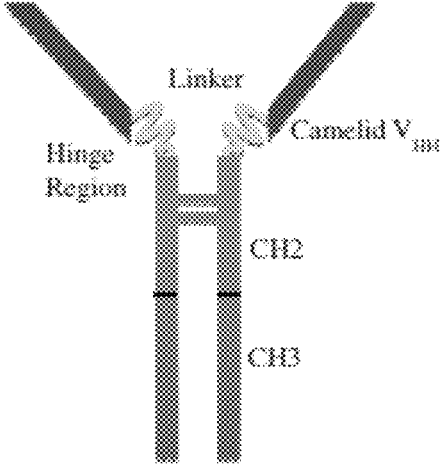

Fig. 9

NM9628 Bispecific Anti-P & Anti-Alb Antibody

| | |
|---|---|
| | NMT16 V_H |
| | EVQLVQSGAEVKKPGASVKVSCKASGYIFTNY PIHWVRQAPGQGLEWMGFIDPGGGYDEPDER FRDRVTMTADTSTSTAYMELSSLRSEDTAVYYCA RRGGGYYLDYWGQGTTVTVSSASTK |
| | NMT16 V_L |
| | DIQMTQSPSSLSASVGDRVTITCRASQDISFFLNW YQQKPGKAPKLLIYYTSRYHSGVPSRFSGSGSGT DFTLTISSLQPEDFATYYCQHGNTLPWTFGQGTK LEIKRTVAAP |
| | Anti-ALB V_H |
| | EVQLLESGGGLVQPGGSLRLSCAVSGIDLSNYAIN WVRQAPGKGLEWIGIIWASGTTFYATWAKGR FTISRDNSKNTVYLQMNSLRAEDTAVYYCARTVP GYSTAPYFDLWGQGTLVTVSSASTK |
| | Anti-ALB V_B |
| | DIQMTQSPSSVSASVGDRVTITCQSSPSYWSNFLSW YQQKPGKAPKLLIYEASKLTSGVPSRFSGSGSGTDF TLTISSLQPEDFATYYCGGGYSSISDFIFGGGTKVEI KRTVAAP |
| | IgG1 Fc |
| | GPSVFPLAPCSRSTSESTAALGCLVKDYFPEPVTVSW NSGALTSGVHTFPAVLQSSGLYSLSSVVTVPSSNFGT QTYTCNVDHKPSNTKVDKTVEPKSCDKTHTCPPCP APELLGGPSVFLFPPKPKDTLMISRTPEVTCVVVDV SHEDPEVKFNWYVDGVEVHNAKTKPREEQYNSTY RVVSVLTVLHQDWLNGKEYKCKVSNKALPAPIEKT ISKAKGQPREPQVYTLPPSRDELTKNQVSLTCLVKG FYPSDIAVEWESNGQPENNYKTTPPVLDSDGSFFLY SKLTVDKSRWQQGNVFSCSVMHEALHNHYTQKSL SLSPGK |
| | Fc - LC |
| | SVFIFPPSDEQLKSGTASVVCLLNNFYPREAKVQWKV DNALQSGNSQESVTEQDSKDSTYSLSSTLTLSKADYE KHKVYACEVTHQGLSSPVTKSFNRGEC |

Fig. 10

NM9629 Bispecific HumRab Anti-P & HumRab Anti-Alb Antibody

| | Presta Humanized Rabbit (2703 H2) V_H |
|---|---|
| | EVQLLESGGGLVQPGGSLRLSCAASGFSFSSGYWIFWVRQAPGKGLELVGGIYSGSSGTTYYADSVKGRFTISKDNSKNTVYLQMNSLRAEDTAVYYCARSVDGHSYDAAFNLWGQGTLVTVSSASTK |
| | Presta Humanized Rabbit (2703 L2) V_L |
| | DIQLTQSPSSLSASVGDRVTITCRASDNIYSLLAWYQQKPGKAPKLLIYRASTLASGVPSRFSGSGSGTDFTLTISSVQPEDFATYYCQQHYDYNYLDVAPGGGTKVEIKRTVAAP |
| | Anti-ALB V_H |
| | EVQLLESGGGLVQPGGSLRLSCAVSGIDLSNYAINWVRQAPGKGLEWIGIIWASGTTFYATWAKGRFTISRDNSKNTVYLQMNSLRAEDTAVYYCARIVPGYSTAPYFDIWGQGTLVTVSSASTK |
| | Anti-ALB V_H |
| | DIQMTQSPSSVSASVGDRVTITCQSSPSVWSNFLSWYQQKPGKAPKLLIYEASKLTSGVPSRFSGSGSGTDFTLTISSLQPEDFATYYCGGGYSSISDTTPGGGTKVEIKRTVAAP |
| | IgG1 Fc (w/ YTE Mutation) |
| | GPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | Fc - LC |
| | SVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

Fig. 11

NM9630 Bispecific Anti-P & Anti-TNF Antibody

| | NMT16 Anti-P V$_H$ |
|---|---|
| | EVQLVQSGAEVKKPGASVKVSCKASGYIFTNYPHHWVRQAPGQGLEWMGFIDPGGGYDFPDERFRDRVTMTADTSTSTAYMELSSLRSEDTAVYYCAKRGGGYYLDYWGQGTTVTVSSASTK |
| | NMT16 Anti-P V$_L$ |
| | DIQMTQSPSSLSASVGDRVTITCRASQDISFFLNWYQQKPGKAPKLLIYYTSRYHSGVPSRFSGSGSGTDFTLTISSLQPEDFATYYCQHGNTLPWTFGQGTKLEIKRTVAAP |
| | Anti-TNF V$_H$ |
| | EVQLVESGGGLVQPGRSLRLSCAASGFTFDDYAMHWVRQAPGKGLEWVSAITWNSGHIDYADSVEGRFTISRDNAKNSLYLQMNSLRAEDTAVYYCAKVSYLSTASSLDYWGQGTLVTVSSASTK |
| | Anti-TNF V$_L$ |
| | DIQMTQSPSSLSASVGDRVTITCRASQGIRNYLAWYQQKPGKAPKLLIYAASTLQSGVPSRFSGSGSGTDFTLTISSLQPEDVATYYCQRYNRAPYTFGQGTKVEIKRTVAAP |
| | IgG1 Fc - HC |
| | GPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | Fc - LC |
| | SVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

Fig. 12

NM9631 Bispecific Anti-P & Anti-VEGF Antibody

| | |
|---|---|
| | NMT16 Anti-P V$_H$ |
| | EVQLVQSGAEVKKPGASVKVSCKASGYIFTNY PIHWVRQAPGQGLEWMGFIDPGGGYDEPDER FRDRVTMTADTSTSTAYMELSSLRSEDTAVYYCA RRGGGYYLDYWGQGTTVTVSSASTK |
| | NMT16 Anti-P V$_L$ |
| | DIQMTQSPSSLSASVGDRVTITCRASQDISFFLNW YQQKPGKAPKLLIYYTSRYHSGVPSRFSGSGSGT DFTLTISSLQPEDFATYYCQHGNTLPWTFGQGT KLEIKRTVAAP |
| | Anti-VEGF V$_H$ |
| | EVQLVESGGGLVQPGGSLRLSCAASGYTFTNY GMNWVRQAPGKGLEWVGWINTYTGEPTYAA DFKRRFTFSLDTSKSTAYLQMNSLRAEDTAVY YCAKYPHYYGSSHWYFDVWGQGTLVTVSSASTK |
| | Anti-VEGF V$_L$ |
| | DIQMTQSPSSLSASVGDRVTITCSASQDISNYLN WYQQKPGKAPKVLIYFTSSLHSGVPSRFSGSGSG TDFTLTISSLQPEDFATYYCQQYSTVPWTFGQGT KVEIKRTVAAP |
| | IgG1 N298A Fc - HC |
| | GPSVFPLAPSSKSTSGGTAALGCLVKDYFPEPVTVSW NSGALTSGVHTFPAVLQSSGLYSLSSVVTVPSSSLGTQ TYICNVNHKPSNTKVDKKVEPKSCDKTHTCPPCPAPEL LGGPSVFLFPPKPKDTLMISRTPEVTCVVVDVSHEDPE VKFNWYVDGVEVHNAKTKPREEQYASTYRVVSVLT VLHQDWLNGKEYKCKVSNKALPAPIEKTISKAKGQPR EPQVYTLPPSRDELTKNQVSLTCLVKGFYPSDIAVEWE SNGQPENNYKTTPPVLDSDGSFFLYSKLTVDKSRWQQ GNVFSCSVMHEALHNHYTQKSLSLSPGK |
| | Fc - LC |
| | SVFIFPPSDEQLKSGTASVVCLLNNFYPREAKVQWKVDN ALQSGNSQESVTEQDSKDSTYSLSSTLTLSKADYEKHKV YACEVTHQGLSSPVTKSFNRGEC |

Fig. 13

Bispecific NMT16 Anti-Properdin fAb – Camelid Anti-Alb Antibody

| | NMT16 Anti-Properdin V$_H$ |
|---|---|
| | EVQLVQSGAEVKKPGASVKVSCKASGYIFTNY PIHWVRQAPGQGLEWMGFIDPGGGYDEPDER FRDRVTMTADTSTSTAYMELSSLRSEDTAVYYCA RRGGGYYLDYWGQGTTVTVSSASTK |
| | NM16 Anti-Properdin V$_L$ |
| | DIQMTQSPSSLSASVGDRVTITCRASQDISFFLNW YQQKPGKAPKLLIYYTSRYHSGVPSRFSGSGSGT DFTLTISSLQPEDFATYYCQHGNTLPWTFGQGT KLEIKRTVAAP |
| | Ablynx Anti-Alb V$_H$ |
| | EVQLVESGGGLVQPGGSLRLSCAASGFTFRSFGMSW VRQAPGKEPEWVSSISGSGSDTLYADSVKGRFTISRD NAKTTLYLQMNSLKPEDTAVYYCTIGGSLSRSSQGT QVTVSS |
| | (G4S)3 Linker |
| | GGGGSGGGGSGGGGS |
| | IgG1 YTE Fc - CH |
| | GPSVFPLAPSSKSTSGGTAALGCLVKDYFPEPVTV SWNSGALTSGVHTFPAVLQSSGLYSLSSVVTVPSS SLGTQTYICNVNHKPSNTKVDKKVEPKSCDKTHT CPPCPAPELLGGPSVFLFPPKPKDTLYITREPEVTCV VVDVSHEDPEVKFNWYVDGVEVHNAKTKPREEQ YNSTYRVVSVLTVLHQDWLNGKEYKCKVSNKAL PAPIEKTISKAKGQPREPQVYTLPPSRDELTKNQVS LTCLVKGFYPSDIAVEWESNGQPENNYKTTPPVLD SDGSFFLYSKLTVDKSRWQQGNVFSCSVMHEALH NHYTQKSLSLSPGK |
| | Fc - CL |
| | SVFIFPPSDEQLKSGTASVVCLLNNFYPREAKVQWK VDNALQSGNSQESVTEQDSKDSTYSLSSTLTLSKAD YEKHKVYACEVTHQGLSSPVTKSFNRGEC |

Fig. 15

Bispecific NMT16 Anti-P fAb – HumRab Anti-Alb fAb Antibody

| | |
|---|---|
| | NMT16 Anti-Properdin V$_H$ |
| | EVQLVQSGAEVKKPGASVKVSCKASGYIFTNY PHHWVRQAPGQGLEWMGFIDPGGGYDEPDER FRDRVTMTADTSTSTAYMELSSLRSEDTAVYYCA RRGGGYYLDYWGQGTTVTVSSASTK |
| | NM16 Anti-Properdin V$_L$ |
| | DIQMTQSPSSLSASVGDRVTITCRASQDISFFLNW YQQKPGKAPKLLIYYTSRYHSGVPSRFSGSGSGT DFTLTISSLQPEDFATYYCQHGNTLPWTFGQGT KLEIKRTVAAP |
| | HumRab Anti-ALB V$_H$ |
| | EVQLLESGGGLVQPGGSLRLSCAVSGIDLSNYA INWVRQAPGKGLEWIGIIWASGTTFYATWA KGRFTISRDNSKNTVYLQMNSLRAEDTAVYY CARTVPGYSTAPYFDLWGQGTLVTVSSASTK |
| | HumRab Anti-ALB V$_B$ |
| | DIQMTQSPSSVSASVGDRVTITCQSSPSVWSNFLS WYQQKPGKAPKLLIYEASKLTSGVPSRFSGSGSG TDFTLTISSLQPEDFATYYCGGGYSSISDTFGGG TKVEIKRTVAAP |
| | IgG1 N297A Fc - CH |
| | GPSVFPLAPSSKSTSGGTAALGCLVKDYFPEPVTVSW NSGALTSGVHTFPAVLQSSGLYSLSSVVTVPSSSLGTQ TYICNVNHKPSNTKVDKKVEPKSCDKTHTCPPCPAPEL LGGPSVFLFPPKPKDTLMISRTPEVTCVVVDVSHEDPE VKFNWYVDGVEVHNAKTKPREEQYASTYRVVSVLT VLHQDWLNGKEYKCKVSNKALPAPIEKTISKAKGQPR EPQVYTLPPSRDELTKNQVSLTCLVKGFYPSDIAVEWE SNGQPENNYKTTPPVLDSDGSFFLYSKLTVDKSRWQQ GNVFSCSVMHEALHNHYTQKSLSLSPGK |
| | Fc - CL |
| | SVFIFPPSDEQLKSGTASVVCLLNNFYPREAKVQWK VDNALQSGNSQESVTEQDSKDSTYSLSSTLTLSKAD YEKHKVYACEVTHQGLSSPVTKSFNRGEC |

Fig. 16

Bispecific Camelid Anti-P – Anti-Alb Antibody

| | |
|---|---|
| ALXN's Camelid Anti-P V$_{HH}$ | |
| | EVQLLESGGGLVQPGGSLRLSCAASGRISSIHMAW FRQAPGKERELVSEISRVGTTYYADSVKGRFTI SRDNSKNTLYLQMNSLKPEDTAVYYCNALQYEK HGGADYWGQGTLVTVSS |
| (G4S)3 Linker | |
| | GGGGSGGGGSGGGGS |
| Dulaglutide's IgG4 Fc (CH2/CH3 Only) | |
| | AESKYGPPCPPCPAPEAAGGPSVFLFPPKPKDTLMI SRTPEVTCVVVDVSQEDPEVQFNWYVDGVEVHNA KTKPREEQFNSTYRVVSVLTVLHQDWLNGKEYKC KVSNKGLPSSIEKTISKAKGQPREPQVYTLPPSQEE MTKNQVSLTCLVKGFYPSDIAVEWESNGQPENNY KTTPPVLDSDGSFFLYSRLTVDKSRWQEGNVFSCS VMHEALHNHYTQKSLSLSLG |
| ALXN's Anti-Alb V$_H$ | |
| | EVQLVESGGGLVKPGGSLRLSCAASGRPVSNYAAAW FRQAPGKEREFVSAINWQKTATYADSVKGRFTISRD NAKNSLYLQMNSLRAEDTAVYYCAAVFRVVAPKT QYDYDYWGQGTLVTVSS |
| (G4S)3 Linker | |
| | GGGGSGGGGSGGGGS |
| Dulaglutide's IgG4 Fc (CH2/CH3 Only) | |
| | AESKYGPPCPPCPAPEAAGGPSVFLFPPKPKDTLMI SRTPEVTCVVVDVSQEDPEVQFNWYVDGVEVHNA KTKPREEQFNSTYRVVSVLTVLHQDWLNGKEYKC KVSNKGLPSSIEKTISKAKGQPREPQVYTLPPSQEE MTKNQVSLTCLVKGFYPSDIAVEWESNGQPENNY KTTPPVLDSDGSFFLYSRLTVDKSRWQEGNVFSCS VMHEALHNHYTQKSLSLSLG |

Fig. 17

C3b/Properdin Deposition (NMT28)
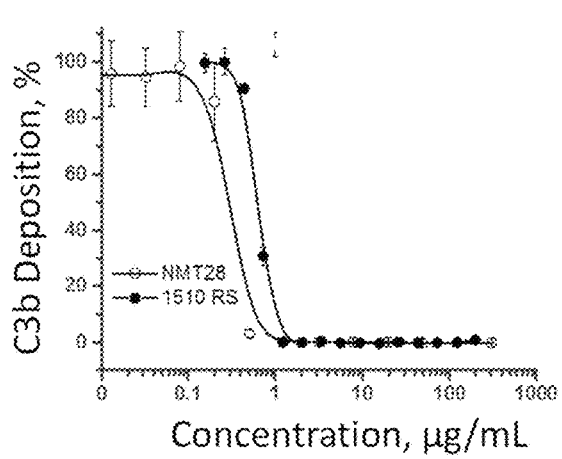 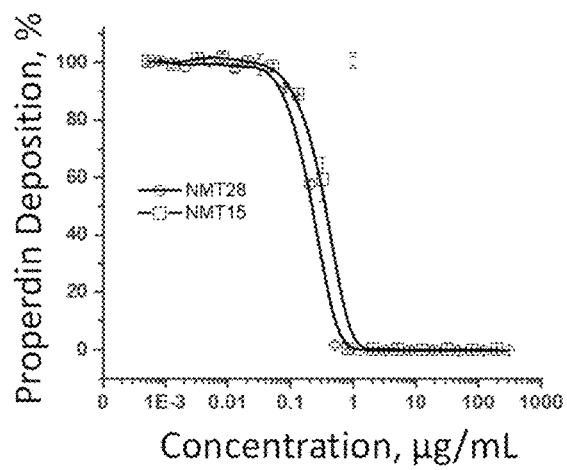
Fig. 34
CP HAGG MAC/C3b 10% NHS (NMT28)
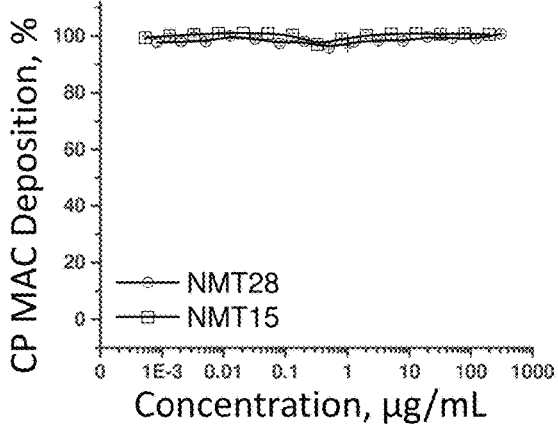 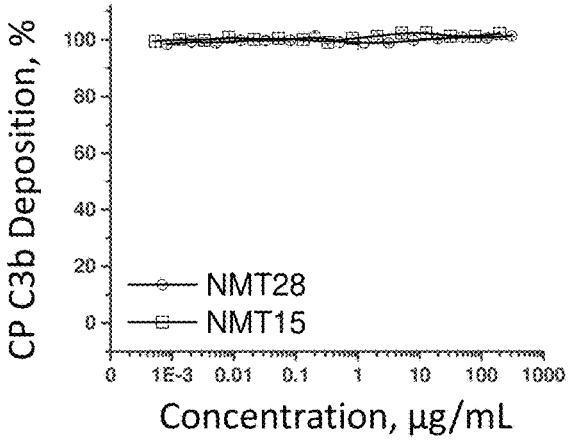
Fig. 35

US 11,981,727 B2

MONOSPECIFIC AND BISPECIFIC ANTIBODIES AND ANTIGEN BINDING FRAGMENTS THEREOF

The instant application contains a Sequence Listing which has been submitted electronically in ASCII format and is hereby incorporated by reference in its entirety. Said ASCII copy, created on Feb. 22, 2023, is named NMT028649USPRISEQUENCELISTING.txt and is 345,063 bytes in size.

FIELD OF THE INVENTION

This disclosure relates to monospecific and bispecific antibodies and antigen-binding fragments thereof that can bind to properdin and selectively inhibit the alternative complement pathway in disease conditions where the alternative pathway contributes to disease pathology.

BACKGROUND

The complement system is important for clearance of pathogens and host defense against pathogens. The complement system is activated via three distinct complement pathways; the classical, the lectin and the alternative pathways. The classical pathway is activated via antigen-antibody complexes. The lectin pathway is a variation of the classical pathway. The alternative pathway (AP) is activated by foreign material, artificial surfaces, dead tissues, bacteria, and dead yeast cells. In disease conditions, AP activation generates C3a, C5a, and C5b-9 (also known as the MAC complex). Elevated levels of C3a, C5a, and C5b-9 have been found to be associated with multiple acute and chronic disease conditions. These inflammatory molecules activate leukocytes, neutrophils, monocytes, platelets, mast cells, and endothelial cells as well as induce vascular permeability, cytolysis, and tissue injury. Activated cells release inflammatory mediators, such as TNF-α, IL-1β, IL-6, IL-8, VEGF, neutrophil elastase, and peroxides. Therefore, inhibition of disease-induced AP activation is important for clinical benefit in diseases where complement activation plays a role in disease pathology.

The initiation of the alternative complement pathway requires the binding of properdin to C3b, which occurs with high affinity. Properdin-bound C3b (PC3b) associates with factor B to form the PC3bB complex, which is then cleaved by factor D into PC3bBb and Ba, in which Ba is released. Properdin-depleted serum completely lacks AP activation activity, showing that properdin is essential for this initiation process to occur. Properdin concentration in blood is nearly 5 μg/ml, and consequently, it is the only non-protease molecule present at much lower concentration than other non-protease molecules.

Inhibiting AP activation is an important therapeutic strategy to mitigate symptoms and slow or prevent disease progression. Depleting, neutralizing, or inactivating properdin can block AP activation without inhibiting the classical complement pathway and, thus, is a viable and promising therapeutic strategy. The benefit of leaving the classical pathway intact is increased protection against infection.

SUMMARY

Embodiments described herein relate to isolated monospecific or bispecific antibodies or antigen binding fragments thereof. The isolated monospecific or bispecific antibodies or antigen binding fragments thereof specifically bind properdin and can selectively block the alternative complement pathway. The isolated monospecific or bispecific antibodies or antigen binding fragments thereof described herein can neutralize properdin functional activity and prevent AP induced production of C3a, C5a, C3b, and Mac complex (C5b-9). As a result, cellular activation, inflammation, and release of inflammatory mediators can also be prevented. Since AP activation is linked to various acute and chronic human diseases, inhibition of AP activation with the isolated monospecific or bispecific antibodies or antigen binding fragments thereof can also inhibit inflammation, providing clinical benefits to human beings treated with the isolated monospecific or bispecific antibodies or antigen binding fragments thereof.

In some embodiments, an isolated monospecific or bispecific antibody or antigen binding fragment can include at least one of:

a)
- a CDR-H1 comprising the amino acid sequence of GYIFTX$_1$YPIH (SEQ ID NO: 201), wherein X$_1$ is N, Q, S, A, or D,
- a CDR-H2 comprising the amino acid sequence of FIX$_1$PGGGX$_2$DEX$_3$X$_4$X$_5$X$_6$X$_7$X$_8$X$_9$ (SEQ ID NO: 202), wherein X$_1$ is D, E, S, or A; X$_2$ is H or Y; X$_3$ is P, S, or Y; X$_4$ is A or D; X$_5$ is D, E, or Q; X$_6$ is K, R, or S; X$_7$ is F or V; X$_8$ is E, K, Q, or R; and X$_9$ is D or G; and
- a CDR-H3 comprising the amino acid sequence of RGGGYYLDY (SEQ ID NO: 203);

b)
- a CDR-L1 comprising the amino acid sequence of RASQDISFFLN (SEQ ID NO: 206),
- a CDR-L2 comprising the amino acid sequence of X$_1$X$_2$SX$_3$YHS (SEQ ID NO: 207), wherein X$_1$ is G or Y; X$_2$ is A or T; and X$_3$ is R or S; and
- a CDR-L3 comprising the amino acid sequence of QHGX$_1$TLPX$_2$T (SEQ ID NO: 208), wherein X$_1$ is A, D, N, Q, or S; and X$_2$ is F, H, R, W, or Y;

c)
- a CDR-H1 comprising the amino acid sequence of GFSLSTSGX$_1$GVG (SEQ ID NO: 211), wherein X$_1$ is I, K, M, or V,
- a CDR-H2 comprising the amino acid sequence of HIX$_1$X$_1$DDVKSYX$_2$ PALKS (SEQ ID NO: 212), wherein X$_1$ is F, H, W, or Y; and X$_2$ is A, N, Q, or S; and
- a CDR-H3 comprising the amino acid sequence of IGX$_1$GYYSFDY (SEQ ID NO: 213), wherein X$_1$ is A, D, E, or S;

d)
- a CDR-L1 comprising the amino acid sequence of X$_1$ASQDVSDAVA (SEQ ID NO: 216), wherein X$_1$ is K or R;
- a CDR-L2 comprising the amino acid sequence of SPSYRYT (SEQ ID NO: 217); and
- a CDR-L3 comprising the amino acid sequence of QQHYSTPX$_1$TF (SEQ ID NO: 218), wherein X$_1$ is F, H, W, or Y;

e)
- a CDR-H1 comprising the amino acid sequence of GFSFSSGYX$_1$IF (SEQ ID NO: 221), wherein X$_1$ is F, H, W, or Y;
- a CDR-H2 comprising the amino acid sequence of GIYSGSSGTTY (SEQ ID NO: 222); and
- a CDR-H3 comprising the amino acid sequence of SVX$_1$GIX$_1$SYX$_1$ AAFX$_2$L (SEQ ID NO: 223), wherein X$_1$ is A, D, E, or S; and X$_2$ is A, N, Q, or S;

f)
a CDR-L1 comprising the amino acid sequence of X$_1$ASDX$_2$IYSLLA (SEQ ID NO: 229), wherein X$_1$ is Q or R; X$_2$ is A, N, Q, or S;
a CDR-L2 comprising the amino acid sequence of RAS-TLAS (SEQ ID NO: 230); and
a CDR-L3 comprising the amino acid sequence of QQHYDYX$_1$YLDVA (SEQ ID NO: 231), wherein X$_1$ is A, N, Q, or S;

g)
a CDR-H1 comprising the amino acid sequence of GFSFSSSYX$_1$IF (SEQ ID NO: 225), wherein X$_1$ is F, H, W, or Y,
a CDR-H2 comprising the amino acid sequence of GIYSSSGRX$_1$Y (SEQ ID NO: 226), wherein X$_1$ is I, K, L, or M; and
a CDR-H3 comprising the amino acid sequence of SAX$_1$GSX$_1$SYX$_1$AYFTL (SEQ ID NO: 227), wherein X$_1$ is A, D, E, or S;

h)
a CDR-L1 comprising the amino acid sequence of X$_1$ASDX$_2$IYSX$_2$LA (SEQ ID NO: 233), wherein X$_1$ is Q or R; X$_2$ is A, N, Q, or S;
a CDR-L2 comprising the amino acid sequence of RAS-TLAS (SEQ ID NO: 234); and
a CDR-L3 comprising the amino acid sequence of QQHX$_1$DYDYIDVA (SEQ ID NO: 235), wherein X$_1$ is F, H, W, or Y;

i)
a CDR-H1 comprising the amino acid sequence of GRIS-SIIHMA (SEQ ID NO: 237), wherein X$_1$ is F, H, W, or Y,
a CDR-H2 comprising the amino acid sequence of RX$_1$GTTX$_1$YAX$_2$SX$_1$X$_3$G (SEQ ID NO: 238), wherein X$_1$ is I or V; X$_2$ is A, D, E, or S; and X$_3$ is A or K; and
a CDR-H3 comprising the amino acid sequence of LQYEX$_1$HGGAX$_2$Y (SEQ ID NO: 239), wherein X$_1$ is A or K; and X$_2$ is A, D, E, or S;

j)
a CDR-H1 comprising the amino acid sequence of GRIFEX$_1$X$_2$MMA (SEQ ID NO: 241), wherein X$_1$ is I or V; and X$_2$ is A, D, N, Q, or S,
a CDR-H2 comprising the amino acid sequence of RX$_1$GTTTYAX$_2$SX$_1$X$_3$G (SEQ ID NO: 242), wherein X$_1$ is I or V; X$_2$ is A, D, E, or S; and X$_3$ is A or K; and
a CDR-H3 comprising the amino acid sequence of LQYX$_1$RYGGAEY (SEQ ID NO: 243), wherein X$_1$ is A, D, E, or S; or k)
or a heavy chain variable region and/or light chain variable region that competitively inhibits binding of an isolated monospecific or bispecific antibody or antigen binding fragment thereof comprising at least one of a), b), c), d), e), f), g), h), i), or j) to monomeric properdin.

In some embodiments, the isolated monospecific or bispecific antibody or antigen binding fragment, can include:
a CDR-H1 comprising the amino acid sequence of GYIFTX$_1$YPIH (SEQ ID NO: 201), wherein X$_1$ is N, Q, S, A, or D,
a CDR-H2 comprising the amino acid sequence of FIX$_1$PGGGX$_2$DEX$_3$X$_4$X$_5$X$_6$X$_7$X$_8$X$_9$ (SEQ ID NO: 202), wherein X$_1$ is D, E, S, or A; X$_2$ is H or Y; X$_3$ is P, S, or Y; X$_4$ is A or D; X$_5$ is D, E, or Q; X$_6$ is K, R, or S; X$_7$ is F or V; X$_8$ is E, K, Q, or R; and X$_9$ is D or G; and
a CDR-H3 comprising the amino acid sequence of RGG-GYYLDY (SEQ ID NO: 203);
a CDR-L1 comprising the amino acid sequence of RASQDISFFLN (SEQ ID NO: 206),
a CDR-L2 comprising the amino acid sequence of X$_1$X$_2$SX$_3$YHS (SEQ ID NO: 207), wherein X$_1$ is G or Y; X$_2$ is A or T; and X$_3$ is R or S; and
a CDR-L3 comprising the amino acid sequence of QHGX$_1$TLPX$_2$T (SEQ ID NO: 208), wherein X$_1$ is A, D, N, Q, or S; and X$_2$ is F, H, R, W, or Y.

In some embodiments, the isolated monospecific or bispecific antibody or antigen binding fragment can include:
a CDR-H1 comprising the amino acid sequence of GFSLSTSGX$_1$GVG (SEQ ID NO: 211), wherein X$_1$ is I, K, M, or V,
a CDR-H2 comprising the amino acid sequence of HIX$_1$X$_1$DDVKSYX$_2$PALKS (SEQ ID NO: 212), wherein X$_1$ is F, H, W, or Y; and X$_2$ is A, N, Q, or S;
a CDR-H3 comprising the amino acid sequence of IGX$_1$GYYSFDY (SEQ ID NO: 213), wherein X$_1$ is A, D, E, or S;
a CDR-L1 comprising the amino acid sequence of X$_1$ASQDVSDAVA (SEQ ID NO: 216), wherein X$_1$ is K or R;
a CDR-L2 comprising the amino acid sequence of SPSYRYT (SEQ ID NO: 217); and
a CDR-L3 comprising the amino acid sequence of QQHYSTPX$_1$TF (SEQ ID NO: 218), wherein X$_1$ is F, H, W, or Y.

In some embodiments, the isolated monospecific or bispecific antibody or antigen binding fragment thereof can include:
a CDR-H1 comprising the amino acid sequence of GFSFSSGYX$_1$IF (SEQ ID NO: 221), wherein X$_1$ is F, H, W, or Y;
a CDR-H2 comprising the amino acid sequence of GIYSGSSGTTY (SEQ ID NO: 222);
a CDR-H3 comprising the amino acid sequence of SVX$_1$GIX$_1$SYX$_1$ AAFX$_2$L (SEQ ID NO: 223), wherein X$_1$ is A, D, E, or S; and X$_2$ is A, N, Q, or S;
a CDR-L1 comprising the amino acid sequence of X$_1$ASDX$_2$IYSLLA (SEQ ID NO: 229), wherein X$_1$ is Q or R; X$_2$ is A, N, Q, or S;
a CDR-L2 comprising the amino acid sequence of RAS-TLAS (SEQ ID NO: 230); and
a CDR-L3 comprising the amino acid sequence of QQHYDYX$_1$YLDVA (SEQ ID NO: 231), wherein X$_1$ is A, N, Q, or S.

In some embodiments, the isolated monospecific or bispecific antibody or antigen binding fragment thereof can include a CDR-H1 comprising the amino acid sequence of GFSFSSSYX$_1$IF (SEQ ID NO: 225), wherein X$_1$ is F, H, W, or Y,
a CDR-H2 comprising the amino acid sequence of GIYSSSGRX$_1$Y (SEQ ID NO: 226), wherein X$_1$ is I, K, L, or M;
a CDR-H3 comprising the amino acid sequence of SAX$_1$GSX$_1$SYX$_1$AYFTL (SEQ ID NO: 227), wherein X$_1$ is A, D, E, or S;
a CDR-L1 comprising the amino acid sequence of X$_1$ASDX$_2$IYSX$_2$LA (SEQ ID NO: 233), wherein X$_1$ is Q or R; X$_2$ is A, N, Q, or S;
a CDR-L2 comprising the amino acid sequence of RAS-TLAS (SEQ ID NO: 234); and
a CDR-L3 comprising the amino acid sequence of QQHX$_1$DYDYIDVA (SEQ ID NO: 235), wherein X$_1$ is F, H, W, or Y.

In some embodiments, the isolated monospecific or bispecific antibody or antigen binding fragment thereof can include a heavy chain variable region that includes the 3 CDRs of one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 40, SEQ ID NO: 41, SEQ ID NO: 42, SEQ ID NO: 43, SEQ ID NO: 44, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 71, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, or SEQ ID NO: 107; or a heavy chain variable region that competitively inhibits binding of an isolated antibody or antigen binding fragment comprising at least one of a heavy chain variable region that includes the 3 CDRs of one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 40, SEQ ID NO: 41, SEQ ID NO: 42, SEQ ID NO: 43, SEQ ID NO: 44, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 71, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, or SEQ ID NO: 107.

In other embodiments, the isolated monospecific or bispecific antibody or antigen binding fragment thereof can include a heavy chain variable region that includes an amino acid sequence at least about 70%, at least about 80%, or at least about 90% identical to the amino acid sequence of one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 40, SEQ ID NO: 41, SEQ ID NO: 42, SEQ ID NO: 43, SEQ ID NO: 44, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 71, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, or SEQ ID NO: 107.

In still other embodiments, the isolated monospecific or bispecific antibody or antigen binding fragment thereof can include a light chain variable region that includes the 3 CDRs of one of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 45, SEQ ID NO: 46, SEQ ID NO: 47, SEQ ID NO: 48, SEQ ID NO: 49, SEQ ID NO: 50, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, or SEQ ID NO: 72; or a light chain variable region that competitively inhibits binding of an isolated antibody or antigen binding fragment comprising at least one of a light chain variable region that includes the 3 CDRs of one of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 45, SEQ ID NO: 46, SEQ ID NO: 47, SEQ ID NO: 48, SEQ ID NO: 49, SEQ ID NO: 50, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, or SEQ ID NO: 72.

In some embodiments, the isolated monospecific or bispecific antibody or antigen binding fragment thereof can include a light chain variable region that includes an amino acid sequence at least about 70%, at least about 80%, or at least about 90% identical to the amino acid sequence of one of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 45, SEQ ID NO: 46, SEQ ID NO: 47, SEQ ID NO: 48, SEQ ID NO: 49, SEQ ID NO: 50, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, or SEQ ID NO: 72.

In some embodiments, the isolated monospecific or bispecific antibody or antigen binding fragment thereof can include at least one of the following:
  a) a heavy chain variable region that includes the 3 CDRs of SEQ ID NO: 1 and a light chain variable region that includes the 3 CDRs of SEQ ID NO: 24;
  b) a heavy chain variable region that includes the 3 CDRs of SEQ ID NO: 2 and a light chain variable region that includes the 3 CDRs of SEQ ID NO: 25;
  c) a heavy chain variable region that includes the 3 CDRs of SEQ ID NO: 3 and a light chain variable region that includes the 3 CDRs of SEQ ID NO: 26;
  d) a heavy chain variable region that includes the 3 CDRs of SEQ ID NO: 4 and a light chain variable region that includes the 3 CDRs of SEQ ID NO: 27;

e) a heavy chain variable region that includes the 3 CDRs of SEQ ID NO: 5 and a light chain variable region that includes the 3 CDRs of SEQ ID NO: 28;
f) a heavy chain variable region that includes the 3 CDRs of SEQ ID NO: 6 and a light chain variable region that includes the 3 CDRs of SEQ ID NO: 29;
g) a heavy chain variable region that includes the 3 CDRs of SEQ ID NO: 7 and a light chain variable region that includes the 3 CDRs of SEQ ID NO: 30;
h) a heavy chain variable region that includes the 3 CDRs of SEQ ID NO: 8 and a light chain variable region that includes the 3 CDRs of SEQ ID NO: 31;
i) a heavy chain variable region that includes the 3 CDRs of SEQ ID NO: 9 and a light chain variable region that includes the 3 CDRs of SEQ ID NO: 32;
j) a heavy chain variable region that includes the 3 CDRs of SEQ ID NO: 10 and a light chain variable region that includes the 3 CDRs of SEQ ID NO: 33;
k) a heavy chain variable region that includes the 3 CDRs of SEQ ID NO: 11 and a light chain variable region that includes the 3 CDRs of SEQ ID NO: 34;
l) a heavy chain variable region that includes the 3 CDRs of SEQ ID NO: 12 and a light chain variable region that includes the 3 CDRs of SEQ ID NO: 35;
m) a heavy chain variable region that includes the 3 CDRs of SEQ ID NO: 13 and a light chain variable region that includes the 3 CDRs of SEQ ID NO: 36;
n) a heavy chain variable region that includes the 3 CDRs of SEQ ID NO: 14 and a light chain variable region that includes the 3 CDRs of SEQ ID NO: 37;
o) a heavy chain variable region that includes the 3 CDRs of SEQ ID NO: 15 and a light chain variable region that includes the 3 CDRs of SEQ ID NO: 38 or SEQ ID NO: 39;
p) a heavy chain variable region that includes the 3 CDRs of SEQ ID NO: 16 and a light chain variable region that includes the 3 CDRs of SEQ ID NO: 38 or SEQ ID NO: 39;
q) a heavy chain variable region that includes the 3 CDRs of SEQ ID NO: 17 and a light chain variable region that includes the 3 CDRs of SEQ ID NO: 38 or SEQ ID NO: 39;
r) a heavy chain variable region that includes the 3 CDRs of SEQ ID NO: 18 and a light chain variable region that includes the 3 CDRs of SEQ ID NO: 38 or SEQ ID NO: 39;
s) a heavy chain variable region that includes the 3 CDRs of SEQ ID NO: 19 and a light chain variable region that includes the 3 CDRs of SEQ ID NO: 38 or SEQ ID NO: 39;
t) a heavy chain variable region that includes the 3 CDRs of SEQ ID NO: 20 and a light chain variable region that includes the 3 CDRs of SEQ ID NO: 38 or SEQ ID NO: 39;
u) a heavy chain variable region that includes the 3 CDRs of SEQ ID NO: 21 and a light chain variable region that includes the 3 CDRs of SEQ ID NO: 38 or SEQ ID NO: 39;
v) a heavy chain variable region that includes the 3 CDRs of SEQ ID NO: 22 and a light chain variable region that includes the 3 CDRs of SEQ ID NO: 38 or SEQ ID NO: 39;
w) a heavy chain variable region that includes the 3 CDRs of SEQ ID NO: 23 and a light chain variable region that includes the 3 CDRs of SEQ ID NO: 38 or SEQ ID NO: 39;
x) a heavy chain variable region that includes the 3 CDRs of SEQ ID NO: 40 and a light chain variable region that includes the 3 CDRs of SEQ ID NO: 45;
y) a heavy chain variable region that includes the 3 CDRs of SEQ ID NO: 41 and a light chain variable region that includes the 3 CDRs of SEQ ID NO: 46;
z) a heavy chain variable region that includes the 3 CDRs of SEQ ID NO: 42 and a light chain variable region that includes the 3 CDRs of SEQ ID NO: 47;
aa) a heavy chain variable region that includes the 3 CDRs of SEQ ID NO: 43 and a light chain variable region that includes the 3 CDRs of SEQ ID NO: 48, SEQ ID NO: 49, or SEQ ID NO: 50;
bb) a heavy chain variable region that includes the 3 CDRs of SEQ ID NO: 44 and a light chain variable region that includes the 3 CDRs of SEQ ID NO: 48, SEQ ID NO: 49, or SEQ ID NO: 50;
cc) a heavy chain variable region that includes the 3 CDRs of SEQ ID NO: 51 and a light chain variable region that includes the 3 CDRs of SEQ ID NO: 61, SEQ ID NO: 62, SEQ ID NO: 63, SEQ ID NO: 64, or SEQ ID NO: 65;
dd) a heavy chain variable region that includes the 3 CDRs of SEQ ID NO: 52 and a light chain variable region that includes the 3 CDRs of SEQ ID NO: 61, SEQ ID NO: 62, SEQ ID NO: 63, SEQ ID NO: 64, or SEQ ID NO: 65;
ee) a heavy chain variable region that includes the 3 CDRs of SEQ ID NO: 53 and a light chain variable region that includes the 3 CDRs of SEQ ID NO: 61, SEQ ID NO: 62, SEQ ID NO: 63, SEQ ID NO: 64, or SEQ ID NO: 65;
ff) a heavy chain variable region that includes the 3 CDRs of SEQ ID NO: 54 and a light chain variable region that includes the 3 CDRs of SEQ ID NO: 61, SEQ ID NO: 62, SEQ ID NO: 63, SEQ ID NO: 64, or SEQ ID NO: 65;
gg) a heavy chain variable region that includes the 3 CDRs of SEQ ID NO: 55 and a light chain variable region that includes the 3 CDRs of SEQ ID NO: 61, SEQ ID NO: 62, SEQ ID NO: 63, SEQ ID NO: 64, or SEQ ID NO: 65;
hh) a heavy chain variable region that includes the 3 CDRs of SEQ ID NO: 56 and a light chain variable region that includes the 3 CDRs of SEQ ID NO: 66, SEQ ID NO: 67, SEQ ID NO: 68, SEQ ID NO: 69, or SEQ ID NO: 70;
ii) a heavy chain variable region that includes the 3 CDRs of SEQ ID NO: 57 and a light chain variable region that includes the 3 CDRs of SEQ ID NO: 66, SEQ ID NO: 67, SEQ ID NO: 68, SEQ ID NO: 69, or SEQ ID NO: 70;
jj) a heavy chain variable region that includes the 3 CDRs of SEQ ID NO: 58 and a light chain variable region that includes the 3 CDRs of SEQ ID NO: 66, SEQ ID NO: 67, SEQ ID NO: 68, SEQ ID NO: 69, or SEQ ID NO: 70;
kk) a heavy chain variable region that includes the 3 CDRs of SEQ ID NO: 59 and a light chain variable region that includes the 3 CDRs of SEQ ID NO: 66, SEQ ID NO: 67, SEQ ID NO: 68, SEQ ID NO: 69, or SEQ ID NO: 70; or
ll) a heavy chain variable region that includes the 3 CDRs of SEQ ID NO: 60 and a light chain variable region that includes the 3 CDRs of SEQ ID NO: 66, SEQ ID NO: 67, SEQ ID NO: 68, SEQ ID NO: 69, or SEQ ID NO: 70.

In some embodiments, the isolated monospecific or bispecific antibody or antigen binding fragment thereof can include at least one of the following:

a) a heavy chain that includes an amino acid sequence at least about 70%, at least about 80%, or at least about 90% identical to the amino acid sequence of SEQ ID NO: 1 and a light chain that includes an amino acid sequence at least about 70%, at least about 80%, or at least about 90% identical to the amino acid sequence of SEQ ID NO: 24;

b) a heavy chain that includes an amino acid sequence at least about 70%, at least about 80%, or at least about 90% identical to the amino acid sequence of SEQ ID NO: 2 and a light chain that includes an amino acid sequence at least about 70%, at least about 80%, or at least about 90% identical to the amino acid sequence of SEQ ID NO: 25;

c) a heavy chain variable that includes an amino acid sequence at least about 70%, at least about 80%, or at least about 90% identical to the amino acid sequence of SEQ ID NO: 3 and a light chain that includes an amino acid sequence at least about 70%, at least about 80%, or at least about 90% identical to the amino acid sequence of SEQ ID NO: 26;

d) a heavy chain that includes an amino acid sequence at least about 70%, at least about 80%, or at least about 90% identical to the amino acid sequence of SEQ ID NO: 4 and a light chain that includes an amino acid sequence at least about 70%, at least about 80%, or at least about 90% identical to the amino acid sequence of SEQ ID NO: 27;

e) a heavy chain that includes an amino acid sequence at least about 70%, at least about 80%, or at least about 90% identical to the amino acid sequence of SEQ ID NO: 5 and a light chain that includes an amino acid sequence at least about 70%, at least about 80%, or at least about 90% identical to the amino acid sequence of SEQ ID NO: 28;

f) a heavy chain that includes an amino acid sequence at least about 70%, at least about 80%, or at least about 90% identical to the amino acid sequence of SEQ ID NO: 6 and a light chain that includes an amino acid sequence at least about 70%, at least about 80%, or at least about 90% identical to the amino acid sequence of SEQ ID NO: 29;

g) a heavy chain that includes an amino acid sequence at least about 70%, at least about 80%, or at least about 90% identical to the amino acid sequence of SEQ ID NO: 7 and a light chain that includes an amino acid sequence at least about 70%, at least about 80%, or at least about 90% identical to the amino acid sequence of SEQ ID NO: 30;

h) a heavy chain that includes an amino acid sequence at least about 70%, at least about 80%, or at least about 90% identical to the amino acid sequence of SEQ ID NO: 8 and a light chain that includes an amino acid sequence at least about 70%, at least about 80%, or at least about 90% identical to the amino acid sequence of SEQ ID NO: 31;

i) a heavy chain that includes an amino acid sequence at least about 70%, at least about 80%, or at least about 90% identical to the amino acid sequence of SEQ ID NO: 9 and a light chain that includes an amino acid sequence at least about 70%, at least about 80%, or at least about 90% identical to the amino acid sequence of SEQ ID NO: 32;

j) a heavy chain that includes an amino acid sequence at least about 70%, at least about 80%, or at least about 90% identical to the amino acid sequence of SEQ ID NO: 10 and a light chain that includes an amino acid sequence at least about 70%, at least about 80%, or at least about 90% identical to the amino acid sequence of SEQ ID NO: 33;

k) a heavy chain that includes an amino acid sequence at least about 70%, at least about 80%, or at least about 90% identical to the amino acid sequence of SEQ ID NO: 11 and a light chain that includes an amino acid sequence at least about 70%, at least about 80%, or at least about 90% identical to the amino acid sequence of SEQ ID NO: 34;

l) a heavy chain that includes an amino acid sequence at least about 70%, at least about 80%, or at least about 90% identical to the amino acid sequence of SEQ ID NO: 12 and a light chain that includes an amino acid sequence at least about 70%, at least about 80%, or at least about 90% identical to the amino acid sequence of SEQ ID NO: 35;

m) a heavy chain that includes an amino acid sequence at least about 70%, at least about 80%, or at least about 90% identical to the amino acid sequence of SEQ ID NO: 13 and a light chain that includes an amino acid sequence at least about 70%, at least about 80%, or at least about 90% identical to the amino acid sequence of SEQ ID NO: 36;

n) a heavy chain that includes an amino acid sequence at least about 70%, at least about 80%, or at least about 90% identical to the amino acid sequence of SEQ ID NO: 14 and a light chain that includes an amino acid sequence at least about 70%, at least about 80%, or at least about 90% identical to the amino acid sequence of SEQ ID NO: 37;

o) a heavy chain that includes an amino acid sequence at least about 70%, at least about 80%, or at least about 90% identical to the amino acid sequence of SEQ ID NO: 15 and a light chain that includes an amino acid sequence at least about 70%, at least about 80%, or at least about 90% identical to the amino acid sequence of SEQ ID NO: 38 or SEQ ID NO: 39;

p) a heavy chain that includes an amino acid sequence at least about 70%, at least about 80%, or at least about 90% identical to the amino acid sequence of SEQ ID NO: 16 and a light chain that includes an amino acid sequence at least about 70%, at least about 80%, or at least about 90% identical to the amino acid sequence of SEQ ID NO: 38 or SEQ ID NO: 39;

q) a heavy chain that includes an amino acid sequence at least about 70%, at least about 80%, or at least about 90% identical to the amino acid sequence of SEQ ID NO: 17 and a light chain that includes an amino acid sequence at least about 70%, at least about 80%, or at least about 90% identical to the amino acid sequence of SEQ ID NO: 38 or SEQ ID NO: 39;

r) a heavy chain that includes an amino acid sequence at least about 70%, at least about 80%, or at least about 90% identical to the amino acid sequence of SEQ ID NO: 18 and a light chain that includes an amino acid sequence at least about 70%, at least about 80%, or at least about 90% identical to the amino acid sequence of SEQ ID NO: 38 or SEQ ID NO: 39;

s) a heavy chain that includes an amino acid sequence at least about 70%, at least about 80%, or at least about 90% identical to the amino acid sequence of SEQ ID NO: 19 and a light chain that includes an amino acid sequence at least about 70%, at least about 80%, or at least about 90% identical to the amino acid sequence of SEQ ID NO: 38 or SEQ ID NO: 39;
t) a heavy chain that includes an amino acid sequence at least about 70%, at least about 80%, or at least about 90% identical to the amino acid sequence of SEQ ID NO: 20 and a light chain that includes an amino acid sequence at least about 70%, at least about 80%, or at least about 90% identical to the amino acid sequence of SEQ ID NO: 38 or SEQ ID NO: 39;
u) a heavy chain that includes an amino acid sequence at least about 70%, at least about 80%, or at least about 90% identical to the amino acid sequence of SEQ ID NO: 21 and a light chain that includes an amino acid sequence at least about 70%, at least about 80%, or at least about 90% identical to the amino acid sequence of SEQ ID NO: 38 or SEQ ID NO: 39;
v) a heavy chain that includes an amino acid sequence at least about 70%, at least about 80%, or at least about 90% identical to the amino acid sequence of SEQ ID NO: 22 and a light chain that includes an amino acid sequence at least about 70%, at least about 80%, or at least about 90% identical to the amino acid sequence of SEQ ID NO: 38 or SEQ ID NO: 39;
w) a heavy chain that includes an amino acid sequence at least about 70%, at least about 80%, or at least about 90% identical to the amino acid sequence of SEQ ID NO: 23 and a light chain that includes an amino acid sequence at least about 70%, at least about 80%, or at least about 90% identical to the amino acid sequence of SEQ ID NO: 38 or SEQ ID NO: 39;
x) a heavy chain that includes an amino acid sequence at least about 70%, at least about 80%, or at least about 90% identical to the amino acid sequence of SEQ ID NO: 40 and a light chain that includes an amino acid sequence at least about 70%, at least about 80%, or at least about 90% identical to the amino acid sequence of SEQ ID NO: 45;
y) a heavy chain that includes an amino acid sequence at least about 70%, at least about 80%, or at least about 90% identical to the amino acid sequence of SEQ ID NO: 41 and a light chain that includes an amino acid sequence at least about 70%, at least about 80%, or at least about 90% identical to the amino acid sequence of SEQ ID NO: 46;
z) a heavy chain that includes an amino acid sequence at least about 70%, at least about 80%, or at least about 90% identical to the amino acid sequence of SEQ ID NO: 42 and a light chain that includes an amino acid sequence at least about 70%, at least about 80%, or at least about 90% identical to the amino acid sequence of SEQ ID NO: 47;
aa) a heavy chain that includes an amino acid sequence at least about 70%, at least about 80%, or at least about 90% identical to the amino acid sequence of SEQ ID NO: 43 and a light chain that includes an amino acid sequence at least about 70%, at least about 80%, or at least about 90% identical to the amino acid sequence of SEQ ID NO: 48, SEQ ID NO: 49, or SEQ ID NO: 50;
bb) a heavy chain that includes an amino acid sequence at least about 70%, at least about 80%, or at least about 90% identical to the amino acid sequence of SEQ ID NO: 44 and a light chain that includes an amino acid sequence at least about 70%, at least about 80%, or at least about 90% identical to the amino acid sequence of SEQ ID NO: 48, SEQ ID NO: 49, or SEQ ID NO: 50;
cc) a heavy chain that includes an amino acid sequence at least about 70%, at least about 80%, or at least about 90% identical to the amino acid sequence of SEQ ID NO: 51 and a light chain that includes an amino acid sequence at least about 70%, at least about 80%, or at least about 90% identical to the amino acid sequence of SEQ ID NO: 61, SEQ ID NO: 62, SEQ ID NO: 63, SEQ ID NO: 64, or SEQ ID NO: 65;
dd) a heavy chain that includes an amino acid sequence at least about 70%, at least about 80%, or at least about 90% identical to the amino acid sequence of SEQ ID NO: 52 and a light chain that includes an amino acid sequence at least about 70%, at least about 80%, or at least about 90% identical to the amino acid sequence of SEQ ID NO: 61, SEQ ID NO: 62, SEQ ID NO: 63, SEQ ID NO: 64, or SEQ ID NO: 65;
ee) a heavy chain that includes an amino acid sequence at least about 70%, at least about 80%, or at least about 90% identical to the amino acid sequence of SEQ ID NO: 53 and a light chain that includes an amino acid sequence at least about 70%, at least about 80%, or at least about 90% identical to the amino acid sequence of SEQ ID NO: 61, SEQ ID NO: 62, SEQ ID NO: 63, SEQ ID NO: 64, or SEQ ID NO: 65;
ff) a heavy chain that includes an amino acid sequence at least about 70%, at least about 80%, or at least about 90% identical to the amino acid sequence of SEQ ID NO: 54 at least about 90% identical to the amino acid sequence of SEQ ID NO: 61, SEQ ID NO: 62, SEQ ID NO: 63, SEQ ID NO: 64, or SEQ ID NO: 65;
gg) a heavy chain that includes an amino acid sequence at least about 70%, at least about 80%, or at least about 90% identical to the amino acid sequence of SEQ ID NO: 55 and a light chain that includes an amino acid sequence at least about 70%, at least about 80%, or at least about 90% identical to the amino acid sequence of SEQ ID NO: 61, SEQ ID NO: 62, SEQ ID NO: 63, SEQ ID NO: 64, or SEQ ID NO: 65;
hh) a heavy chain that includes an amino acid sequence at least about 70%, at least about 80%, or at least about 90% identical to the amino acid sequence of SEQ ID NO: 56 and a light chain that includes an amino acid sequence at least about 70%, at least about 80%, or at least about 90% identical to the amino acid sequence of SEQ ID NO: 66, SEQ ID NO: 67, SEQ ID NO: 68, SEQ ID NO: 69, or SEQ ID NO: 70;
ii) a heavy chain that includes an amino acid sequence at least about 70%, at least about 80%, or at least about 90% identical to the amino acid sequence of SEQ ID NO: 57 and a light chain that includes an amino acid sequence at least about 70%, at least about 80%, or at least about 90% identical to the amino acid sequence of SEQ ID NO: 66, SEQ ID NO: 67, SEQ ID NO: 68, SEQ ID NO: 69, or SEQ ID NO: 70;
jj) a heavy chain that includes an amino acid sequence at least about 70%, at least about 80%, or at least about 90% identical to the amino acid sequence of SEQ ID NO: 58 and a light chain that includes an amino acid sequence at least about 70%, at least about 80%, or at least about 90% identical to the amino acid sequence of SEQ ID NO: 66, SEQ ID NO: 67, SEQ ID NO: 68, SEQ ID NO: 69, or SEQ ID NO: 70;
kk) a heavy chain that includes an amino acid sequence at least about 70%, at least about 80%, or at least about 90% identical to the amino acid sequence of SEQ ID NO: 59 and a light chain that includes an amino acid sequence at least about 70%, at least about 80%, or at least about 90% identical to the amino acid sequence of SEQ ID NO: 66, SEQ ID NO: 67, SEQ ID NO: 68, SEQ ID NO: 69, or SEQ ID NO: 70; or ll) a heavy chain that includes an amino acid sequence at least about 70%, at least about 80%, or at least about 90% identical to the amino acid sequence of SEQ ID NO: 60 and a light chain that includes an amino acid sequence at least about 70%, at least about 80%, or at least about 90% identical to the amino acid sequence of SEQ ID NO: 66, SEQ ID NO: 67, SEQ ID NO: 68, SEQ ID NO: 69, or SEQ ID NO: 70.

In some embodiments, the isolated monospecific or bispecific antibody or antigen binding fragment thereof can include a constant chain region and wherein the antibody or antigen binding fragment thereof including the constant chain region has enhanced in vivo half-live and/or reduced immunogenicity compared to the antibody or antigen binding fragment thereof without the constant chain region.

In some embodiments, the constant chain region includes an amino acid sequence at least about 70%, at least about 80%, or at least about 90% identical to the amino acid sequence of SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, or SEQ ID NO: 139.

In some embodiments, the isolated monospecific or bispecific antibody or antigen binding fragment thereof can include at least one of the following:

a heavy chain that includes an amino acid sequence at least about 70%, at least about 80%, or at least about 90% identical to the amino acid sequence of SEQ ID NO: 156 and a light chain that includes an amino acid sequence at least about 70%, at least about 80%, or at least about 90% identical to the amino acid sequence of SEQ ID NO: 157;

a heavy chain that includes an amino acid sequence at least about 70%, at least about 80%, or at least about 90% identical to the amino acid sequence of SEQ ID NO: 166 and a light chain that includes an amino acid sequence at least about 70%, at least about 80%, or at least about 90% identical to the amino acid sequence of SEQ ID NO: 167;

a heavy chain that includes an amino acid sequence at least about 70%, at least about 80%, or at least about 90% identical to the amino acid sequence of SEQ ID NO: 170 and a light chain that includes an amino acid sequence at least about 70%, at least about 80%, or at least about 90% identical to the amino acid sequence of SEQ ID NO: 171;

a heavy chain that includes an amino acid sequence at least about 70%, at least about 80%, or at least about 90% identical to the amino acid sequence of SEQ ID NO: 178 and a light chain that includes an amino acid sequence at least about 70%, at least about 80%, or at least about 90% identical to the amino acid sequence of SEQ ID NO: 179;

a heavy chain that includes an amino acid sequence at least about 70%, at least about 80%, or at least about 90% identical to the amino acid sequence of SEQ ID NO: 182;

a heavy chain that includes an amino acid sequence at least about 70%, at least about 80%, or at least about 90% identical to the amino acid sequence of SEQ ID NO: 184 and a light chain that includes an amino acid sequence at least about 70%, at least about 80%, or at least about 90% identical to the amino acid sequence of SEQ ID NO: 185;

a heavy chain that includes an amino acid sequence at least about 70%, at least about 80%, or at least about 90% identical to the amino acid sequence of SEQ ID NO: 187 and a light chain that includes an amino acid sequence at least about 70%, at least about 80%, or at least about 90% identical to the amino acid sequence of SEQ ID NO: 188;

a heavy chain that includes an amino acid sequence at least about 70%, at least about 80%, or at least about 90% identical to the amino acid sequence of SEQ ID NO: 191;

a heavy chain that includes an amino acid sequence at least about 70%, at least about 80%, or at least about 90% identical to the amino acid sequence of SEQ ID NO: 193 and a light chain that includes an amino acid sequence at least about 70%, at least about 80%, or at least about 90% identical to the amino acid sequence of SEQ ID NO: 194; or a heavy chain that includes an amino acid sequence at least about 70%, at least about 80%, or at least about 90% identical to the amino acid sequence of SEQ ID NO: 197 and a light chain that includes an amino acid sequence at least about 70%, at least about 80%, or at least about 90% identical to the amino acid sequence of SEQ ID NO: 198.

In some embodiments, the isolated monospecific or bispecific antibody or antigen binding fragment thereof can include a peptide linker. The peptide linker can include the amino acid sequence of SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 245, or SEQ ID NO: 246.

In some embodiments, the antibody or antigen binding fragment thereof is humanized.

In other embodiments, the antibody or antigen binding fragment thereof binds to human properdin.

In some embodiments, the antibody or antigen binding fragment thereof inhibits alternative complement pathway activation in a mammal without inhibiting classical complement pathway activation.

In some embodiments, the isolated monospecific or bispecific antibody or antigen binding fragment thereof can include a first heavy chain variable region that binds to properdin and a second heavy chain variable region that binds to a different epitope than the first heavy chain variable region.

In some embodiments, the second heavy chain variable region increases the in vivo half-life of the antibody or antigen binding fragment thereof to about 3 week to about 8 weeks.

In other embodiments, the second heavy chain variable region binds to one of albumin, TNF, or VEGF.

In some embodiments, the second antibody or antigen binding fragment thereof comprises an amino acid sequence at least about 70%, at least about 80%, or at least about 90% identical to the amino acid sequence of SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 150, or SEQ ID NO: 152.

In some embodiments, the isolated monospecific or bispecific antibody or antigen binding fragment thereof can inhibit C3b and Mac complex (C5b-9) formation in vivo.

Other embodiments described herein relate to an isolated monospecific or bispecific anti-properdin antibody or antigen binding fragment that includes:

an anti-properdin heavy chain variable region that includes an amino acid sequence at least about 70%, at least about 80%, or at least about 90% identical to the amino acid sequence of SEQ ID NO: 2 and an anti-properdin light chain variable region that includes an amino acid sequence at least about 70%, at least about 80%, or at least about 90% identical to the amino acid sequence of SEQ ID NO: 25 and wherein the heavy chain variable region includes:
a CDR-H1 comprising the amino acid sequence of GYIFTX$_1$YPIH (SEQ ID NO: 201), wherein X$_1$ is N, Q, S, A, or D (e.g., X$_1$ is Q, S, A, or D)
a CDR-H2 comprising the amino acid sequence of FIX$_1$PGGGX$_2$DEX$_3$X$_4$X$_5$X$_6$X$_7$X$_8$X$_9$ (SEQ ID NO: 202), wherein X$_1$ is D, E, S (e.g., E or S), or A; X$_2$ is H or Y; X$_3$ is P, S, or Y; X$_4$ is A or D; X$_5$ is D, E, or Q; X$_6$ is K, R, or S; X$_7$ is F or V; X$_8$ is E, K, Q, or R; and X$_9$ is D or G; and
a CDR-H3 comprising the amino acid sequence of RGG-GYYLDY (SEQ ID NO: 203); and the light chain variable region includes:
a CDR-L1 comprising the amino acid sequence of RASQDISFFLN (SEQ ID NO: 206),
a CDR-L2 comprising the amino acid sequence of X$_1$X$_2$SX$_3$YHS (SEQ ID NO: 207), wherein X$_1$ is G or Y; X$_2$ is A or T; and X$_3$ is R or S; and
a CDR-L3 comprising the amino acid sequence of QHGX$_1$TLPX$_2$T (SEQ ID NO: 208), wherein X$_1$ is N, A, D, Q, or S (e.g., A, D, Q, or S); and X$_2$ is F, H, R, W, or Y (e.g., F, H, R, or Y).

In some embodiments, the isolated monospecific or bispecific antibody or antigen binding fragment thereof can include at least one of a constant chain region or a second heavy chain variable region binds that binds to a different epitope than the anti-properdin heavy chain region and wherein the antibody or antigen binding fragment including the constant chain region or second heavy chain variable region has enhanced in vivo half-live and/or reduced immunogenicity compared to the antibody or antigen binding fragment thereof without the constant chain region or second heavy chain variable region.

In some embodiments, the constant chain region includes an amino acid sequence at least about 70%, at least about 80%, or at least about 90% identical to the amino acid sequence of SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, or SEQ ID NO: 139; and the second heavy chain variable region includes an amino acid sequence at least about 70%, at least about 80%, or at least about 90% identical to the amino acid sequence of SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 150, or SEQ ID NO: 152.

In some embodiments, the isolated monospecific or bispecific antibody or antigen binding fragment thereof can include a heavy chain having an amino acid sequence at least 90% identical to SEQ ID NO: 247, and a light chain having an amino acid sequence at least 90% identical to SEQ ID NO: 248.

Other embodiments described herein relate to a method of treating a complement mediated disease or disorder in a subject in need thereof. The method includes administering a therapeutically effective amount of the antibody or antigen binding fragment thereof as described herein to a subject in need thereof.

In some embodiments, the subject has a disease or disorder in which activation of the alternative complement pathway plays a role, and wherein the step of administering the antibody or antigen binding fragment thereof treats the disease or disorder.

In another aspect, the method includes the step of treating a disease or disorder in which activation of the alternative complement pathway plays a role, comprising administering antibody or antigen binding fragment thereof described herein to an individual that has, or is at risk of developing, said disease or disorder.

In a further aspect, the method includes the step of treating a disease or disorder selected from the group consisting of inflammatory diseases and inflammatory disorders.

In another aspect, the method includes the step of treating a disease or disorder selected from the group consisting of autoimmune diseases and autoimmune disorders.

In a further aspect, the method includes the step of treating an autoimmune disease or autoimmune disorder selected from the group consisting of systemic lupus erythematosus, myasthenia gravis, arthritis condition, Alzheimer's disease and multiple sclerosis.

In another aspect, the method includes the step of treating an arthritis condition. The arthritis condition can be selected from the group consisting of rheumatoid arthritis, osteoarthritis, and juvenile arthritis.

In a further aspect, the method includes the step of treating a complement-associated disease or disorder selected from a group consisting of ocular diseases and ocular disorders. The ocular disease or ocular disorder can be selected from the group consisting of diabetic retinopathy, histoplasmosis of the eye, age-related macular degeneration, diabetic retinopathy, choroidal neo-vascularization (CNV), uveitis, diabetic macular edema, pathological myopia, von Hippel-Lindau disease, histoplasmosis of the eye, Central Retinal Vein Occlusion (CRVO), corneal neo-vascularization, and retinal neovascularization. The age-related macular degeneration can be selected from the group consisting of intermediate dry AMD and geographic atrophy.

In another aspect, the step of treating a complement-associated disorder is selected from the group consisting of asthmatic disorders and airway inflammation disorders. The airway inflammation disorder can be selected from the group consisting of: asthma, chronic obstructive pulmonary disease ("COPD"), allergic broncho-pulmonary aspergillosis, hypersensitivity pneumonia, eosinophilic pneumonia, emphysema, bronchitis, allergic bronchitis bronchiecstasis, cyctic fibrosis, tuberculosis, hypersensitivity pneumonitis, occupational asthma, sarcoid, reactive airway disease syndrome, interstitial lung disease, hyper-eosinophilic syndrome, rhinitis, sinusitis, exercise-induced asthma, pollution-induced asthma, cough variant asthma, parasitic lung disease, respiratory syncytial virus ("RSV") infection, parainfluenza virus ("PIV") infection, rhinovirus ("RV") infection, and adenovirus infection.

In another aspect, the step of treating a complement-associated disorder is selected Central and Peripheral Nervous System/Neurological diseases and disorders including multiple sclerosis (MS), myasthenia gravis (MG), myasthenia gravis, multiple sclerosis, Guillain Barre syndrome, Miller-Fisher syndrome, stroke, reperfusion following stroke, Alzheimer's disease, multifocal motor neuropathy (MMN), demyelination, Huntington's disease, amyotrophic lateral sclerosis (ALS), Parkinson's disease, degenerative disc disease (DDD), meningitis, cranial nerve damage from meningitis, variant Creutzfeldt-Jakob Disease (vCJD), idiopathic polyneuropathy, brain/cerebral trauma (including, but not limited to, hemorrhage, inflammation, and edema), neuromyelitis optica (NMO), including those serologically positive for aquaporin-4 (AQP4)-IgG autoantibody, and neuropathic pain.

BRIEF DESCRIPTION OF THE DRAWINGS

FIG. 1 illustrates a schematic showing the structure of a monospecific anti-properdin antibody and a table listing the amino acid sequences of the $V_H$ regions (SEQ ID NOs: 204 and 205) and $V_L$ regions (SEQ ID NOs: 209 and 210) of the monospecific anti-properdin antibody in accordance with an embodiment.

FIG. 4 illustrates a table showing variable and constant chain linkers (SEQ ID NOs: 140-149).

FIG. 5 illustrates a schematic showing the structure of a bispecific anti-properdin/anti-albumin antibody and a table listing the amino acid sequences of the camelid anti-properdin portion (SEQ ID NOs: 240 and 244) and anti-albumin portion (SEQ ID NOs: 108 and 119) of the bispecific anti-properdin/anti-albumin antibody in accordance with another embodiment.

FIG. 6 illustrates a schematic showing the structure of single chain camelid anti-properdin/anti-albumin antibodies (NMT1001 and NMT1002) and a table listing the amino acid sequences of the camelid anti-properdin $V_{HH}$ region (SEQ ID NO: 108), linker (SEQ ID NO: 143), and anti-albumin region (SEQ ID NO: 75) of NMT1001 (SEQ ID NOs: 108, 143 and 75) and the camelid anti-properdin $V_{HH}$ region (SEQ ID NO: 110), linker (SEQ ID NO: 143), and anti-albumin region (SEQ ID NO: 75) of NMT 1002.

FIG. 7 illustrates a schematic showing the structure of a monospecific anti-properdin (Fab)2 (NMT1003) and a table listing the amino acid sequences of the $V_H$ and $V_L$ regions (SEQ ID NOs: 1 and 24), Fc-CH1 (SEQ ID NO: 138), Fc-LC (SEQ ID NO: 139) of NMT1003.

FIG. 8 illustrates a schematic showing the structure of bispecific anti-albumin/anti-properdin Fabs (NMT1004 and NMT1005) and a table listing the amino acid sequences of the anti-properdin VH (SEQ ID NO: 1), Fc-CH1 (SEQ ID NO: 138), VL (SEQ ID NO: 24), and Fc-LC (SEQ ID NO: 139), linker (SEQ ID NO: 143), and anti-albumin region (SEQ ID NO: 110) of NMT1004 and the anti-properdin VH (SEQ ID NO: 1), Fc-CH1 (SEQ ID NO: 138), VL (SEQ ID NO: 24), and Fc-LC (SEQ ID NO: 139), linker (SEQ ID NO: 143), and anti-albumin region (SEQ ID NO: 108) of NMT1005.

FIG. 9 illustrates a schematic showing the structure of a monospecific camelid anti-properdin antibody and a table listing the amino acid sequences of the camelid anti-properdin $V_{HH}$ (SEQ ID NO: 74), linker (SEQ ID NO: 143), and IgG4 Fc with hinge region (SEQ ID NO: 137) of the monospecific camelid anti-properdin antibody (SEQ ID NO: 162) in accordance with another embodiment.

FIG. 10 illustrates a schematic showing the structure of a bispecific anti-properdin/anti-albumin antibody and a table listing the amino acid sequences of anti-properdin $V_H$ (SEQ ID NO: 2), IG1 Fc (SEQ ID NO: 129), VL (SEQ ID NO: 25), and Fc-LC (SEQ ID NO: 139) and anti-albumin $V_H$ (SEQ ID NO: 71), IG1 Fc (SEQ ID NO: 129), VL (SEQ ID NO: 72), and Fc-LC (SEQ ID NO: 139) of the bispecific anti-properdin/anti-albumin antibody in accordance with another embodiment.

FIG. 11 illustrates a schematic showing the structure of a bispecific anti-properdin/anti-albumin antibody and a table listing the amino acid sequences of anti-properdin $V_H$ (SEQ ID NO: 52), IG1 Fc (SEQ ID NO: 131), VL (SEQ ID NO: 62), and Fc-LC (SEQ ID NO: 139) and anti-albumin $V_H$ (SEQ ID NO: 71), IG1 Fc (SEQ ID NO: 131), VL (SEQ ID NO: 72), and Fc-LC (SEQ ID NO: 139) of the bispecific anti-properdin/anti-albumin antibody in accordance with another embodiment.

FIG. 12 illustrates a schematic showing the structure of a bispecific anti-properdin/anti-TNF antibody and a table listing the amino acid sequences of anti-properdin $V_H$ (SEQ ID NO: 2), IG1 Fc (SEQ ID NO: 129), VL (SEQ ID NO: 25), and Fc-LC (SEQ ID NO: 139) and anti-TNF $V_H$ (SEQ ID NO: 150), IG1 Fc (SEQ ID NO: 129), VL (SEQ ID NO: 151), and Fc-LC (SEQ ID NO: 139) of the bispecific anti-properdin/anti-TNF antibody in accordance with another embodiment.

FIG. 13 illustrates a schematic showing the structure of a bispecific anti-properdin/anti-VEGF antibody and a table listing the amino acid sequences of anti-properdin $V_H$ (SEQ ID NO: 2), IG1 Fc (SEQ ID NO: 130), VL (SEQ ID NO: 25), and Fc-LC (SEQ ID NO: 139) and anti-VEGF $V_H$ (SEQ ID NO: 152), IG1 Fc (SEQ ID NO: 130), VL (SEQ ID NO: 153), and Fc-LC (SEQ ID NO: 139) of the bispecific anti-properdin/anti-VEGF antibody in accordance with another embodiment.

FIG. 15 illustrates a schematic showing the structure of a bispecific anti-properdin/anti-albumin antibody and a table listing the amino acid sequences of anti-properdin $V_H$ (SEQ ID NO: 2), IG1 Fc (SEQ ID NO: 131), VL (SEQ ID NO: 25), and Fc-LC (SEQ ID NO: 139) and anti-albumin $V_H$ (SEQ ID NO: 110), linker (SEQ ID NO: 143), and IgG1 Fc (SEQ ID NO: 131) of the bispecific anti-properdin/anti-albumin antibody in accordance with another embodiment.

FIG. 16 illustrates a schematic showing the structure of a bispecific anti-properdin/anti-albumin antibody and a table listing the amino acid sequences of anti-properdin $V_H$ (SEQ ID NO: 2), IG1 Fc (SEQ ID NO: 130), VL (SEQ ID NO: 25), and Fc-LC (SEQ ID NO: 139) and anti-albumin $V_H$ (SEQ ID NO: 71), IG1 Fc (SEQ ID NO: 130), VL (SEQ ID NO: 72), and Fc-LC (SEQ ID NO: 139) of the bispecific anti-properdin/anti-albumin antibody in accordance with another embodiment.

FIG. 17 illustrates a schematic showing the structure of a bispecific camelid anti-properdin/anti-albumin antibody and a table listing the amino acid sequences of the camelid anti-properdin $V_{HH}$ (SEQ ID NO: 75), linker (SEQ ID NO: 143), and IgG4 Fc with hinge region (SEQ ID NO: 137) and anti-albumin $V_H$ (SEQ ID NO: 108), linker (SEQ ID NO: 143), and IgG4 Fc (SEQ ID NO: 137) of the bispecific camelid anti-properdin/anti-albumin antibody in accordance with another embodiment.

FIG. 34. illustrates plots showing inhibition of AP mediated C3 convertase formation and Deposition by NMT28.

FIG. 35 illustrates plots showing CP mediated C3b Formation and Deposition by NMT28.

DETAILED DESCRIPTION OF THE INVENTION

Figure 2:
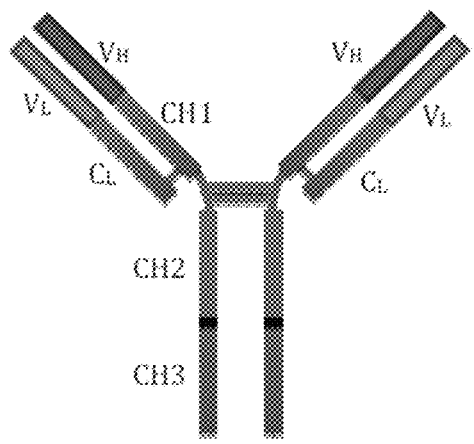
FIG. 2 illustrates a schematic showing the structure of a monospecific anti-properdin antibody and a table listing the amino acid sequences of the $V_H$ regions (SEQ ID NOs: 214 and 215) and $V_L$ regions (SEQ ID NOs: 219 and 220) of the monospecific anti-properdin antibody in accordance with another embodiment.

As used herein, the term "acceptor human framework" refers to a framework comprising the amino acid sequence of a VL or VH framework derived from a human immunoglobulin framework, or from a human consensus framework.

As used herein, the term "antibody" covers full length monoclonal antibodies, polyclonal antibodies, nanobodies and multi-specific antibodies. Biological antibodies are usually hetero-tetrameric glycoproteins of about 150,000 Daltons, composed of two identical light (L) chains and two identical heavy (H) chains. The two heavy chains are linked together by disulfide bonds, and each heavy chain is linked to a light chain by a disulfide bond. Each full-length IgG molecule contains at least two binding sites for a specific target or antigen. Light chains are either kappa or the lambda. Both light chains contain a domain of variable amino acid sequences, called the variable region (variously referred to as a "$V_L$," "$V_{kappa}$," or "$V_{lambda}$-region") and a domain of relatively conserved amino acid sequences, called the constant region ("CL-region"). Similarly, each heavy chain contains a variable region ("$V_H$-region") and three constant domains ("$C_{H1}$-," "$C_{H2}$-," and "$C_{H3}$-regions") and a hinge region.

As used herein, the term "antibody fragment" refers to a segment of a full-length antibody, generally called as the target binding or variable region. Other antibodies include diabodies, linear antibodies, single-chain antibody molecules and multispecific antibodies formed from antibody fragments. Examples include Fab, Fab', F(ab')2, Fv, or scFv fragments. An "Fv" fragment is the minimum antibody fragment which contains a complete target recognition and binding site.

As used herein, the term "antigen binding fragment" refers to a fragment or fragments of an antibody molecule that contain the antibody variable regions responsible for antigen binding.

Antigen-binding fragments can be prepared from full-length antibody by protease digestion. Antigen-binding fragments may be produced using standard recombinant DNA methodology by those skilled in the art. Examples of antigen binding fragments:
"Fab" fragments (single chain variable regions with VH and VL)
"Monovalent Fragments" (antibody fragments consisting of the VL, VH, CL and CH1 domains)
"F(ab')2" fragments (bivalent fragments comprising two Fab fragments linked by a disulfide bridge at the hinge region);
"Fd" fragments (which consist of the VH and CH1 domains of an antibody);
"Fv" fragment (which consist of the VL and VH domains of a single arm of an antibody);
single domain antibody ("dAb"), which consist of a VH domain or a VL domain; and
an isolated Complementarity Determining Region ("CDR").

As used herein, complementarity-determining region ("CDR") are the key binding regions of the antibody. CDR refers to a specific region within variable regions of the heavy and the light chain. Generally, the variable region consists of four framework regions (FR1, FR2, FR3, FR4) and three CDRs arranged in the following manner: NH2-FR1-CDR1-FR2-CDR2-FR3-CDR3-FR4-COOH. The term "framework regions" refers to those variable domain residues other than the CDR residues herein defined.

CDRs, as antigen binding fragments, can also be incorporated into single domain antibodies, maxi bodies, mini bodies, intrabodies, diabodies, triabodies, tetra bodies, v-NAR and bis-scFv. Antigen binding fragments of antibodies can be grafted into scaffolds based on polypeptides. Antigen binding fragments can be incorporated into single chain molecules comprising a pair of tandem Fv segments (VH-CH1-VH-CH1) which, together with complementary light chain polypeptides, form a pair of antigen binding regions.

As used herein, a "single chain Fv" or "scFv" antibody fragment comprises the VH and VL domains of an antibody, wherein these domains are present in a single polypeptide chain.

As used herein "effector functions" refer to those biological activities attributable to the native Fc region of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); lack of activation of platelets that express Fc receptor; and B cell activation. In order to minimize or eliminate side effects of a therapeutic antibody, it may be preferable to minimize or eliminate effector functions.

In the context of this application "undesired effector functions" include ADCC, CDC, classical pathway activation, cell activation, and antibody mediated inflammation.

An "engineered antibody" is an antibody that is not naturally produced, and which has been altered or created to achieve a specific purpose or to have a specific characteristic. For example, antibodies which have undergone deliberate modifications to their wild type forms, to have reduced effector functions, are engineered antibodies.

As used herein, the term "Fc region" refers to the region of the antibody that provides defense to a given antigen.

As used herein, the term "first portion of the antibody" refers to a portion of a whole antibody, a portion less than the whole, which contains the antigen binding regions of the antibody. "Second portion of the antibody" refers to a portion of a whole antibody, a portion less than the whole, which consists of the portion of the antibody which is not included in the first portion.

The terms "Fc receptor" or "FcγR" describe a receptor that binds to the Fc region of an IgG. "FcγRI," "FcγRII," and "FcγRIII" are subclasses of FcγRs.

As used herein, the term "reduced Fc effector function(s)" refers to the function(s) of an antibody wherein the antibody does not act against an antigen that recognizes the Fc region of the antibody. Examples of reduced Fc effector functions can include, but are not limited to, reduced Fc binding to the antigen, lack of Fc activation against an antigen, an Fc region that contains mutations to prevent normal Fc effector functions, or prevention of the activation of platelets and other cells that have Fc receptors.

A "modification" to an antibody, antibody fragment, and/or Fc region of an antibody, refers to a substitution, insertion, or deletion of one or more amino acids in the protein's wild type polypeptide sequence. A modified antibody, antibody fragment, and/or Fc region is one in which a modification has been artificially made.

As used herein, "competitively inhibits" refers to competitive inhibition of binding of a isolated antibody or antigen binding portion thereof to properdin by any other molecule.

As used herein, the term "epitope" refers to a site on properdin to which antibody and fragments thereof bind and perform the functional activity. The term epitope is the same as "antigenic site", and "antibody binding site,". One skilled in the art can align the sequence of properdin of a human with the sequence of properdin from another animal species and determine the positions of the epitope.

As used herein, "Fab fragment" refers to the constant domain of the light chain and the first constant domain of the heavy chain. Fab' fragments differ from Fab fragments by the few extra residues at the carboxyl terminus of the heavy chain CH1 domain including one or more cysteines from the antibody hinge region. F(ab') fragments are produced by cleavage of the disulfide bond at the hinge cysteines of the F(ab')2 pepsin digestion product.

As used herein, the term "antigen binding fragment thereof" of an antibody refers to an antibody fragment having qualitative biological activity in common with a full-length antibody. For example, an antigen binding fragment thereof of an antibody is one which can bind to properdin in such a manner so as to prevent or substantially reduce the alternative complement activation.

As used herein, the term "human consensus framework" refers to a framework which represents the most commonly occurring amino acid residue in a selection of human immunoglobulin VL or VH framework sequences. Generally, the selection of human immunoglobulin VL or VH sequences is from a subgroup of variable domain sequences.

As used herein, a "humanized antibody" refers to an antibody consisting of mostly human sequences, except for CDR1, CDR2, and CDR3. All framework regions are also humanized. A chimeric antibody comprises murine CDRs, murine framework regions, and human constant regions. Collectively, chimeric antibodies contain murine both variable regions and human constant regions.

As used herein, the term "monovalent antibody or antigen binding fragment thereof" refers to an antibody or antigen binding fragment thereof comprising a single binding domain, e.g., $V_H$ or $V_{HH}$, for an antigen, e.g., a single properdin molecule. In one embodiment, the bound antigen molecule is part of a multimer, e.g., a trimer or higher order multimer of properdin monomers. Antibodies generally, including monovalent antibodies or antibody fragments thereof, bind with a high degree of specificity to a particular antigen.

As used herein, the term "single domain antibody" defines molecules where the antigen binding site is present on, and formed by, a single immunoglobulin domain. Generally, the antigen binding site of an immunoglobulin single variable domain is formed by no more than three CDRs. The single variable domain may, for example, include a light chain variable domain sequence (a $V_L$ sequence) or a suitable fragment thereof; or a heavy chain variable domain sequence (e.g., a $V_H$ sequence or $V_{HH}$ sequence) or a suitable fragment thereof; as long as it is capable of forming a single antigen binding unit (i.e., a functional antigen binding unit that essentially is the single variable domain, such that the single antigen binding domain does not need to interact with another variable domain to form a functional antigen binding unit).

As used herein, the term "camelid antibody" refers to an antibody derived from a camelid species, for example, in a camel, dromedary, llama, alpaca or guanaco. Camelid antibodies differ from those of most other mammals in that they lack a light chain, and thus include only heavy chains with complete and diverse antigen binding capabilities (Hamers-Casterman, C. et al., Nature, 363:446-8, 1993).

As used herein, the term "$V_{HH}$" refers to a single heavy chain variable domain antibody devoid of light chains. Vmi chains, for example, can be of the type that can be found in Camelidae or cartilaginous fish that are naturally devoid of light chains or to a synthetic and non-immunized $V_{HH}$ that can be constructed accordingly. Each heavy chain includes a variable region encoded by V-, D- and J-exons. A $V_{HH}$ may be a natural $V_{HH}$ antibody, e.g., a camelid antibody, or a recombinant protein including a heavy chain variable domain.

As used herein, the term an "isolated antibody" refers to an antibody that is substantially free of other antibodies having different antigenic specificities (e.g., an isolated antibody that binds to properdin is substantially free of contaminants, e.g., antibodies that do not bind to properdin). In addition, an "isolated" antibody is one that has been identified and separated and/or recovered from a component of its natural environment. Contaminant components of its natural environment are materials that could interfere with diagnostic or therapeutic uses for the antibody, and may include enzymes, hormones, and other proteinaceous or nonproteinaceous solutes.

As used herein, the term "specific binding" of an antibody or fragment thereof, polypeptide, or peptidomimetic is binding to a target molecule that is measurably different from binding to molecules that are not target molecules. As used herein, specific binding refers to a greater than 95% preference for binding a particular antigen versus background ("non-specific") binding. "Substantially specific" binding refers to a greater than about 80% preference for binding a particular antigen versus background. Binding can be measured using a variety of methods including, but not limited to, Western blot, immunoblot, enzyme-linked immunosorbant assay ("ELISA"), radioimmunoassay ("RIA"), immunoprecipitation, surface plasmon resonance, bio-layer interferometry, chemiluminescence, fluorescent polarization, phosphorescence, immunohistochemical analysis, matrix-assisted laser desorption/ionization time-of-flight ("MALDI-TOF") mass spectrometry, microcytometry, microarray, microscopy, fluorescence activated cell sorting ("FACS") and flow cytometry.

As used herein, the term "human properdin" refers to a 469 amino acid soluble glycoprotein found in plasma that has seven thrombospondin type I repeats (TSR) with the N-terminal domain, TSR0, being a truncated domain. Human properdin, a 53 kDa protein, includes a signal peptide (amino acids 1-28), and six, non-identical TSR repeats about 60 amino acids each, as follows: amino acids 80-134 (TSR1), amino acids 139-191 (TSR2), amino acids 196-255 (TSR3), amino acids 260-313 (TSR4), amino acids 318-377 (TSR5), and amino acids 382-462 (TSR6). Properdin is formed by oligomerization of a rod-like monomer into cyclic dimers, trimers, and tetramers. The amino acid sequence of human properdin is found in the GenBank database under the following accession numbers: for human properdin, see, e.g., GenBank Accession Nos. AAA36489, NP_002612, AAH15756, AAP43692, S29126 and CAA40914. Properdin is a positive regulator of the alternative complement activation cascade. Known binding ligands for properdin include C3b, C3bB and C3bBb (Blatt, A. et al., Immunol. Rev., 274:172-90, 2016).

As used herein, the term "mouse properdin" refers to a 457 amino acid soluble glycoprotein found in plasma that has seven TSRs with the N-terminal domain, TSR0, being truncated. Mouse properdin, a 50 kDa protein, includes a signal peptide (amino acids 1-24), and six, non-identical TSRs of about 60 amino acids each, as follows: amino acids 73-130 (TSR1), amino acids 132-187 (TSR2), amino acids 189-251 (TSR3), amino acids 253-309 (TSR4), amino acids 311-372 (TSR5), and amino acids 374-457 (TSR6). Mouse properdin is formed by oligomerization of a rod-like monomer into cyclic dimers, trimers, and tetramers. The amino acid sequence of mouse properdin is found, for example, in the GenBank database (Gen Bank Accession Nos. P11680 and S05478).

As used herein, the term "TSR0 domain" refers to the truncated domain of properdin that precedes the TSR1 domain of properdin. For example, the TSR0 domain of human properdin includes amino acids 28-76.

As used herein, the term "TSR1 domain" refers to the domain of properdin adjacent to the TSR0 domain of properdin. For example, the TSR0 domain of human properdin includes amino acids 77-134.

As used herein, the term "an activity of properdin" refers to the biological activity of properdin including, but not limited to, binding interactions that lead to the stability of the C3/C5 convertase. Properdin binds most avidly to C3b,Bb—the alternative pathway C3/C5 convertase, but also binds to C3b; C3b,B and C3b,Bb. One function is to stabilize the C3b,Bb complex allowing increased alternative pathway activation (Pangburn, M., Methods Enzymol., 162:639-53, 1988; Nolan, K. & Reid, K., Methods Enzymol., 223:35-46, 1993). Properdin enhances formation of the alternative pathway C3 convertase by increasing binding of factor B to P,C3b complexes. Thus, properdin is an accelerator (positive regulator) of complement activation. Properdin also has been implicated in initiating activation of the alternative pathway by binding to the target surface and initiating C3/C5 convertase formation (Kemper C. & Hourcade, D., Mol. Immunol., 45:4048-56, 2008).

As used herein, the term "alternative complement pathway" refers to one of three pathways of complement activation (the others being the classical pathway and the lectin pathway). The alternative complement pathway is typically activated by bacteria, parasites, viruses or fungi, although IgA Abs and certain IgL chains have also been reported to activate this pathway.

As used herein, the term "alternative complement pathway dysregulation" refers to any aberration in the ability of the alternative complement pathway to provide host defense against pathogens and clear immune complexes and damaged cells and for immunoregulation. Alternative complement pathway dysregulation can occur both in fluid phase as well as at cell surface and can lead to excessive complement activation or insufficient regulation, both causing tissue injury.

As used herein, the term "a disease mediated by alternative complement pathway dysregulation" refers to an interruption, cessation or disorder of body functions, systems or organs caused by alternative complement pathway dysregulation. Such diseases would benefit from treatment with a composition or formulation described herein. In some embodiments, the disease is caused by any aberration in the ability of the alternative complement pathway to provide host defense against pathogens and clear immune complexes and damaged cells, and for immunoregulation. Also encompassed herein are diseases, directly or indirectly, mediated by dysregulation of one or more components of the alternative complement pathway, or a product generated by the alternative complement pathway.

As used herein, the term "alternative complement pathway-dependent membrane attack complex assembly" refers to a terminal complex formed as a result of alternative complement pathway activation and includes complement components C5, C6, C7, C8 and C9. Assembly of the membrane attack complex (MAC) leads to cell lysis.

As used herein, the term "alternative complement pathway dependent hemolysis" refers to the lysis of red blood cells mediated by increased alternative complement pathway-dependent MAC assembly and/or deposition on red blood cells.

As used herein, the term "linker" refers to a linkage between two elements, e.g., protein domains. A linker can be a covalent bond or a spacer. The term "bond" refers to a chemical bond, e.g., an amide bond or a disulfide bond, or any kind of bond created from a chemical reaction, e.g., chemical conjugation. A linker may refer to a moiety (e.g., a polyethylene glycol (PEG) polymer) or an amino acid sequence (e.g., a 3-200 amino acid, 3-150 amino acid, or 3-100 amino acid sequence) occurring between two polypeptides or polypeptide domains to provide space and/or flexibility between the two polypeptides or polypeptide domains. An amino acid spacer may be part of the primary sequence of a polypeptide (e.g., joined to the spaced polypeptides or polypeptide domains via the polypeptide backbone). A linker may comprise one or more glycine and serine residues.

As used herein, the term "identical" or "substantially identical" with respect to an antibody chain polypeptide sequence may be construed as an antibody chain exhibiting at least 65%, 70%, 80%, 90% or 95% sequence identity to the reference polypeptide sequence present in the variable region of the antigen binding fragment. The term with respect to a nucleic acid sequence may be construed as a sequence of nucleotides exhibiting at least about 65%, 75%, 85%, 90%, 95% or 97% sequence identity to the reference nucleic acid sequence.

As used herein, the term "individual" refers to a vertebrate, preferably a mammal and more preferably a human. Individuals amenable to treatment include those who are presently asymptomatic, but who are at risk of developing a symptomatic disorder in which the alternative complement pathway plays a role, or in which activation of the alternative complement pathway plays a role.

As used herein, the term "mammal" refers to any animal classified as a mammal includes humans, higher primates, domestic and farm animals, horses, pigs, cattle, dogs, cats and ferrets, etc. In one embodiment of the invention, the mammal is a human.

As used herein, "monoclonal antibody" refers to a homogeneous population of antibodies. Such antibodies are highly specific and are directed against a single target antigen. These monoclonal antibodies are homogeneously produced by the hybridoma culture, uncontaminated by other immunoglobulins. Monoclonal antibodies can also be produced by other procedures such as phase display by well known methods.

As used herein, the term "selectively inhibit the alternative complement pathway" refers to preferentially and exclusively inhibits the alternative complement pathway, but does not inhibit other pathways for complement activation, including the classical complement pathway. For example, the humanized and chimerized antibodies and their antigen-binding fragments selectively inhibits the alternative complement pathway. This definition applies to other methods described herein wherein the alternative complement pathway is selectively inhibited.

As used herein, the term "therapeutically effective amount" refers to the amount of a "properdin antagonist" which is required to achieve a measurable improvement in the state, for example, pathology, of the target disease or condition, such as, for example, a complement-associated eye condition.

As used herein, the term "treatment" refers to both therapeutic treatment and prophylactic or preventative measures.

Described herein are novel anti-properdin antibodies and antigen binding fragments thereof that are useful for the prevention and treatment of complement-mediated and/or associated conditions. These anti-properdin antibodies and antigen binding fragments can include, but are not limited to, anti-properdin antibodies and antibody variants thereof, antigen-binding fragments thereof, other binding polypeptides, and/or peptides. These anti-properdin antibodies and antigen binding fragments can bind to properdin and can be capable of neutralizing, blocking, partially or fully inhibiting, abrogating, reducing or interfering with properdin functional activities, for example the ability of properdin to participate in the pathology of any complement-associated inflammatory disease or disorder.

Anti-Properdin Antibodies and Antigen Binding Fragments Thereof

The Anti-Properdin Antibodies and Antigen Binding Fragments thereof can Prevent the binding of properdin to C3b to form the PC3b complex by selectively binding to properdin. As a result, the PC3b complex and the PC3bBb complex will not form. Since the PC3bBb complex cleaves C5 into C5a and C5b, the MAC complex (C5b-9) also will not form. Thus, by inhibiting the binding of properdin to C3b, the anti-properdin antibodies and antigen binding fragments thereof will inhibit the formation of the MAC complex. Elevated levels of the MAC complex have been found to be associated with multiple acute and chronic disease conditions. Therefore, inhibition of the MAC complex via the anti-properdin antibodies and antigen binding fragments thereof is important for clinical benefit in the diseases where complement activation plays a role in disease pathology.

The PC3b complex, the PC3bB complex, and the PC3bBb complex can all be polymerized. The anti-properdin antibodies and antigen binding fragments thereof described herein can inhibit the polymerization of each of these complexes, where the molar ratio of properdin to each of C3b, factor B, or factor Bb can be 1:1. The anti-properdin antibodies and antigen binding fragments thereof can inhibit the polymerization of each of these complexes, where each of these complexes comprises at least one more mole properdin than to each of, C3b, factor B, and factor Bb in each complex respectively. In one example, for the PC3b complex, the molar ratio between properdin and C3b can be expressed as $(P)x(C3b)_y$, where $X=Y+1$. In another example, for the PC3bB complex, the molar ratio between properdin, C, C3b, and factor B can be expressed as $(P)x(C3b)_y(B)_z$, where $X=Y+Z$. This example also can express the molar ratio of properdin to C3b and factor Bb in the PC3bBb complex.

The anti-properdin antibodies and antigen binding fragments thereof can have the ability to inhibit any biological activity of properdin. Such activity can bring a measurable improvement in the state of pathology of a properdin-associated disease or condition, for example, a complement-associated inflammatory disease or disorder. The activity can be evaluated in in vitro or in vivo tests, including, but not limited to, binding assays, alternative pathway hemolysis assays using a relevant animal model, or human clinical trials.

In another embodiment, anti-properdin antibodies and antigen binding fragments thereof can bind to a specific epitope located on properdin to inhibit AP activation. In one example, the anti-properdin agent can bind to the N-terminal domain of properdin to inhibit the binding of properdin to C3b.

The anti-properdin antibodies or antigen binding fragments thereof described herein can be produced by using full-length properdin, properdin polypeptides, and/or using antigenic properdin epitope-bearing peptides, for example, a fragment of the properdin polypeptide. Properdin peptide and polypeptides can be isolated and used to generate antibodies as natural polypeptides, recombinant or synthetic recombinant polypeptides. All antigens useful for producing anti-properdin antibodies can be used to generate monospecific and bispecific antibodies.

The anti-properdin antibody may be a monoclonal antibody or derived from a monoclonal antibody. Suitable monoclonal antibodies to selected antigens may be prepared by known techniques ("Monoclonal Antibodies: A manual of techniques," Zola (CRC Press, 1988); "Monoclonal Hybridoma Antibodies: Techniques and Applications," Hurrell (CRC Press, 1982), the entire contents of which are incorporated herein by reference).

The anti-properdin antibodies and antigen binding fragments thereof can include humanized monoclonal anti-properdin antibodies or antigen-binding fragments thereof that selectively bind to properdin and selectively inhibit activation of the alternative complement pathway. The anti-properdin antibodies and antigen binding fragments thereof can be used to treat any alternative pathway associated inflammatory diseases or disorders in humans or other mammals.

Methods for making humanized non-human antibodies are well known in the art. Humanization is essentially performed by substituting rodent CDRs or CDR sequences for the corresponding sequences of a human antibody. The choice of human variable domains, both light and heavy, to be used in making the humanized antibodies can, in some instances, be important to reduce antigenicity and/or human anti-mouse antibody (HAMA) response. In some embodiments, the anti-properdin antibodies and antigen binding fragments thereof are humanized such that HAMA response is reduced or eliminated.

Ordinarily, properdin can have a range of percentages of amino acid sequence identity, ranging from at least about 60%, to at least about 70%, to at least about 80%, to at least about 85%, to at least about least about 90%, to at least about 95%, to at least about 98%, to at least about 99% amino acid sequence identity with the mature human amino acid sequence.

The variable domain of the antibodies refers to certain portions of the variable domains that differ in sequence among antibodies. The variability in the anti-properdin antibodies and antigen binding fragments thereof can be concentrated in three CDR segments, located in both the light chain and the heavy chain variable domains. The highly conserved portions of variable domains are called framework (FR) regions. In the anti-properdin antibodies described herein, there are four FR regions, connected by three CDRs, that can comprise a variable chain. The CDRs in each of the light and heavy chains are held together in close proximity by the FR regions and, with the CDRs from the other chain, can contribute to the formation of the target binding site of antibodies.

Antibody Humanization is a process that can generate engineered human antibodies with variable region ("V-region") sequences that are substantially similar to actual human germ-line sequences, while retaining the binding specificity and affinity of a reference antibody. This process can graft, for example, the CDR1, CDR2, and CDR3 regions of the heavy and the light chain sequences into humanized human framework that is both optimized and previously identified prior to the start of the grafting process. The variable region containing humanized framework can be produced into Fab, Fab', Fab2, or single chain antigen binding fragments thereof. The resulting engineered humanized antibody fragments can retain the binding specificity of the parent murine antibody for the antigen properdin, and can have an equivalent or higher binding affinity for a specific antigen than the parent antibody. The engineered antigen binding fragments can have heavy and light chain V-regions with a high degree of amino acid sequence identity compared to the closest human germline antibody genes. For example, additional maturational changes can be introduced in the CDR3 regions of each chain during construction in order to identify antibodies with optimal binding kinetics.

In some embodiments, the antibody may be a single-domain antibody, such as a $V_{HH}$. Such antibodies exist naturally in camelids and sharks (Saerens, D. et al., Curr. Opin. Pharmacol., 8:600-8, 2008). Camelid antibodies are described in, for example. U.S. Pat. Nos. 5,759,808; 5,800,988; 5,840,526; 5,874,541; 6,005,079; and 6,015,695, the entire contents of each of which are incorporated herein by reference. The cloned and isolated $V_{HH}$ domain is a stable polypeptide that features the full antigen-binding capacity of the original heavy-chain antibody. $V_{HH}$ domains, with their unique structural and functional properties, combine the advantages of conventional antibodies (high target specificity, high target affinity and low inherent toxicity) with important features of small molecule drugs (the ability to inhibit enzymes and access receptor clefts). Furthermore, they are stable, have the potential to be administered by means other than injection, are easier to manufacture.

In some embodiments, the anti-properdin antibodies and antigen binding fragments thereof can bind to the same epitope on properdin as the antibodies recited in this application. Such antibodies can be identified based on their ability to cross-compete with or competitively inhibit the anti-properdin antibodies and antigen binding fragments thereof in standard properdin binding assays. Thus, all anti-properdin antibodies and antigen binding fragments thereof that competitively inhibit the binding of anti-properdin antibodies and the antigen binding fragments thereof are encompassed by this disclosure.

The antigen binding fragments of antibodies can be identified following protease digestion. These include, for example, the "Fab fragment", "Fab' fragment" (a Fab with the heavy chain hinge region), and "F(ab')$_2$ fragment" (a dimer of Fab' fragments joined by the heavy chain hinge region). Recombinant methods have been used to generate such fragments and to generate even smaller antibody fragments, e.g., those referred to as "single chain Fv" (variable fragment) or "scFv," consisting of $V_L$ and $V_H$ joined by a synthetic peptide linker ($V_L$-linker-$V_H$). Fab fragments, Fab' fragments and scFv fragments are monovalent or monospecific for antigen binding, as they each include only one antigen binding domain including one $V_H$/$V_L$ dimer. Even smaller monovalent antibody fragments are the dAbs, which include only a single immunoglobulin variable domain, e.g., $V_H$ or $V_L$, that alone specifically binds antigen, i.e., without the need for a complementary $V_L$ or $V_H$ domain, respectively. A dAb binds antigen independently of other V domains; however, a dAb can be present in a homo- or hetero-multimer with other $V_H$ or $V_L$ domains where the other domains are not required for antigen binding by the dAb, i.e., where the dAb binds antigen independently of the additional $V_H$ or $V_L$ domains.

In some embodiments, the anti-properdin antibody or antigen binding fragment thereof can be a monospecific antibody or antigen binding fragment thereof that includes at least one of:

a)
- a CDR-H1 comprising the amino acid sequence of GYIFTX$_1$YPIH (SEQ ID NO: 201), wherein X$_1$ is N, Q, S, A, or D,
- a CDR-H2 comprising the amino acid sequence of FIX$_1$PGGGX$_2$DEX$_3$X$_4$X$_5$X$_6$X$_7$X$_8$X$_9$ (SEQ ID NO: 202), wherein X$_1$ is D, E, S, or A; X$_2$ is H or Y; X$_3$ is P, S, or Y; X$_4$ is A or D; X$_5$ is D, E, or Q; X$_6$ is K, R, or S; X$_7$ is F or V; X$_8$ is E, K, Q, or R; and X$_9$ is D or G; and
- a CDR-H3 comprising the amino acid sequence of RGGGYYLDY (SEQ ID NO: 203);

b)
- a CDR-L1 comprising the amino acid sequence of RASQDISFFLN (SEQ ID NO: 206),
- a CDR-L2 comprising the amino acid sequence of X$_1$X$_2$SX$_3$YHS (SEQ ID NO: 207), wherein X$_1$ is G or Y; X$_2$ is A or T; and X$_3$ is R or S; and
- a CDR-L3 comprising the amino acid sequence of QHGX$_1$TLPX$_2$T (SEQ ID NO: 208), wherein X$_1$ is A, D, N, Q, or S; and X$_2$ is F, H, R, W, or Y;

c)
- a CDR-H1 comprising the amino acid sequence of GFSLSTSGX$_1$GVG (SEQ ID NO: 211), wherein X$_1$ is I, K, M, or V,
- a CDR-H2 comprising the amino acid sequence of HIX$_1$X$_1$DDVKSYX$_2$PALKS (SEQ ID NO: 212), wherein X$_1$ is F, H, W, or Y; and X$_2$ is A, N, Q, or S; and
- a CDR-H3 comprising the amino acid sequence of IGX$_1$GYYSFDY (SEQ ID NO: 213), wherein X$_1$ is A, D, E, or S;

d)
- a CDR-L1 comprising the amino acid sequence of X$_1$ASQDVSDAVA (SEQ ID NO: 216), wherein X$_1$ is K or R;
- a CDR-L2 comprising the amino acid sequence of SPSYRYT (SEQ ID NO: 217); and
- a CDR-L3 comprising the amino acid sequence of QQHYSTPX$_1$TF (SEQ ID NO: 218), wherein X$_1$ is F, H, W, or Y;

e)
- a CDR-H1 comprising the amino acid sequence of GFSFSSGYX$_1$IF (SEQ ID NO: 221), wherein X$_1$ is F, H, W, or Y;
- a CDR-H2 comprising the amino acid sequence of GIYSGSSGTTY (SEQ ID NO: 222); and
- a CDR-H3 comprising the amino acid sequence of SVX$_1$GIX$_1$SYX$_1$AAFX$_2$L (SEQ ID NO: 223), wherein X$_1$ is A, D, E, or S; and X$_2$ is A, N, Q, or S;

f)
- a CDR-L1 comprising the amino acid sequence of X$_1$ASDX$_2$IYSLLA (SEQ ID NO: 229), wherein X$_1$ is Q or R; X$_2$ is A, N, Q, or S;
- a CDR-L2 comprising the amino acid sequence of RASTLAS (SEQ ID NO: 230); and
- a CDR-L3 comprising the amino acid sequence of QQHYDYX$_1$YLDVA (SEQ ID NO: 231), wherein X$_1$ is A, N, Q, or S;

g)
- a CDR-H1 comprising the amino acid sequence of GFSFSSSYX$_1$IF (SEQ ID NO: 225), wherein X$_1$ is F, H, W, or Y,
- a CDR-H2 comprising the amino acid sequence of GIYSSSGRX$_1$Y (SEQ ID NO: 226), wherein X$_1$ is I, K, L, or M; and
- a CDR-H3 comprising the amino acid sequence of SAX$_1$GSX$_1$SYX$_1$AYFTL (SEQ ID NO: 227), wherein X$_1$ is A, D, E, or S;

h)
- a CDR-L1 comprising the amino acid sequence of X$_1$ASDX$_2$IYSX$_2$LA (SEQ ID NO: 233), wherein X$_1$ is Q or R; X$_2$ is A, N, Q, or S;
- a CDR-L2 comprising the amino acid sequence of RASTLAS (SEQ ID NO: 234); and
- a CDR-L3 comprising the amino acid sequence of QQHX$_1$DYDYIDVA (SEQ ID NO: 235), wherein X$_1$ is F, H, W, or Y;

i)
- a CDR-H1 comprising the amino acid sequence of GRISSIIHMA (SEQ ID NO: 237), wherein X$_1$ is F, H, W, or Y,
- a CDR-H2 comprising the amino acid sequence of RX$_1$GTTX$_1$YAX$_2$SX$_1$X$_3$G (SEQ ID NO: 238), wherein X$_1$ is I or V; X$_2$ is A, D, E, or S; and X$_3$ is A or K; and
- a CDR-H3 comprising the amino acid sequence of LQYEX$_1$HGGAX$_2$Y (SEQ ID NO: 239), wherein X$_1$ is A or K; and X$_2$ is A, D, E, or S;

j)
- a CDR-H1 comprising the amino acid sequence of GRIFEX$_1$X$_2$MMA (SEQ ID NO: 241), wherein X$_1$ is I or V; and X$_2$ is A, D, N, Q, or S,
- a CDR-H2 comprising the amino acid sequence of RX$_1$GTTTYAX$_2$SX$_1$X$_3$G (SEQ ID NO: 242), wherein X$_1$ is I or V; X$_2$ is A, D, E, or S; and X$_3$ is A or K; and
- a CDR-H3 comprising the amino acid sequence of LQYX$_1$RYGGAEY (SEQ ID NO: 243), wherein X$_1$ is A, D, E, or S; or k)
or a heavy chain variable region and/or light chain variable region that competitively inhibits binding of an isolated monospecific or bispecific antibody or antigen binding fragment thereof comprising at least one of a), b), c), d), e), f), g), h), i), or j) to monomeric properdin.

In other embodiments, the anti-properdin antibody or antigen binding fragment thereof, can include:
- a CDR-H1 comprising the amino acid sequence of GYIFTX$_1$YPIH (SEQ ID NO: 201), wherein X$_1$ is N, Q, S, A, or D,
- a CDR-H2 comprising the amino acid sequence of FIX$_1$PGGGX$_2$DEX$_3$X$_4$X$_5$X$_6$X$_7$X$_8$X$_9$ (SEQ ID NO: 202), wherein X$_1$ is D, E, S, or A; X$_2$ is H or Y; X$_3$ is P, S, or Y; X$_4$ is A or D; X$_5$ is D, R, or Q; X$_6$ is K, R, or S; X$_7$ is F or V; X$_8$ is E, K, Q, or R; and X$_9$ is D or G; and
- a CDR-H3 comprising the amino acid sequence of RGGGYYLDY (SEQ ID NO: 203);
- a CDR-L1 comprising the amino acid sequence of RASQDISFFLN (SEQ ID NO: 206),
- a CDR-L2 comprising the amino acid sequence of X$_1$X$_2$SX$_3$YHS (SEQ ID NO: 207), wherein X$_1$ is G or Y; X$_2$ is A or T; and X$_3$ is R or S; and
- a CDR-L3 comprising the amino acid sequence of QHGX$_1$TLPX$_2$T (SEQ ID NO: 208), wherein X$_1$ is A, D, N, Q, or S; and X$_2$ is F, H, R, W, or Y.

In some embodiments, the anti-properdin antibody or antigen binding fragment thereof can include:
- a CDR-H1 comprising the amino acid sequence of GFSLSTSGX$_1$GVG (SEQ ID NO: 211), wherein X$_1$ is I, K, M, or V,
- a CDR-H2 comprising the amino acid sequence of HIX$_1$X$_1$DDVKSYX$_2$PALKS (SEQ ID NO: 212), wherein X$_1$ is F, H, W, or Y; and X$_2$ is A, N, Q, or S;
- a CDR-H3 comprising the amino acid sequence of IGX$_1$GYYSFDY (SEQ ID NO: 213), wherein X$_1$ is A, D, E, or S;
- a CDR-L1 comprising the amino acid sequence of X$_1$ASQDVSDAVA (SEQ ID NO: 216), wherein X$_1$ is K or R;
- a CDR-L2 comprising the amino acid sequence of SPSYRYT (SEQ ID NO: 217); and
- a CDR-L3 comprising the amino acid sequence of QQHYSTPX$_1$TF (SEQ ID NO: 218), wherein X$_1$ is F, H, W, or Y.

In some embodiments, the anti-properdin antibody or antigen binding fragment thereof can include:
- a CDR-H1 comprising the amino acid sequence of GFSFSSGYX$_1$IF (SEQ ID NO: 221), wherein X$_1$ is F, H, W, or Y;
- a CDR-H2 comprising the amino acid sequence of GIYSGSSGTTY (SEQ ID NO: 222);
- a CDR-H3 comprising the amino acid sequence of SVX$_1$GIX$_1$SYX$_1$ AAFX$_2$L (SEQ ID NO: 223), wherein X$_1$ is A, D, E, or S; and X$_2$ is A, N, Q, or S;
- a CDR-L1 comprising the amino acid sequence of X$_1$ASDX$_2$IYSLLA (SEQ ID NO: 229), wherein X$_1$ is Q or R; X$_2$ is A, N, Q, or S;
- a CDR-L2 comprising the amino acid sequence of RASTLAS (SEQ ID NO: 230); and
- a CDR-L3 comprising the amino acid sequence of QQHYDYX$_1$YLDVA (SEQ ID NO: 231), wherein X$_1$ is A, N, Q, or S.

In some embodiments, the anti-properdin antibody or antigen binding fragment thereof can include:
- a CDR-H1 comprising the amino acid sequence of GFSFSSSYX$_1$IF (SEQ ID NO: 225), wherein X$_1$ is F, H, W, or Y,
- a CDR-H2 comprising the amino acid sequence of GIYSSSGRX$_1$Y (SEQ ID NO: 226), wherein X$_1$ is I, K, L, or M;
- a CDR-H3 comprising the amino acid sequence of SAX$_1$GSX$_1$SYX$_1$AYFTL (SEQ ID NO: 227), wherein X$_1$ is A, D, E, or S;
- a CDR-L1 comprising the amino acid sequence of X$_1$ASDX$_2$IYSX$_2$LA (SEQ ID NO: 233), wherein X$_1$ is Q or R; X$_2$ is A, N, Q, or S;
- a CDR-L2 comprising the amino acid sequence of RASTLAS (SEQ ID NO: 234); and
- a CDR-L3 comprising the amino acid sequence of QQHX$_1$DYDYIDVA (SEQ ID NO: 235), wherein X$_1$ is F, H, W, or Y.

In some embodiments, the anti-properdin antibody or antigen binding fragment thereof can include a heavy chain variable region that includes the 3 CDRs of one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 40, SEQ ID NO: 41, SEQ ID NO: 42, SEQ ID NO: 43, SEQ ID NO: 44, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 71, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, or SEQ ID NO: 107; or a heavy chain variable region that competitively inhibits binding of an isolated antibody or antigen binding fragment comprising at least one of a heavy chain variable region that includes the 3 CDRs of one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 40, SEQ ID NO: 41, SEQ ID NO: 42, SEQ ID NO: 43, SEQ ID NO: 44, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 71, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, or SEQ ID NO: 107.

In other embodiments, the anti-properdin antibody or antigen binding fragment thereof can include a heavy chain variable region that includes an amino acid sequence at least about 70%, at least about 80%, or at least about 90% identical to the amino acid sequence of one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 40, SEQ ID NO: 41, SEQ ID NO: 42, SEQ ID NO: 43, SEQ ID NO: 44, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 71, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, or SEQ ID NO: 107.

In still other embodiments, the anti-properdin antibody or antigen binding fragment thereof can include a light chain variable region that includes the 3 CDRs of one of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 45, SEQ ID NO: 46, SEQ ID NO: 47, SEQ ID NO: 48, SEQ ID NO: 49, SEQ ID NO: 50, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, or SEQ ID NO: 72; or a light chain variable region that competitively inhibits binding of an isolated antibody or antigen binding fragment comprising at least one of a light chain variable region that includes the 3 CDRs of one of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 45, SEQ ID NO: 46, SEQ ID NO: 47, SEQ ID NO: 48, SEQ ID NO: 49, SEQ ID NO: 50, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, or SEQ ID NO: 72.

In some embodiments, the anti-properdin antibody or antigen binding fragment thereof can include a light chain variable region that includes an amino acid sequence at least about 70%, at least about 80%, or at least about 90% identical to the amino acid sequence of one of SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 45, SEQ ID NO: 46, SEQ ID NO: 47, SEQ ID NO: 48, SEQ ID NO: 49, SEQ ID NO: 50, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, or SEQ ID NO: 72.

In some embodiments, the anti-properdin antibody or antigen binding fragment thereof can include at least one of the following:
  a) a heavy chain variable region that includes the 3 CDRs of SEQ ID NO: 1 and a light chain variable region that includes the 3 CDRs of SEQ ID NO: 24;
  b) a heavy chain variable region that includes the 3 CDRs of SEQ ID NO: 2 and a light chain variable region that includes the 3 CDRs of SEQ ID NO: 25;
  c) a heavy chain variable region that includes the 3 CDRs of SEQ ID NO: 3 and a light chain variable region that includes the 3 CDRs of SEQ ID NO: 26;
  d) a heavy chain variable region that includes the 3 CDRs of SEQ ID NO: 4 and a light chain variable region that includes the 3 CDRs of SEQ ID NO: 27;
  e) a heavy chain variable region that includes the 3 CDRs of SEQ ID NO: 5 and a light chain variable region that includes the 3 CDRs of SEQ ID NO: 28;

f) a heavy chain variable region that includes the 3 CDRs of SEQ ID NO: 6 and a light chain variable region that includes the 3 CDRs of SEQ ID NO: 29;
g) a heavy chain variable region that includes the 3 CDRs of SEQ ID NO: 7 and a light chain variable region that includes the 3 CDRs of SEQ ID NO: 30;
h) a heavy chain variable region that includes the 3 CDRs of SEQ ID NO: 8 and a light chain variable region that includes the 3 CDRs of SEQ ID NO: 31;
i) a heavy chain variable region that includes the 3 CDRs of SEQ ID NO: 9 and a light chain variable region that includes the 3 CDRs of SEQ ID NO: 32;
j) a heavy chain variable region that includes the 3 CDRs of SEQ ID NO: 10 and a light chain variable region that includes the 3 CDRs of SEQ ID NO: 33;
k) a heavy chain variable region that includes the 3 CDRs of SEQ ID NO: 11 and a light chain variable region that includes the 3 CDRs of SEQ ID NO: 34;
l) a heavy chain variable region that includes the 3 CDRs of SEQ ID NO: 12 and a light chain variable region that includes the 3 CDRs of SEQ ID NO: 35;
m) a heavy chain variable region that includes the 3 CDRs of SEQ ID NO: 13 and a light chain variable region that includes the 3 CDRs of SEQ ID NO: 36;
n) a heavy chain variable region that includes the 3 CDRs of SEQ ID NO: 14 and a light chain variable region that includes the 3 CDRs of SEQ ID NO: 37;
o) a heavy chain variable region that includes the 3 CDRs of SEQ ID NO: 15 and a light chain variable region that includes the 3 CDRs of SEQ ID NO: 38 or SEQ ID NO: 39;
p) a heavy chain variable region that includes the 3 CDRs of SEQ ID NO: 16 and a light chain variable region that includes the 3 CDRs of SEQ ID NO: 38 or SEQ ID NO: 39;
q) a heavy chain variable region that includes the 3 CDRs of SEQ ID NO: 17 and a light chain variable region that includes the 3 CDRs of SEQ ID NO: 38 or SEQ ID NO: 39;
r) a heavy chain variable region that includes the 3 CDRs of SEQ ID NO: 18 and a light chain variable region that includes the 3 CDRs of SEQ ID NO: 38 or SEQ ID NO: 39;
s) a heavy chain variable region that includes the 3 CDRs of SEQ ID NO: 19 and a light chain variable region that includes the 3 CDRs of SEQ ID NO: 38 or SEQ ID NO: 39;
t) a heavy chain variable region that includes the 3 CDRs of SEQ ID NO: 20 and a light chain variable region that includes the 3 CDRs of SEQ ID NO: 38 or SEQ ID NO: 39;
u) a heavy chain variable region that includes the 3 CDRs of SEQ ID NO: 21 and a light chain variable region that includes the 3 CDRs of SEQ ID NO: 38 or SEQ ID NO: 39;
v) a heavy chain variable region that includes the 3 CDRs of SEQ ID NO: 22 and a light chain variable region that includes the 3 CDRs of SEQ ID NO: 38 or SEQ ID NO: 39;
w) a heavy chain variable region that includes the 3 CDRs of SEQ ID NO: 23 and a light chain variable region that includes the 3 CDRs of SEQ ID NO: 38 or SEQ ID NO: 39;
x) a heavy chain variable region that includes the 3 CDRs of SEQ ID NO: 40 and a light chain variable region that includes the 3 CDRs of SEQ ID NO: 45;
y) a heavy chain variable region that includes the 3 CDRs of SEQ ID NO: 41 and a light chain variable region that includes the 3 CDRs of SEQ ID NO: 46;
z) a heavy chain variable region that includes the 3 CDRs of SEQ ID NO: 42 and a light chain variable region that includes the 3 CDRs of SEQ ID NO: 47;
aa) a heavy chain variable region that includes the 3 CDRs of SEQ ID NO: 43 and a light chain variable region that includes the 3 CDRs of SEQ ID NO: 48, SEQ ID NO: 49, or SEQ ID NO: 50;
bb) a heavy chain variable region that includes the 3 CDRs of SEQ ID NO: 44 and a light chain variable region that includes the 3 CDRs of SEQ ID NO: 48, SEQ ID NO: 49, or SEQ ID NO: 50;
cc) a heavy chain variable region that includes the 3 CDRs of SEQ ID NO: 51 and a light chain variable region that includes the 3 CDRs of SEQ ID NO: 61, SEQ ID NO: 62, SEQ ID NO: 63, SEQ ID NO: 64, or SEQ ID NO: 65;
dd) a heavy chain variable region that includes the 3 CDRs of SEQ ID NO: 52 and a light chain variable region that includes the 3 CDRs of SEQ ID NO: 61, SEQ ID NO: 62, SEQ ID NO: 63, SEQ ID NO: 64, or SEQ ID NO: 65;
ee) a heavy chain variable region that includes the 3 CDRs of SEQ ID NO: 53 and a light chain variable region that includes the 3 CDRs of SEQ ID NO: 61, SEQ ID NO: 62, SEQ ID NO: 63, SEQ ID NO: 64, or SEQ ID NO: 65;
ff) a heavy chain variable region that includes the 3 CDRs of SEQ ID NO: 54 and a light chain variable region that includes the 3 CDRs of SEQ ID NO: 61, SEQ ID NO: 62, SEQ ID NO: 63, SEQ ID NO: 64, or SEQ ID NO: 65;
gg) a heavy chain variable region that includes the 3 CDRs of SEQ ID NO: 55 and a light chain variable region that includes the 3 CDRs of SEQ ID NO: 61, SEQ ID NO: 62, SEQ ID NO: 63, SEQ ID NO: 64, or SEQ ID NO: 65;
hh) a heavy chain variable region that includes the 3 CDRs of SEQ ID NO: 56 and a light chain variable region that includes the 3 CDRs of SEQ ID NO: 66, SEQ ID NO: 67, SEQ ID NO: 68, SEQ ID NO: 69, or SEQ ID NO: 70;
ii) a heavy chain variable region that includes the 3 CDRs of SEQ ID NO: 57 and a light chain variable region that includes the 3 CDRs of SEQ ID NO: 66, SEQ ID NO: 67, SEQ ID NO: 68, SEQ ID NO: 69, or SEQ ID NO: 70;
jj) a heavy chain variable region that includes the 3 CDRs of SEQ ID NO: 58 and a light chain variable region that includes the 3 CDRs of SEQ ID NO: 66, SEQ ID NO: 67, SEQ ID NO: 68, SEQ ID NO: 69, or SEQ ID NO: 70;
kk) a heavy chain variable region that includes the 3 CDRs of SEQ ID NO: 59 and a light chain variable region that includes the 3 CDRs of SEQ ID NO: 66, SEQ ID NO: 67, SEQ ID NO: 68, SEQ ID NO: 69, or SEQ ID NO: 70; or
ll) a heavy chain variable region that includes the 3 CDRs of SEQ ID NO: 60 and a light chain variable region that includes the 3 CDRs of SEQ ID NO: 66, SEQ ID NO: 67, SEQ ID NO: 68, SEQ ID NO: 69, or SEQ ID NO: 70.

In some embodiments, the anti-properdin antibody or antigen binding fragment thereof can include at least one of the following:

a) a heavy chain that includes an amino acid sequence at least about 70%, at least about 80%, or at least about 90% identical to the amino acid sequence of SEQ ID NO: 1 and a light chain that includes an amino acid sequence at least about 70%, at least about 80%, or at least about 90% identical to the amino acid sequence of SEQ ID NO: 24;

b) a heavy chain that includes an amino acid sequence at least about 70%, at least about 80%, or at least about 90% identical to the amino acid sequence of SEQ ID NO: 2 and a light chain that includes an amino acid sequence at least about 70%, at least about 80%, or at least about 90% identical to the amino acid sequence of SEQ ID NO: 25;

c) a heavy chain variable that includes an amino acid sequence at least about 70%, at least about 80%, or at least about 90% identical to the amino acid sequence of SEQ ID NO: 3 and a light chain that includes an amino acid sequence at least about 70%, at least about 80%, or at least about 90% identical to the amino acid sequence of SEQ ID NO: 26;

d) a heavy chain that includes an amino acid sequence at least about 70%, at least about 80%, or at least about 90% identical to the amino acid sequence of SEQ ID NO: 4 and a light chain that includes an amino acid sequence at least about 70%, at least about 80%, or at least about 90% identical to the amino acid sequence of SEQ ID NO: 27;

e) a heavy chain that includes an amino acid sequence at least about 70%, at least about 80%, or at least about 90% identical to the amino acid sequence of SEQ ID NO: 5 and a light chain that includes an amino acid sequence at least about 70%, at least about 80%, or at least about 90% identical to the amino acid sequence of SEQ ID NO: 28;

f) a heavy chain that includes an amino acid sequence at least about 70%, at least about 80%, or at least about 90% identical to the amino acid sequence of SEQ ID NO: 6 and a light chain that includes an amino acid sequence at least about 70%, at least about 80%, or at least about 90% identical to the amino acid sequence of SEQ ID NO: 29;

g) a heavy chain that includes an amino acid sequence at least about 70%, at least about 80%, or at least about 90% identical to the amino acid sequence of SEQ ID NO: 7 and a light chain that includes an amino acid sequence at least about 70%, at least about 80%, or at least about 90% identical to the amino acid sequence of SEQ ID NO: 30;

h) a heavy chain that includes an amino acid sequence at least about 70%, at least about 80%, or at least about 90% identical to the amino acid sequence of SEQ ID NO: 8 and a light chain that includes an amino acid sequence at least about 70%, at least about 80%, or at least about 90% identical to the amino acid sequence of SEQ ID NO: 31;

i) a heavy chain that includes an amino acid sequence at least about 70%, at least about 80%, or at least about 90% identical to the amino acid sequence of SEQ ID NO: 9 and a light chain that includes an amino acid sequence at least about 70%, at least about 80%, or at least about 90% identical to the amino acid sequence of SEQ ID NO: 32;

j) a heavy chain that includes an amino acid sequence at least about 70%, at least about 80%, or at least about 90% identical to the amino acid sequence of SEQ ID NO: 10 and a light chain that includes an amino acid sequence at least about 70%, at least about 80%, or at least about 90% identical to the amino acid sequence of SEQ ID NO: 33;

k) a heavy chain that includes an amino acid sequence at least about 70%, at least about 80%, or at least about 90% identical to the amino acid sequence of SEQ ID NO: 11 and a light chain that includes an amino acid sequence at least about 70%, at least about 80%, or at least about 90% identical to the amino acid sequence of SEQ ID NO: 34;

l) a heavy chain that includes an amino acid sequence at least about 70%, at least about 80%, or at least about 90% identical to the amino acid sequence of SEQ ID NO: 12 and a light chain that includes an amino acid sequence at least about 70%, at least about 80%, or at least about 90% identical to the amino acid sequence of SEQ ID NO: 35;

m) a heavy chain that includes an amino acid sequence at least about 70%, at least about 80%, or at least about 90% identical to the amino acid sequence of SEQ ID NO: 13 and a light chain that includes an amino acid sequence at least about 70%, at least about 80%, or at least about 90% identical to the amino acid sequence of SEQ ID NO: 36;

n) a heavy chain that includes an amino acid sequence at least about 70%, at least about 80%, or at least about 90% identical to the amino acid sequence of SEQ ID NO: 14 and a light chain that includes an amino acid sequence at least about 70%, at least about 80%, or at least about 90% identical to the amino acid sequence of SEQ ID NO: 37;

o) a heavy chain that includes an amino acid sequence at least about 70%, at least about 80%, or at least about 90% identical to the amino acid sequence of SEQ ID NO: 15 and a light chain that includes an amino acid sequence at least about 70%, at least about 80%, or at least about 90% identical to the amino acid sequence of SEQ ID NO: 38 or SEQ ID NO: 39;

p) a heavy chain that includes an amino acid sequence at least about 70%, at least about 80%, or at least about 90% identical to the amino acid sequence of SEQ ID NO: 16 and a light chain that includes an amino acid sequence at least about 70%, at least about 80%, or at least about 90% identical to the amino acid sequence of SEQ ID NO: 38 or SEQ ID NO: 39;

q) a heavy chain that includes an amino acid sequence at least about 70%, at least about 80%, or at least about 90% identical to the amino acid sequence of SEQ ID NO: 17 and a light chain that includes an amino acid sequence at least about 70%, at least about 80%, or at least about 90% identical to the amino acid sequence of SEQ ID NO: 38 or SEQ ID NO: 39;

r) a heavy chain that includes an amino acid sequence at least about 70%, at least about 80%, or at least about 90% identical to the amino acid sequence of SEQ ID NO: 18 and a light chain that includes an amino acid sequence at least about 70%, at least about 80%, or at least about 90% identical to the amino acid sequence of SEQ ID NO: 38 or SEQ ID NO: 39;

s) a heavy chain that includes an amino acid sequence at least about 70%, at least about 80%, or at least about 90% identical to the amino acid sequence of SEQ ID NO: 19 and a light chain that includes an amino acid sequence at least about 70%, at least about 80%, or at least about 90% identical to the amino acid sequence of SEQ ID NO: 38 or SEQ ID NO: 39;

t) a heavy chain that includes an amino acid sequence at least about 70%, at least about 80%, or at least about 90% identical to the amino acid sequence of SEQ ID NO: 20 and a light chain that includes an amino acid sequence at least about 70%, at least about 80%, or at least about 90% identical to the amino acid sequence of SEQ ID NO: 38 or SEQ ID NO: 39;

u) a heavy chain that includes an amino acid sequence at least about 70%, at least about 80%, or at least about 90% identical to the amino acid sequence of SEQ ID NO: 21 and a light chain that includes an amino acid sequence at least about 70%, at least about 80%, or at least about 90% identical to the amino acid sequence of SEQ ID NO: 38 or SEQ ID NO: 39;

v) a heavy chain that includes an amino acid sequence at least about 70%, at least about 80%, or at least about 90% identical to the amino acid sequence of SEQ ID NO: 22 and a light chain that includes an amino acid sequence at least about 70%, at least about 80%, or at least about 90% identical to the amino acid sequence of SEQ ID NO: 38 or SEQ ID NO: 39;

w) a heavy chain that includes an amino acid sequence at least about 70%, at least about 80%, or at least about 90% identical to the amino acid sequence of SEQ ID NO: 23 and a light chain that includes an amino acid sequence at least about 70%, at least about 80%, or at least about 90% identical to the amino acid sequence of SEQ ID NO: 38 or SEQ ID NO: 39;

x) a heavy chain that includes an amino acid sequence at least about 70%, at least about 80%, or at least about 90% identical to the amino acid sequence of SEQ ID NO: 40 and a light chain that includes an amino acid sequence at least about 70%, at least about 80%, or at least about 90% identical to the amino acid sequence of SEQ ID NO: 45;

y) a heavy chain that includes an amino acid sequence at least about 70%, at least about 80%, or at least about 90% identical to the amino acid sequence of SEQ ID NO: 41 and a light chain that includes an amino acid sequence at least about 70%, at least about 80%, or at least about 90% identical to the amino acid sequence of SEQ ID NO: 46;

z) a heavy chain that includes an amino acid sequence at least about 70%, at least about 80%, or at least about 90% identical to the amino acid sequence of SEQ ID NO: 42 and a light chain that includes an amino acid sequence at least about 70%, at least about 80%, or at least about 90% identical to the amino acid sequence of SEQ ID NO: 47;

aa) a heavy chain that includes an amino acid sequence at least about 70%, at least about 80%, or at least about 90% identical to the amino acid sequence of SEQ ID NO: 43 and a light chain that includes an amino acid sequence at least about 70%, at least about 80%, or at least about 90% identical to the amino acid sequence of SEQ ID NO: 48, SEQ ID NO: 49, or SEQ ID NO: 50;

bb) a heavy chain that includes an amino acid sequence at least about 70%, at least about 80%, or at least about 90% identical to the amino acid sequence of SEQ ID NO: 44 and a light chain that includes an amino acid sequence at least about 70%, at least about 80%, or at least about 90% identical to the amino acid sequence of SEQ ID NO: 48, SEQ ID NO: 49, or SEQ ID NO: 50;

cc) a heavy chain that includes an amino acid sequence at least about 70%, at least about 80%, or at least about 90% identical to the amino acid sequence of SEQ ID NO: 51 and a light chain that includes an amino acid sequence at least about 70%, at least about 80%, or at least about 90% identical to the amino acid sequence of SEQ ID NO: 61, SEQ ID NO: 62, SEQ ID NO: 63, SEQ ID NO: 64, or SEQ ID NO: 65;

dd) a heavy chain that includes an amino acid sequence at least about 70%, at least about 80%, or at least about 90% identical to the amino acid sequence of SEQ ID NO: 52 and a light chain that includes an amino acid sequence at least about 70%, at least about 80%, or at least about 90% identical to the amino acid sequence of SEQ ID NO: 61, SEQ ID NO: 62, SEQ ID NO: 63, SEQ ID NO: 64, or SEQ ID NO: 65;

ee) a heavy chain that includes an amino acid sequence at least about 70%, at least about 80%, or at least about 90% identical to the amino acid sequence of SEQ ID NO: 53 and a light chain that includes an amino acid sequence at least about 70%, at least about 80%, or at least about 90% identical to the amino acid sequence of SEQ ID NO: 61, SEQ ID NO: 62, SEQ ID NO: 63, SEQ ID NO: 64, or SEQ ID NO: 65;

ff) a heavy chain that includes an amino acid sequence at least about 70%, at least about 80%, or at least about 90% identical to the amino acid sequence of SEQ ID NO: 54 and a light chain that includes an amino acid sequence at least about 70%, at least about 80%, or at least about 90% identical to the amino acid sequence of SEQ ID NO: 61, SEQ ID NO: 62, SEQ ID NO: 63, SEQ ID NO: 64, or SEQ ID NO: 65;

gg) a heavy chain that includes an amino acid sequence at least about 70%, at least about 80%, or at least about 90% identical to the amino acid sequence of SEQ ID NO: 55 and a light chain that includes an amino acid sequence at least about 70%, at least about 80%, or at least about 90% identical to the amino acid sequence of SEQ ID NO: 61, SEQ ID NO: 62, SEQ ID NO: 63, SEQ ID NO: 64, or SEQ ID NO: 65;

hh) a heavy chain that includes an amino acid sequence at least about 70%, at least about 80%, or at least about 90% identical to the amino acid sequence of SEQ ID NO: 56 and a light chain that includes an amino acid sequence at least about 70%, at least about 80%, or at least about 90% identical to the amino acid sequence of SEQ ID NO: 66, SEQ ID NO: 67, SEQ ID NO: 68, SEQ ID NO: 69, or SEQ ID NO: 70;

ii) a heavy chain that includes an amino acid sequence at least about 70%, at least about 80%, or at least about 90% identical to the amino acid sequence of SEQ ID NO: 57 at least about 90% identical to the amino acid sequence of SEQ ID NO: 66, SEQ ID NO: 67, SEQ ID NO: 68, SEQ ID NO: 69, or SEQ ID NO: 70;

jj) a heavy chain that includes an amino acid sequence at least about 70%, at least about 80%, or at least about 90% identical to the amino acid sequence of SEQ ID NO: 58 and a light chain that includes an amino acid sequence at least about 70%, at least about 80%, or at least about 90% identical to the amino acid sequence of SEQ ID NO: 66, SEQ ID NO: 67, SEQ ID NO: 68, SEQ ID NO: 69, or SEQ ID NO: 70;

kk) a heavy chain that includes an amino acid sequence at least about 70%, at least about 80%, or at least about 90% identical to the amino acid sequence of SEQ ID NO: 59 and a light chain that includes an amino acid sequence at least about 70%, at least about 80%, or at least about 90% identical to the amino acid sequence of SEQ ID NO: 66, SEQ ID NO: 67, SEQ ID NO: 68, SEQ ID NO: 69, or SEQ ID NO: 70; or ll) a heavy chain that includes an amino acid sequence at least about 70%, at least about 80%, or at least about 90% identical to the amino acid sequence of SEQ ID NO: 60 and a light chain that includes an amino acid sequence at least about 70%, at least about 80%, or at least about 90% identical to the amino acid sequence of SEQ ID NO: 66, SEQ ID NO: 67, SEQ ID NO: 68, SEQ ID NO: 69, or SEQ ID NO: 70.

In some embodiments, the antibody or antigen binding fragment thereof can include a constant chain region and wherein the antibody or antigen binding fragment including the constant chain region has enhanced in vivo half-live and/or reduced immunogenicity compared to the antibody or antigen binding fragment thereof without the constant chain region.

In some embodiments, the constant chain region includes an amino acid sequence at least about 70%, at least about 80%, or at least about 90% identical to the amino acid sequence of SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, or SEQ ID NO: 139.

In some embodiments, the anti-properdin antibody or antigen binding fragment thereof can include at least one of the following:
  a heavy chain that includes an amino acid sequence at least about 70%, at least about 80%, or at least about 90% identical to the amino acid sequence of SEQ ID NO: 156 and a light chain that includes an amino acid sequence at least about 70%, at least about 80%, or at least about 90% identical to the amino acid sequence of SEQ ID NO: 157;
  a heavy chain that includes an amino acid sequence at least about 70%, at least about 80%, or at least about 90% identical to the amino acid sequence of SEQ ID NO: 166 and a light chain that includes an amino acid sequence at least about 70%, at least about 80%, or at least about 90% identical to the amino acid sequence of SEQ ID NO: 167;
  a heavy chain that includes an amino acid sequence at least about 70%, at least about 80%, or at least about 90% identical to the amino acid sequence of SEQ ID NO: 170 and a light chain that includes an amino acid sequence at least about 70%, at least about 80%, or at least about 90% identical to the amino acid sequence of SEQ ID NO: 171;
  a heavy chain that includes an amino acid sequence at least about 70%, at least about 80%, or at least about 90% identical to the amino acid sequence of SEQ ID NO: 178 and a light chain that includes an amino acid sequence at least about 70%, at least about 80%, or at least about 90% identical to the amino acid sequence of SEQ ID NO: 179;
  a heavy chain that includes an amino acid sequence at least about 70%, at least about 80%, or at least about 90% identical to the amino acid sequence of SEQ ID NO: 182;
  a heavy chain that includes an amino acid sequence at least about 70%, at least about 80%, or at least about 90% identical to the amino acid sequence of SEQ ID NO: 184 and a light chain that includes an amino acid sequence at least about 70%, at least about 80%, or at least about 90% identical to the amino acid sequence of SEQ ID NO: 185;
  a heavy chain that includes an amino acid sequence at least about 70%, at least about 80%, or at least about 90% identical to the amino acid sequence of SEQ ID NO: 187 and a light chain that includes an amino acid sequence at least about 70%, at least about 80%, or at least about 90% identical to the amino acid sequence of SEQ ID NO: 188;
  a heavy chain that includes an amino acid sequence at least about 70%, at least about 80%, or at least about 90% identical to the amino acid sequence of SEQ ID NO: 191;
  a heavy chain that includes an amino acid sequence at least about 70%, at least about 80%, or at least about 90% identical to the amino acid sequence of SEQ ID NO: 193 and a light chain that includes an amino acid sequence at least about 70%, at least about 80%, or at least about 90% identical to the amino acid sequence of SEQ ID NO: 194; or
  a heavy chain that includes an amino acid sequence at least about 70%, at least about 80%, or at least about 90% identical to the amino acid sequence of SEQ ID NO: 197 and a light chain that includes an amino acid sequence at least about 70%, at least about 80%, or at least about 90% identical to the amino acid sequence of SEQ ID NO: 198.

Linkers

In some embodiments, the anti-properdin antibody or antigen binding fragment thereof can include a linker. The linker can be used as a linkage or connection between polypeptides or protein domains and/or associated non-protein moieties of the anti-properdin antibody or antigen binding fragment thereof. In some embodiments, a linker is a linkage or connection between at least two polypeptide constructs, e.g., such that the two polypeptide constructs are joined to each other in tandem series (e.g., an antibody or antigen binding fragment thereof linked to a second polypeptide or antibody). A linker can attach the N-terminus or C-terminus of one antibody construct to the N-terminus or C-terminus of a second polypeptide construct.

A linker can be a simple covalent bond, e.g., a peptide bond, a synthetic polymer, e.g., a polyethylene glycol (PEG) polymer, or any kind of bond created from a chemical reaction, e.g., chemical conjugation. In the case that a linker is a peptide bond, the carboxylic acid group at the C-terminus of one protein domain can react with the amino group at the N-terminus of another protein domain in a condensation reaction to form a peptide bond. Specifically, the peptide bond can be formed from synthetic means through a conventional organic chemistry reaction well-known in the art, or by natural production from a host cell, wherein a polynucleotide sequence encoding the DNA sequences of both proteins, e.g., two antibody constructs, in tandem series can be directly transcribed and translated into a contiguous polypeptide encoding both proteins by the necessary molecular machineries, e.g., DNA polymerase and ribosome, in the host cell.

In the case that a linker is a synthetic polymer, e.g., a PEG polymer, the polymer can be functionalized with reactive chemical functional groups at each end to react with the terminal amino acids at the connecting ends of two proteins.

In the case that a linker (except peptide bond mentioned above) is made from a chemical reaction, chemical functional groups, e.g., amine, carboxylic acid, ester, azide, or other functional groups commonly used in the art, can be attached synthetically to the C-terminus of one protein and the N-terminus of another protein, respectively. The two functional groups can then react to through synthetic chemistry means to form a chemical bond, thus connecting the two proteins together. Such chemical conjugation procedures are routine for those skilled in the art.

A linker between two peptide constructs can be an amino acid linker including from 1-200 (e.g., 1-4, 1-10, 1-20, 1-30, 1-40, 2-10, 2-12, 2-16, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, 100, 150, 200) amino acids. Suitable peptide linkers are known in the art, and include, for example, peptide linkers containing flexible amino acid residues such as glycine and serine. In certain embodiments, the peptide linker can include the amino acid sequence of SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 245, or SEQ ID NO: 246.

Bispecific, Enhanced Stability, and Modified Antibodies or Antigen Binding Fragments Thereof In some embodiments, the antibody or antigen binding fragment thereof can include a first heavy chain variable region that binds to properdin and a second polypeptide, such as a second antibody or antigen binding fragment thereof having second heavy chain variable region that binds to a different epitope than the first heavy chain variable region so as to form a bispecific antibody or antigen binding fragment thereof.

In some embodiments, the second heavy chain variable region increases the in vivo half-life of the antibody or antigen binding fragment thereof to about 3 week to about 8 weeks.

In other embodiments, the second heavy chain variable region binds to one of albumin, TNF, or VEGF.

In some embodiments, the second polypeptide is an albumin binding molecule, an albumin binding peptide, or an anti-albumin antibody (e.g., a monovalent antibody), or a modified form thereof. Albumin binding peptides are known in the art and are described, for example, in WO 2007/106120 (see Tables 1 to 9) and Dennis et al., 2002, J Biol. Chem. 277: 35035-35043, the disclosures of which are hereby incorporated by reference.

In some embodiments, the second polypeptide is a Fc domain that enhances in vivo stability of the construct.

In some embodiments, the second antibody or antigen binding fragment thereof comprises an amino acid sequence at least about 70%, at least about 80%, or at least about 90% identical to the amino acid sequence of SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 150, or SEQ ID NO: 152.

In some embodiments, the isolated monospecific or bispecific antibody or antigen binding fragment thereof can inhibit C3b and Mac complex (C5b-9) formation in vivo.

Other embodiments described herein relate to an isolated monospecific or bispecific antibody or antigen binding fragment that includes:

an anti-properdin heavy chain variable region that includes an amino acid sequence at least about 70%, at least about 80%, or at least about 90% identical to the amino acid sequence of SEQ ID NO: 2 and anti-properdin light chain variable region that includes an amino acid sequence at least about 70%, at least about 80%, or at least about 90% identical to the amino acid sequence of SEQ ID NO: 25 and wherein the heavy chain variable region includes:
a CDR-H1 comprising the amino acid sequence of GYIFTX$_1$YPIH (SEQ ID NO: 201), wherein X$_1$ is N, Q, S, A, or D (e.g., X$_1$ is Q, S, A, or D)
a CDR-H2 comprising the amino acid sequence of FIX$_1$PGGGX$_2$DEX$_3$X$_4$X$_5$X$_6$X$_7$X$_8$X$_9$ (SEQ ID NO: 202), wherein X$_1$ is D, E, S (e.g., E or S), or A; X$_2$ is H or Y; X$_3$ is P, S, or Y; X$_4$ is A or D; X$_5$ is D, E, or Q; X$_6$ is K, R, or S; X$_7$is F or V; X$_8$ is E, K, Q, or R; and X$_9$ is D or G; and
a CDR-H3 comprising the amino acid sequence of RGG-GYYLDY (SEQ ID NO: 203); and
the light chain variable region includes:
a CDR-L1 comprising the amino acid sequence of RASQDISFFLN (SEQ ID NO: 206),
a CDR-L2 comprising the amino acid sequence of X$_1$X$_2$SX$_3$YHS (SEQ ID NO: 207), wherein X$_1$ is G or Y; X$_2$ is A or T; and X$_3$ is R or S; and
a CDR-L3 comprising the amino acid sequence of QHGX$_1$TLPX$_2$T (SEQ ID NO: 208), wherein X$_1$ is N, A, D, Q, or S (e.g., A, D, Q, or S); and X$_2$ is F, H, R, W, or Y (e.g., F, H, R, or Y).

In some embodiments, the antibody or antigen binding fragment thereof can include at least one of a constant chain region or a second heavy chain variable region binds that binds to a different epitope than the anti-properdin heavy chain region and wherein the antibody or antigen binding fragment including the constant chain region or second heavy chain variable region has enhanced in vivo half-live and/or reduced immunogenicity compared to the antibody or antigen binding fragment thereof without the constant chain region or second heavy chain variable region.

In some embodiments, the constant chain region includes an amino acid sequence at least about 70%, at least about 80%, or at least about 90% identical to the amino acid sequence of SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, or SEQ ID NO: 139; and the second heavy chain variable region includes an amino acid sequence at least about 70%, at least about 80%, or at least about 90% identical to the amino acid sequence of SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 150, or SEQ ID NO: 152.

In some embodiments, the isolated monospecific or bispecific antibody or antigen binding fragment thereof can include a heavy chain having an amino acid sequence at least 90% identical to SEQ ID NO: 247, and light chain having an amino acid sequence at least 90% identical to SEQ ID NO: 248.

Generation of Single Domain Antibodies

In some embodiments, an isolated monospecific or bispecific antibody or antigen binding fragment thereof use a single domain antibody that is a heavy chain variable domain (V$_H$, e.g., V$_{HH}$) or a light chain domain (V$_L$). Thus, one means of generating single domain antibodies specific for properdin is to amplify and express the V$_H$ and V$_L$ regions of the heavy chain and light chain gene sequences isolated, for example, from a hybridoma (e.g., a mouse hybridoma) that expresses anti-properdin monoclonal antibody. The boundaries of V$_H$ and V$_L$ domains are set out, for example, by Kabat et al. (Sequences of Proteins of Immunological Interest (National Institutes of Health, Bethesda, Md., 1991). The information regarding the boundaries of the $V_H$ and $V_L$ domains of heavy and light chain genes is used to design PCR primers that amplify the V domain from a heavy or light chain coding sequence encoding an antibody known to bind properdin. The amplified V domains are inserted into a suitable expression vector, e.g., pHEN-1 (Hoogenboom, H. et al., Nucleic Acids Res., 19:4133-7, 1991) and expressed, for example, as a fusion of the V.sub.H and V.sub.L in a scFv or other suitable monovalent format. The resulting polypeptide can then be screened for high affinity monovalent binding to properdin. Screening for binding can be performed by methods known in the art. Single domain antibodies can be generated using methods known in the art (WO2005118642; Ward, E. et al., Nature, 341:544-6, 1989; Holt, L. et al., Trends Biotechnol., 21:484-90, 2003). Each light chain domain may be either of the kappa or lambda subgroup. Methods for isolating $V_H$ and $V_L$ domains have been described in the art (EP0368684).

In one embodiment, the antibody or antigen binding fragment thereof can include a single domain antibody that is obtained from a human, humanized rodent, camelid or shark. Any such single domain antibody can be optionally humanized. Humanization of camelid single domain antibodies requires the introduction and mutagenesis of a limited number of amino acids in a single polypeptide chain. This is in contrast to humanization of scFv, Fab, (Fab')2 and IgG, which requires the introduction of amino acid changes in two chains, the light and the heavy chain and the preservation of the assembly of both chains. In some embodiments, the single domain antibody includes $V_{HH}$ domains. In some embodiments, the $V_{HH}$ domains correspond to the $V_{HH}$ domains of naturally occurring heavy chain antibodies directed against properdin. Such $V_{HH}$ sequences can be generated, for example, by suitably immunizing a species of camelid with properdin (i.e., so as to raise an immune response and/or heavy chain antibodies directed against properdin), by obtaining a suitable biological sample from said camelid (such as a blood sample, serum sample or sample of B-cells), and by generating $V_{HH}$ sequences directed against properdin, starting from said sample, using any suitable technique known in the art (e.g., the gene encoding the single domain antibody may be cloned by single cell PCR, or the B-cell(s) encoding the single domain antibody may be immortalized by EBV transformation, or by fusion to an immortal cell line).

Alternatively, such naturally occurring $V_{HH}$ domains against properdin, can be obtained from naive libraries of camelid $V_{HH}$ sequences, for example by screening such a library using properdin, or at least one part, fragment, antigenic determinant or epitope thereof using one or more screening techniques known in the art (WO 99/37681, WO 01/90190, WO 03/025020 and WO 03/035694). Alternatively, improved synthetic or semi-synthetic libraries derived from naive $V_{HH}$ libraries may be used, such as $V_{HH}$ libraries obtained from naive $V_{HH}$ libraries by techniques such as random mutagenesis and/or CDR shuffling (WO 00/43507). In a certain embodiment, a $V_{HH}$ library is constructed and expressed on phages after infection with helper phages. After several rounds of bio-panning, single domain antibodies against human properdin can be isolated and efficiently expressed.

A library of fusion proteins including $V_{HH}$ or $V_{HH}$ fragments can be displayed on a phage, phagemid, ribosome or suitable microorganism (such as yeast), to facilitate screening. Suitable methods, techniques and host organisms for displaying and screening (a set, collection or library of) fusion proteins including $V_{HH}$ or $V_{HH}$ fragments are known in the art (WO 03/054016; Hoogenboom, H., Nat. Biotechnol., 23:1105-16, 2005).

In an additional embodiment, a method for generating fusion proteins including $V_{HH}$ or $V_{HH}$ fragment sequences includes at least the steps of: a) providing a collection or sample of cells derived from a species of camelid that express immunoglobulin sequences; b) screening the collection or sample of cells for (i) cells that express an immunoglobulin sequence that can bind to and/or have affinity for properdin; and (ii) cells that express heavy chain antibodies, in which substeps (i) and (ii) can be performed essentially as a single screening step or in any suitable order as two separate screening steps, to provide at least one cell that expresses a heavy chain antibody that can bind to and/or has affinity for properdin; and c) either (i) isolating from the cell the $V_{HH}$ sequence present in the heavy chain antibody; or (ii) isolating from the cell a nucleic acid sequence that encodes the $V_{HH}$ sequence present in the heavy chain antibody, followed by expressing the $V_{HH}$ domain.

The method for generating an amino acid sequence directed against properdin can include at least the steps of: a) providing a set, collection or library of nucleic acid sequences encoding heavy chain antibodies or $V_{HH}$ sequences; b) screening the set, collection or library of nucleic acid sequences for nucleic acid sequences that encode a heavy chain antibody or a fusion protein including the $V_{HH}$ sequence that can bind to and/or has affinity for properdin; and c) isolating the nucleic acid sequence, followed by expressing the $V_{HH}$ sequence present in the heavy chain antibody or by expressing the fusion protein including the $V_{HH}$ sequence, respectively.

Other suitable methods and techniques for obtaining the single domain antibodies and/or nucleic acids encoding the same, starting from naturally occurring $V_H$ sequences or $V_{HH}$ sequences may, for example, include combining one or more parts of one or more naturally occurring VHH sequences (such as one or more framework region (FR) sequences and/or CDR sequences), one or more parts of one or more naturally occurring $V_{HH}$ sequences (such as one or more framework region sequences or CDR sequences), and/or one or more synthetic or semi-synthetic sequences, in a suitable manner, so as to provide a monovalent anti-properdin single domain antibody or a nucleotide sequence or nucleic acid encoding the same. Nucleotide sequences encoding framework sequences of $V_{HH}$ or single domain antibodies are known in the art and may alternatively be obtained polymerase chain reaction (PCR) starting from the nucleotide sequences obtained using the methods described herein. Such compositions can be suitably combined with nucleotide sequences that encode the desired CDRs (for example, by PCR assembly using overlapping primers), to provide a single domain antibody, or antibody fragment fused with a regulator of the alternative complement pathway or fragment thereof.

Antibody antigen binding fragments that recognize the same epitope as a parent antibody can be generated by known techniques. For example, antibody antigen binding fragments can be prepared by proteolytic hydrolysis of an antibody or by expression in E. coli of the DNA coding for the fragment. The antibody antigen binding fragments are antigen binding portions of an antibody, such as Fab, F(ab')2, and scFV can be obtained by pepsin or papain digestion of whole antibodies by conventional methods or by genetic engineering techniques.

An antibody antigen binding fragment can be produced by enzymatic cleavage of antibodies with pepsin to provide a 100 kDa fragment denoted F(ab')2. This fragment can be further cleaved using a thiol reducing agent, and optionally a blocking group for the sulfhydryl groups resulting from cleavage of disulfide linkages, to produce 50 kDa Fab' monovalent fragments. Alternatively, an enzymatic cleavage using papain produces two monovalent Fab fragments and an Fc fragment directly (U.S. Pat. Nos. 4,036,945 and 4,331,647; Nisonoff, A. et al., Arch. Biochem. Biophys., 89:230-44, 1960; Porter, R., Biochem. J., 73:119-26, 1959; Edelman et al., in Methods in Enzymology Vol. I, page 422 (Academic Press 1967), and Coligan el al., Current Protocols in Immunology, Vol. 1, pages 2.8.1-2.8.10 and 2.10.-2.10.4 (John Wiley & Sons 1991).

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

Another form of an antibody antigen binding fragment is a peptide coding for a single complementarity-determining region (CDR). CDR peptides can be obtained by constructing genes encoding the CDR of an antibody of interest. Such genes are prepared, for example, by using the polymerase chain reaction to synthesize the variable region from RNA of antibody producing cells (Larrick, J & Fry, K. METHODS—a companion to Methods in Enzymology Volume: New Techniques in Antibody Generation, 2:106-110, 1991); Courtenay-Luck, "Genetic Manipulation of Monoclonal Antibodies," in Monoclonal Antibodies: Production, Engineering and Clinical Application, Ritter et al. (eds.), pages 166-179 (Cambridge University Press 1995); and Ward et al., "Genetic Manipulation and Expression of Antibodies," in Monoclonal Antibodies: Principles And Applications, Birch et al., (eds.), pages 137-185 (Wiley-Liss, Inc. 1995)).

Other antibody antigen binding fragments, for example single domain antibody fragments, are known in the art and may be used in the claimed constructs (Muyldermans, S. et al., Trends Biochem. Sci., 26:230-5, 2001; Yau, K. et al., J. Immunol. Methods, 281:161-75, 2003; Maass, D. et al., J. Immunol. Methods, 324:13-25, 2007). The $V_{HH}$ may have potent antigen binding capacity and can interact with novel epitopes that are inaccessible to conventional $V_H$-$V_L$ pairs. Camelidae may be immunized with known antigens, such as properdin, and $V_{HH}$s can be isolated that bind to and neutralize the target antigen.

Screening of Antibodies or Antigen Binding Fragments Thereof for Properdin Binding Library screening methods can be used to identify properdin-specific binding antibodies or antigen binding fragments thereof. Phage display technology provides an approach for the selection of antibodies that bind a desired target (e.g., human properdin) from among large, diverse repertoires of antibodies (Smith, G., Science, 228:1315-7, 1985; Scott, J. & Smith, G., Science, 249:386-90, 1990; McCafferty, J. et al., Nature, 348:552-4, 1990). These phage-antibody libraries can be grouped into two categories: natural libraries that use rearranged V genes harvested from human B-cells (Marks, J. et al., J. Mol. Biol., 222:581-97, 1991; Vaughan, T. et al., Nat. Biotechnol., 14:309-14, 1996) or synthetic libraries whereby germline V gene segments or other antibody polypeptide coding sequences are 'rearranged' in vitro (Hoogenboom, H. & Winter, G., J. Mol. Biol., 227:381-8, 1992; Nissim, A. et al., EMBO J., 13:692-8, 1994; Griffiths, A. et al., EMBO J., 13:3245-60, 1994; de Kruif, J. et al., J. Mol. Biol., 248:97-105, 1995) or where synthetic CDRs are incorporated into a single rearranged V gene (Barbas, C. et al., Proc. Natl. Acad. Sci. USA, 89:4457-61, 1992). Methods involving genetic display packages (e.g., phage display, polysome display) are suited for the selection of properdin-specific antibody constructs because they generally express only fragments, rather than whole, antibodies, on the display packages. Methods for the preparation of phage display libraries displaying various antibody fragments are described in the preceding references and, for example, in U.S. Pat. No. 6,696,245, which is incorporated herein by reference in its entirety.

Following expression of a repertoire of antibodies on the surface of phage, selection is performed by contacting the phage repertoire with immobilized target antigen (e.g., properdin), washing to remove unbound phage, and propagation of the bound phage, the whole process frequently referred to as "panning." This process is applicable to the screening of antibodies and antigen binding fragments thereof that can be expressed on a display library (e.g., scFv, Fab, (Fab')2, and $V_{HH}$; Harrison, J. et al., Meth. Enzymol., 267:83-109, 1996). Alternatively, phages are pre-selected for the expression of properly folded member variants by panning against an immobilized generic ligand (e.g., protein A or protein L) that is only bound by folded members (WO 99/20749). This has the advantage of reducing the proportion of non-functional members, thereby increasing the proportion of members likely to bind a target antigen. The screening of phage antibody libraries is generally described, for example, by.

Screening is commonly performed using purified antigen immobilized on a solid support, for example, plastic tubes or wells, or on a chromatography matrix, for example Sepharose™ (Pharmacia). Screening or selection can also be performed on complex antigens, such as the surface of cells (Marks, J. et al., Biotechnology (NY), 11:1145-9, 1993; de Kruif, J. et al., Proc. Natl. Acad. Sci. USA, 92:3938-42, 1995). Another alternative involves selection by binding biotinylated antigen in solution, followed by capture on streptavidin-coated beads.

Pharmaceutical Compositions

Other embodiments relate to formulations or compositions comprising an inhibitor of the alternative complement pathway and a selective inhibitor including, but not limited to, a murine, chimeric, or human antibody that prevents alternative pathway activation in a mammal. The formulation comprises: (a) an inhibitor of the alternative complement pathway as described herein; and (b) a pharmaceutically acceptable carrier. In one embodiment, the formulation or composition can include one or more additional agents, such as an anti-inflammatory agent suitable for reducing inflammation in a mammal that has, or is at risk of developing, an inflammatory disorder. In another embodiment, the formulation or composition can include one or more additional agents, such as an additional agent suitable for preventing or reducing ischemia-reperfusion injury in a mammal. In yet another embodiment, the formulation or composition can include one or more additional agents, such as an additional agent suitable for treatment of another disease or condition associated with activation of the alternative complement pathway.

A monospecific or bispecific anti-properdin antibody or antigen binding fragment thereof described herein can be included with a pharmaceutically acceptable carrier, including, but not limited to, pharmaceutically acceptable excipients and/or pharmaceutically acceptable delivery vehicles, which are suitable for use in the administration of a formulation or composition to a suitable in vivo site.

One type of pharmaceutically acceptable carrier can include a controlled-release formulation that is capable of slowly releasing a composition of the present invention into a mammal. As used herein, a controlled-release formulation comprises an agent of the present invention in a controlled-release vehicle. Suitable controlled-release vehicles can include, but are not limited to, biocompatible polymers, other polymeric matrices, capsules, microcapsules, microparticles, bolus preparations, osmotic pumps, diffusion devices, liposomes, lipospheres, and transdermal delivery systems. Other suitable carriers can include any carrier that can be bound to or incorporated with the monospecific or bispecific anti-properdin antibody or antigen binding fragment thereof described herein that extends that half-life of the monospecific or bispecific anti-properdin antibody or antigen binding fragment thereof described herein to be delivered. Such a carrier can include any suitable protein carrier or a fusion segment that extends the half-life of a protein when delivered in vivo. Suitable delivery vehicles can include, but are not limited to liposomes, viral vectors or other delivery vehicles, including ribozymes, and natural lipid-containing delivery vehicles such as cells and cellular membranes.

Intravenous, intraperitoneal, intramuscular and intramuscular administrations can be performed using methods standard in the art. Aerosol delivery can be performed using methods standard in the art. Devices for delivery of aerosolized formulations can include, but are not limited to, pressurized metered dose inhalers ("MDI"), dry powder inhalers ("DPI"), and metered solution devices ("MSI"), and include devices that are nebulizers and inhalers.

Another type of dose of a monospecific or bispecific anti-properdin antibody or antigen binding fragment thereof described herein or a particularly when the antibody formulation is delivered by nebulization, comprises a collection of ranges between about 200 ng/kg and about 600 µg/kg body weight of the mammal, between about 200 ng/kg and about 500 µg/kg, between about 200 ng/kg and about 400 µg/kg, between about 200 ng/kg and about 300 µg/kg, between about 200 ng/kg and about 200 µg/kg, between about 200 ng/kg and about 100 µg/kg, and preferably, between about 200 ng/kg and about 50 µg/kg body weight of the mammal.

The monospecific or bispecific anti-properdin antibody or antigen binding fragment thereof described herein can be conjugated with a synthetic or biological entity at the —SH group, or any other position which does not interfere with the binding. Such conjugates can also be covered in the present invention.

Uses of Anti-Properdin Antibody or Antigen Binding Fragment

In some embodiments, the anti-properdin antibody or antigen binding fragment can be used to inhibit complement activation via the alternative pathway in vivo in subjects, including humans, suffering from an acute or chronic pathological injury. For example, anti-properdin antibody or antigen binding fragment can be used to treat the following complement mediated or associated diseases, disorders, or conditions, including but not limited to:

Extracorporeal circulation diseases and disorders: Post-cardiopulmonary bypass inflammation, post-operative pulmonary dysfunction, cardiopulmonary bypass, hemodialysis, leukopheresis, plasmapheresis, plateletpheresis, heparin-induced extracorporeal LDL precipitation (HELP), postperfusion syndrome, extracorporeal membrane oxygenation (ECMO), cardiopulmonary bypass (CPB), post-perfusion syndrome, systemic inflammatory response, and multiple organ failure.

Cardiovascular diseases and disorders: acute coronary syndromes, Kawaski disease (arteritis), Takayasu's arteritis, Henoch-Schonlein purpura nephritis, vascular leakage syndrome, percutaneous coronary intervention (PCI), myocardial infarction, ischemia-reperfusion injury following acute myocardial infarction, atherosclerosis, vasculitis, immune complex vasculitis, vasculitis associated with rheumatoid arthritis (also called malignant rheumatoid arthritis), systemic lupus erythematosus-associated vasculitis, sepsis, arteritis, aneurysm, cardiomyopathy, dilated cardiomyopathy, cardiac surgery, peripheral vascular conditions, renovascular conditions, cardiovascular conditions, cerebrovascular conditions, mesenteric/enteric vascular conditions, diabetic angiopathy, venous gas embolus (VGE), Wegener's granulomatosis, heparin-induced extracorporeal membrane oxygenation, and Behcet's syndrome.

Bone/Musculoskeletal diseases and disorders: arthritis, inflammatory arthritis, non-inflammatory arthritis, rheumatoid arthritis, juvenile rheumatoid arthritis, systemic juvenile rheumatoid arthritis, osteoarthritis, osteoporosis, systemic lupus erythematosus (SLE), Behcet's syndrome, and Sjogren's syndrome.

Transplantation diseases and disorders: transplant rejection, xenograft rejection, graft versus host disease, xenotransplantation of organs or grafts, allotransplantation of organs or grafts, and hyperacute rejection.

Eye/Ocular diseases and disorders: wet and dry age-related macular degeneration (AMD), choroidal neurovascularization (CNV), retinal damage, diabetic retinopathy, diabetic retinal microangiopathy, histoplasmosis of the eye, uveitis, diabetic macular edema, diabetic retinopathy, diabetic retinal microangiopathy, pathological myopia, central retinal vein occlusion (CRVO), corneal neovascularization, retinal neovascularization, retinal pigment epithelium (RPE), histoplasmosis of the eye, and Purtscher's retinopathy.

Hemolytic/Blood diseases and disorders: sepsis, systemic inflammatory response syndrome" (SIRS), hemorrhagic shock, acute respiratory distress syndrome (ARDS), catastrophic anti-phospholipid syndrome (CAPS), cold agglutinin disease (CAD), autoimmune thrombotic thrombocytopenic purpura (TTP), endotoxemia, hemolytic uremic syndrome (HUS), atypical hemolytic uremic syndrome (aHUS), paroxysmal nocturnal hemoglobinuria (PNH), sepsis, septic shock, sickle cell anemia, hemolytic anemia, hypereosinophilic syndrome, and anti-phospholipid syndrome (APLS).

Respiratory/Pulmonary diseases and disorders: asthma, Wegener's granulomatosis, transfusion-related acute lung injury (TRALI), antiglomerular basement membrane disease (Goodpasture's disease), eosinophilic pneumonia, hypersensitivity pneumonia, allergic bronchitis bronchiectasis, reactive airway disease syndrome, respiratory syncytial virus (RSV) infection, parainfluenza virus infection, rhinovirus infection, adenovirus infection, allergic bronchopulmonary aspergillosis (ABPA), tuberculosis, parasitic lung disease, adult respiratory distress syndrome, chronic obstructive pulmonary disease (COPD), sarcoidosis, emphysema, bronchitis, cystic fibrosis, interstitial lung disease, acute respiratory distress syndrome (ARDS), transfusion-related acute lung injury, ischemia/reperfusion acute lung injury, byssinosis, heparin-induced extracorporeal membrane oxygenation, anaphylactic shock, and asbestos-induced inflammation.

Central and Peripheral Nervous System/Neurological diseases and disorders: multiple sclerosis (MS), myasthenia gravis (MG), myasthenia gravis, multiple sclerosis, Guillain Barre syndrome, Miller-Fisher syndrome, stroke, reperfusion following stroke, Alzheimer's disease, multifocal motor neuropathy (MMN), demyelination, Huntington's disease, amyotrophic lateral sclerosis (ALS), Parkinson's disease, degenerative disc disease (DDD), meningitis, cranial nerve damage from meningitis, variant Creutzfeldt-Jakob Disease (vCJD), idiopathic polyneuropathy, brain/cerebral trauma (including, but not limited to, hemorrhage, inflammation, and edema), neuromyelitis optica (NMO), including those serologically positive for aquaporin-4 (AQP4)-IgG autoantibody, and neuropathic pain.

Trauma-induced injuries and disorders: hemorrhagic shock, hypovolemic shock, spinal cord injury, neuronal injury, cerebral trauma, cerebral ischemia reperfusion, crush injury, wound healing, severe burns, and frostbite.

Renal diseases and disorders: renal reperfusion injury, poststreptococcal glomerulonephritis (PSGN), Goodpasture's disease, membranous nephritis, Berger's Disease/IgA nephropathy, mesangioproliferative glomerulonephritis, membranous glomerulonephritis, membranoproliferative glomerulonephritis (mesangiocapillary glomerulonephritis), acute postinfectious glomerulonephritis, cryoglobulinemic glomerulonephritis, lupus nephritis, Henoch-Schonlein purpura nephritis, and renal cortical necrosis (RCN).

Reperfusion injuries and disorders of organs: including but not limited to heart, brain, kidney, and liver.

Reproduction and urogenital diseases and disorders: painful bladder diseases and disorders, sensory bladder diseases and disorders, spontaneous abortion, male and female diseases from infertility, diseases from pregnancy, fetomaternal tolerance, pre-eclampsia, urogenital inflammatory diseases, diseases and disorders from placental dysfunction, diseases and disorders from miscarriage, chronic abacterial cystitis, and interstitial cystitis.

Skin/Dermatologic diseases and disorders: burn injuries, psoriasis, atopic dermatitis (AD), eosinophilic spongiosis, urticaria, thermal injuries, pemphigoid, epidermolysis bullosa acquisita, autoimmune bullous dermatoses, bullous pemphigoid, scleroderma, angioedema, hereditary angioneurotic edema (HAE), erythema multiforme, herpes gestationis, Sjogren's syndrome, dermatomyositis, and dermatitis herpetiformis.

Gastrointestinal diseases and disorders: Crohn's disease, Celiac Disease/gluten-sensitive enteropathy, Whipple's disease, intestinal ischemia, inflammatory bowel disease, and ulcerative colitis.

Endocrine diseases and disorders: Hashimoto's thyroiditis, juvenile lymphocytic thyroiditis, stress anxiety, and other diseases affecting prolactin, growth or insulin-like growth factor, adrenocorticotropin release, pancreatitis, Addison's disease, diabetic conditions including, but not limited to, type 1 and type 2 diabetes, type I diabetes mellitus, sarcoidosis, diabetic retinal microangiopathy, non-obese diabetes (IDDM), angiopathy, neuropathy or retinopathy complications of IDDM or Type-2 diabetes, and insulin resistance.

Treatment of Malignancies: diseases and disorders arising from chemotherapeutics and radiation therapy.

EXAMPLES

Properdin is an activator of the complement system. It is the only endogenous activator of the alternative pathway (AP). Additionally, properdin has no effect on the classical pathway (CP); therefore, blocking the formation of properdin still leaves many essential mechanisms of the CP intact.

The following anti-properdin antibodies and antigen binding fragments thereof were constructed using variable chains, constant chains, and linkers. Substitutions were made in each of these sequences and linkers in order to generate multiple variants and embodiments of Anti-properdin antibodies.

Example 1

Example 1 describes the structure and amino acid sequences of anti-properdin antibodies NMT16-NMT28. The CDR regions of the variable light and heavy chain sequences for NMT16-NMT28 (SEQ ID NOs: 2-14 & 24-37) are shown in FIG. 1 and Table 1. The framework regions are from NMT16's heavy chain (SEQ ID NO: 2) and light chain (SEQ ID NO: 24) sequences. The CDR regions for the $V_H$ Region (SEQ ID NO: 204) and $V_L$ region (SEQ ID NOs: 209) contain multiple substitutions across variants of the anti-properdin antibody NM5072 where the amino acids that can be substituted in the CDR regions are marked as X.

The Presta humanized mouse variable sequences anti-properdin antibody 9401 (SEQ ID NOs: 15-23 & 38-39) are presented in the same manner. The CDR regions contain multiple substitutions across all humanized 9401 sequences, and the framework regions used are from Presta h9401-H1 heavy chain (SEQ ID NO: 15) and h9401-L1 light chain (SEQ ID NO: 38). The CDR regions for the $V_H$ Region (SEQ ID NO: 205) and $V_L$ region (SEQ ID NO: 210) contain multiple substitutions where the amino acids that can be substituted in the CDR regions are marked as X. The full list of amino acid substitutions for NM5072 and Presta 9401 can be found in the table below.

NM5072 Example 1 (NMT16-NMT28)
and Presta Mouse 9401
CDR Regions for SEQ ID NOs: 204 and 209

|  | CDR1 | CDR2 | CDR3 |
|---|---|---|---|
| Heavy Chain | GYIFTX$_1$YPIH (SEQ ID NO: 201) Wherein X$_1$ is N, Q, S, A, D | FIX$_1$PGGGX$_2$DEX$_3$ X$_4$X$_5$X$_6$X$_7$X$_8$X$_9$ (SEQ ID NO: 202) Wherein X$_1$ is D, E, S, or A; X$_2$ is H or Y; X$_3$ is P, S, or Y; X$_4$ is A or D; X$_5$ is D, E, or Q; X$_6$ is K, R, or S; X$_7$ is F or V; X$_8$ is E, K, Q, or R; X$_9$ is D or G | RGGGYYLDY (SEQ ID NO: 203) No substitutions |
| Light Chain | RASQDISFFLN (SEQ ID NO: 206) No substitutions | X$_1$X$_2$SX$_3$YHS (SEQ ID NO: 207) Wherein X$_1$ is G or Y; X$_2$ is A or T; or S X$_3$ is R | QHGX$_1$TLPX$_2$T (SEQ ID NO: 208) Wherein X$_1$ is A, D, N, Q, or S; X$_2$ is F, H, R, W, or Y |

The Ab structure of FIG. 1 is a monospecific antibody that contains fAb regions from the $V_H$ and $V_L$ of NM5072 or Presta humanized mouse 9401. Different combinations of the variable chain sequences can be utilized with different amino acid CDR substitutions and framework variations. Further combinations can be implemented when linking the $V_H$ to an Fc region. The heavy chain can be linked to any of the Fc's present in Table 6 using any of the linkers from Table 7 with the most common being the ASTK linker (SEQ ID NO: 245), whereas the $V_L$ will be linked to the CL (SEQ ID NO: 246) using the RTVAAP linker (SEQ ID NO 247). The heavy and light chain sequences are joined together by a disulfide bond that occurs between the CH1 and CL chains at the Cystine residues. Similarly, disulfide bonds are formed between the hinge regions of the two fAbs creating a full monoclonal antibody. The antibody can be made bispecific by replacing one of the NM5072 or Presta fAbs with an Anti-Alb sequence or a fAb that binds to a different target.

For NM5072, the most important factor was identifying substitutions in the CDR regions of the sequences. The CDR region allows the antibody to recognize its specific binding site, in this case Properdin, in order to block the activation of the Alternative Pathway. Four main heavy chain substitutions were made. One substitution had the replacement of amino acid V with I; another substitution had the replacement of amino acid K with A; the third substitution had the replacement of amino acid D with E, S, or A also known as a Asn/Pro fragmentation substitution; the final substitution had the replacement of amino acid N with Q, S, A, or D also known as a deamidation substitution.

The light chain had three main substitutions. One substitution had the replacement of amino acid A with T; another substitution had the deamidation substitution; the final substitution had the replacement of amino acid W with H, Y, or F also known as a tryptophan oxidation substitution.

All other substitutions are based off of slight changes in the CDR regions when comparing all NM5072 sequences (NMT16-NMT28) with respect to each other. Differences in the framework regions are listed as separate sequences.

Additional CDR variants and differences in the framework regions are listed as separate sequences in Table 1.

TABLE 1

| HEAVY CHAIN | |
|---|---|
| NMT15-HC | QVQLVQSAPEVAKPGTSVKMSCKASGYIFTNYPIHWVKQAPGQ GLEWIGFIDPGGGYDEPDERFRDRATLTADKSTSTAYMELSSLR SEDTAIYYCARRGGGYYLDYWGQGTLVTVSS (SEQ ID NO: 1) |
| NMT16-HC | EVQLVQSGAEVKKPGASVKVSCKASGYIFT NYPIHWVRQA PGQGLEWMGF IDPGGGYDEPDERFRDRVTM TADTSTSTAY MELSSLRSED TAVYYCARRG GGYYLDYWGQ GTTVTVSS (SEQ ID NO: 2) |
| NMT17-HC | EVQLVQSGAE VKKPGASVKV SCKASGYIFT NYPIHWVRQA PGQGLEWMGF IDPGGGYDEP DERFRDRVTM TADTSTSTAY MELSSLRSED TAVYYCARRG GGYYLDYWGQ GTTVTVSS (SEQ ID NO: 3) |
| NMT18-HC | EVQLVQSGAE VKKPGASVKV SCKASGYIFT NYPIHWVRQA PGQGLEWMGF IDPGGGYDEP DERFRDRVTM TADTSTSTAY MELSSLRSED TAVYYCARRG GGYYLDYWGQ GTTVTVSS (SEQ ID NO: 4) |
| NMT19-HC | EVQLVQSGAE VKKPGASVKV SCKASGHIFT NYPIHWVRQA PGQGLEWMGF IDPGGGHDEP DERFRDRVTM TADTSTSTAY MELSSLRSED TAVYYCARRG GGYYLDYWGQ GTTVTVSS (SEQ ID NO: 5) |
| NMT20-HC | EVQLVQSGAE VKKPGASVKV SCKASGYIFT NYPIHWVRQA PGQGLEWMGF IDPGGGYDEP DERFRDRVTM TADTSTSTAY MELSSLRSED TAVYYCARRG GGYYLDYWGQ GTTVTVSS (SEQ ID NO: 6) |
| NMT21-HC | EVQLVQSGAE VKKPGASVKV SCKASGYIFT NYPIHWVRQA PGQGLEWMGF IDPGGGYDEY AQKFQGRVTL TADTSTSTAY MELSSLRSED TAVYYCARRG GGYYLDYWGQ GTTLTVSS (SEQ ID NO: 7) |
| NMT22-HC | EVQLVQSGAE VKKPGASVKV SCKASGYIFT NYPIHWVRQA PGQGLEWMGF IDPGGGYDES AQKFRGRVTL TADTSTSTVY MELSSLRSED TAVYYCARRG GGYYLDYWGQ GTTLTVSS (SEQ ID NO: 8) |
| NMT23-HC | EVQLVQSGAE VKKPGASVKV SCKASGYIFT NYPIHWVRQA PGKGLEWMGF IDPGGGHDEY ADSVKGRVTM TRDTSTSTVY MELSSLRSED TAVYYCARRG GGYYLDYWGQ GTLVTVSS (SEQ ID NO: 9) |
| NMT24-HC | EVQLVQSGAE VKKPGASVKV SCKASGYIFT NYPIHWVRQA PGKGLEWMGF IDPGGGHDEY ADSVKGRVTM TRDTSTSTVY MELSSLRSED TAVYYCARRG GGYYLDYWGQ GTLVTVSS (SEQ ID NO: 10) |
| NMT25-HC | EVQLLESGGG LVQPGGSLRL SCAASGYIFT NYPIHWVRQA PGKGLEWVSF IDPGGGYDEY ADSVKGRFTI SRDNSKNTLY LQMNSLRAED TAVYYCAKRG GGYYLDYWGQ GTLVTVSS (SEQ ID NO: 11) |

TABLE 1-continued

| | |
|---|---|
| NMT26-HC | EVQLVESGGG LVQPGRSLRL SCAASGYIFT NYPIHWVRQA PGKGLEWVSF IDPGGHIDY ADSVEGRFTI SRDNAKNSLY LQMNSLRAED TAVYYCAKRG GGYYLDYWGQ GTLVTVSS (SEQ ID NO: 12) |
| NMT27-HC | EVQLVQSGAE VKKPGASVKV SCKASGYIFT NYPIHWVRQA PGKGLEWMGF IDPGGYDEP DERFRDRVTM TRDTSTSTVY MELSSLRSED TAVYYCARRG GGYYLDYWGQ GTLVTVSS (SEQ ID NO: 13) |
| NMT28-HC | EVQLVQSGAE VKKPGASVKV SCKASGYIFT NYPIHWVRQA PGQGLEWMGF IDPGGYDEP DERFRDRVTM TADTSTSTAY MELSSLRSED TAVYYCARRG GGYYLDYWGQ GTLVTVSS (SEQ ID NO: 14) |
| h9401-H1_HC | QVQLVQSGAE VKKPGASVKV SCKASGYIFT NYPIHWVRQA PGQGLEWMGF IDPGGYDEP DERFRDRVTM TRDTSTSTVY MELSSLRSED TAVYYCARRG GGYYLDYWGQ GTTVTVSS (SEQ ID NO: 15) |
| h9401-H2_HC | QVQLVQSGAE VKKPGASVKV SCKASGYIFT NYPIHWVRQA PGQGLEWMGF IDPGGYDEP DERFRDRVTM TADTSTSTAY MELSSLRSED TAVYYCARRG GGYYLDYWGQ GTTVTVSS (SEQ ID NO: 16) |
| h9401-H3_HC | QVQLVQSGAE VKKPGASVKM SCKASGYIFT NYPIHWVRQA PGQGLEWMGF IDPGGYDEP DERFRDRATL TADTSTSTAY MELSSLRSED TAVYYCARRG GGYYLDYWGQ GTTLTVSS (SEQ ID NO: 17) |
| h9401-H2b_HC | QVQLVQSGAE VKKPGASVKV SCKASGYIFT NYPIHWVRQA PGQGLEWMGF IDPGGYDEP DERFRDRVTM TADKSTSTAY MELSSLRSED TAVYYCARRG GGYYLDYWGQ GTTVTVSS (SEQ ID NO: 18) |
| h9401-H3b_HC | QVQLVQSGAE VKKPGASVKM SCKASGYIFT NYPIHWVRQA PGQGLEWMGF IDPGGYDEP DERFRDRATL TADKSTSTAY MELSSLRSED TAVYYCARRG GGYYLDYWGQ GTTLTVSS (SEQ ID NO: 19) |
| h9401-H2c_HC | QVQLVQSGAE VKKPGASVKV SCKASGYIFT NYPIHWVRQA PGQGLEWMGF IDPGGGYDEY AQKFQGRVTM TADTSTSTAY MELSSLRSED TAVYYCARRG GGYYLDYWGQ GTTVTVSS (SEQ ID NO: 20) |
| h9401-H3c_HC | QVQLVQSGAE VKKPGASVKM SCKASGYIFT NYPIHWVRQA PGQGLEWMGF IDPGGGYDEY AQKFQGRATL TADTSTSTAY MELSSLRSED TAVYYCARRG GGYYLDYWGQ GTTLTVSS (SEQ ID NO: 21) |
| h9401-H2d_HC | QVQLVQSGAE VKKPGASVKV SCKASGYIFT NYPIHWVRQA PGQGLEWMGF IDPGGGYDEY AQKFQGRVTM TADKSTSTAY MELSSLRSED TAVYYCARRG GGYYLDYWGQ GTTVTVSS (SEQ ID NO: 22) |
| h9401-H3d_HC | QVQLVQSGAE VKKPGASVKM SCKASGYIFT NYPIHWVRQA PGQGLEWMGF IDPGGGYDEY AQKFQGRATL TADTSTSTAY MELSSLRSED TAVYYCARRG GGYYLDYWGQ GTTLTVSS (SEQ ID NO: 23) |
| LIGHT CHAIN | |
| NMT15-LC | DIQMTQSPSS LSASLGDRVT ITCRASQDIS FFLNWYQQKP DGTVKLLIYY TSRYHSGVPS RFSGSGSGTD FTLTISSLQP EDFATYFCQH GNTLPWTFGQ GTKLEIK (SEQ ID NO: 24) |
| NMT16-LC | DIQMTQSPSS LSASVGDRVT ITCRASQDIS FFLNWYQQKP GKAPKLLIYY TSRYHSGVPS RFSGSGSGTD FTLTISSLQP EDFATYYCQH GNTLPWTFGQ GTKLEIK (SEQ ID NO: 25) |
| NMT17-LC | DIQMTQSPSS LSASVGDRVT ITCRASQDIS FFLNWYQQKP GKAPKLLIYY TSRYHSGVPS RFSGSGSGTD FTLTISSLQP EDFATYYCQH GSTLPWTFGQ GTKLEIK (SEQ ID NO: 26) |
| NMT18-LC | DIQMTQSPSS LSASVGDRVT ITCRASQDIS FFLNWYQQKP GKAPKLLIYY TSRYHSGVPS RFSGSGSGTD FTLTISSLQP EDFATYYCQH GQTLPWTFGQ GTKLEIK (SEQ ID NO: 27) |

TABLE 1-continued

```
NMT19-LC       DIQMTQSPSS LSASVGDRVT ITCRASQDIS FFLNWYQQKP
               GKAPKLLIYY TSRYHSGVPS RFSGSGSGTD FTLTISSLQP
               EDFATYYCQH GQTLPWTFGQ GTKLEIK (SEQ ID NO: 28)

NMT20-LC       DIQMTQSPSS LSASVGDRVT ITCRASQDIS FFLNWYQQKP
               GKAPKLLIYY TSRYHSGVPS RFSGSGSGTD FTLTISSLQP
               EDFATYYCQH GSTLPYTFGQ GTKLEIK (SEQ ID NO: 29)

NMT21-LC       DIQMTQSPSS LSASVGDRVT ITCRASQDIS FFLNWYQQKP
               GKAPKLLIYY TSRYHSGVPS RFSGSGSGTD FTLTISSLQP
               EDFATYYCQH GQTLPWTFGQ GTKLEIK (SEQ ID NO: 30)

NMT22-LC       DIQMTQSPSS LSASVGDRVT ITCRASQDIS FFLNWYQQKP
               GKAPKLLIYY TSRYHSGVPS RFSGSGSGTD FTLTISSLQP
               EDFATYYCQH GSTLPYTFGQ GTKLEIK (SEQ ID NO: 31)

NMT23-LC       DIQMTQSPSS LSASVGDRVT ITCRASQDIS FFLNWYQQKP
               GKAPKLLIYY TSRYHSGVPS RFSGSGSGTD FTLTISSLQP
               EDFATYYCQH GSTLPWTFGQ GTKVEIK (SEQ ID NO: 32)

NMT24-LC       DIQMTQSPSS LSASVGDRVT ITCRASQDIS FFLNWYQQKP
               GKAPKLLIYG ASSYHSGVPS RFSGSGSGTD FTLTISSLQP
               EDFATYYCQH GQTLPRTFGQ GTKVEIK (SEQ ID NO: 33)

NMT25-LC       EIVLTQSPGT LSLSPGERAT LSCRASQDIS FFLNWYQQKP
               GQAPRLLIYY TSRYHSGIPD RFSGSGSGTD FTLTISRLEP
               EDFAVFYCQH GSTLPRTFGQ GTKVEIK (SEQ ID NO: 34)

NMT26-LC       DIQMTQSPSS LSASVGDRVT ITCRASQDIS FFLNWYQQKP
               GKAPKLLIYY TSRYHSGVPS RFSGSGSGTD FTLTISSLQP
               EDVATYYCQH GSTLPYTFGQ GTKVEIK (SEQ ID NO: 35)

NMT27-LC       DIQMTQSPSS LSASVGDRVT ITCRASQDIS FFLNWYQQKP
               GKAPKLLIYY TSRYHSGVPS RFSGSGSGTD FTLTISSLQP
               EDFATYYCQH GSTLPRTFGQ GTKVEIK (SEQ ID NO: 36)

NMT28-LC       DIQMTQSPSS LSASVGDRVT ITCRASQDIS FFLNWYQQKP
               GKAPKLLIYY TSRYHSGVPS RFSGSGSGTD FTLTISSLQP
               EDFATYYCQH GQTLPWTFGQ GTKVEIK (SEQ ID NO: 37)

h9401-L1_LC    DIQMTQSPSS LSASVGDRVT ITCRASQDIS FFLNWYQQKP
               GKAPKLLIYY TSRYHSGVPS RFSGSGSGTD FTLTISSLQP
               EDFATYYCQH GNTLPWTFGQ GTKLEIKR (SEQ ID NO: 38)

h9401-L2_LC    DIQMTQSPSS LSASVGDRVT ITCRASQDIS FFLNWYQQKP
               GKAVKLLIYY TSRYHSGVPS RFSGSGSGTD FTLTISSLQP
               EDFATYYCQH GNTLPWTFGQ GTKLEIKR (SEQ ID NO: 39)
```

Example 2

Example 2 describes structure and amino acid sequences of anti-properdin antibodies NMT-29-NMT31. The CDR substitutions for the variable light and heavy chain regions of NMT29-NMT31 (SEQ ID NO: 40-42 & 45-47) are listed in FIG. 2. The framework regions are from NMT29's heavy chain (SEQ ID NO: 40) and light chain (SEQ ID NO: 45) sequences. The CDR regions for the $V_H$ Region (SEQ ID NO: 214) and $V_L$ region (SEQ ID NOs: 219) contain multiple substitutions across variants of the anti-properdin antibody, where X represents the positions in the CDR's that are prone to substitutions.

The Presta humanized mouse 3196 variable light and heavy chain sequence CDR's are presented in the same manner. The framework regions are Presta h3196-H2 heavy chain (SEQ ID NO: 43) and h3196-L3 light chain (SEQ ID NO: 48). The CDR regions for the $V_H$ Region (SEQ ID NO: 215) and $V_L$ region (SEQ ID NOs: 220) contain multiple substitutions across variants of the anti-properdin antibody, where X represents the positions in the CDR's that are prone to substitutions. A full list of substitutions for NM3196 and Presta 3196 can be found below.

| | NM3196 (NMT29-NMT31) and Presta Mouse 3196 CDR Regions for SEQ ID NOs: 214 and 219 | | |
|---|---|---|---|
| | CDR1 | CDR2 | CDR3 |
| Heavy Chain | GFSLSTSGX$_1$GVG (SEQ ID NO: 211) Wherein X$_1$ is 1, K, M, or V | HIX$_1$X$_1$DDVKSYX$_2$PALKS (SEQ ID NO: 212) Wherein X$_1$ is F, H, W, or Y; X$_2$ is A, N, Q, or S | IGX$_1$GYYSFDY (SEQ ID NO: 213) Wherein X$_1$ is A, D, E, or S |

| | NM3196 (NMT29-NMT31) and Presta Mouse 3196 CDR Regions for SEQ ID NOs: 214 and 219 | | |
|---|---|---|---|
| | CDR1 | CDR2 | CDR3 |
| Light Chain | X₁ASQDVSDAVA (SEQ ID NO: 216) Wherein X₁ is K or R | SPSYRYT (SEQ ID NO: 217) No substitutions | QQHYSTPX₁TF (SEQ ID NO: 218) Wherein X₁ is F, H, W, or Y |

The Ab structure is the same as the one presented in FIG. 1. In this case the fAb regions are made from the variable chains from NM3196 and Presta 3196. Multiple combinations of this antibody can be formed by using the CDR substitutions listed above. The $V_H$ can be linked to any of the constant heavy chain Fc regions found in Table 6 using any of the linkers found in Table 7, the most common being the ASTK linker (SEQ ID NO: 245). The $V_L$ is usually linked to the CL (SEQ ID NO: 246) with the RTVAAP (SEQ ID NO: 247) linker. A bispecific antibody can be generated by replacing a 3196 fAb with anti-Alb or a fAb that binds to a different target.

For NM3196, the CDR substitutions were based off of Presta's humanized mouse 3196. In the heavy chain sequence 5 main substitutions were presented. One substitution had the replacement of amino acid V with L; another substitution had the replacement of amino acid M with V, I, or K also known as a methionine substitution; another substitution had the same tryptophan substitution present in NM5072; the fourth substitution had the replacement of N with Q, S, or A also known as the Asn/Pro Fragmentation substitution for NM3196; the final substitution had the replacement of D with E, S, or A also known as an isoaspartate substitution for NM3196.

For the light chain sequence four main substitutions were presented. One substitution had the replacement of amino acid L with M or V; another substitution had the replacement of amino acid A with S or T; the third substitution had the replacement of amino acid R with K; the final substitution was a tryptophan substitution.

Additional CDR variants and differences in the framework regions are listed as separate sequences in Table 2.

TABLE 2

| HEAVY CHAIN | |
|---|---|
| NMT29-HC | EVTLKESGPT LVKPTQTLTL TCTFSGFSLS TSGMGVGWIR QPPGKALEWL AHIWWDDVKS YNPALKSRLT ITKDTSKNQV VLTMTNMDPV DTATYYCARI GDGYYSFDYW GQGTTVTVSS (SEQ ID NO: 40) |
| NMT30-HC | EVTLKESGPT LVKPTQTLTL TCTFSGFSLS TSGMGVGWIR QPPGKALEWL AHIWWDDVKS YNPALKSRLT ITKDTSKNQV VLTITNVDPV DTATYYCARI GDGYYSFDYW GQGTTLTVSS (SEQ ID NO: 41) |
| NMT31-HC | EVTLKESGPT LVKPTQTLTL TCTFSGFSLS TSGMGVGWIR QPPGKALEWL AHIWWDDVKS YNPALKSRLT ITKDTSKNQV VLTMTNMDPV DTATYYCARI GDGYYSFDYW GQGTTVTVSS (SEQ ID NO: 42) |
| Prest_h3196-H1_HC | QVTLKESGPT LVKPTQTLTL TCTFSGFSLS TSGMGVGWIR QPPGKALEWL AHIWWDDVKS YNPALKSRLT ITKDTSKNQV VLTMTNMDPV DTATYYCARI GDGYYSFDYW GQGTTVTVSS (SEQ ID NO: 43) |
| Prest_h3196-H2_HC | QVTLKESGPT LVKPTQTLTL TCTFSGFSLS TSGMGVGWIR QPPGKALEWL AHIWWDDVKS YNPALKSRLT ITKDTSKNQV VLTITNVDPV DTATYYCARI GDGYYSFDYW GQGTTLTVSS (SEQ ID NO: 44) |
| LIGHT CHAIN | |
| NMT29-LC | DIQMTQSPSS LSASVGDRVT ITCRASQDVS DAVAWYQQKP GKAPKLLIYS PSYRYTGVPS RFSGSGSGTD FTLTISSLQP EDFATYYCQQ HYSTPWTFGQ GTKLEIK (SEQ ID NO: 45) |
| NMT30-LC | DIQMTQSPSS LSASVGDRVT ITCRASQDVS DAVAWFQQKP GKAPKLLIYS PSYRYTGVPS RFSGSGSGTD FTFTISSLQP EDFATYYCQQ HYSTPWTFGQ GTKLEIK (SEQ ID NO: 46) |
| NMT31-LC | DIQMTQSPSS LSASVGDRVT ITCRASQDVS DAVAWFQQKP GKAPKLLIYS PSYRYTGVPS RFSGSGSGTD FTFTISSLQP EDLATYYCQQ HYSTPWTFGQ GTKLEIK (SEQ ID NO: 47) |
| Prest_h3196-L1_LC | DIQMTQSPSS LSASVGDRVT ITCRASQDVS DAVAWYQQKP GKAPKLLIYS PSYRYTGVPS RFSGSGSGTD FTLTISSLQP EDFATYYCQQ HYSTPWTFGQ GTKLEIK (SEQ ID NO: 48) |

TABLE 2-continued

```
Prest_h3196-L2_LC   DIQMTQSPSS LSASVGDRVT ITCRASQDVS DAVAWFQQKP
                    GKAPKLLIYS PSYRYTGVPS RFSGSGSGTD FTFTISSLQP
                    EDFATYYCQQ HYSTPWTFGQ GTKLEIK (SEQ ID NO: 49)

Prest_h3196-L3_LC   DIQMTQSPSS LSASVGDRVT ITCRASQDVS DAVAWFQQKP
                    GKAPKLLIYS PSYRYTGVPS RFSGSGSGTD FTFTISSLQP
                    EDLATYYCQQ HYSTPWTFGQ GTKLEIK (SEQ ID NO: 50)
```

Example 3

Example 3 describes the structure and amino acid sequences of anti-Properdin antibodies that include CDR's for two different humanized rabbit variable light and heavy chain sequences. The humanized rabbit variable light and heavy chain sequences are listed in FIG. 3 (Rabbit 27-03 and Rabbit 86-06). For rabbit 27-03, the framework regions were from Presta report's h2703-H1 heavy chain (SEQ ID NO: 51) and h2703-L1 light chain (SEQ ID NO: 61). For rabbit 86-06, the framework regions were from Presta report's h8606-H2 heavy chain (SEQ ID NO: 56) and h8606-L3 light chain (SEQ ID NO: 66). The CDR regions for the $V_H$ Regions (SEQ ID NO: 224 and 232) and $V_L$ regions (SEQ ID NOs: 228 and 236) contain multiple substitutions across variants of the anti-properdin antibody, where X represents the positions in the CDR's that are prone to substitutions. A full list of CDR substitutions for both 27-03 and 86-06 can be found in the table below.

247) linker. The antibody can be made bispecific by replacing one of the fAbs with anti-albumin or a fAb with a different target.

For rabbit 27-03, the heavy chain CDR's had 6 main substitutions. One substitution had the replacement of amino acid D with T; another substitution had the replacement of N with T; yet another substitution had the replacement of V with T; one substitution was the tryptophan substitution; one substitution was the isoaspartate formation substitution present in NM3196; the final substitution was the replacement of N with Q, S, or A also known as a deamidation substitution for rabbit 27-03.

Humanized rabbit 27-03 light chain CDR's had 6 main substitutions. One substitution had the replacement of amino acid L with V; one substitution had the replacement of R with Q; another substitution had the replacement of A with P; one substitution was the deamidation substitution; one substitution had the replacement of S with K; the final substitution had the replacement of I with V.

For rabbit 86-06, the heavy chain CDR's had 6 main substitutions as well. One substitution was the replacement

| Presta Humanized Rabbit Anti-P Sequences |||
|---|---|---|
| CDR1 | CDR2 | CDR3 |
| CDR Regions for 27-03 SEQ ID NOs: 221-223 (VH) & SEQ ID NO: 229-231 (VL) |||
| Heavy Chain GFSFSSGYX₁IF (SEQ ID NO: 221) Wherein X₁ is F, H, W, or Y | GIYSGSSGTTY (SEQ ID NO: 222) No substitutions | SVX₁GIX₁SYX₁ AAFX₂L (SEQ ID NO: 223) Wherein X₁ is A, D, E, or S; X₂ is A, N, Q, or S |
| Light Chain X₁ASDX₂IYSLLA (SEQ ID NO: 229) Wherein X₁ is Q or R; X₂ is A, N, Q, or S | RASTLAS (SEQ ID NO: 230) No substitutions | QQHYDYX₁YLDVA (SEQ ID NO: 231) Wherein X₁ is A, N, Q, or S |
| CDR Regions for 86-06 SEQ ID NOs: 225-227 (VH) & SEQ ID NO: 233-235 (VL) |||
| Heavy Chain GFSFSSSYX₁IF (SEQ ID NO: 225) Wherein X₁ is F, H, W, or Y | GIYSSSGRXiY (SEQ ID NO: 226) Wherein X₁ is I, K, L, or M | SAX₁GSX₁SYX₁AYFTL (SEQ ID NO: 227) Wherein X₁ is A, D, E, or S |
| Light Chain X₁ASDX₂IYSX₂LA (SEQ ID NO: 233) Wherein X₁ is Q or R; X₂ is A, N, Q, or S | RASTLAS (SEQ ID NO: 234) No substitutions | QQHX₁DYDYIDVA (SEQ ID NO: 235) Wherein X₁ is F, H, W, or Y |

The Ab structure is a monospecific antibody much like NM5072 and NM3196. Different antibody sequence combinations can be made using the CDR substitutions. The $V_H$ can be linked to a variation of different IgG Fc's found in Table 6. The linkers that can be used to join these two regions are in Table 7 with the most common being the ASTK (SEQ ID NO: 245) linker. The $V_L$ is usually joined to the CL (SEQ ID NO: 246) using the RTVAAP (SEQ ID NO:

of amino acid V with A or T; another was the tryptophan substitution; one was the replacement of M with L, I, or K also known as a methionine substitution for rabbit 86-06; another substitution had the replacement of D with T; yet another substitution had the replacement of N with S, or T; the final substitution was an isoaspartate substitution present in NM3196.

Humanized rabbit 86-06 light chain CDR's also contained 6 main substitutions. L can be replaced by V; R can be replaced by Q; one substitution was the deamidation substitution; A can be replaced by R; one substitution was the tryptophan substitution; and the final substitution had the replacement of I with V.

Additional CDR variants and differences in the framework regions are listed as separate sequences in Table 3.

TABLE 3

| | Humanized RabMab-HC |
|---|---|
| h2703-H1 | EVQLLESGGG LVQPGGSLRL SCAASGFSFS SGYWIFWVRQ APGKGLEWVS GIYSGSSGTT YYADSVKGRF TISRDNSKNT LYLQMNSLRA EDTAVYYCAK SVDGIDSYDA AFNLWGQGTL VTVSS (SEQ ID NO: 51) |
| h2703-H2 | EVQLLESGGG LVQPGGSLRL SCAASGFSFS SGYWIFWVRQ APGKGLELVG GIYSGSSGTT YYADSVKGRF TISKDNSKNT VYLQMNSLRA EDTAVYYCAR SVDGIDSYDA AFNLWGQGTL VTVSS (SEQ ID NO: 52) |
| h2703-H3 | EVQLLESGGG LVQPGGSLRL SCAASGFSFS SGYWIFWVRQ APGKGLELVG GIYSGSSGTT YYADWAKGRF TISKDNSKNT VYLQMNSLRA EDTAVYYCAR SVDGIDSYDA AFNLWGQGTL VTVSS (SEQ ID NO: 53) |
| h2703-H2a | EVQLLESGGG LVQPGGSLRL SCAASGFSFS SGYWIFWVRQ APGKGLELVG GIYSGSSGTT YYADSVKGRF TISKDSSKNT VYLQMNSLRA EDTAVYYCAR SVDGIDSYDA AFNLWGQGTL VTVSS (SEQ ID NO: 54) |
| h2703-H3a | EVQLLESGGG LVQPGGSLRL SCAASGFSFS SGYWIFWVRQ APGKGLELVG GIYSGSSGTT YYADWAKGRF TISKDSSKNT VYLQMNSLRA EDTAVYYCAR SVDGIDSYDA AFNLWGQGTL VTVSS (SEQ ID NO: 55) |
| h8606-H1 | EVQLLESGGG LVQPGGSLRL SCAASGFSFS SSYWIFWVRQ APGKGLEWVS GIYSSSGRMY YADSVKGRFT ISRDNSKNTL YLQMNSLRAE DTAVYYCAKS ADGSDSYDAY FTLWGQGTLV TVSSS (SEQ ID NO: 56) |
| h8606-H2 | EVQLLESGGG LVQPGGSLRI SCAASGFSFS SSYWIFWVRQ APGKGLELIG GIYSSSGRMY YADSVKGRFT ISKDNSKNTM YLQMNSLRAE DTAVYYCARS ADGSDSYDAY FTLWGQGTLV TVSSS (SEQ ID NO: 57) |
| h8606-H3 | EVQLLESGGG LVQPGGSLRI SCAASGFSFS SSYWIFWVRQ APGKGLELIG GIYSSSGRMY YADWAKGRFT ISKDNSKNTM YLQMNSLRAE DTAVYYCARS ADGSDSYDAY FTLWGQGTLV TVSSS (SEQ ID NO: 58) |
| h8606-H2a | EVQLLESGGG LVQPGGSLRI SCAASGFSFS SSYWIFWVRQ APGKGLELIG GIYSSSGRMY YADSVKGRFT ISKDSSKNTM YLQMNSLRAE DTAVYYCARS ADGSDSYDAY FTLWGQGTLV TVSSS (SEQ ID NO: 59) |
| h8606-H3a | EVQLLESGGG LVQPGGSLRI SCAASGFSFS SSYWIFWVRQ APGKGLELIG GIYSSSGRMY YADWAKGRFT ISKDSSKNTM YLQMNSLRAE DTAVYYCARS ADGSDSYDAY FTLWGQGTLV TVSSS (SEQ ID NO: 60) |
| | Rabbit mAb-LC |
| h2703-L1 | DIQMTQSPSS LSASVGDRVT ITCRASDNIY SLLAWYQQKP GKAPKLLIYR ASTLASGVPS RFSGSGSGTD FTLTISSLQP EDFATYYCQQ HYDYNYLDVA FGGGTKVEIK (SEQ ID NO: 61) |
| h2703-L2 | DIQLTQSPSS LSASVGDRVT ITCRASDNIY SLLAWYQQKP GKAPKLLIYR ASTLASGVPS RFSGSGSGTD FTLTISSVQP EDFATYYCQQ HYDYNYLDVA FGGGTKVEIK (SEQ ID NO: 62) |
| h2703-L3 | DYQLTQSPSS LSASVGDRVT ITCRASDNIY SLLAWYQQKP GKAPKLLIYR ASTLASGVPS RFSGSGSGTD FTLTISSVQP EDFATYYCQQ HYDYNYLDVA FGGGTKVEIK (SEQ ID NO: 63) |

TABLE 3-continued

| | |
|---|---|
| h2703-L2a | DIQLTQSPSS LSASVGDRVT ITCRASDNIY SLLAWYQQKP GKAPKLLIYR ASTLASGVPS RFSGSGSGTD FTLTISSVQP EDAATYYCQQ HYDYNYLDVA FGGGTKVEIK (SEQ ID NO: 64) |
| h2703-L3a | DYQLTQSPSS LSASVGDRVT ITCRASDNIY SLLAWYQQKP GKAPKLLIYR ASTLASGVPS RFSGSGSGTD FTLTISSVQP EDAATYYCQQ HYDYNYLDVA FGGGTKVEIK (SEQ ID NO: 65) |
| h8606-L1 | DIQMTQSPSS LSASVGDRVT ITCRASQNIY SNLAWYQQKP GKAPKLLIYR ASTLASGVPS RFSGSGSGTD FTLTISSLQP EDFATYYCQQ HWDYDYIDVA FGGGTKVEIK (SEQ ID NO: 66) |
| h8606-L2 | DIQMTQSPSS LSASVGDRVT ITCRASQNIY SNLAWYQQKP GKAPKLLIYR ASTLASGVPS RFSGSGSGTD FTLTISSVQP EDFATYYCQQ HWDYDYIDVA FGGGTKVEIK (SEQ ID NO: 67) |
| h8606-L3 | DYQMTQSPSS LSASVGDRVT ITCRASQNIY SNLAWYQQKP GKAPKLLIYR ASTLASGVPS RFSGSGSGTD FTLTISSVQP EDFATYYCQQ HWDYDYIDVA FGGGTKVEIK (SEQ ID NO: 68) |
| h8606-L2a | DIQMTQSPSS LSASVGDRVT ITCRASQNIY SNLAWYQQKP GKAPKLLIYR ASTLASGVPS RFSGSGSGTD FTLTISSVQP EDAATYYCQQ HWDYDYIDVA FGGGTKVEIK (SEQ ID NO: 69) |
| h8606-L3a | DYQMTQSPSS LSASVGDRVT ITCRASQNIY SNLAWYQQKP GKAPKLLIYR ASTLASGVPS RFSGSGSGTD FTLTISSVQP EDAATYYCQQ HWDYDYIDVA FGGGTKVEIK (SEQ ID NO: 70) |
| Fv-(VH HumRab Anti-ALB) | EVQLLESGGG LVQPGGSLRL SCAVSGIDLS NYAINWVRQA PGKGLEWIGI IWASGTTFYA TWAKGRFTIS RDNSKNTVYL QMNSLRAEDT AVYYCARTVP GYSTAPYFDL WGQGTLVTVS SASTK (SEQ ID NO: 71) |
| Fv-(VL HumRab Anti-ALB) | DIQMTQSPSS VSASVGDRVT ITCQSSPSVW SNFLSWYQQK PGKAPKLLIY EASKLTSGVP SRFSGSGSGT DFTLTISSLQ PEDFATYYCG GGYSSISDTT FGGGTKVEIK RTVAAP (SEQ ID NO: 72) |

IgG Fc Constant Chain Variations

Figure 3:
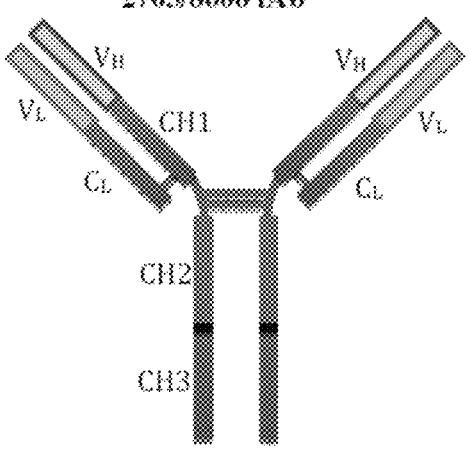
FIG. 3 illustrates a schematic showing the structure of a monospecific anti-properdin antibody and a table listing the amino acid sequences of the $V_H$ regions (SEQ ID NOs: 224 and 228) and $V_L$ regions (SEQ ID NOs: 232 and 236) of the monospecific anti-properdin antibody in accordance with another embodiment.

The variable chains in FIG. 1, FIG. 2, and FIG. 3 can be combined into full fAb regions and linked to full IgG constant chain regions. Full constant chain regions (Fc's) are listed in Table 6. The CH regions contain variations that are present in their sequences. The IgG N298A Fc, as described in the name, has a point mutation at position 298, which replaces amino acid N with A. The mutation does not always occur at position 298 in the sequence. It is dependent on the length of the $V_H$ and the linker.

The YTE Fc contains three point mutations: M253Y, S255T, and T257E. Like the N298A Fc, the mutations are not always guaranteed to occur at the listed positions. The length of the $V_H$ and linker will influence the location.

IgG2 is a commonly used Fc sequence for monospecific and bispecific complement targeting antibodies.

There is no variation in the IgG constant light chain. The $C_L$ is almost always the same for every antibody.

The common linkers used to join the variable chain regions to the constant chain regions are listed in Table 7. The most commonly used variable heavy chain linker is the ASTK linker (SEQ ID NO: 245) and the most commonly used variable light chain linker is the RTVAAP linker (SEQ ID NO: 247). All other linkers are normally used to link the variable heavy chain to the constant heavy chain. In some embodiments the linkers can be used to link two variable heavy chains together directly with a CH1 region separating them.

Example 4

Example 4 describes the structure and amino acid sequences of monospecific and bispecific camelid anti-properdin antibodies. CDR substitutions for the camelid sequences (LVP058 and $V_{HH}$) along with selected framework regions are shown in FIG. 4. The framework regions for the sequences are from SEQ ID NOs: 45-51, 59, and 61 of U.S. Patent Application Publication No US20190352381A1, which is herein incorporate by reference in its entirety. The CDR regions for the $V_{HH}$ Regions (SEQ ID NO: 240 and 244) contain multiple substitutions across variants of the camelid anti-properdin antibody, where X represents the positions in the CDR's that are prone to substitutions. Also listed are the humanized Anti-ALB sequences. A full list of CDR substitutions for the camelid anti-properdin sequences can be found in the table below.

| Humanized Camelid Heavy Chain Fv | | |
|---|---|---|
| CD1 | CDR2 | CDR3 |
| SEQ ID NO: 237-239 | | |
| Heavy Chain GRISSIIHMA (SEQ ID NO: 237) No substitutions | RX$_1$GTTX$_1$YAX$_2$SX$_1$X$_3$G (SEQ ID NO: 238) Wherein X$_1$ is 1 or V; X$_2$ is A, D, E, or S; X$_3$ is A or K | LQYEX$_1$HGGAX$_2$Y (SEQ ID NO: 239) Wherein X$_1$ is A or K; X$_2$ is A, D, E, or S |
| SEQ ID NO: 241-243 | | |
| Heavy Chain GRIFEX$_1$X$_2$MMA (SEQ ID NO: 241) Wherein X$_1$ is I or V; X$_2$ is A, D, N, Q, or S | RX$_1$GTTTYAX$_2$SX$_1$X$_3$G (SEQ ID NO: 242) Wherein X$_1$ is 1 or V; X$_2$ is A, D, E, or S; X$_3$ is A or K | LQYX$_1$RYGGAEY (SEQ ID NO: 243) X$_1$ is A, D, E, or S |

The structure in FIG. 5 is a bispecific antibody that binds both properdin and Albumin. This embodiment has the fAb regions directly linked to the CH2 region of the Fc. The CH1 region is not present due to the fact that a V$_L$ is not required for camelid species. The addition of the Alb will help increase the half-life and decrease the clearance rate of this antibody in the body. Using the Presta substitutions, different combinations of camelid heavy chain sequences can be attached to the Fc region.

Additionally, these heavy chain regions can be linked to any of the heavy chain Fc's shown in Table 6 with the CH1 region removed. For these embodiments, any linker can be utilized from Table 7 with the most common being the (G$_4$S)$_3$ linker.

For the camelid anti-properdin sequences, there is no light chain region. Camelid species contains only the heavy chain domain (V$_{HH}$). There were four main substitutions that were given to the CDR regions. The substitutions were based off of Presta substitutions found in humanized mouse 9401 and 3196. One substitution had the replacement of amino acid V with I; another substitution had the replacement of amino acid K with A; one substitution was the presence of the deamidation substitution from Presta report 9401; the final substitution was the isoaspartate formation substitution from Presta report 3196.

These substitutions do not cover all the changes in the CDR's for the camelid heavy chain sequences. Additional CDR variants and differences in the framework regions are listed as separate sequences in Table 4 below.

TABLE 4

| Camelid Anti-P | |
|---|---|
| Anti-P (from LPV058) | EVQLVESGGG LVQAGGSLRL SCAASGRISS IIHMAWYRQA PGKQRELVAE ISRVGTTVYA DSVKGRFTIS RDDAKNTVTL QMNSLKPEDT AVYYCNALQY EKHGGADYWG QGTQVTVSS (SEQ ID NO: 73) |
| Anti-P (from LPV058) | EVQLLESGGG LVQPGGSLRL SCAASGRISS IIHMAWFRQA PGKERELVSE ISRVGTTVYA DSVKGRFTIS RDNSKNTLYL QMNSLKPEDT AVYYCNALQY EKHGGADYWG QGTLVTVSS (SEQ ID NO: 74) |
| Anti-P (from LPV058) | EVQLVESGGG LVQPGGSLRL SCAASGRISS IIHMAWVRQA PGKQRELVSE ISRVGTTVYA DSVKGRFTIS RDNSKNTLYL QMNSLRAEDT AVYYCNALQY EKHGGADYWG QGTLVTVSS (SEQ ID NO: 75) |
| V$_{HH}$ on Silent Human Fc | EVQLLESGGG LVQAGGSLRL SCAASGRISS IIHMAWYRQA PGKQRELVSE ISRVGTTVYA DSVKGRFTIS RDDAKNTVTL QMNSLKPEDT AVYYCNALQY EAHGGASYWG QGTQVTVSS (SEQ ID NO: 76) |
| Anti-Properdin-V$_{HH}$ | QVQLVESGGG LVQAGGSLRL SCAASGRISS IIHMAWYRQA PGKQRELVAE ISRIGTTVYA ESVAGRFTIS RDDAKNTVTL QMNSLKPEDT AVYYCNALQY EKHGGASYWG QGTQVTVSG (SEQ ID NO: 77) |
| Anti-Properdin-V$_{HH}$ | QVQVVESGGG LRQTGGSLRL SCTASGRIFE VNMMAWYRQA PGKQRELVAE ISRVGTTVYA DSVKGRFTIS RDSAKNTVTL QMNSLKSEDT AVYYCNALQY DRYGGAEYWG QGTQVTVSS (SEQ ID NO: 78) |
| Anti-Properdin-V$_{HH}$ | QVQLVESGGG LRQTGESLRL SCTASGRIFE VNMMAWYRQA PGKQRELVAE ISRVGTTTYA DSVKGRFTIS RDSAKNTVTL QMNSLKSEDT AVYYCNALQY DRYGGAEYWG QGTQVTVSG (SEQ ID NO: 79) |

TABLE 4-continued

Camelid Anti-P

| | |
|---|---|
| Anti-Properdin-V$_{HH}$ | QVQLAESGGG LVQAGDSLKL SCTASGRIFE VNMMAWYRQA PGKDRELVAE ISRVGTTTYA DSVKGRFTIS RDSAKNTVTL QMNSLKSEDT AVYYCNALQY SRYGGAEYWG QGTQVTVSG (SEQ ID NO: 80) |
| Fab-Vhh Domain | QVQLVESGGG LVQAGGSLRL SCAASGGTFS SYSMGWFRQA PGKEREFVAA ITWNGVSTYY ADSVKGRFTI SRDNAKNTVY LQMNSLKPTD TAVYYCAAEI TTRYSGFYYY EDNKSYDYWG QGTQVTVSS (SEQ ID NO: 81) |
| Fab-Vhh Domain | QVQLIESGGG LVQAGDSLRL SCATSEGTFS RFAMGWFRQA PGKEREFVAA INWSGGITYY ADSIAGRFTI SRDNAKNTVY LQMNSLKPED TADYYCAAET TTRYSGYYYY EDNKSYDYWG QGTLVTVSG (SEQ ID NO: 82) |
| Fab-Vhh Domain | QVQLVESGGG LVQAGGSLRL SCAASGRTFS TLGMGWFRQA PGKERQFVAA INWSGSSTYY ANSVKGRFTI SRDNAQSTMY LQMNSLKPED TAVYYCAADL DSRYSAYYYY SDESQYDYWG QGTLVTVSG (SEQ ID NO: 83) |
| Fab-Vhh Domain | QVQLVESGGG LVQAGGSLRL SCAASGRTFS SYAMGWFRQP PGKEREFVAA ITWRGASTYY ADPIKGRFTI SRDNAKNTVY LQMSSLKPED TAVYYCAAEE PSYYSGSYYY MMGESYAYWG QGTLVTVSG (SEQ ID NO: 84) |
| Fab-Vhh Domain | QVHLVESGGG LVQAGGSLRL SCAASGRTFS SYAMGWFRQP PGKERQFVAA ITWSGSSIYY ADSIKGRFTI SRDNAKNTVY LQMNSLKPED TAVYYCAAEE TSAYSGSYYY MMGDSYSYWG QGTQVTVSG (SEQ ID NO: 85) |
| Fab-Vhh Domain | QVQLVESGGG LVQPGGSLSL SCAASGRTFS SYAMGWFRQA PGKEREWVAA ITWSGANIYY ADSIKGRFTL SRDNAENTVW LQLNSLKPED TAVYYCAAAE SGRYSGRAYY SAPGVYLYWG QGTLVTVSG (SEQ ID NO: 86) |
| Fab-Vhh Domain | QVQLVESGGG LVQAGGSLRL SCAASGRTFS NYAMAWFRQA PGKEREFVAS ISGSGDSRYY ADSVKGRFTI SRDNAKNTVY LQTNSPKPED TAVYYCAAVL PTRYSGFYYY SDGTQYHYWG QGTQVTVSS (SEQ ID NO: 87) |
| Fab-Vhh Domain | QVRLVESGGG LVQAGDSLRL SCATSGRTLS SYAMGWFRQA PGKEREFVAA TTWRDTSTYY ADSVKGRFTI SRDNAKNTVY LQTNSLKPED TAAYYCAAEE PSKYSGRSYY MMGASYDYWG QGTQVTVSS (SEQ ID NO: 88) |
| Fab-Vhh Domain | QVQLVESGGG LVQPGGSLRL SCATSGGTFS SYAMGWFRQA PGKEREFVAA TTWQGSNRYY AESVAGRFTI SRDNAKSTVW LQMNSLKPED TAVYYCAAEH STRYSGFYYY TRGETYHYWG QGTQVTVSG (SEQ ID NO: 89) |
| Fab-Vhh Domain | QVQLVESGGG LVQPGGSLRL SCATSGGTFS SYAMGWFRQA PGKEREFVAA TTWQGSNRYY AESVAGRFTI SRDNAKSTVW LQMNSLKPED TAVYYCAAEH STRYSGFYYY TRGETYHYWG QGTQVTVSG (SEQ ID NO: 90) |
| Fab-Vhh Domain | QVQLVESGGG LVQAGDSLRF SCAASGFTFS SYAMGWFRQA PGKEREFVAA ITWSGVSTYY ADSIAGRFTI SRDNAKNRVY LQMNSLKPED TADYSCAADG SGRYSGMEYY NRDWVYDYWG QGTQVTVSS (SEQ ID NO: 91) |
| Fab-Vhh Domain | QVQLIESGGG LVQAGDSLRF SCAASGFTFS SYAMGWFRQA PGKEREFVAA ITWSGVSTYY ADSIAGRFTI SRDNAKNRVY LQMNSLKPED TADYSCAADG SGRYSGMEYY NRDWVYDYWG QGTQVTVSS (SEQ ID NO: 92) |
| Fab-Vhh Domain | EVQLVESGGG LVQPGGSLRL SCAASGFTFG SADMSWVRQA PGKGPEWVSA INSNGGSTYY AASVKGRFTI SRDNAKNTLY LQMNSLKPED TAVYYCAQGN WYTEEYHYWG QGTQVTVSG (SEQ ID NO: 93) |
| Fab-Vhh Domain | QVQLVESGGG LVQAGGSLRL SCAASGRTFS SYAMGWFRQA PGKEREFVAA IGWNGEIYY ADSVKGRFTI SRDNAKNTGY LQMNSLKPED TAVYYCAADS EGVVPGFPIA YWGQGTQVTV SG (SEQ ID NO: 94) |

TABLE 4-continued

| Camelid Anti-P | |
|---|---|
| Fab-Vhh Domain | EVQLVESGGG LVQPGGSLRL SCATSGRPFS SYAMGWFRQA<br>PGKEREIVAG LSWSGGQIYY ADSVKGRFTI SRDNAKNTGD<br>LQMNSLKPED TAVYYCAIGP ALTTGPTAYR<br>YWGQGTQVTV SS (SEQ ID NO: 95) |
| Fab-Vhh Domain | QVHLVESGGG LVQAGGSLRL SCTASGGTVG<br>DYAVGWFRQA PGKERELIGV VSRLGARTGY ADSVLGRFTI<br>SRDDVKNTVF LQMDSVKPED TAVYYCAARR<br>DYSFEVVPYD YWGQGTQVTV SG (SEQ ID NO: 96) |
| Fab-Vhh Domain | QVQLVESGGG LVQPGGSLRL SCAASGRTFS SYSMGWFRQR<br>HGNEREFVAA ISWSGRSTYY AESVKGRFAI SRDNANTTVY<br>LQMNSLKPED SAVYYCAAST RGWYGTQESD<br>YNFWGQGTQV TVSG (SEQ ID NO: 97) |
| Fab-Vhh Domain | QVQLIESGGG LVQAGGSLRL SCTASGRTFS NYAMGWFRQA<br>PGKEREFLAA ISRSGESTQY ATFVKGRFAI ARDNAKNTVS<br>LQMNSLKPED TAVYFCAAKI AVLVSTTYNS QYEYWGQGTL<br>VTVSS (SEQ ID NO: 98) |
| Fab-Vhh Domain | QVQLIESGGG LVQEGASLRL SCAGSGPMFS RLAVGWFRQA<br>PGKEREFVAV INWSGSADFY TNSVKGRFTI SRDNAKNTVY<br>LEMNTLKPED SAVYYCAADQ NPLTLRTGVR<br>DVGRQWGQGT EVTVSS (SEQ ID NO: 99) |
| Fab-Vhh Domain | EVQLVESGGG LVQPGGSLRL SCAASGFTLD YYAIGWFRQA<br>PGKEREGVSC ISRTDGSTYY ADSVKGRFTI SRDNAKNTVY<br>LQMNSLKPED TAVYYCAVDD SYPTGGISCL FGHFGSWGQG<br>TQVTVSS (SEQ ID NO: 100) |
| Fab-Vhh Domain | QVQLVESGGG LVQAGGSLRL SCAASGRTFS<br>SYAMGWFRQA PGKEREFVAA VPWTYGSKYY<br>ADSVKGRFTI SRDDAKNTVY LQMNNLKPED<br>TAVYYCAADS SAGYYSGFDY YSAATPYDLW<br>GQGTQVTVSG (SEQ ID NO: 101) |
| Fab-Vhh Domain | QVQMVESGGG LVQAGGSLRL SCAASGLTNR<br>IRIMGWYRQA PGKLRELVAT ITNDGSTHYA DSVKGRFTIS<br>TDNAKNTVFL QMNSLKPEDT AVYICNVGEN<br>WGPAYWGQGT QVTVSG (SEQ ID NO: 102 |
| Fab-Vhh Domain | QVQLVESGGG LVQAGGSLXL SCAASGSDRR<br>INGMGWYRHP PGKQRELVAA ITSGGSTNYA DSVKGRFTIS<br>TNNANNMMYL QMNSLKPEDT AVYYCAIDEF<br>GTGWLDYCGQ GTQVTVSG (SEQ ID NO: 103) |
| Fab-Vhh Domain | QVLLEESGGG LERTGGSLRL SCAASGSIFS VNSMTWYRQA<br>PGKRREFLGT ITEEGRTNYA DSVKGRFTIS RDNAKNTMYL<br>QMNSLKPEDT AVYYCYANLI SSEDRTFGVW GQGTQVTVSS<br>(SEQ ID NO: 104) |
| Fab-Vhh Domain | QVHMVESGGG LVQAGGSLRF SCAASGNIFT ISTLDWYRQA<br>PGEQRELVAT LTPDGITDYA GSVKGRFTIS RDNAKNTVYL<br>QMNSLKPEDT AVYYCNAWRY SDDYRGRVDY<br>WGQGTQVTVS G (SEQ ID NO: 105) |
| Fab-Vhh Domain | QVQLMESGGG EVQAGGSLRL SCAASGSIFD ISAMGWYRQA<br>PGKQRELVAD ITSSGSTQYA DSVKGRFTIS RDNAKNTVYL<br>QMNSLKPEDT AVYTCAAESI RESQNRHQLG<br>YMGPLYDYWG QGTQVTVSG (SEQ ID NO: 106) |
| Fab-Vhh Domain | QVQLVESGGG LVQPGGSLRL SCAASGSDYY AIGWFRQAPG<br>KEREGVSCMS RTDGSTYYAD SVKDRFTISR DYAKNTVYLQ<br>MNSLKPEDTA VYYCGLDRSY PTGGISCLFG DFGSWGQGTQ<br>VTVSG (SEQ ID NO: 107) |
| Human-Anti-Alb | EVQLVESGGG LVKPGGSLRL SCAASGRPVS NYAAAWFRQA<br>PGKEREFVSA INWQKTATYA DSVKGRFTIS RDNAKNSLYL<br>QMNSLRAEDT AVYYCAAVFR VVAPKTQYDY<br>DYWGQGTLVT VSS (SEQ ID NO: 108) |

Example 5

Example 5 describes the structure and amino acid sequences of additional bispecific anti-properdin antibodies. The sequences contain variations of an anti-albumin chain, camelid anti-properdin heavy chain, and NovelMed's NMT15 light and heavy chains.

Anti-Properdin Antibodies

| Sequence Number | mAb | Sequence Layout |
|---|---|---|
| 1 | Single Chain | Human anti-albumin with camelid anti-properdin |
| 2 | Single Chain | Humanized anti-albumin with camelid anti-properdin |
| 3 | (Fab)2 Linker | Two NMT15 light and heavy chain Fab regions |
| 4 | Alb-Fab Linker | Human anti-albumin with NMT15 Fab |
| 5 | Alb-Fab Linker | Humanized anti-albumin with NMT15 Fab region |

The camelid anti-properdin heavy chain sequence for these antibodies was modified from U.S. Patent Application Publication No. 20190352381A1 as well as the human anti-albumin sequence in the first and fourth constructs. The humanized anti-albumin sequence in constructs two and five were modified from U.S. Patent Application Publication No. 2007/0269422A1, which is incorporated by reference in its entirety. The NMT15 light and heavy chains were generated through humanization of a mouse anti-properdin Fab region of the original Presta sequences described above. The anti-albumin is used in the synthesis of these new construct to aid in extending the half-life and bioavailability of the drug. Examples of anti-albumin amino acid sequences are listed in Table 5. The full sequences of each construct can be found in FIGS. 6-8.

For all sequences in the tables above, the sequences were connected using a (G4S)3 linker (GGGSGGGSGGGS) (SEQ ID NO: 143). In FIG. 6, the anti-albumin is linked with the camelid anti-properdin. Similarly, in FIG. 7, two identical Fab regions (NMT15 HC/LC) are linked together to create a full mAb. In FIG. 8, the anti-albumin sequences from FIG. 6 are linked with the Fab region in FIG. 7 to form a full mAb. Specifically for sequence NMT1003-NMT1005, the heavy chain regions were connected to an Fc that only contained the CH1 region (SEQ ID NO 138) and the light chain regions were connected to a CL (SEQ ID NO 139).

TABLE 5

| Anti-ALB | | |
|---|---|---|
| ALB1 (PMP6A6) | AVQLVESGGG LVQPGNSLRL SCAASGFTFR SFGMSWVRQA PGKEPEWVSS ISGSGSDTLY ADSVKGRFTI SRDNAKTTLY LQMNSLKPED TAVYYCTIGG SLSRSSQGTQ VTVSS (SEQ ID NO: 109) | |
| ALB3 (ALB1, HUM1) | EVQLVESGGG LVQPGGSLRL SCAASGFTFR SFGMSWVRQA PGKEPEWVSS ISGSGSDTLY ADSVKGRFTI SRDNAKTTLY LQMNSLKPED TAVYYCTIGG SLSRSSQGTQ VTVSS (SEQ ID NO: 110) | |
| ALB4 (ALB1, HUM2) | EVQLVESGGG LVQPGGSLRL SCAASGFTFS SFGMSWVRQA PGKEPEWVSS ISGSGSDTLY ADSVKGRFTI SRDNAKTTLY LQMNSLKPED TAVYYCTIGG SLSRSSQGTQ VTVSS (SEQ ID NO: 111) | |
| ALB5 (ALB1, HUM3) | EVQLVESGGG LVQPGGSLRL SCAASGFTFR SFGMSWVRQA PGKGLEWVSS ISGSGSDTLY ADSVKGRFTI SRDNAKTTLY LQMNSLKPED TAVYYCTIGG SLSRSSQGTQ VTVSS (SEQ ID NO: 112) | |
| ALB6 (ALB1, HUM1) | EVQLVESGGG LVQPGNSLRL SCAASGFTFR SFGMSWVRQA PGKGLEWVSS ISGSGSDTLY ADSVKGRFTI SRDNAKTTLY LQMNSLKPED TAVYYCTIGG SLSRSSQGTL VTVSS (SEQ ID NO: 113) | |
| ALB7 (ALB1, HUM2) | EVQLVESGGG LVQPGNSLRL SCAASGFTFR SFGMSWVRQA PGKGLEWVSS ISGSGSDTLY ADSVKGRFTI SRDNAKTTLY LQMNSLRPED TAVYYCTIGG SLSRSSQGTL VTVSS (SEQ ID NO: 114) | |
| ALB8 (ALB1,HUM3) | EVQLVESGGG LVQPGNSLRL SCAASGFTFS SFGMSWVRQA PGKGLEWVSS ISGSGSDTLY ADSVKGRETI SRDNAKTTLY LQMNSLRPED TAVYYCTIGG SLSRSSQGTL VTVSS (SEQ ID NO: 115) | |
| ALB9 (ALB1, HUM4) | EVQLVESGGG LVQPGNSLRL SCAASGFTFS SFGMSWVRQA PGKGLEWVSS ISGSGSDTLY ADSVKGRETI SRDNAKNTLY LQMNSLRPED TAVYYCTIGG SLSRSSQGTL VTVSS (SEQ ID NO: 116) | |
| ALB10 (ALB1, HUM5) | EVQLVESGGG LVQPGNSLRL SCAASGFTFS SFGMSWVRQA PGKGLEWVSS ISGSGSDTLY ADSVKGRFTI SRDNAKNTLY LQMNSLRPED TAVYYCTIGG SLSRSGQGTL VTVSS (SEQ ID NO: 117) | |

TABLE 5-continued

Anti-ALB

| | |
|---|---|
| ALB11 | EVQLVESGGG LVQPGNSLRL SCAASGFTFS SFGMSWVRQA PGKGLEWVSS ISGSGSDTLY ADSVKGRFTI SRDNAKTTLY LQMNSLRPED TAVYYCTIGG SLSRSSQGTL VTVSS (SEQ ID NO: 118) |
| ALB23 | EVQLLESGGG LVQPGGSLRL SCAASGFTFR SFGMSWVRQA PGKGPEWVSS ISGSGSDTLY ADSVKGRFTI SRDNSKNTLY LQMNSLRPED TAVYYCTIGG SLSRSSQGTL VTVSS (SEQ ID NO: 119) |
| ALB23A | AWQLLESGGG LVQPGGSLRL SCAASGFTFR SFGMSWVRQA PGKGPEWVSS ISGSGSDTLY ADSVKGRFTI SRDNSKNTLY LQMNSLRPED TAVYYCTIGG SLSRSSQGTL VTVSS (SEQ ID NO: 120) |
| ALB23B | AWQLLESGGG LVQPGGSLRL SCAASGFTFR SFGMSWVRQA PGKGPEWVSS ISGSGSDTLY ADSVKGRFTI SRDNSKNTLY LQMNSLRPED TAVYYCTIGG SLSRSSQGTQ WTVSS (SEQ ID NO: 121) |
| ALB23C | EVQLLESGGG LVQPGGSLRL SCAASGFTFR SFGMSWVRQA PGKGPEWVSS ISGSGSDTLY ADSVKGRFTI SRDNSKNTLY LQMNSLRPED TAVYYCTIGG SLSRSSQGTQ VTVSS (SEQ ID NO: 122) |
| ALB23D | EVQLLESGGG LVQPGGSLRL SCAASGFTFR SFGMSWVRQA PGKGPEWVSS ISGSGSDTLY ADSVKGRFTI SRDNSKNTLY LQMNSLRPED TAVYYCTIGG SLSRSSQGTL VTVSS (SEQ ID NO: 123) |
| ALB23E | EVQLLESGGG LVQPGGSLRL SCAASGFTFR SFGMSWVRQA PGKGPEWVSS ISGSGSDTLY ADSVKGRFTI SRDNSKNTLY LQMNSLRPED TAVYYCTIGG SLSRSSQGTL WTVSS (SEQ ID NO: 124) |
| ALB23F | EVQLLESGGG LVQPGGSLRL SCAASGFTFR SFGMSWVRQA PGKGPEWVSS ISGSGSDTLY ADSVKGRFTI SRDNSKNTLY LQMNSLRPED TAVYYCTIGG SLSRSSQGTL WTVSS (SEQ ID NO: 125) |
| ALB23G | EVQLLESGGG LVQPGGSLRL SCAASGFTFR SFGMSWVRQA PGKGPEWVSS ISGSGSDTLY ADSVKGRFTI SRDNSKNTLY LQMNSLRPED TAVYYCTIGG SLSRSSQGTL VTVSS (SEQ ID NO: 126) |
| ALB23H | EVQLLESGGG LVQPGGSLRL SCAASGFTFR SFGMSWVRQA PGKGPEWVSS ISGSGSDTLY ADSVKGRFTI SRDNSKNTLY LQMNSLRPED TAVYYCTIGG SLSRSSQGTL VTVSS (SEQ ID NO: 127) |
| ALB23I | EVQLLESGGG LVQPGGSLRL SCAASGFTFR SFGMSWVRQA PGKGPEWVSS ISGSGSDTLY ADSVKGRFTI SRDNSKNTLY LQMNSLRPED TAVYYCTIGG SLSRSSQGTL WTVSS (SEQ ID NO: 128) |

Example 6

Example 6 describes the structure and amino acid sequences of bispecific anti-properdin antibodies. The bispecific anti-properdin antibodies described in this example and the table below were designed to be more stable and longer lasting in circulation. Attaching an anti-albumin sequence to an anti-properdin antibody or antigen binding fragment thereof allowed the antibody to bind to serum albumin giving it a longer half-life and circulation time. Furthermore, the addition of the Fc region can also aid in increasing the half-life of the antibody and improves the stability of the overall structure. Multiple embodiments of the bispecific Anti-P antibody constructed using different Fc's listed in Table 6, linkers listed in Table 7, and fAB binding regions listed in Table 8, are described generally in the Table and embodiments below.

Monospecific LVP058 w/IgG4 Fc
Bispecific LVP058 - Anti-ALB w/IgG 4 Fc
Bispecific LVP058 - ALXN Anti-ALB w/(US20190002568A1) IgG1 Fc
Bispecific NMT16 Anti-P Fab - HumRab Anti-ALB w/(US20190002568A1) IgG1 Fc
Bispecific Presta HumRab Anti-P - HumRab Anti-ALB w/(US20190002568A1) IgG2 Fc
Bispecific NMT16 Anti-P Fab - Anti-TNF Fab w/IgG Fc
Bispecific NMT16 Anti-P Fab - Anti-VEGF Fab w/N298A IgG Fc NM9625 is a monospecific antibody that binds to properdin. Using a camelid Anti-P sequence, it is attached to a variation of the IgG4 Fc using a $(G_4S)_3$ linker. In this embodiment of the IgG4 Fc, there is no CH1 region, and the camelid variable heavy chain domain is directly linked to the hinge region of the Fc. The full sequence listing and the antibody structure can be found in FIG. 9.

NM9626 and NM9627 are bispecific antibodies that bind to both properdin and serum albumin. The sequence and structure of these antibodies in FIG. 4. A variation of the camelid Anti-P sequence is used along with a humanized camelid anti-albumin sequence. These variable heavy chain sequences are attached to a variation of the IgG Fc with a (G$_4$S)$_3$ linker. In these embodiments of the IgG Fc's, there is no CH1 region, and both the camelid Anti-P and Anti-Alb are directly linked to the hinge region of the IgG Fc. The major difference between these two antibodies is that NM9626 is formulated using the same IgG4 Fc as NM9625 (SEQ ID NO: 163 & 164) and NM9627 is formulated using an IgG1 Fc (SEQ ID NO: 165 & 166).

NM9628 is a bispecific antibody that binds to both properdin and serum albumin. The full sequence listing and the antibody structure can be found in FIG. 10. NovelMed's NMT16 Anti-P fAb region is combined with a humanized rabbit serum albumin fAb. The heavy chain regions for NMT16 and Anti-Alb are joined to a full IgG1 Fc. The light chain regions for NMT16 and Anti-ALB are joined to the CL.

NM9629 is a bispecific antibody that binds both properdin and serum albumin. The full sequence listing and the antibody structure can be found in FIG. 11. Presta's humanized rabbit 27-03 Anti-P sequence is combined with a humanized rabbit anti-albumin sequence. The heavy chain regions for Presta humanized rabbit and anti-albumin are joined to the IgG1 Full Fc with the YTE mutation (SEQ ID NO: 131). The light chain regions for Presta humanized rabbit and Anti-Alb are joined to the CL.

NM9630 is a bispecific antibody that binds both properdin and TNF. The full sequence listing and the antibody sequence can be found in FIG. 12. NovelMed's NMT16 fAb is combined with an anti-TNF fAb. The heavy chains are connected to an IgG1 Fc pulled from an anti-TNF antibody: Humira (SEQ ID NO: 129), and the light chains are connected to the CL.

NM9631 is a bispecific antibody that binds both properdin and VEGF-A. A full sequence listing and the antibody structure can be found in FIG. 13.

TABLE 6

| | Half-Lif Fc NM5072 |
|---|---|
| | Heavy Chain |
| Fc-CH | GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PELLGGPSVF LFPPKPKDTL MISRTPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSRDELTKN QVSLTCLVKG FYPSDIAVEW ESNGQPENNY KTTPPVLDSD GSFFLYSKLT VDKSRWQQGN VFSCSVMHEA LHNHYTQKSL SLSPGK (SEQ ID NO: 129) |
| Fc-CH | GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PELLGGPSVF LFPPKPKDTL MISRTPEVTC VVVDVSHEDP EVKFNWYVDG VEVHNAKTKP REEQYASTYR VVSVLTVLHQ DWLNGKEYKC KVSNKALPAP IEKTISKAKG QPREPQVYTL PPSRDELTKN QVSLTCLVKG FYPSDIAVEW ESNGQPENNY KTTPPVLDSD GSFFLYSKLT VDKSRWQQGN VFSCSVMHEA LHNHYTQKSL SLSPGK (SEQ ID NO: 130) |
| Fc-CH | GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PELLGGPSVF LFPPKPKDTL YITREPEVTC VVVDVSHEDP EVKFNWYVDG VEVHNAKTKP REEQYASTYR VVSVLTVLHQ DWLNGKEYKC KVSNKALPAP IEKTISKAKG QPREPQVYTL PPSRDELTKN QVSLTCLVKG FYPSDIAVEW ESNGQPENNY KTTPPVLDSD GSFFLYSKLT VDKSRWQQGN VFSCSVMHEA LHNHYTQKSL SLSPGK (SEQ ID NO: 131) |

TABLE 6-continued

| | Half-Lif Fc NM5072 |
|---|---|
| Fc-CH | GPSVFPLAPC SRSTSESTAA LGCLVKDYFP EPVTVSWNSG ALTSGVHTFP AVLQSSGLYS LSSVVTVPSS NFGTQTYTCN VDHKPSNTKV DKTVERKCCV ECPPCPAPPV AGPSVFLFPP KPKDTLMISR TPEVTCVVVD VSQEDPEVQF NWYVDGVEVH NAKTKPREEQ FNSTYRVVSV LTVLHQDWLN GKEYKCKVSN KGLPSSIEKT ISKAKGQPRE PQVYTLPPSQ EEMTKNQVSL TCLVKGFYPS DIAVEWESNG QPENNYKTTP PVLDSDGSFF LYSRLTVDKS RWQEGNVFSC SVLHEALHSH YTQKSLSLSL GK (SEQ ID NO: 132) |
| Fc-CH | GPSVFPLAPC SRSTSESTAA LGCLVKDYFP EPVTVSWNSG ALTSGVHTFP AVLQSSGLYS LSSVVTVPSS NFGTQTYTCN VDHKPSNTKV DKTVERKCCV ECPPCPAPPV AGPSVFLFPP KPKDTLMISR TPEVTCVVVD VSQEDPEVQF NWYVDGVEVH NAKTKPREEQ FNSTYRVVSV LTVLHQDWLN GKEYKCKVSN KGLPSSIEKT ISKAKGQPRE PQVYTLPPSQ EEMTKNQVSL TCLVKGFYPS DIAVEWESNG QPENNYKTTP PVLDSDGSFF LYSRLTVDKS RWQEGNVFSC SVMHEALHNH YTQKSLSLSL GK (SEQ ID NO: 133) |
| IgG1 Fc-CH | EPKSCDKTHT CPPCPAPELL GGPSVFLFPP KPKDTLMISR TPEVTCVVVD VSHEDPEVKF NWYVDGVEVH NAKTKPREEQ YNSTYRVVSV LTVLHQDWLN GKEYKCKVSN KALPAPIEKT ISKAKGQPRE PQVYTLPPSR DELTKNQVSL TCLVKGFYPS DIAVEWESNG QPENNYKTTP PVLDSDGSFF LYSKLTVDKS RWQQGNVFSC SVMHEALHNH YTQKSLSLSP GK (SEQ ID NO: 134) |
| IgG2 Fc-CH | ERKCCVECPP CPAPPVAGPS VFLFPPKPKD TLMISRTPEV TCVVVDVSHE DPEVQFNWYV DGMEVHNAKT KPREEQFNST FRVVSVLTVV HQDWLNGKEY KCKVSNKGLP APIEKTISKT KGQPREPQVY TLPPSREEMT KNQVSLTCLV KGFYPSDIAV EWESNGQPEN NYKTTPPMLD SDGSFFLYSK LTVDKSRWQQ GNVFSCSVMH EALHNHYTQK SLSLSPGK (SEQ ID NO: 135) |
| IgG4 Fc-CH | ESKYGPPCPS CPAPEFLGGP SVFLFPPKPK DTLMISRTPE VTCVVVDVSQ EDPEVQFNWY VDGVEVHNAK TKPREEQFNS TYRVVSVLTV LHQDWLNGKE YKCKVSNKGL PSSIEKTISK AKGQPREPQV YTLPPSQEEM TKNQVSLTCL VKGFYPSDIA VEWESNGQPE NNYKTTPPVL DSDGSFFLYS RLTVDKSRWQ EGNVFSCSVM HEALHNHYTQ KSLSLSLGK (SEQ ID NO: 136) |
| Fc (gG4) | AESKYGPPCP PCPAPEAAGG PSVFLFPPKP KDTLMISRTP EVTCVVVDVS QEDPEVQFNW YVDGVEVHNA KTKPREEQFN STYRVSVLT VLHQDWLNGK EYKCKVSNKG LPSSIEKTIS KAKGQPREPQ VYTLPPSQEE MTKNQVSLTC LVKGFYPSDIAVEWESNGQP ENNYKTTPPV LDSDGSFFLY SRLTVDKSRW QEGNVFSCSV MHEALHNHYT QKSLSLSLG (SEQ ID NO: 137) |
| Fc-CH1 | GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD (SEQ ID NO: 138) |
| | Light Chain |
| Fc-LC | SVFIFPPSDE QLKSGTASVV CLLNNFYPRE AKVQWKVDNA LQSGNSQESV TEQDSKDSTY SLSSTLTLSK ADYEKHKVYA CEVTHQGLSS PVTKSFNRGE C (SEQ ID NO: 139 |

TABLE 7

| LINKERS | |
|---|---|
| G4S | GGGGS (SEQ ID NO: 140) |
| G3SG | GGGSG (SEQ ID NO: 141) |

TABLE 7-continued

| | LINKERS |
|---|---|
| SG4 | SGGG (SEQ ID NO: 142) |
| (G4S)3 | GGGGSGGGGS GGGGS (SEQ ID NO: 143) |
| (G4D)3 | GGGGDGGGGD GGGG (SEQ ID NO: 144) |
| G4E | GGGGEGGGGE GGGG (SEQ ID NO: 145) |
| G3D | GGGE (SEQ ID NO: 146) |
| G3E | GGGD (SEQ ID NO: 147) |
| G4A | GGGGA (SEQ ID NO: 148) |
| G4A/S | GGGGAGGGGA GGGGS (SEQ ID NO: 149) |

TABLE 8

| | Anti-TNF Anti VEGF fAb |
|---|---|
| Fv-(VH Anti-TNF) | EVQLVESGGG LVQPGRSLRL SCAASGFTFD DYAMHWVRQA PGKGLEWVSA ITWNSGHIDY ADSVEGRFTI SRDNAKNSLY LQMNSLRAED TAVYYCAKVS YLSTASSLDY WGQGTLVTVS SASTK (SEQ ID No: 150) |
| Fv-(VL Anti-TNF) | DIQMTQSPSS LSASVGDRVT ITCRASQGIR NYLAWYQQKP GKAPKLLIYA ASTLQSGVPS RFSGSGSGTD FTLTISSLQP EDVATYYCQR YNRAPYTFGQ GTKVEIKRTV AAP (SEQ ID NO: 151) |
| Fv-(VH Anti-VEGF) | EVQLVESGGG LVQPGGSLRL SCAASGYTFT NYGMNWVRQA PGKGLEWVGW INTYTGEPTY AADFKRRFTF SLDTSKSTAY LQMNSLRAED TAVYYCAKYP HYYGSSHWYF DVWGQGTLVT VSSASTK (SEQ ID NO: 152 |
| Fv-(VL Anti-VEGF) | DIQMTQSPSS LSASVGDRVT ITCSASQDIS NYLNWYQQKP GKAPKVLIYF TSSLHSGVPS RFSGSGSGTD FTLTISSLQP EDFATYYCQQ YSTVPWTFGQ GTKVEIKRTV AAP (SEQ ID NO: 153) |

Example 7

Example 7 describes the structure and amino acid sequences of antibodies that were modified and reconstructed from Example 5 and Example 6. Specifically, NMT1003, the (fAb)2 monospecific antibody from Example 5 is listed along with a couple bispecific fAb regions from Example 6 (Anti-P/Anti-Alb, Anti-P/Anti-TNF, Anti-P/Anti-VEGF). The main difference is the variations of the Fc's used to attach to these heavy chain regions. By varying the Fc, the ability to get monospecific and bispecific antibodies with better binding, half-life, and circulation time can be generated. The table below shows the list of antibodies that have been developed for Example 7.

1. Monospecific NMT15 Anti-P (fAb)₂ with CH1 Fc Only
2. Bispecific Camelid Anti-P - Anti-Alb w/IgG1 N297A Fc
3. Bispecific NMT16 Anti-P - Anti-Alb w/IgG1 YTE Fc
4. Bispecific NMT16 Anti-P - HumRab Anti-Alb w/IgG1 N297A Fc
5. Bispecific Camelid Anti-P - ALXN Anti-Alb w/IgG4 (CH2/CH3 only)
6. Bispecific NMT16 Anti-P - Anti-TNF w/IgG1 YTE Fc
7. Bispecific NMT16 Anti-P - Anti-VEGF w/IgG1 YTE Fc FIG. 7 shows a monospecific antibody that only binds to Properdin. This antibody contains NMT15 for its variable heavy and light chains (fAb). The variable heavy chain is attached to Fc CH1 region only. The light chain is attached to the Fc CL. The two identical NMT15 fAb regions will be joined together with a (G₄S)₃ linker. A structure of the antibody is presented as well with the two ovals representing the NMT15 fAb regions along with the CH1 and CL regions. The green line between the two represents the linker joining them together.

Figure 14:
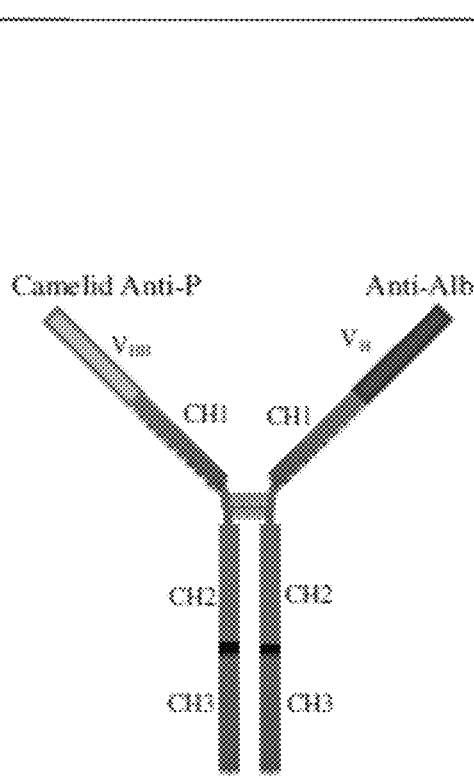
FIG. 14 illustrates a schematic showing the structure of a bispecific camelid anti-properdin/anti-albumin antibody and a table listing the amino acid sequences of the camelid anti-properdin $V_{HH}$ (SEQ ID NO: 74), linker (SEQ ID NO: 143), and IgG1 Fc with hinge region (SEQ ID NO: 130) and anti-albumin $V_H$ (SEQ ID NO: 108), linker (SEQ ID NO: 143), and IgG1 Fc (SEQ ID NO: 143) of the bispecific camelid anti-properdin/anti-albumin antibody in accordance with another embodiment.

FIG. 14 illustrates the sequences and structure of a bispecific antibody that binds to both properdin and serum albumin. Both the anti-properdin and anti-albumin variable heavy chain sequences are derived from camelid species. Additionally, both are attached the an IgG1 full Fc with a N297A mutation (a mutation of Aparagine to Alanine at position 297). However, this position is subject to change depending on the variable heavy chain it is attached to. A (G4S)3 linker is used to connect the variable chains to the constant chains.

FIG. 15 shows the sequences and structure of a bispecific antibody that binds to both properdin and serum albumin. NMT16 variable heavy and light chains are combined with a camelid Anti-Alb single variable heavy chain. NMT16's variable heavy chain region is attached to an IgG1 Fc with a YTE mutation to help induce a longer half-life. Ablynx's camelid anti-alb is attached to the same Fc using a (G4S)3 linker. NMT16's light chain is attached to the CL Fc.

FIG. 16 shows the sequences and structure of a bispecific antibody that binds to both properdin and serum albumin. NMT16 Anti-P fAb region is combined with humanized rabbit serum albumin. This is similar to the NM9628 construct from Example 6. The difference is that the heavy chain regions for NMT16 and Anti-ALB are joined to a IgG1 N297A Fc (mutation might not always occur at position 297, it depends on the VH to which it is attached). The light chain regions for NMT16 and Anti-ALB are joined to the CL.

FIG. 17 shows the sequences and structure of a bispecific antibody that binds both properdin and serum albumin. A camelid anti-properdin single variable heavy chain is combined with camelid anti-alb single heavy chain. These two variable heavy chain regions are joined to Dulaglutide's IgG4 Fc (CH2/CH3 regions only) with a (G4S)3 linker.

Figure 18:
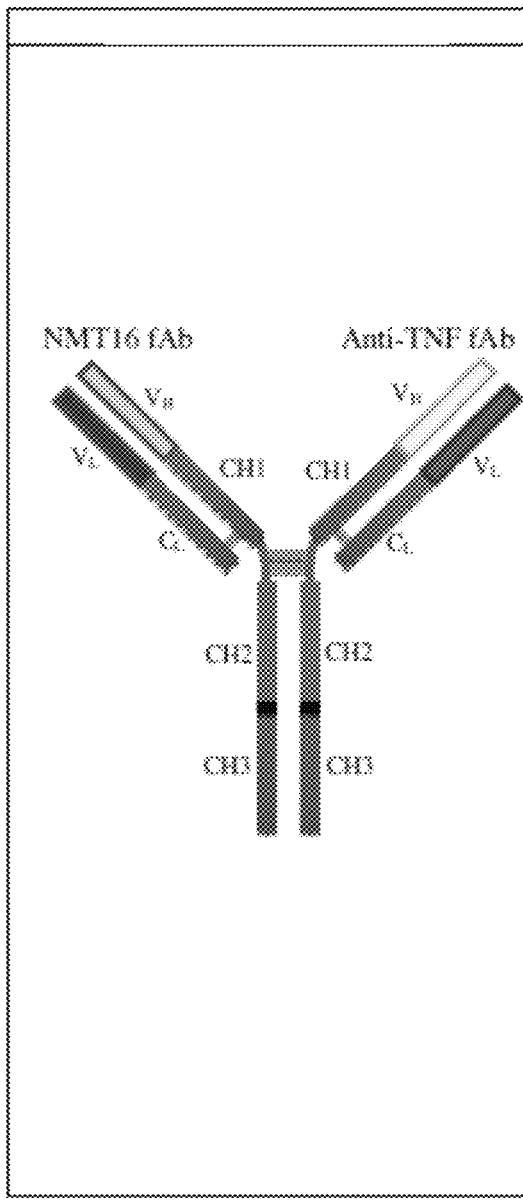
FIG. 18 illustrates a schematic showing the structure of a bispecific anti-properdin/anti-TNF antibody and a table listing the amino acid sequences of anti-properdin $V_H$ (SEQ ID NO: 2), IG1 Fc (SEQ ID NO: 131), VL (SEQ ID NO: 25), and Fc-LC (SEQ ID NO: 139) and anti-TNF $V_H$ (SEQ ID NO: 150), IG1 Fc (SEQ ID NO: 131), VL (SEQ ID NO: 151), and Fc-LC (SEQ ID NO: 139) of the bispecific anti-properdin/anti-TNF antibody in accordance with another embodiment.

FIG. 18 shows the sequences and structure of a bispecific antibody that binds both properdin and TNF. This is similar to Example 6's NM9630. NMT16 fAb is combined with an anti-TNF fAb. The difference is that the variable heavy chain sequences are connected to an IgG1 YTE Fc. The light chains are attached to the CL.

Figure 19:
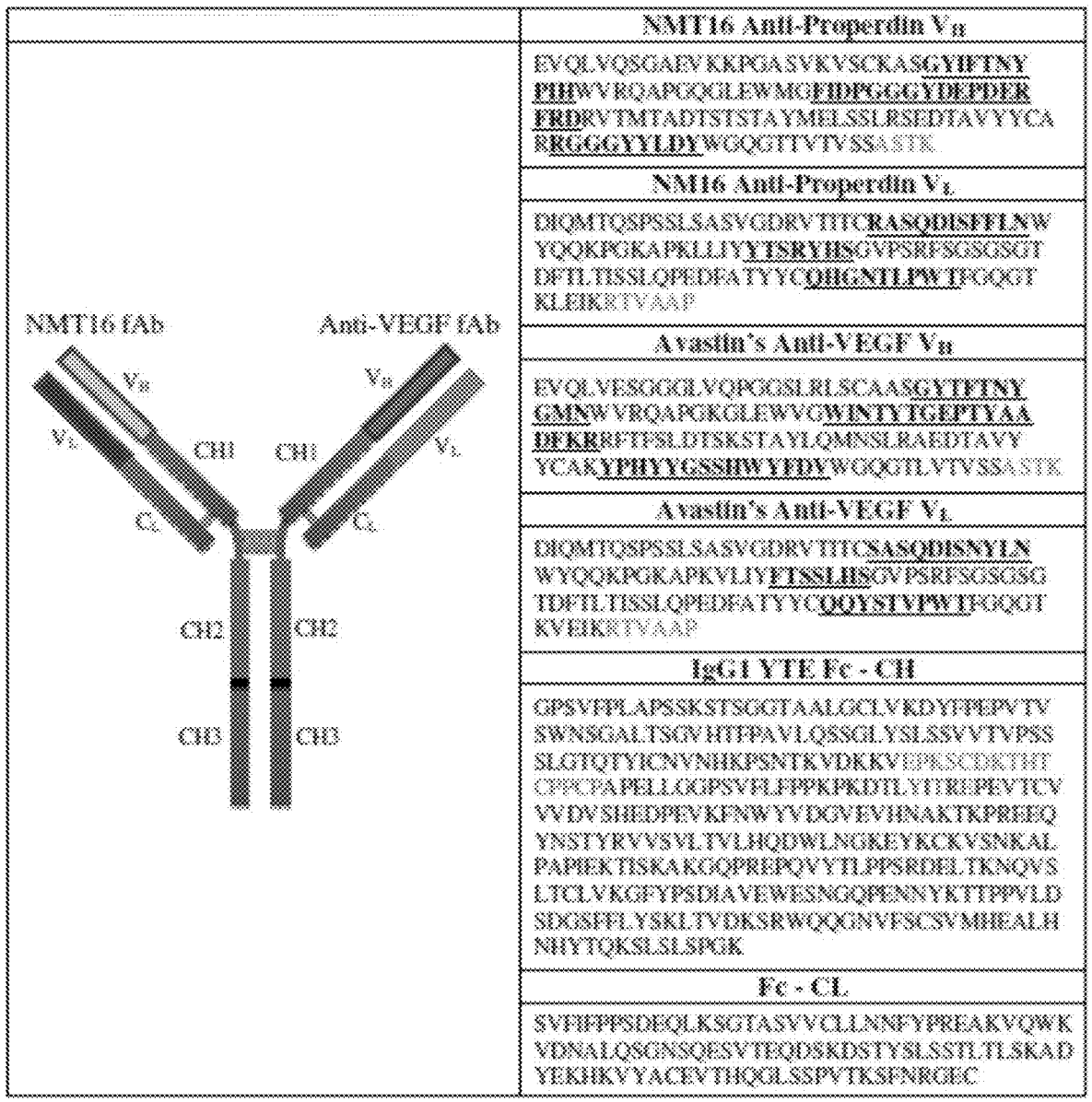
FIG. 19 illustrates a schematic showing the structure of a bispecific anti-properdin/anti-VEGF antibody and a table listing the amino acid sequences of anti-properdin $V_H$ (SEQ ID NO: 2), IG1 Fc (SEQ ID NO: 131), VL (SEQ ID NO: 25), and Fc-LC (SEQ ID NO: 139) and anti-VEGF $V_H$ (SEQ ID NO: 152), IG1 Fc (SEQ ID NO: 131), VL (SEQ ID NO: 153), and Fc-LC (SEQ ID NO: 139) of the bispecific anti-properdin/anti-VEGF antibody in accordance with another embodiment.

FIG. 19 shows the sequences and structure of a bispecific antibody that binds both properdin and VEGF-A. This is similar to Example 6's NM9631 construct. NMT16 fAb is combined with an anti-VEGF-A fAb. The difference is that the heavy chains are to an IgG1 YTE Fc, just like the bispecific construct above. The light chains are connected to the CL.

Using the Presta substitutions, multiple different combinations of variable chain sequences can be generated. These sequences can be utilized to formulate and test how different substitutions can affect the affinity, hemolysis, and potency of different antibody structures. Additionally, the ability to create bispecific molecules using anti-Alb, anti-TNF, anti-VEGF, and the mutation of the IgG Fc's can help increase the half-life and circulation time of these antibodies in vivo.

Amino acid sequences of these anti-properdin antibodies and other monospecific and bispecific anti-properdin antibodies are listed in Tables 9, 10, and 11.

TABLE 9

| Full Chain SEQ ID NQs | |
|---|---|
| NMT 1001-Single Chain mAb Anti-Alb/Camelid Anti-P (LPV058) | EVQLVESGGG LVKPGGSLRL SCAASGRPVS NYAAAWFRQA PGKEREFVSA INWQKTATYA DSVKGRFTIS RDNAKNSLYL QMNSLRAEDT AVYYCAAVFR VVAPKTQYDY DYWGQGTLVT VSSGGGSGGG SGGGSEVQLV ESGGGLVQPG GSLRLSCAAS GRISSIIHMA WVRQAPGKQR ELVSEISRVG TTVYADSVKG RFTISRDNSK NTLYLQMNSL RAEDTAVYYC NALQYEKHGG ADYWGQGTLV TVSS (SEQ ID NO: 154) |
| NMT 1002-Single Chain mAb Anti-Alb/Camelid Anti-P (LPV058) | EVQLVESGGG LVQPGGSLRL SCAASGFTFR SFGMSWVRQA PGKEPEWVSS ISGSGSDTLY ADSVKGRFTI SRDNAKTTLY LQMNSLKPED TAVYYCTIGG SLSRSSQGTQ VTVSSGGGSG GGSGGGSEVQ LVESGGGLVQ PGGSLRLSCA ASGRISSIIH MAWVRQAPGK QRELVSEISR VGTTVYADSV KGRFTISRDN SKNTLYLQMN SLRAEDTAVY YCNALQYEKH GGADYWGQGT LVTVSS (SEQ ID NO: 155) |
| NMT 1003-(Fab)2 Fv (VH NMT15) Fc-CH1 | QVQLVQSAPE VAKPGTSVKM SCKASGYIFT NYPIHWVKQA PGQGLEWIGF IDPGGYDEP DERFRDRATL TADKSTSTAY MELSSLRSED TAIYYCARRG GGYYLDYWGQ GTLVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CD (SEQ ID NO: 156) |
| NMT-1003-(Fab)2 Fv (VL NMT15) Fc-CL | DIQMTQSPSS LSASLGDRVT ITCRASQDIS FFLNWYQQKP DGTVKLLIYY TSRYHSGVPS RFSGSGSGTD FTLTISSLQP EDFATYFCQH GNTLPWTFGQ GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC (SEQ ID NO: 157) |
| NMT1004-NMT15 fAb-Camelid Anti-Alb Fv (VHNMT15) Fc-CH1 (G4S)3 Linker Hum Anti-Alb | QVQLVQSAPE VAKPGTSVKM SCKASGYIFT NYPIHWVKQA PGQGLEWIGF IDPGGYDEP DERFRDRATL TADKSTSTAY MELSSLRSED TAIYYCARRG GGYYLDYWGQ GTLVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDGGGGSGGG GSGGGGSEVQ LVESGGGLVK PGGSLRLSCA ASGRPVSNYA AAWFRQAPGK EREFVSAINW QKTATYADSV KGRFTISRDN AKNSLYLQMN SLRAEDTAVY YCAAVFRVVA PKTQYDYDYW GQGTLVTVSS (SEQ ID NO: 158) |
| Fv (VL NMT15) Fc-CL | DIQMTQSPSS LSASLGDRVT ITCRASQDIS FFLNWYQQKP DGTVKLLIYY TSRYHSGVPS RFSGSGSGTD FTLTISSLQP EDFATYFCQH GNTLPWTFGQ GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC (SEQ ID NO: 159) |
| NMT1005-NMT15 fAb-Camelid Anti-Alb Fv (VHNMT15) Fc-CH1 (G4S)3 Linker Human-Anti-Alb | QVQLVQSAPE VAKPGTSVKM SCKASGYIFT NYPIHWVKQA PGQGLEWIGF IDPGGYDEP DERFRDRATL TADKSTSTAY MELSSLRSED TAIYYCARRG GGYYLDYWGQ GTLVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDGGGGSGGG GSGGGGSEVQ LVESGGGLVQ PGGSLRLSCA ASGFTFRSFG MSWVRQAPGK EPEWVSSISG SGSDTLYADS VKGRFTISRD NAKTTLYLQM NSLKPEDTAV YYCTIGGSLS RSSQGTQVTV SS (SEQ ID NO: 160) |

TABLE 9-continued

Full Chain SEQ ID NQs

| | |
|---|---|
| Fv (VL NMT15) | DIQMTQSPSS LSASLGDRVT ITCRASQDIS FFLNWYQQKP DGTVKLLIYY TSRYHSGVPS RFSGSGSGTD FTLTISSLQP EDFATYFCQH GNTLPWTFGQ GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC (SEQ ID NO: 161) |

TABLE 10

Full Chain SEQ ID NQs

| | |
|---|---|
| NM9625-Camelid Anti-P w/ IgG4 (fAb)2 Camelid (Anti-P) Linker Fc (IgG4) | EVQLLESGGG LVQPGGSLRL SCAASGRISS IIHMAWFRQA PGKERELVSE ISRVGTTVYA DSVKGRFTIS RDNSKNTLYL QMNSLKPEDT AVYYCNALQY EKHGGADYWG QGTLVTVSSG GGGSGGGGSG GGGSAESKYG PPCPPCPAPE AAGGPSVFLF PPKPKDTLMI SRTPEVTCVV VDVSQEDPEV QFNWYVDGVE VHNAKTKPRE EQFNSTYRVV SVLTVLHQDW LNGKEYKCKV SNKGLPSSIE KTISKAKGQP REPQVYTLPP SQEEMTKNQV SLTCLVKGFY PSDIAVEWES NGQPENNYKT TPPVLDSDGS FFLYSRLTVD KSRWQEGNVF SCSVMHEALH NHYTQKSLSL SLG (SEQ ID NO: 162) |
| NM9626-Camelid Anti-P-Anti-Alb w/ IgG4 Camelid (Anti-P) (G4S)3 Linker Fc (IgG4) | EVQLLESGGG LVQPGGSLRL SCAASGRISS IIHMAWFRQA PGKERELVSE ISRVGTTVYA DSVKGRFTIS RDNSKNTLYL QMNSLKPEDT AVYYCNALQY EKHGGADYWG QGTLVTVSSG GGGSGGGGSG GGGSAESKYG PPCPPCPAPE AAGGPSVFLF PPKPKDTLMI SRTPEVTCVV VDVSQEDPEV QFNWYVDGVE VHNAKTKPRE EQFNSTYRVV SVLTVLHQDW LNGKEYKCKV SNKGLPSSIE KTISKAKGQP REPQVYTLPP SQEEMTKNQV SLTCLVKGFY PSDIAVEWES NGQPENNYKT TPPVLDSDGS FFLYSRLTVD KSRWQEGNVF SCSVMHEALH NHYTQKSLSL SLG (SEQ ID NO: 162) |
| Anti-ALB (G4S)3 Linker Fc (IgG4) | EVQLVESGGG LVKPGGSLRL SCAASGRPVS NYAAAWFRQA PGKEREFVSA INWQKTATYA DSVKGRFTIS RDNAKNSLYL QMNSLRAEDT AVYYCAAVFR VVAPKTQYDY DYWGQGTLVT VSSGGGGSGG GGSGGGGSAE SKYGPPCPPC PAPEAAGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLG (SEQ ID NO: 163) |
| NM9627-Camelid Anti-P-Anti-Alb w/ IgG1 Camelid (Anti-P) (G4S)3 Linker IgG1-Fc | EVQLLESGGG LVQPGGSLRL SCAASGRISS IIHMAWFRQA PGKERELVSE ISRVGTTVYA DSVKGRFTIS RDNSKNTLYL QMNSLKPEDT AVYYCNALQY EKHGGADYWG QGTLVTVSSG GGGSGGGGSG GGGSEPKSCD KTHTCPPCPA PELLGGPSVF LFPPKPKDTL MISRTPEVTC VWDVSHEDP EVKFNWYVDG VEVHNAKTKP REEQYNSTYR VVSVLTVLHQ DWLNGKEYKC KVSNKALPAP IEKTISKAKG QPREPQVYTL PPSRDELTKN QVSLTCLVKG FYPSDIAVEW ESNGQPENNY KTTPPVLDSD GSFFLYSKLT VDKSRWQQGN VFSCSVMHEA LHNHYTQKSL SLSPGK (SEQ ID NO: 164) |
| Anti-ALB (G4S)3 Linker IgG1-Fc | EVQLVESGGG LVKPGGSLRL SCAASGRPVS NYAAAWFRQA PGKEREFVSA INWQKTATYA DSVKGRFTIS RDNAKNSLYL QMNSLRAEDT AVYYCAAVFR VVAPKTQYDY DYWGQGTLVT VSSGGGGSGG GGSGGGGSEP KSCDKTHTCP PCPAPELLGG PSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK (SEQ ID NO: 165) |

TABLE 10-continued

| Full Chain SEQ ID NQs | |
|---|---|
| NM9628-NMT16 fAb-LIT HumRab Anti-ALB fAb w/ IgG1<br>Fv-(VH NMT16)<br>Fc-IgG1 | EVQLVQSGAE VKKPGASVKV SCKASGYIFT<br>NYPIHWVRQA PGQGLEWMGF IDPGGGYDEP<br>DERFRDRVTM TADTSTSTAY MELSSLRSED<br>TAVYYCARRG GGYYLDYWGQ GTTVTVSSAS<br>TKGPSVFPLA PCSRSTSEST AALGCLVKDY FPEPVTVSWN<br>SGALTSGVHT FPAVLQSSGL YSLSSVVTVP SSNFGTQTYT<br>CNVDHKPSNT KVDKTVEPKS CDKTHTCPPC PAPELLGGPS<br>VFLFPPKPKD TLMISRTPEV TCVVVDVSHE<br>DPEVKFNWYV DGVEVHNAKT KPREEQYNST<br>YRVVSVLTVL HQDWLNGKEY KCKVSNKALP<br>APIEKTISKA KGQPREPQVY TLPPSRDELT KNQVSLTCLV<br>KGFYPSDIAV EWESNGQPEN NYKTTPPVLD SDGSFFLYSK<br>LTVDKSRWQQ GNVFSCSVMH EALHNHYTQK SLSLSPGK<br>(SEQ ID NO: 166) |
| Fv-(VL NMT16)<br>Fc-CL | DIQMTQSPSS LSASVGDRVT ITCRASQDIS FFLNWYQQKP<br>GKAPKLLIYY TSRYHSGVPS RFSGSGSGTD FTLTISSLQP<br>EDFATYYCQH GNTLPWTFGQ GTKLEIKRTV AAPSVFIFPP<br>SDEQLKSGTA SVVCLLNNFY PREAKVQWKV<br>DNALQSGNSQ ESVTEQDSKD STYSLSSTLT LSKADYEKHK<br>VYACEVTHQG LSSPVTKSFN RGEC (SEQ ID NO: 167) |
| Fv-(VH HumRab Anti-ALB)<br>Fc-IgG1 | EVQLLESGGG LVQPGGSLRL SCAVSGIDLS<br>NYAINWVRQA PGKGLEWIGIIWASGTTFYA<br>TWAKGRFTIS RDNSKNTVYL QMNSLRAEDT<br>AVYYCARTVP GYSTAPYFDL WGQGTLVTVS<br>SASTKGPSVF PLAPCSRSTS ESTAALGCLV KDYFPEPVTV<br>SWNSGALTSG VHTFPAVLQS SGLYSLSSVV TVPSSNFGTQ<br>TYTCNVDHKP SNTKVDKTVE PKSCDKTHTC<br>PPCPAPELLG GPSVFLFPPK PKDTLMISRT PEVTCVVVDV<br>SHEDPEVKFN WYVDGVEVHN AKTKPREEQY<br>NSTYRVVSVL TVLHQDWLNG KEYKCKVSNK<br>ALPAPIEKTI SKAKGQPREP QVYTLPPSRD ELTKNQVSLT<br>CLVKGFYPSD IAVEWESNGQ PENNYKTTPP VLDSDGSFFL<br>YSKLTVDKSR WQQGNVFSCS VMHEALHNHY<br>TQKSLSLSPG K (SEQ ID NO: 168) |
| Fv-(VL HumRab Anti-ALB)<br>Fc-CL | DIQMTQSPSS VSASVGDRVT ITCQSSPSVW SNFLSWYQQK<br>PGKAPKLLIY EASKLTSGVP SRFSGSGSGT DFTLTISSLQ<br>PEDFATYYCG GYSSISDTT FGGGTKVEIK RTVAAPSVFI<br>FPPSDEQLKS GTASVVCLLN NFYPREAKVQ<br>WKVDNALQSG NSQESVTEQD SKDSTYSLSS<br>TLTLSKADYE KHKVYACEVT HQGLSSPVTK SFNRGEC<br>(SEQ ID NO: 169) |
| NM9629-NMT HumRab Anti-P-LIT HumRab Anti-ALB fAb w/ IgG1 YTE<br>Fv-(VH HumRab 2703 H2)<br>Fc-IgG1 YTE Mutation | EVQLLESGGG LVQPGGSLRL SCAASGFSFS SGYWIFWVRQ<br>APGKGLELVG GIYSGSSGTT YYADSVKGRF TISKDNSKNT<br>VYLQMNSLRA EDTAVYYCAR SVDGIDSYDA<br>AFNLWGQGTL VTVSSASTKG PSVFPLAPSS KSTSGGTAAL<br>GCLVKDYFPE PVTVSWNSGA LTSGVHTFPA<br>VLQSSGLYSL SSVVTVPSSS LGTQTYICNV NHKPSNTKVD<br>KKVEPKSCDK THTCPPCPAP ELLGGPSVFL FPPKPKDTLY<br>ITREPEVTCV VVDVSHEDPE VKFNWYVDGV<br>EVHNAKTKPR EEQYNSTYRV VSVLTVLHQD<br>WLNGKEYKCK VSNKALPAPIEKTISKAKGQ PREPQVYTLP<br>PSRDELTKNQ VSLTCLVKGF YPSDIAVEWE<br>SNGQPENNYK TTPPVLDSDG SFFLYSKLTV<br>DKSRWQQGNV FSCSVMHEAL HNHYTQKSLS LSPGK (SEQ<br>ID NO: 170) |
| Fv-(VL HumRab 2703 L2)<br>Fc-CL | DIQLTQSPSS LSASVGDRVT ITCRASDNIY SLLAWYQQKP<br>GKAPKLLIYR ASTLASGVPS RFSGSGSGTD FTLTISSVQP<br>EDFATYYCQQ HYDYNYLDVA FGGGTKVEIK<br>RTVAAPSVFI FPPSDEQLKS GTASVVCLLN NFYPREAKVQ<br>WKVDNALQSG NSQESVTEQD SKDSTYSLSS<br>TLTLSKADYE KHKVYACEVT HQGLSSPVTK SFNRGEC<br>(SEQ ID NO: 171) |
| Fv-(VH HumRab Anti-ALB)<br>Fc-IgG1 YTE Mutation | DIQMTQSPSS VSASVGDRVT ITCQSSPSVW SNFLSWYQQK<br>PGKAPKLLIY EASKLTSGVP SRFSGSGSGT DFTLTISSLQ<br>PEDFATYYCG GYSSISDTT FGGGTKVEIK RTVAAPSVFI<br>FPPSDEQLKS GTASVVCLLN NFYPREAKVQ<br>WKVDNALQSG NSQESVTEQD SKDSTYSLSS<br>TLTLSKADYE KHKVYACEVT HQGLSSPVTK SFNRGEC<br>(SEQ ID NO: 172) |

TABLE 10-continued

| Full Chain SEQ ID NOs | |
|---|---|
| Fv-(VL HumRab Anti-ALB) Fc-CL | DIQMTQSPSS VSASVGDRVT ITCQSSPSVW SNFLSWYQQK PGKAPKLLIY EASKLTSGVP SRFSGSGSGT DFTLTISSLQ PEDFATYYCG GGYSSISDTT FGGGTKVEIK RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC (SEQ ID NO: 173) |
| NM9630-NMT16 fAb-Anti-TNF w/ IgG1 Fv-(VH NMT16) Fc-IgG1 | EVQLVQSGAE VKKPGASVKV SCKASGYIFT NYPIHWVRQA PGQGLEWMGF IDPGGGYDEP DERFRDRVTM TADTSTSTAY MELSSLRSED TAVYYCARRG GGYYLDYWGQ GTTVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVMH EALHNHYTQK SLSLSPGK (SEQ ID NO: 174) |
| Fv-(VL NMT16) Fc-CL | DIQMTQSPSS LSASVGDRVT ITCRASQDIS FFLNWYQQKP GKAPKLLIYY TSRYHSGVPS RFSGSGSGTD FTLTISSLQP EDFATYYCQH GNTLPWTFGQ GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC (SEQ ID NO: 175) |
| Fv-(VH Anti-TNF) Fc-IgG1 | EVQLVESGGG LVQPGRSLRL SCAASGFTFD DYAMHWVRQA PGKGLEWVSA ITWNSGHIDY ADSVEGRFTI SRDNAKNSLY LQMNSLRAED TAVYYCAKVS YLSTASSLDY WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSCDKTHTC PPCPAPELLG GPSVFLFPPK PKDTLMISRT PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRD ELTKNQVSLT CLVKGFYPSD IAVEWESNGQ PENNYKTTPP VLDSDGSFFL YSKLTVDKSR WQQGNVFSCS VMHEALHNHY TQKSLSLSPG K (SEQ ID NO: 176) |
| Fv-(VL Anti-TNF) Fc-CL | DIQMTQSPSS LSASVGDRVT ITCRASQGIR NYLAWYQQKP GKAPKLLIYA ASTLQSGVPS RFSGSGSGTD FTLTISSLQP EDVATYYCQR YNRAPYTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC (SEQ ID NO: 177) |
| NM9631-NMT16fAb-Anti-VEGF w/ IgG1 N298A Fv-(VH NMT16) Fc-IgG1 N298A | EVQLVQSGAE VKKPGASVKV SCKASGYIFT NYPIHWVRQA PGQGLEWMGF IDPGGGYDEP DERFRDRVTM TADTSTSTAY MELSSLRSED TAVYYCARRG GGYYLDYWGQ GTTVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYAST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVMH EALHNHYTQK SLSLSPGK (SEQ ID NO: 178) |
| Fv-(VL NMT16) Fc-CL | DIQMTQSPSS LSASVGDRVT ITCRASQDIS FFLNWYQQKP GKAPKLLIYY TSRYHSGVPS RFSGSGSGTD FTLTISSLQP EDFATYYCQH GNTLPWTFGQ GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC (SEQ ID NO: 179) |
| Fv-(VH Anti-VEGF) Fc-IgG1 N298A | EVQLVESGGG LVQPGGSLRL SCAASGYTFT NYGMNWVRQA PGKGLEWVGW INTYTGEPTY AADFKRRFTF SLDTSKSTAY LQMNSLRAED TAVYYCAKYP HYYGSSHWYF DVWGQGTLVT |

TABLE 10-continued

Full Chain SEQ ID NQs

| | |
|---|---|
| | VSSASTKGPS VFPLAPSSKS TSGGTAALGC LVKDYFPEPV TVSWNSGALT SGVHTFPAVL QSSGLYSLSS VVTVPSSSLG TQTYICNVNH KPSNTKVDKK VEPKSCDKTH TCPPCPAPEL LGGPSVFLFP PKPKDTLMIS RTPEVTCVVV DVSHEDPEVK FNWYVDGVEV HNAKTKPREE QYASTYRVVS VLTVLHQDWL NGKEYKCKVS NKALPAPIEK TISKAKGQPR EPQVYTLPPS RDELTKNQVS LTCLVKGFYP SDIAVEWESN GQPENNYKTT PPVLDSDGSF FLYSKLTVDK SRWQQGNVFS CSVMHEALHN HYTQKSLSLS PGK (SEQ ID NO: 180) |
| Fv-(VL Anti-VEGF) Fc-CL | DIQMTQSPSS LSASVGDRVT ITCSASQDIS NYLNWYQQKP GKAPKVLIYF TSSLHSGVPS RFSGSGSGTD FTLTISSLQP EDFATYYCQQ YSTVPWTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC (SEQ ID NO: 181) |

TABLE 11

Full Chain SEQ ID NQs

| | |
|---|---|
| Anti-P-Anti-Alb w/ N297A Fc<br>Camelid Anti-P-VHH<br>Linker<br>IgG1 N297A Fc-Full CH | EVQLVESGGG LVQPGGSLRL SCAASGRISS IIHMAWVRQA PGKQRELVSE ISRVGTTVYA DSVKGRFTIS RDNSKNTLYL QMNSLRAEDT AVYYCNALQY EKHGGADYWG QGTLVTVSSG GGGSGGGGSG GGGSGPSVFP LAPSSKSTSG GTAALGCLVK DYFPEPVTVS WNSGALTSGV HTFPAVLQSS GLYSLSSVVT VPSSSLGTQT YICNVNHKPS NTKVDKKVEP KSCDKTHTCP PCPAPELLGG PSVFLFPPKP KDTLMISRTP EVTCVVVDVS HEDPEVKFNW YVDGVEVHNA KTKPREEQYA STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK (SEQ ID NO: 182) |
| Anti-Alb<br>Linker<br>IgG1 N297A Fc-Full CH | EVQLVESGGG LVKPGGSLRL SCAASGRPVS NYAAAWFRQA PGKEREFVSA INWQKTATYA DSVKGRFTIS RDNAKNSLYL QMNSLRAEDT AVYYCAAVFR VVAPKTQYDY DYWGQGTLVT VSSGGGGSGG GGSGGGGSGP SVFPLAPSSK STSGGTAALG CLVKDYFPEP VTVSWNSGAL TSGVHTFPAV LQSSGLYSLS SVVTVPSSSL GTQTYICNVN HKPSNTKVDK KVEPKSCDKT HTCPPCPAPE LLGGPSVFLF PPKPKDTLMI SRTPEVTCVV VDSHEDPEV KFNWYVDGVE VHNAKTKPRE EQYASTYRVV SVLTVLHQDW LNGKEYKCKV SNKALPAPIE KTISKAKGQP REPQVYTLPP SRDELTKNQV SLTCLVKGFY PSDIAVEWES NGQPENNYKT TPPVLDSDGS FFLYSKLTVD KSRWQQGNVF SCSVMHEALH NHYTQKSLSL SPGK (SEQ ID NO: 183) |
| NMT16 fAb-Alb w/ YTE Fc<br>NMT16 Fv-VH<br>IgG1 YTE Fc-Full CH | EVQLVQSGAE VKKPGASVKV SCKASGYIFT NYPIHWVRQA PGQGLEWMGF IDPGGGYDEP DERFRDRVTM TADTSTSTAY MELSSLRSED TAVYYCARRG GGYYLDYWGQ GTTVTVSSAS TKEVQLVQSG AEVKKPGASV KVSCKASGYI FTNYPIHWVR QAPGQGLEWM GFIDPGGGYD EPDERFRDRV TMTADTSTST AYMELSSLRS EDTAVYYCAR RGGGYYLDYW GQGTTVTVSS ASTK (SEQ ID NO: 184) |
| NMT16 Fv-VL Fc-CL | DIQMTQSPSS LSASVGDRVT ITCRASQDIS FFLNWYQQKP GKAPKLLIYY TSRYHSGVPS RFSGSGSGTD FTLTISSLQP EDFATYYCQH GNTLPWTFGQ GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC (SEQ ID NO: 185) |
| Anti-Alb Fv-VH<br>Linker<br>IgG1 YTE Fc-Full CH | EVQLVESGGG LVQPGGSLRL SCAASGFTFR SFGMSWVRQA PGKEPEWVSS ISGSGSDTLY ADSVKGRFTI SRDNAKTTLY LQMNSLKPED |

TABLE 11-continued

| Full Chain SEQ ID NQs | |
|---|---|
| | TAVYYCTIGG SLSRSSQGTQ VTVSSGGGGS GGGGSGGGGS GPSVFPLAPS SKSTSGGTAA LGCLVKDYFP EPVTVSWNSG ALTSGVHTFP AVLQSSGLYS LSSVVTVPSS SLGTQTYICN VNHKPSNTKV DKKVEPKSCD KTHTCPPCPA PELLGGPSVF LFPPKPKDTL YITREPEVTC VVVDVSHEDP EVKFNWYVDG VEVHNAKTKP REEQYNSTYR VVSVLTVLHQ DWLNGKEYKC KVSNKALPAP IEKTISKAKG QPREPQVYTL PPSRDELTKN QVSLTCLVKG FYPSDIAVEW ESNGQPENNY KTTPPVLDSD GSFFLYSKLT VDKSRWQQGN VFSCSVMHEA LHNHYTQKSL SLSPGK (SEQ ID NO: 186) |
| NMT16 fAb-HumRab Anti-Alb w/ N297A NMT16 Fv-VH IgG1 N297A Fc-Full CH | EVQLVQSGAE VKKPGASVKV SCKASGYIFT NYPIHWVRQA PGQGLEWMGF IDPGGGYDEP DERFRDRVTM TADTSTSTAY MELSSLRSED TAVYYCARRG GGYYLDYWGQ GTTVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKKVEPKS CDKTHTCPPC PAPELLGGPS VFLFPPKPKD TLMISRTPEV TCVVVDVSHE DPEVKFNWYV DGVEVHNAKT KPREEQYAST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVMH EALHNHYTQK SLSLSPGK (SEQ ID NO: 187) |
| NMT16 Fv-VL Fc-CL | DIQMTQSPSS LSASVGDRVT ITCRASQDIS FFLNWYQQKP GKAPKLLIYY TSRYHSGVPS RFSGSGSGTD FTLTISSLQP EDFATYYCQH GNTLPWTFGQ GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC (SEQ ID NO: 188) |
| HumRab Anti-Alb Fv-VH IgG1 N297A Fc-Full CH | EVQLLESGGG LVQPGGSLRL SCAVSGIDLS NYAINWVRQA PGKGLEWIGIIWASGTTFYA TWAKGRFTIS RDNSKNTVYL QMNSLRAEDT AVYYCARTVP GYSTAPYFDL WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSCDKTHTC PPCPAPELLG GPSVFLFPPK PKDTLMISRT PEVTCVVVDV SHEDPEVKFN WYVDGVEVHN AKTKPREEQY ASTYRVVSVL TVLHQDWLNG KEYKCKVSNK ALPAPIEKTI SKAKGQPREP QVYTLPPSRD ELTKNQVSLT CLVKGFYPSD IAVEWESNGQ PENNYKTTPP VLDSDGSFFL YSKLTVDKSR WQQGNVFSCS VMHEALHNHY TQKSLSLSPG K (SEQ ID NO: 189) |
| HumRab Anti-Alb Fv-VL Fc-CL | DIQMTQSPSS VSASVGDRVT ITCQSSPSVW SNFLSWYQQK PGKAPKLLIY EASKLTSGVP SRFSGSGSGT DFTLTISSLQ PEDFATYYCG GYSSISDTT FGGGTKVEIK RTVAAPSVFI FPPSDEQLKS GTASVVCLLN NFYPREAKVQ WKVDNALQSG NSQESVTEQD SKDSTYSLSS TLTLSKADYE KHKVYACEVT HQGLSSPVTK SFNRGEC (SEQ ID NO: 190) |
| ALXN Anti-P-Anti-Alb w/ IgG4 Camelid Anti-P VHH Linker IgG4 Fc-CH2/CH3 Only | EVQLVESGGG LVQPGGSLRL SCAASGRISS IIHMAWVRQA PGKQRELVSE ISRVGTTVYA DSVKGRFTIS RDNSKNTLYL QMNSLRAEDT AVYYCNALQY EKHGGADYWG QGTLVTVSSG GGGSGGGGSG GGGSAESKYG PPCPPCPAPE AAGGPSVFLF PPKPKDTLMI SRTPEVTCVV VDVSQEDPEV QFNWYVDGVE VHNAKTKPRE EQFNSTYRVV SVLTVLHQDW LNGKEYKCKV SNKGLPSSIE KTISKAKGQP REPQVYTLPP SQEEMTKNQV SLTCLVKGFY PSDIAVEWES NGQPENNYKT TPPVLDSDGS FFLYSRLTVD KSRWQEGNVF SCSVMHEALH NHYTQKSLSL SLG (SEQ ID NO: 191) |
| Anti-Alb Linker IgG4 Fc-CH2/CH3 Only | EVQLVESGGG LVKPGGSLRL SCAASGRPVS NYAAAWFRQA PGKEREFVSA INWQKTATYA DSVKGRFTIS RDNAKNSLYL QMNSLRAEDT AVYYCAAVFR VVAPKTQYDY DWGQGTLVT VSSGGGGSGG GGSGGGGSAE SKYGPPCPPC |

TABLE 11-continued

| Full Chain SEO ID NQs |
| --- |

|  |  |
| --- | --- |
|  | PAPEAAGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLG (SEQ ID NO: 192) |
| Anti-TNF-NMT16 fAb w/ YTE Fc NMT16 Fv-VH IgG1Fc-Full CH | EVQLVQSGAE VKKPGASVKV SCKASGYIFT NYPIHWVRQA PGQGLEWMGF IDPGGGYDEP DERFRDRVTM TADTSTSTAY MELSSLRSED TAVYYCARRG GGYYLDYWGQ GTTVTVSSAS TKEVQLVQSG AEVKKPGASV KVSCKASGYI FTNYPIHWVR QAPGQGLEWM GFIDPGGGYD EPDERFRDRV TMTADTSTST AYMELSSLRS EDTAVYYCAR RGGGYYLDYW GQGTTVTVSS ASTK (SEQ ID NO: 193) |
| NMT16 Fv-VL Fc-CL | DIQMTQSPSS LSASVGDRVT ITCRASQDIS FFLNWYQQKP GKAPKLLIYY TSRYHSGVPS RFSGSGSGTD FTLTISSLQP EDFATYYCQH GNTLPWTFGQ GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC (SEQ ID NO: 194) |
| Anti-TNF Fv-VH IgG1 Fc-Full CH | EVQLVESGGG LVQPGRSLRL SCAASGFTFD DYAMHWVRQA PGKGLEWVSA ITWNSGHIDY ADSVEGRFTI SRDNAKNSLY LQMNSLRAED TAVYYCAKVS YLSTASSLDY WGQGTLVTVS SASTKGPSVF PLAPSSKSTS GGTAALGCLV KDYFPEPVTV SWNSGALTSG VHTFPAVLQS SGLYSLSSVV TVPSSSLGTQ TYICNVNHKP SNTKVDKKVE PKSCDKTHTC PPCPAPELLG GPSVFLFPPK PKDTLYITRE PEVTCVVVDV SHEDPEVKFN WYVDGVEVHN AKTKPREEQY NSTYRVVSVL TVLHQDWLNG KEYKCKVSNK ALPAPIEKTI SKAKGQPREP QVYTLPPSRD ELTKNQVSLT CLVKGFYPSD IAVEWESNGQ PENNYKTTPP VLDSDGSFFL YSKLTVDKSR WQQGNVFSCS VMHEALHNHY TQKSLSLSPG K (SEQ ID NO: 195) |
| Anti-TNF Fv-VL Fc-CL | DIQMTQSPSS LSASVGDRVT ITCRASQGIR NYLAWYQQKP GKAPKLLIYA ASTLQSGVPS RFSGSGSGTD FTLTISSLQP EDVATYYCQR YNRAPYTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC (SEQ ID NO: 196) |
| Anti-VEGF-NMT16 fAb w/ Fc NMT16 Fv-VH IgG1 YTE Fc-Full CH | EVQLVQSGAE VKKPGASVKV SCKASGYIFT NYPIHWVRQA PGQGLEWMGF IDPGGGYDEP DERFRDRVTM TADTSTSTAY MELSSLRSED TAVYYCARRG GGYYLDYWGQ GTTVTVSSAS TKEVQLVQSG AEVKKPGASV KVSCKASGYI FTNYPIHWVR QAPGQGLEWM GFIDPGGGYD EPDERFRDRV TMTADTSTST AYMELSSLRS EDTAVYYCAR RGGGYYLDYW GQGTTVTVSS ASTK (SEQ ID NO: 197) |
| NMT16 Fv-VL Fc-CL | DIQMTQSPSS LSASVGDRVT ITCRASQDIS FFLNWYQQKP GKAPKLLIYY TSRYHSGVPS RFSGSGSGTD FTLTISSLQP EDFATYYCQH GNTLPWTFGQ GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC (SEQ ID NO: 198) |
| Anti-VEGF Fv-VH IgG1 Fc-Full CH | EVQLVESGGG LVQPGGSLRL SCAASGYTFT NYGMNWVRQA PGKGLEWVGW INTYTGEPTY AADFKRRFTF SLDTSKSTAY LQMNSLRAED TAVYYCAKYP HYYGSSHWYF DVWGQGTLVT VSSASTKGPS VFPLAPSSKS TSGGTAALGC LVKDYFPEPV TVSWNSGALT SGVHTFPAVL QSSGLYSLSS VVTVPSSSLG TQTYICNVNH KPSNTKVDKK VEPKSCDKTH TCPPCPAPEL LGGPSVFLFP PKPKDTLYIT REPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS RDELTKNQVS |

TABLE 11-continued

| Full Chain SEQ ID NQs | |
|---|---|
| | LTCLVKGFYP SDIAVEWESN GQPENNYKTT PPVLDSDGSF FLYSKLTVDK SRWQQGNVFS CSVMHEALHN HYTQKSLSLS PGK (SEQ ID NO: 199) |
| Anti-VEGF Fv-VL Fc-CL | DIQMTQSPSS LSASVGDRVT ITCSASQDIS NYLNWYQQKP GKAPKVLIYF TSSLHSGVPS RFSGSGSGTD FTLTISSLQP EDFATYYCQQ YSTVPWTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC (SEQ ID NO: 200) |

Example 8

NMT15-NMT22 Binding Potency and Functional Assays
Binding Affinity to Properdin

Polystyrene microtiter plates were coated with human (2.0 µg/50 µl per well) properdin in phosphate buffered saline (PBS) overnight at 4° C. After aspirating the properdin solution, the wells were blocked with PBS containing 1% bovine serum albumin (BSA) (Sigma-Aldrich, St. Louis, Mo.) for 2 hours at room temperature. Wells without peptide or properdin coating served as background controls. Aliquots of the test antibody in blocking solution were added to the properdin coated wells and allowed to incubate for 1 hour to allow binding to occur. Following a 1 hour incubation at room temperature, the plate was rinsed with PBS five times and incubated with 1:2000 diluted anti-properdin polyclonal antibody.

Figure 20:
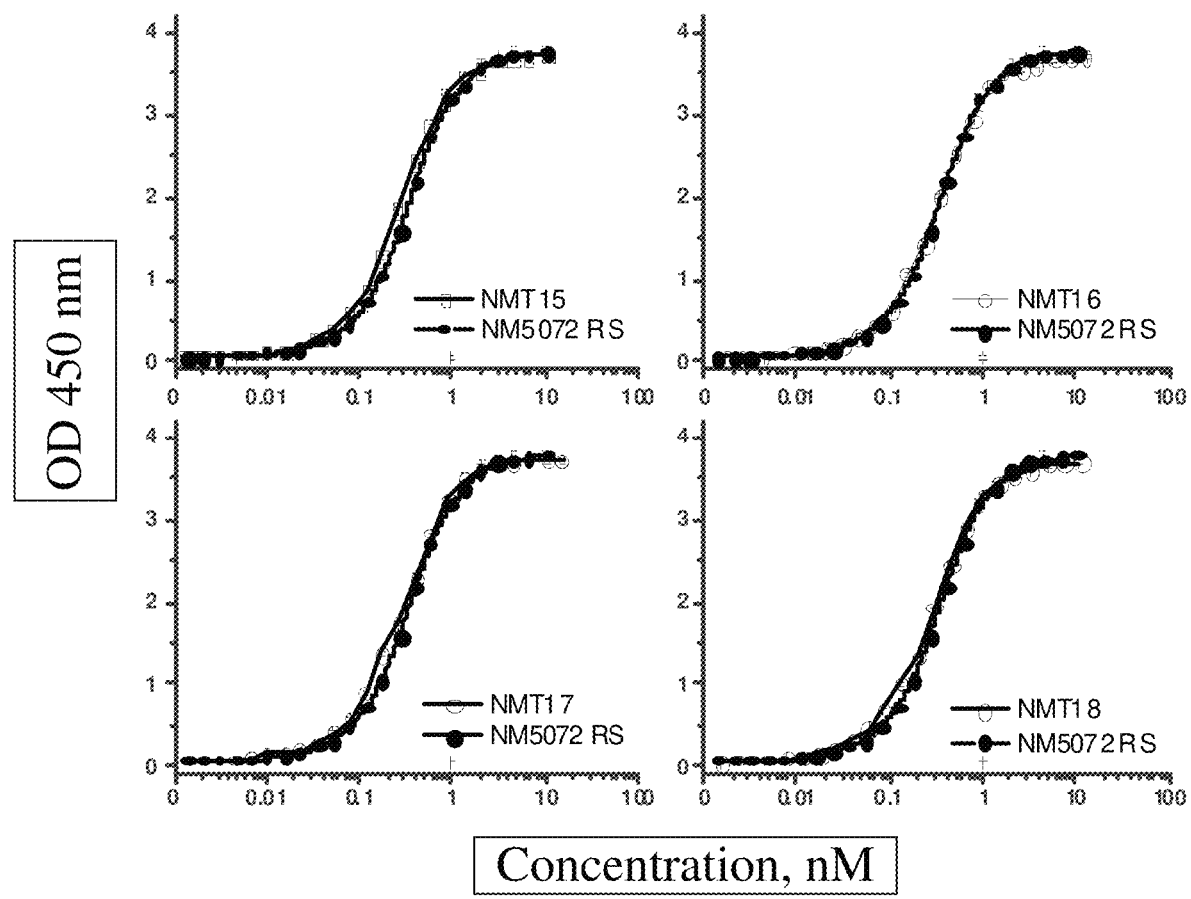
FIG. 20 illustrates plots showing binding affinity of NMT15, NMT16, NMT17, and NMT18 to properdin.

As shown in FIG. 20, NMT15, NMT16, NMT17, and NMT18 bind to properdin with high affinity. The affinity values of NMT15, NMT16, NMT17, and NMT18 were similar to NMT5072.

Figure 21:
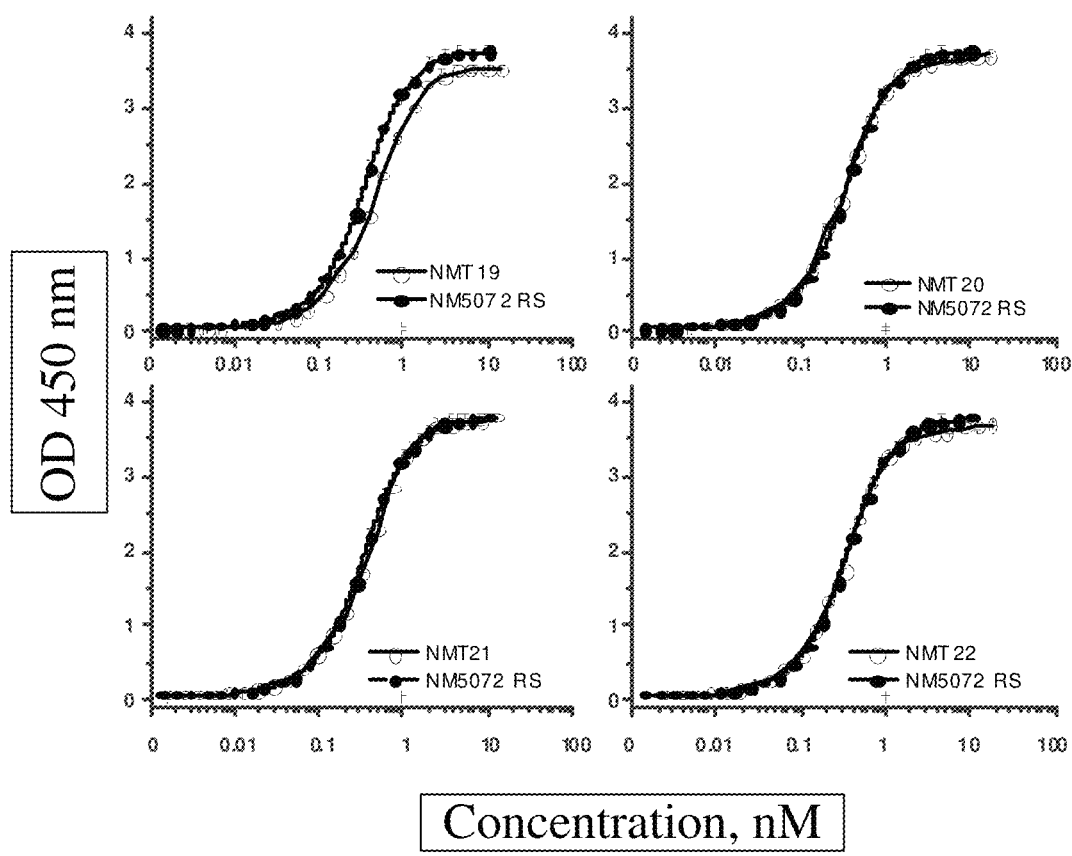
FIG. 21 illustrates plots showing binding affinity of NMT19, NMT20, NMT21, and NMT22 to properdin.

As shown in FIG. 21, NMT19, NMT20, NMT21, and NMT22 bind to properdin with high affinity. The affinity values of NMT19, NMT20, NMT21, and NMT22 were similar to NMT5072.

Inhibition of AP Hemolysis

This cellular assay is based on the formation of terminal complement complex on the surface of the rRBC. As a result, the rRBC are lysed. The evidence of lysed cells is reflected in progressive decrease in light scatter at 700 nm. rRBC are incubated in normal human serum in AP buffer. The surface of rRBC triggers the activation of AP in normal human serum. AP cascade begins and leads to the formation of C5b-9 complex on the surface of the rRBC. Agents that inhibit the activation are expected to inhibit cellular lysis.

To evaluate the effect of the test antibody on AP activation, various concentrations of the test antibody in AP buffer were incubated with normal human serum (10% NHS) at 37° C. with a fixed number of rabbit erythrocytes (Covance) in a temperature controlled ELISA plate reader capable of reading at 700 nm A progressive decrease in light scatter (due to lysis of intact cells) was measured at 700 nm as a function of time. The data were recorded and analyzed with a SpectraMax 190 plate reader and SoftMax Pro software. For calculation total inhibition was calculated at each concentration of the antibody and the results were expressed as a % of unlysed controls. Data at each concentration was plotted in a sigmoidal plot with MicroCal Origin Software.

Figure 22:
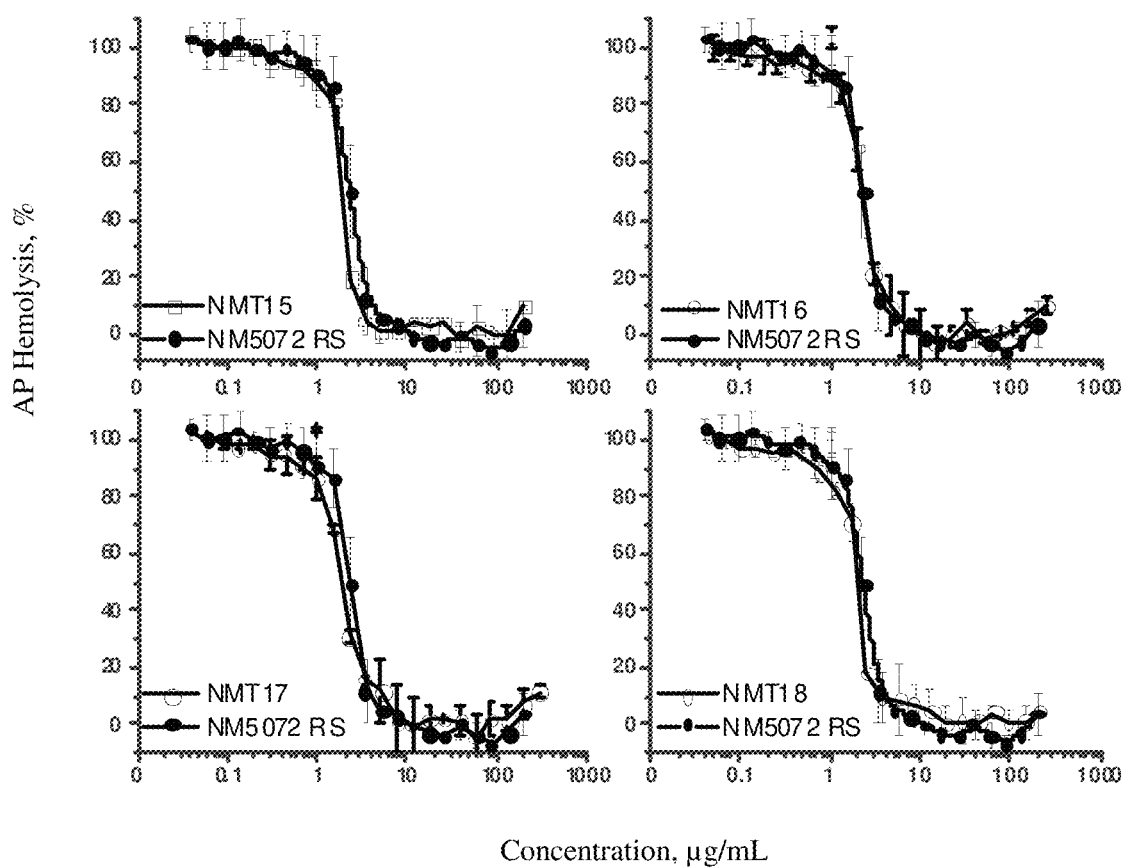
FIG. 22 illustrates plots showing inhibition of AP Hemolysis by NMT15, NMT16, NMT17, and NMT18.

FIG. 22 demonstrates the potent activity of NMT15, NMT16, NMT17, and NMT18 in inhibiting erythrocyte lysis. NMT15, NMT16, NMT17, and NMT18 were able to inhibit lysis at a similar concentration as NM5072.

Figure 23:
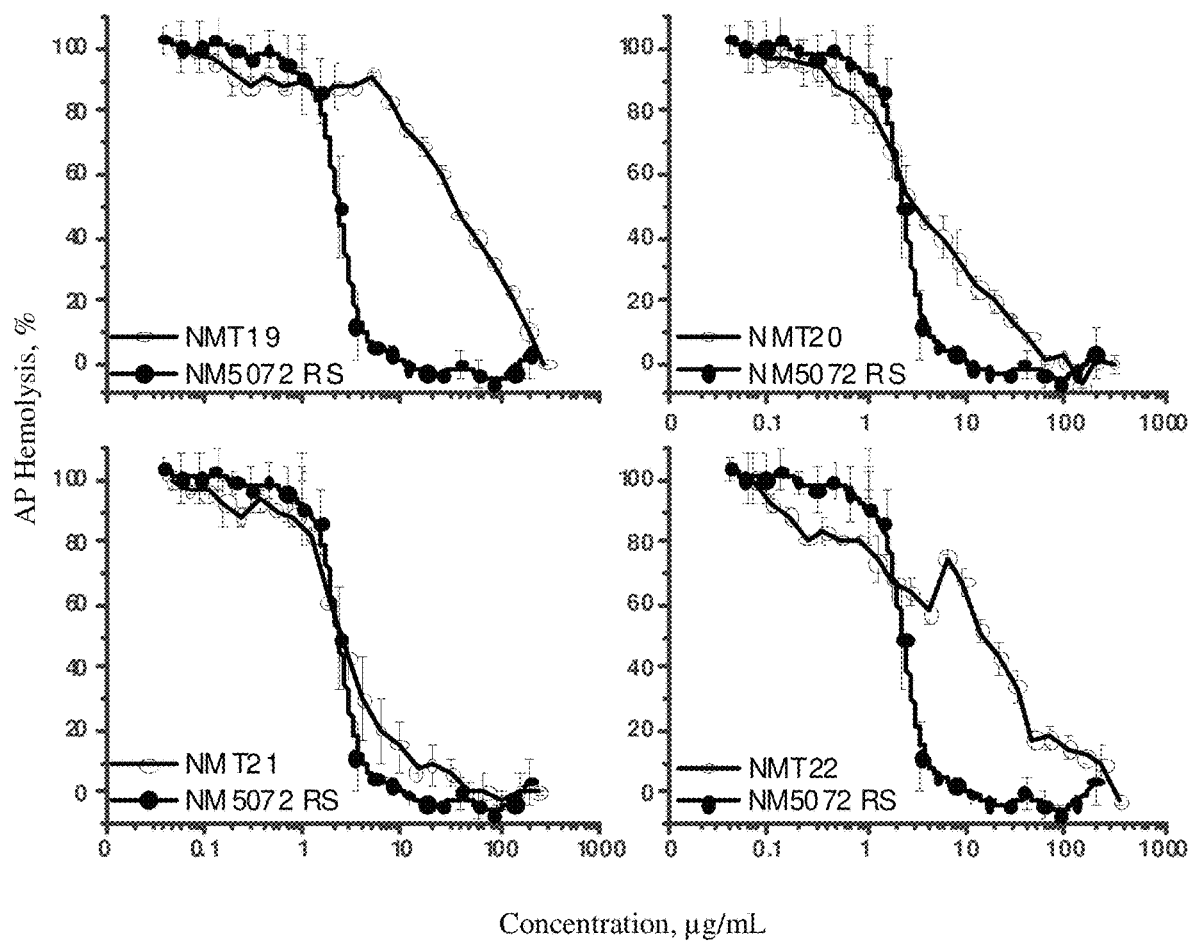
FIG. 23. Illustrates plots showing inhibition of AP Hemolysis by NMT19, NMT20, NMT21, and NMT22.

FIG. 23 demonstrates the potent activity of NMT19, NMT20, NMT21, and NMT22 in inhibiting erythrocyte lysis. NMT21 was able to inhibit lysis at a similar concentration as NM5072.

Inhibition of MAC Formation

C5b-9 Formation Assay: Microtiter wells were coated with LPS (2 µg/50 upper well) in PBS overnight at 4° C. Uncoated wells served as background controls. After aspirating the LPS solution, wells were treated with 1% BSA in phosphate buffered saline, pH 7.4 (PBS) for 2-hours. Following a 2 hour incubation, wells were rinsed with PBS and incubated with various concentrations of the antibody in AP buffer containing 10% Normal Human Serum (NHS). Following a 2-hour incubation at 37° C. to allow AP activation to occur, deposited MAC(C5b-9) was detected with 1:2000 diluted mouse anti-human soluble neo-05b-9 monoclonal antibody. All dilutions of the antibody were made in blocking solution and all antibody incubations were done for 1 hour at room temperature. The primary antibody was detected with goat anti mouse monoclonal. Following each incubation the plate was rinsed five times with PBS. The plate was developed with TMB and the blue color reaction was quenched with 1M phosphoric acid.

Figure 24:
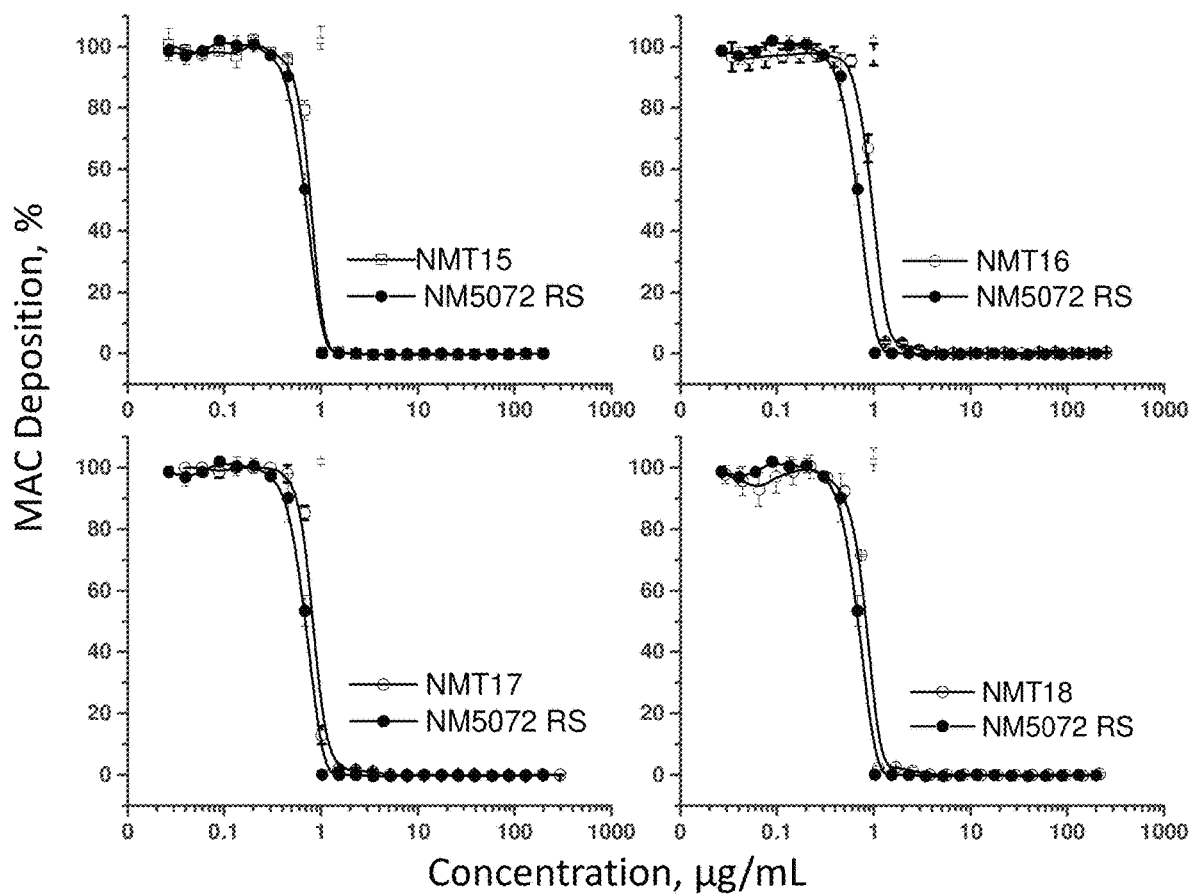
FIG. 24 illustrates plots showing inhibition of MAC Formation by NMT15, NMT16, NMT17, and NMT18.

FIG. 24 illustrates plots showing inhibition of MAC Formation by NMT15, NMT16, NMT17, and NMT18. NMT15, NMT16, NMT17, and NMT18 were able to inhibit MAC formation and deposition at a similar concentration as NM5072.

Figure 25:
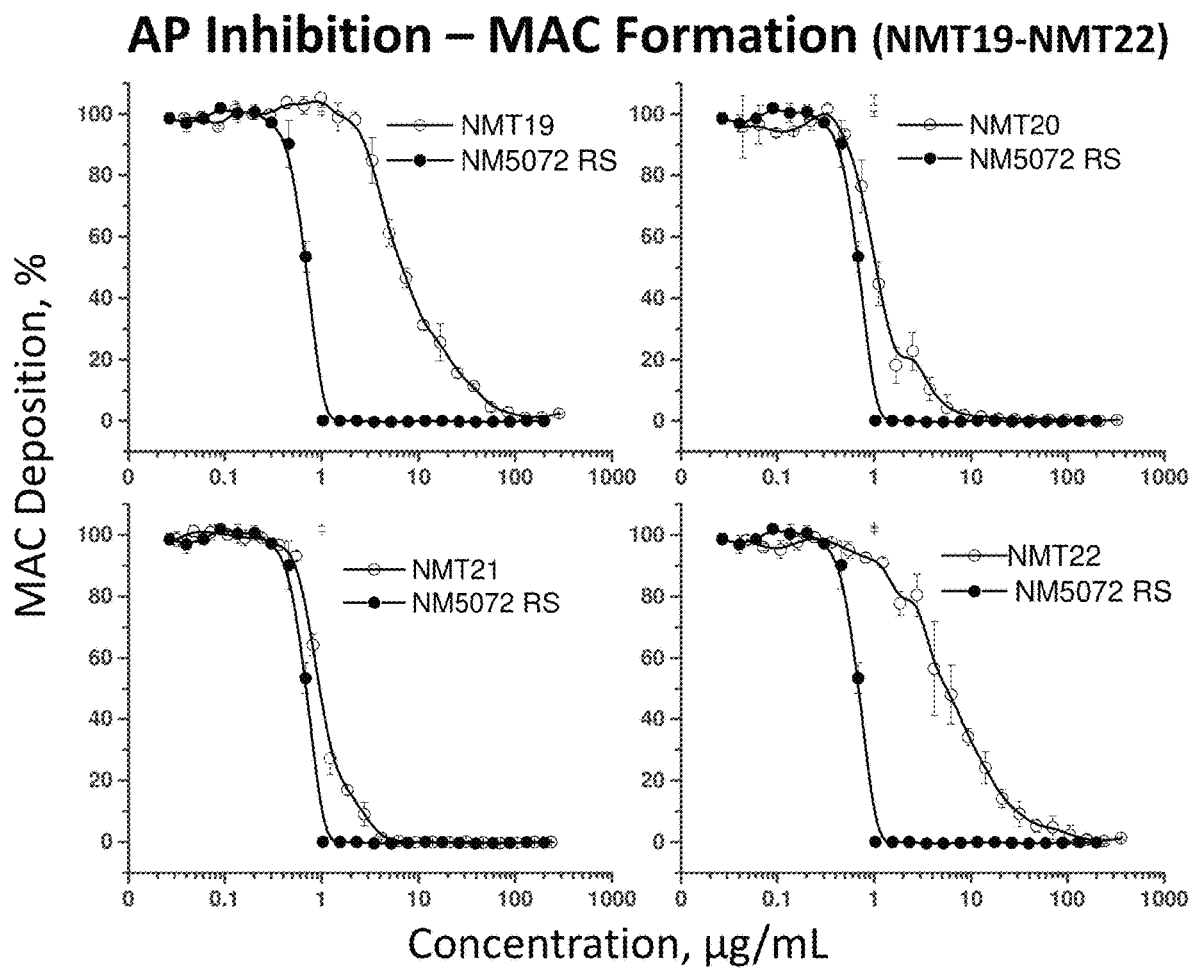
FIG. 25 illustrates plots showing inhibition of MAC Formation by NMT19, NMT20, NMT21, and NMT22.

FIG. 25 illustrates plots showing inhibition of MAC Formation by NMT19, NMT20, NMT21, and NMT22. NMT20 and NMT21 were able to MAC formation and deposition at a similar concentration as NM5072.

Inhibition of Properdin-C3b Binding

AP activation generates C3a and C3b as a result of C3 cleavage by the C3 convertase of the alternative complement pathway. Alternative complement pathway is activated in normal human serum by lip polysaccharide from Salmonella Typhosa under conditions that allow the activation of the alternative complement pathway. We have utilized this assay to demonstrate whether anti-properdin antibody of this invention would inhibit the formation and deposition of C3b. Deposition of C3b initiates the start of the alternative complement pathway. As a way of mechanism, activated and deposited C3b provides high affinity binding to properdin. Properdin-C3b complexes bind factor B and the complex is cleaved by factor D to generate PC3bBb, an alternative pathway C3 convertase. As the alternative pathway proceeds, C5b-9 complexes are formed and deposited.

The formation and deposition of C3b is inhibited. Because C3b formation and deposition is inhibited, the deposition of other components, such as properdin, is also inhibited.

In a typical assay, polystyrene microtiter plate wells were coated with LPS (Lip polysaccharide from Salmonella Typhosa) at 2 µg/50 µl in PBS overnight. The wells were incubated with BSA in PBS to block the unoccupied sites in the wells. Following a 2-hour blocking at room temperature and rinsing with PBS, normal human serum (10%) in AP buffer was mixed with varying concentrations of the anti-properdin antibody and derived fragments. The mixture was incubated onto LPS coated wells. The plate was incubated for 2 hours at 37° C. to allow complement AP activation to occur. Following incubation, the plates were extensively washed with PBS, and components of the C3 convertase were detected with the appropriate antibodies. We detected C3b with rabbit anti-human C3c at 1:2000 in blocking solution, properdin was detected with goat anti-human P, Bb was detected with goat anti-human factor Bb at 1:500 in blocking solution and C5b-9 was detected with HRPO-conjugated neo-anti-human C5b-9 at 1:2000 in blocking solution. Plates were incubated with their respective antibodies for 1-hour at room temperature. Following the incubation, the plates were rinsed with PBS and the bound antibodies were detected with peroxidase labeled goat anti-rabbit at 1:2000 for C3b and peroxidase labeled rabbit anti-goat at 1:2000 in blocking solution for P detection. All plates were developed with TMB following extensive washing with PBS. The blue color was quenched with 1 M orthophosphoric acid. The presence of C3b, P and Bb and MAC together are indicative of AP C3 convertase formation. The antibodies of the present invention are shown to inhibit C3b formation and therefore deposition. This data provides direct evidence that anti-properdin monoclonal antibodies prevent C3 convertase formation and thus AP activation.

Figure 26:
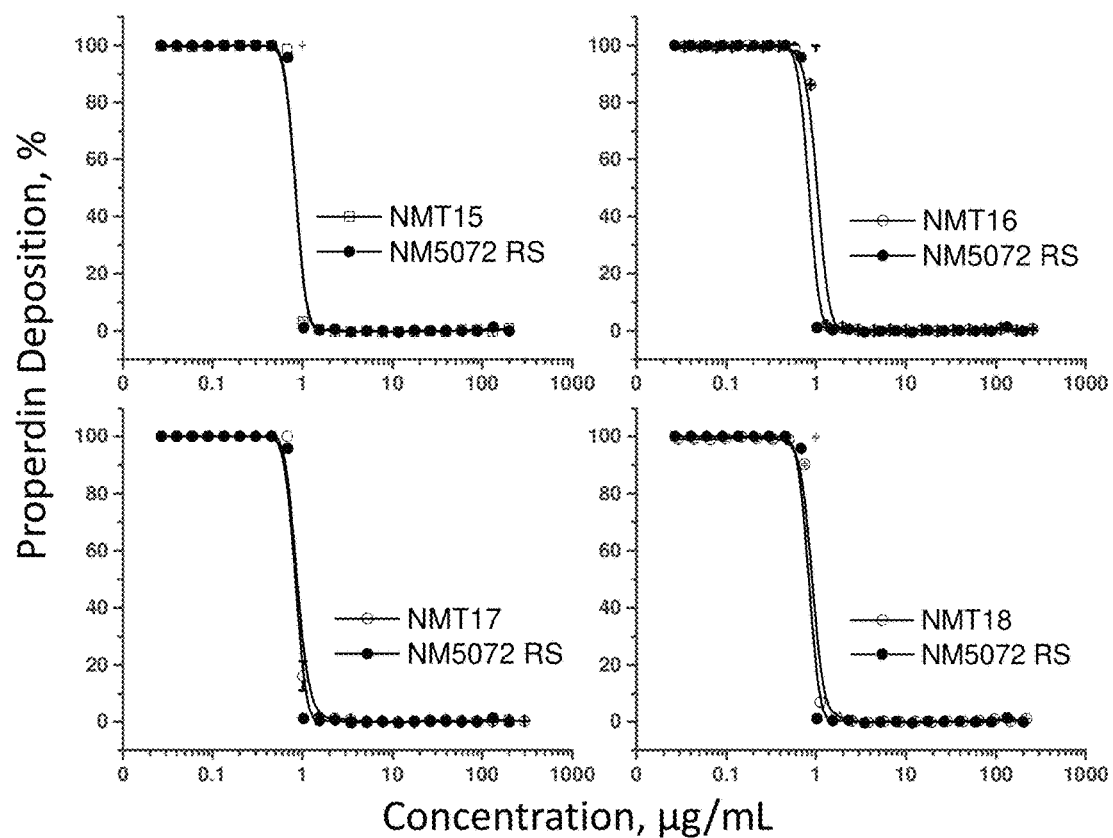
FIG. 26 illustrates plots showing inhibition of Properdin-C3b Binding by NMT15, NMT16, NMT17, and NMT18.

FIG. 26 illustrates plots showing inhibition of deposition of properdin by NMT15, NMT16, NMT17, and NMT18. NMT15, NMT16, NMT17, and NMT18 were able to inhibit properdin binding to C3b and deposition of properdin at a similar concentration as NM5072.

Figure 27:
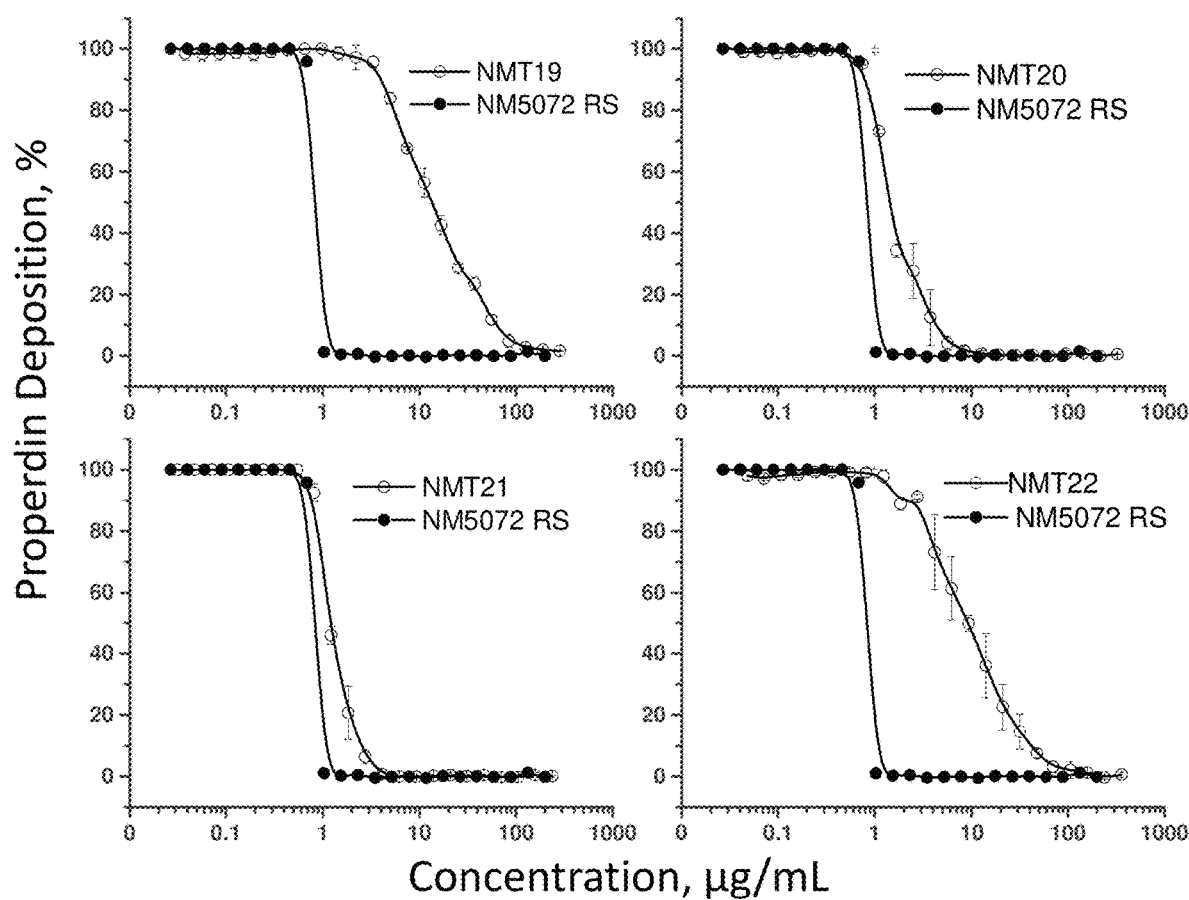
FIG. 27 illustrates plots showing inhibition of Properdin-C3b Binding by NMT19, NMT20, NMT21, and NMT22.

FIG. 27 illustrates plots showing inhibition of deposition of properdin by NMT15, NMT19, NMT20, NMT21, and NMT22. NMT20 and NMT21 were able to inhibit properdin binding to C3b and deposition of properdin at a similar concentration as NM5072.

Figure 28:
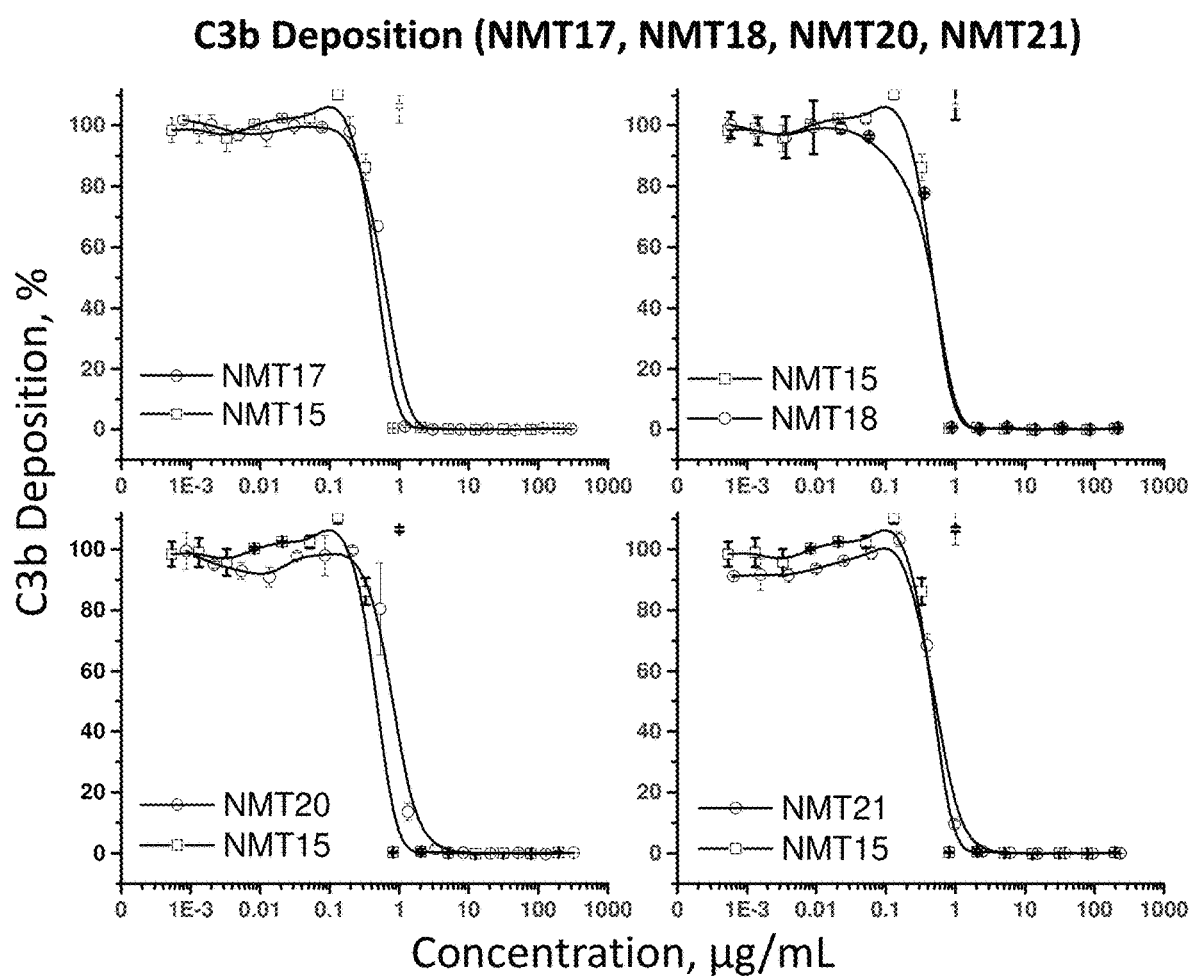
FIG. 28 illustrates plots showing inhibition of AP mediated C3b Formation and Deposition by NMT15, NMT17, NMT18, NMT20, and NMT21.

FIG. 28 illustrates plots showing inhibition of AP mediated C3b Formation and Deposition by NMT15, NMT17, NMT18, NMT20, and NMT21. NMT15, NMT17, NMT18, NMT20, and NMT21 were able to inhibit properdin binding to C3b and C3b deposition at a similar concentrations.

Inhibition of Classical Pathway Activation

To test the activity of the antibodies for CP inhibition, antibody-sensitized, sheep erythrocytes (sRBC) were incubated in 1% normal human serum in CP buffer ($Ca^{2+}/Mg^{2+}$). These sRBCs activate the CP, which induces lysis of cell membranes. Lysis of the cell membranes results in a gradual decrease in light scattered by cells. When an alternative pathway specific antibody of the present invention was incubated with sRBCs at 37° C. in 1% NHS with a buffer containing $Ca^{2+}$ and $Mg^{2+}$ ("the CP buffer") no effect on hemolysis was observed within the time period beginning with the start of hemolysis and concluding with maximal hemolysis. This implies that the antibodies not affect CP hemolytic activity in NHS and is not expected to compromise the CP's expected contribution to host defense against pathogens.

Antibodies described herein irrespective of the target antigen against which they have been raised, do not inhibit the classical pathway. In a typical assay, antibody sensitized sheep erythrocytes are incubated with Normal Human Serum, with CP buffer containing Ca2+. These conditions allow for selective activation of the classical pathway. Mechanistically, the antigen-Antibody complex on the surface of the sheep cells activates the classical complement pathway which causes erythrocyte lysis.

Figure 29:
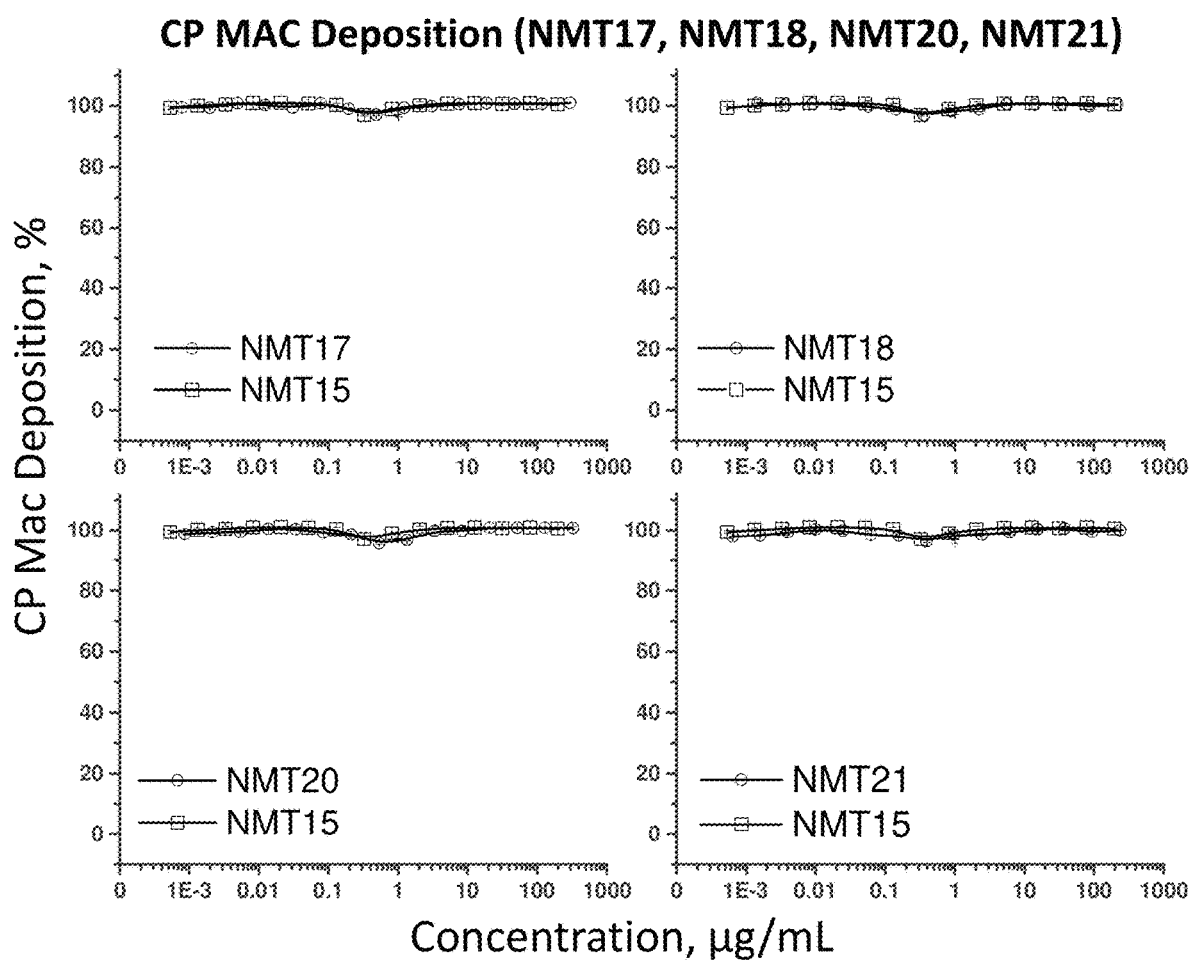
FIG. 29 illustrates plots showing CP mediated MAC Formation and Deposition by NMT15, NMT17, NMT18, NMT20, and NMT21.

FIG. 29 illustrates plots showing CP mediated MAC Formation and Deposition by NMT15, NMT17, NMT18, NMT20, and NMT21. NMT15, NMT17, NMT18, NMT20, and NMT21 did not inhibit CP mediated MAC formation and deposition.

Figure 30:
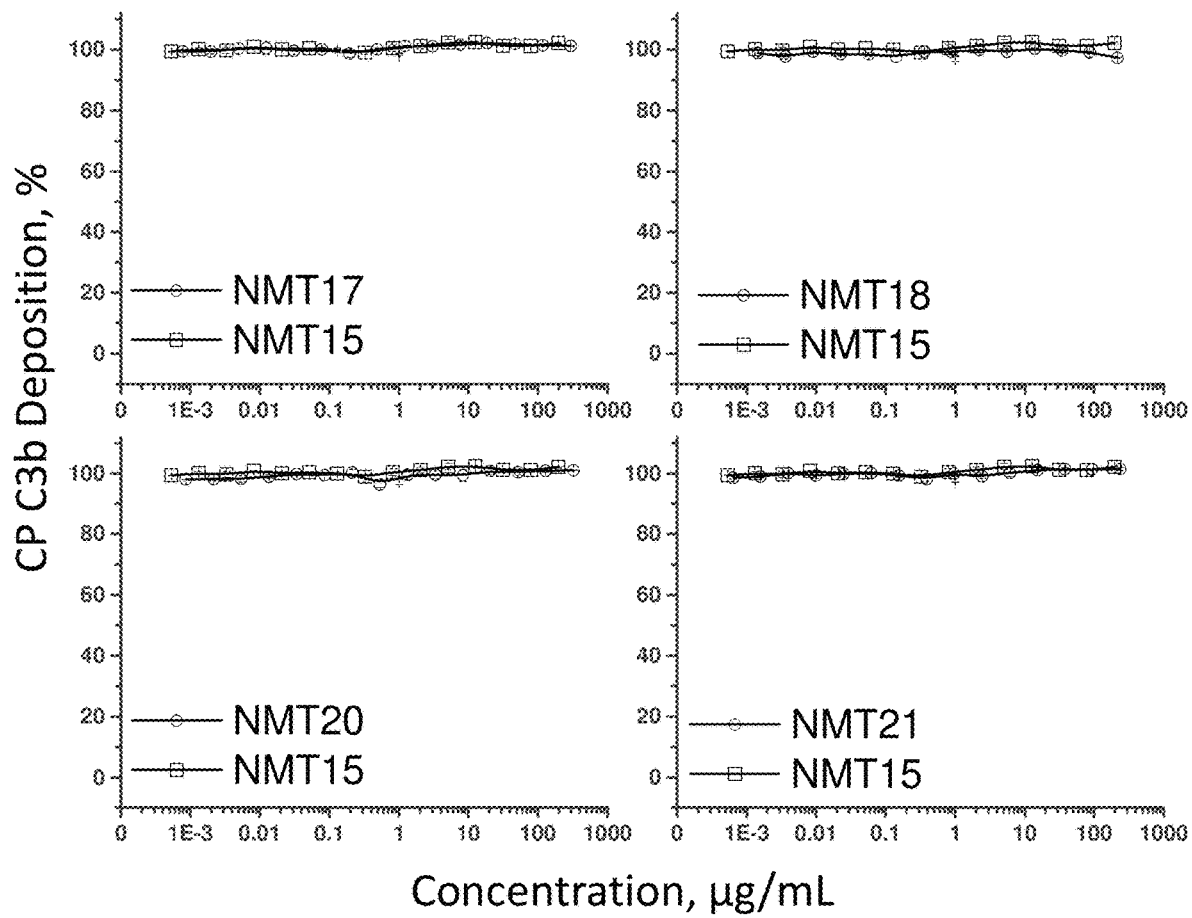
FIG. 30 illustrates plots showing CP mediated C3b Formation and Deposition by NMT15, NMT17, NMT18, NMT20, and NMT21.

FIG. 30 illustrates plots showing CP mediated C3b Formation and Deposition by NMT15, NMT17, NMT18, NMT20, and NMT21. NMT15, NMT17, NMT18, NMT20, and NMT21 did not inhibit CP mediated C3b Formation and Deposition.

Table 12 provides a summary of the binding potency and functional assays for NMT15-NMT22.

TABLE 12

| Variant | Binding Affinity (pM) | AP Hemolysis (µg/mL) | MAC (µg/Ml) | Properdin (µg/mL) |
|---|---|---|---|---|
| NMT#15 | 270 | 5 | 1 | 2 |
| NMT#16 | 315 | 13 | 3 | 4 |
| NMT#17 | 283 | 10 | 5 | 4 |
| NMT#18 | 289 | 20 | 9 | 3 |
| NMT#19 | 486 | — | — | — |
| NMT#20 | 297 | 65 | 25 | 30 |
| NMT#21 | 353 | 50 | 8 | 8 |
| NMT#22 | 335 | — | — | — |

Example 9

NMT23-NMT28 Binding Affinity and Functional Assays

Binding Affinity to Properdin

Figure 31:
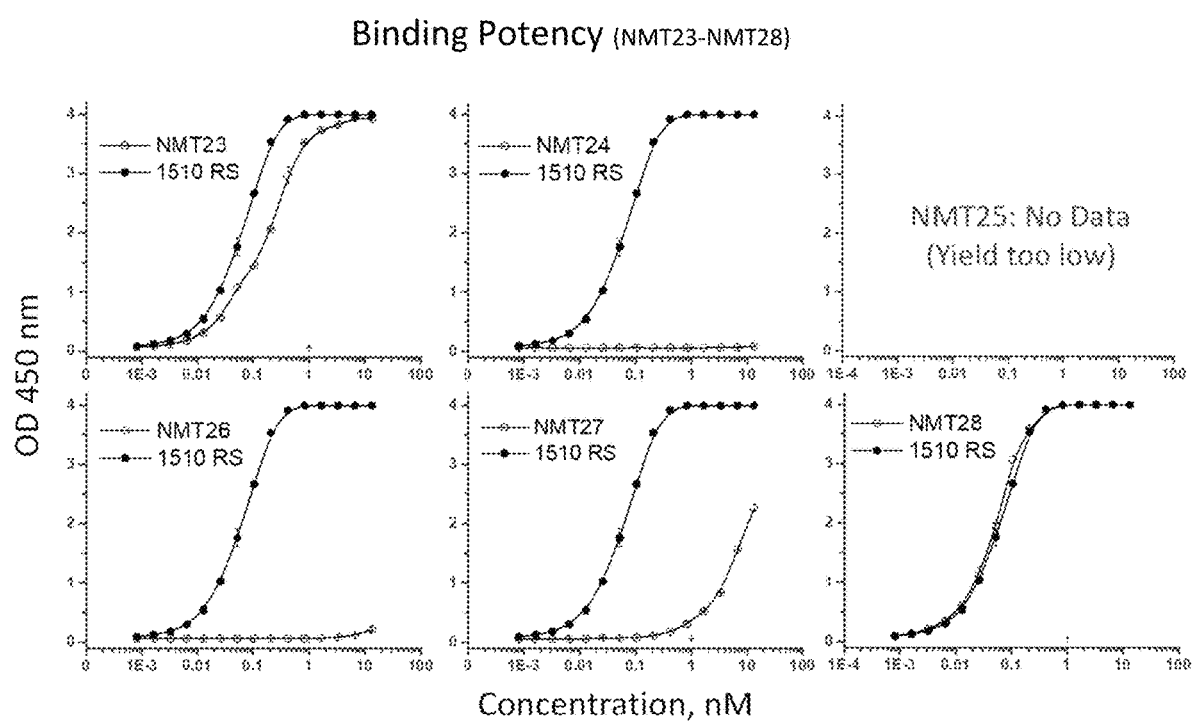
FIG. 31 illustrates plots showing binding affinity of NMT23, NMT24, NMT25, NMT26, NMT27, and NMT28 to properdin.

FIG. 31 illustrates plots showing binding Affinity of NMT23, NMT24, NMT25, NMT26, NMT27, and NMT28 to properdin. The properdin affinity values of NMT23 and NMT 28 were similar to NMT1510.

Inhibition of MAC Formation

Figure 32:
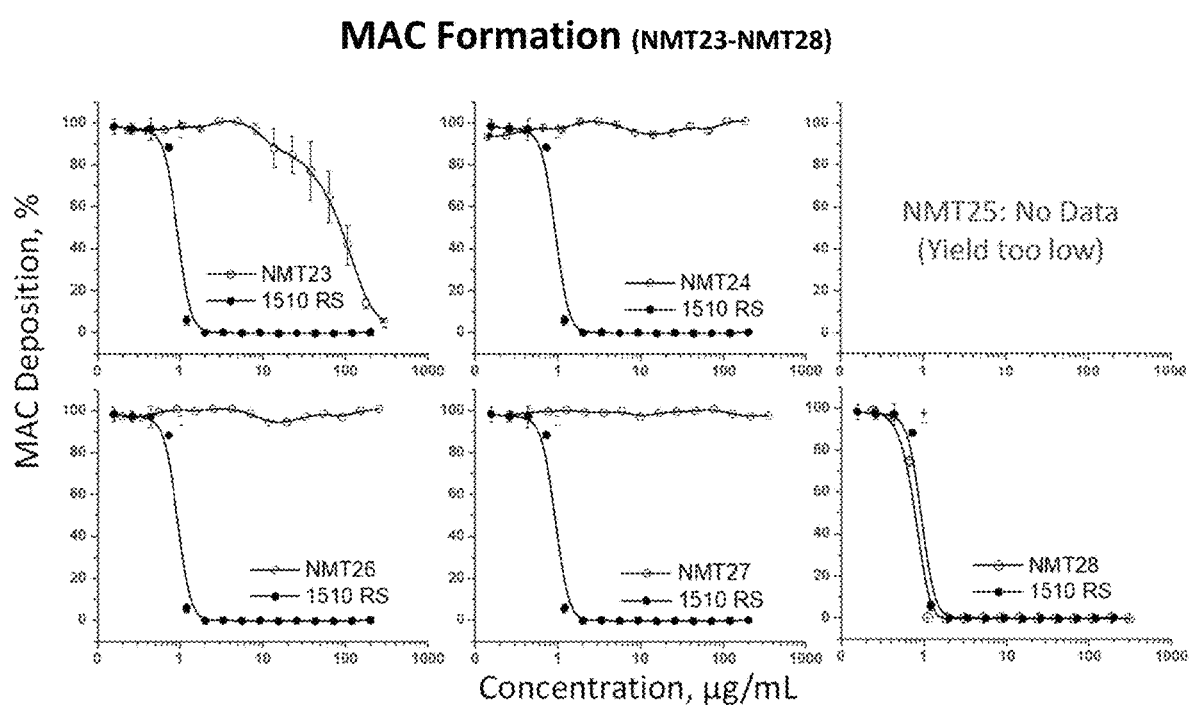
FIG. 32 illustrates plots showing inhibition of MAC Formation and Deposition by NMT23, NMT24, NMT25, NMT26, NMT27, and NMT28.

FIG. 32 illustrates plots showing inhibition of MAC Formation and Deposition by NMT23, NMT24, NMT25, NMT26, NMT27, and NMT28. NMT28 was able to inhibit MAC formation and deposition at a similar concentration as NMT1510.

Inhibition of AP Hemolysis

Figure 33:
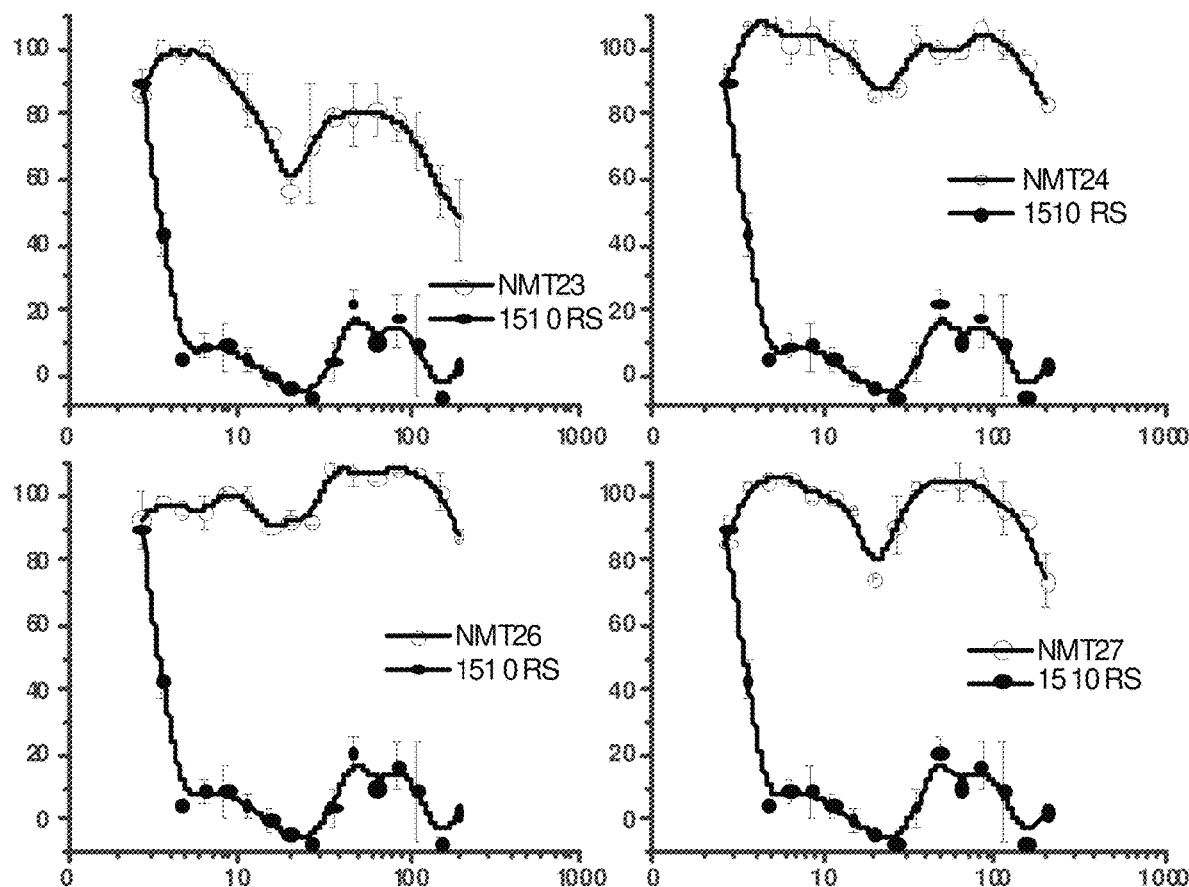
FIG. 33 illustrates plots showing inhibition of AP Hemolysis by NMT23, NMT24, NMT25, NMT26, and NMT27.

FIG. 33 illustrates plots showing inhibition of AP Hemolysis by NMT23, NMT24, NMT26, and NMT27. NMT15, NMT16, NMT17, and NMT28 were not able to inhibit lysis at a similar concentration as NMT1510.

Inhibition of Properdin-C3b Binding

FIG. 34 illustrates plots showing inhibition of AP mediated C3 convertase formation and Deposition of properdin and C3b by NMT28. NMT28 was able to inhibit properdin binding to C3b and deposition of properdin and C3b at a similar concentration as NMT1510.

Inhibition of Classical Pathway Activation

FIG. 35 illustrates plots showing CP mediated MAC Formation and Deposition by NMT28. NMT28 did not inhibit CP mediated MAC formation and deposition.

Table 13 provides a summary of the binding potency and functional assays for NMT23-NMT28.

TABLE 13

| Variants | Binding Affinity | AP Hemolysis (µg/mL) | MAC (µg/mL) |
|---|---|---|---|
| NMT#23 | 176 | — | — |
| NMT#24 | — | — | — |
| NMT#25 | — | — | — |
| NMT#26 | — | — | — |
| NMT#27 | — | — | — |
| NMT#28 | 53 | 8 | 3 |

Figure 36:
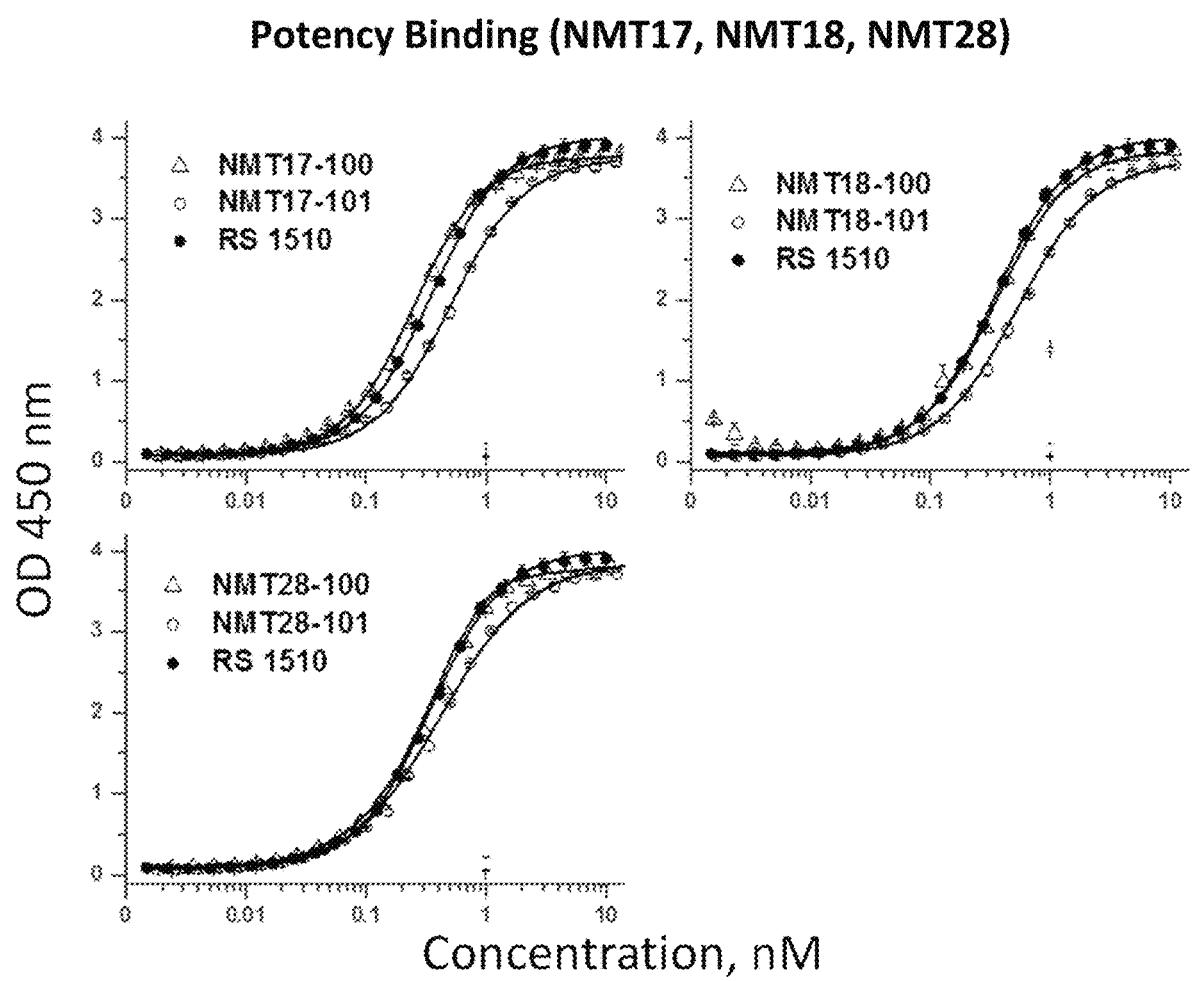
FIG. 36 illustrates plots showing binding affinity of NMT17-100, NMT17-101, NMT18-100, NMT18-101, NMT28-100, and NMT28-101 to Properdin.
Figure 37:
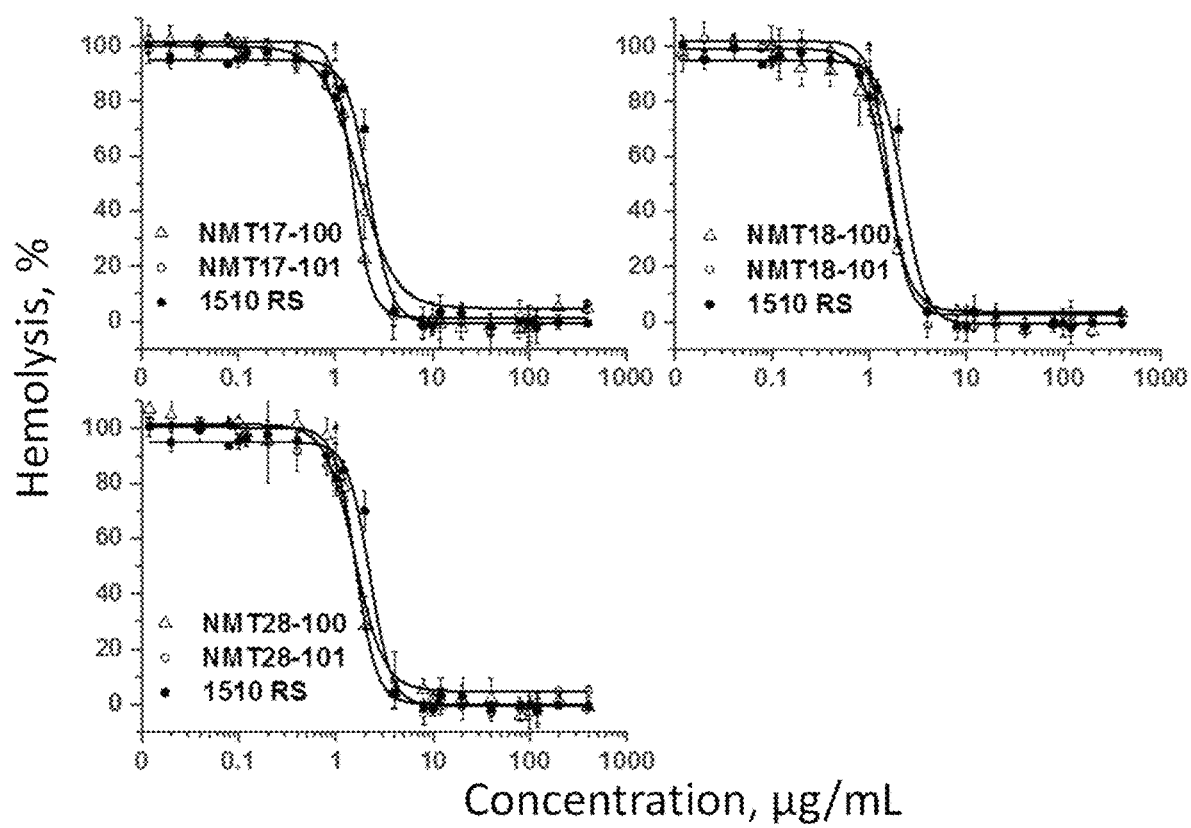
FIG. 37 illustrates plots showing inhibition of AP Hemolysis by NMT17-100, NMT17-101, NMT18-100, NMT18-101, NMT28-100, and NMT28-101.
Figure 38:
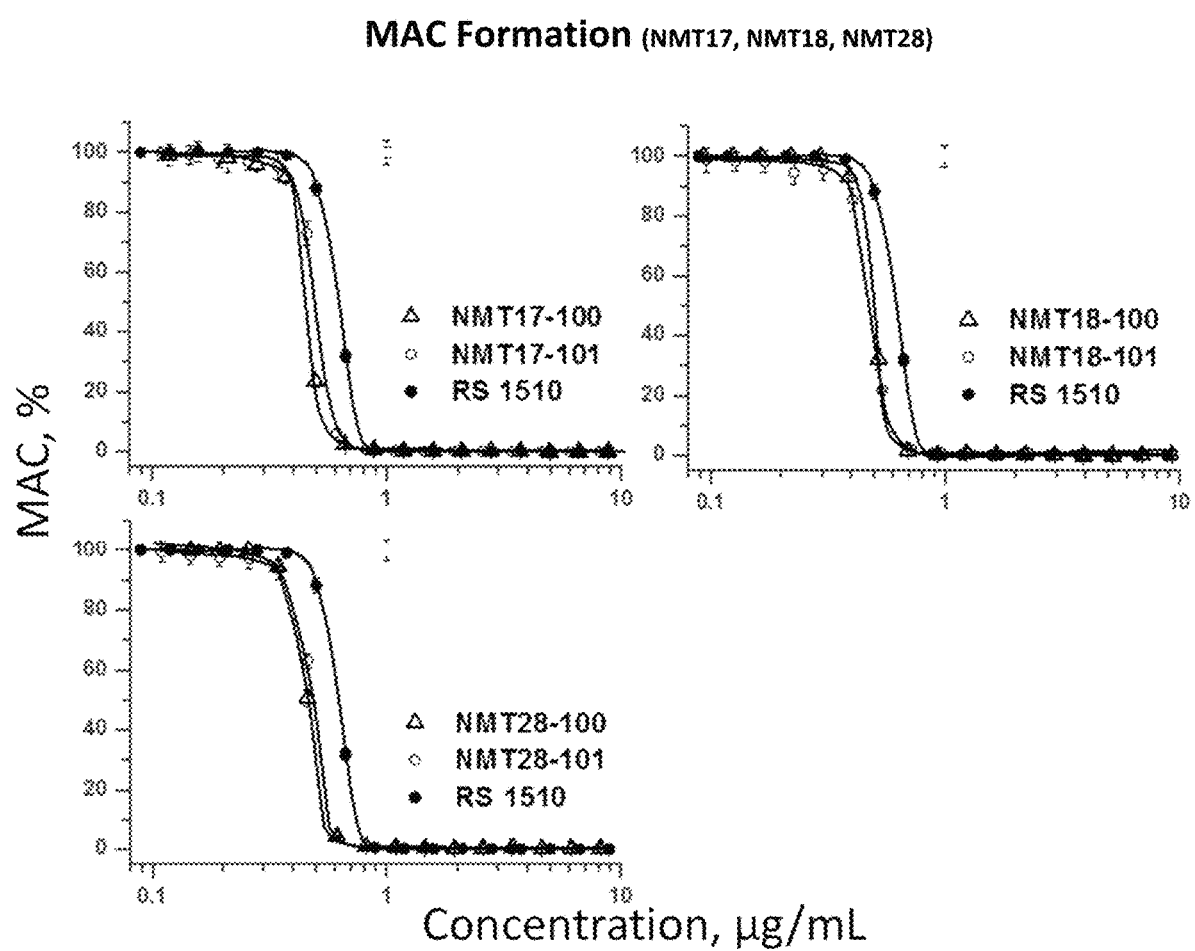
FIG. 38 illustrates plots showing inhibition of Mac Formation by NMT17-100, NMT17-101, NMT18-100, NMT18-101, NMT28-100, and NMT28-101.
Figure 39:
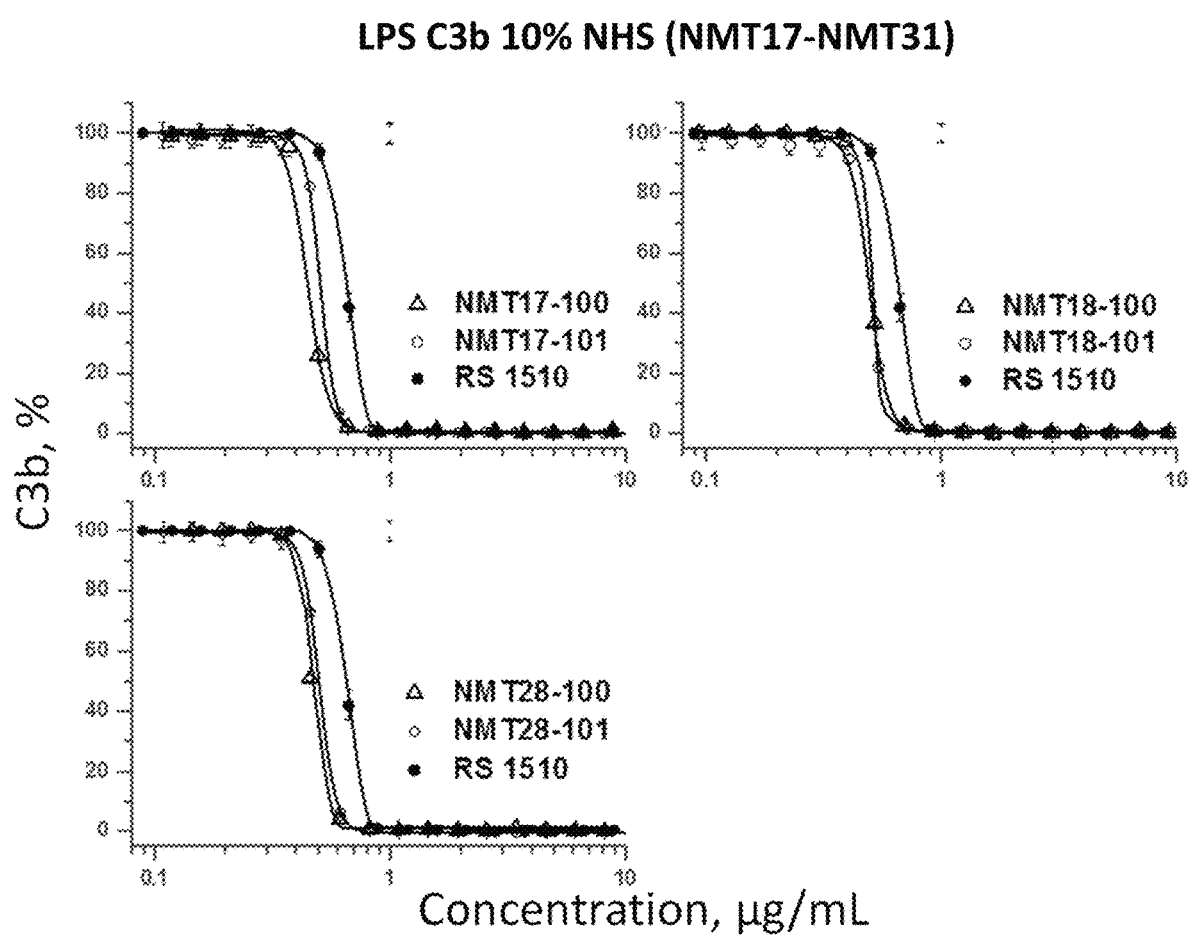
FIG. 39 illustrates plots showing inhibition of AP mediated C3b Formation and Deposition by NMT17-100, NMT17-101, NMT18-100, NMT18-101, NMT28-100, and NMT28-101.

NMT17, NMT18, NMT28 with Modified Fc Regions Binding Potency and Functional Assays
Binding Affinity to Properdin FIG. 36 illustrates plots showing binding Affinity of NMT17-100, NMT17-101, NMT18-100, NMT18-101, NMT28-100, and NMT28-101 to Properdin. Properdin binding affinity values of NMT17-100, NMT17-101, NMT18-100, NMT18-101, NMT28-100, and NMT28-101 were similar to NMT1510.
Inhibition of AP Hemolysis FIG. 37 illustrates plots showing inhibition of AP Hemolysis by NMT17-100, NMT17-101, NMT18-100, NMT18-101, NMT28-100, and NMT28-101. NMT17-100, NMT17-101, NMT18-100, NMT18-101, NMT28-100, and NMT28-101 were able to inhibit lysis at a similar concentration as NMT1510.
Inhibition of MAC Formation FIG. 38 illustrates plots showing inhibition of Mac Formation by NMT17-100, NMT17-101, NMT18-100, NMT18-101, NMT28-100, and NMT28-101. NMT17-100, NMT17-101, NMT18-100, NMT18-101, NMT28-100, and NMT28-101 were able to inhibit MAC formation and deposition at a similar concentration as NMT1510.
Inhibition of Properdin-C3b Binding FIG. 39 illustrates plots showing inhibition of AP mediated C3b Formation and Deposition by NMT17-100, NMT17-101, NMT18-100, NMT18-101, NMT28-100, and NMT28-101. NMT17-100, NMT17-101, NMT18-100, NMT18-101, NMT28-100, and NMT28-101 were able to inhibit properdin binding to C3b and deposition C3b at a similar concentration as NMT1510.

Table 14 provides a summary of the binding potency and functional assays for NMT17-100, NMT17-101, NMT18-100, NMT18-101, NMT28-100, and NMT28-101.

TABLE 14

| Construct | Affinity (pM) | AP Hemolysis (µg/mL) | MAC (µg/mL) | C3b (µg/mL) |
|---|---|---|---|---|
| NMT17-100 | 263 | 5 | 1 | 1 |
| NMT17-101 | 499 | 5 | 1 | 1 |
| NMT18-100 | 322 | 4 | 1 | 1 |
| NMT18-101 | 590 | 5 | 3 | 1 |
| NMT28-100 | 318 | 5 | 3 | 1 |
| NMT28-101 | 425 | 4 | 3 | 1 |

Example 10

Figure 40:
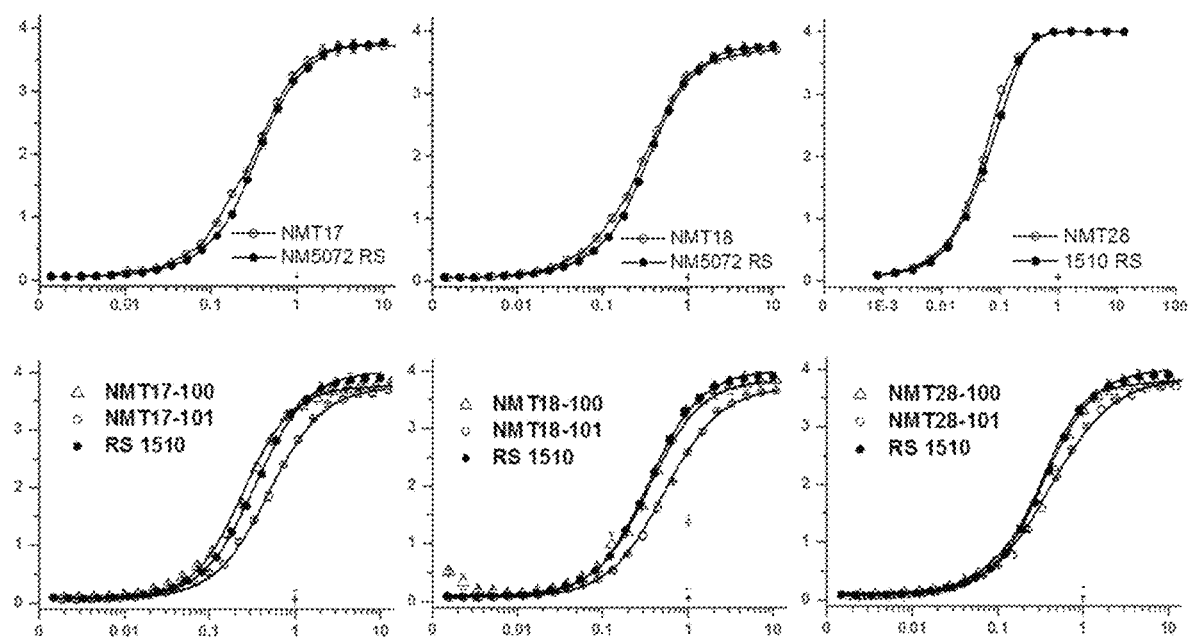
FIG. 40 illustrates plots showing binding Affinity Comparison of N297 and Xtend Fc regions—NMT17, NMT18, NMT28, NMT17-100, NMT17-101, NMT18-100, NMT18-101, NMT28-100, and NMT28-101 to Properdin.
Figure 41:
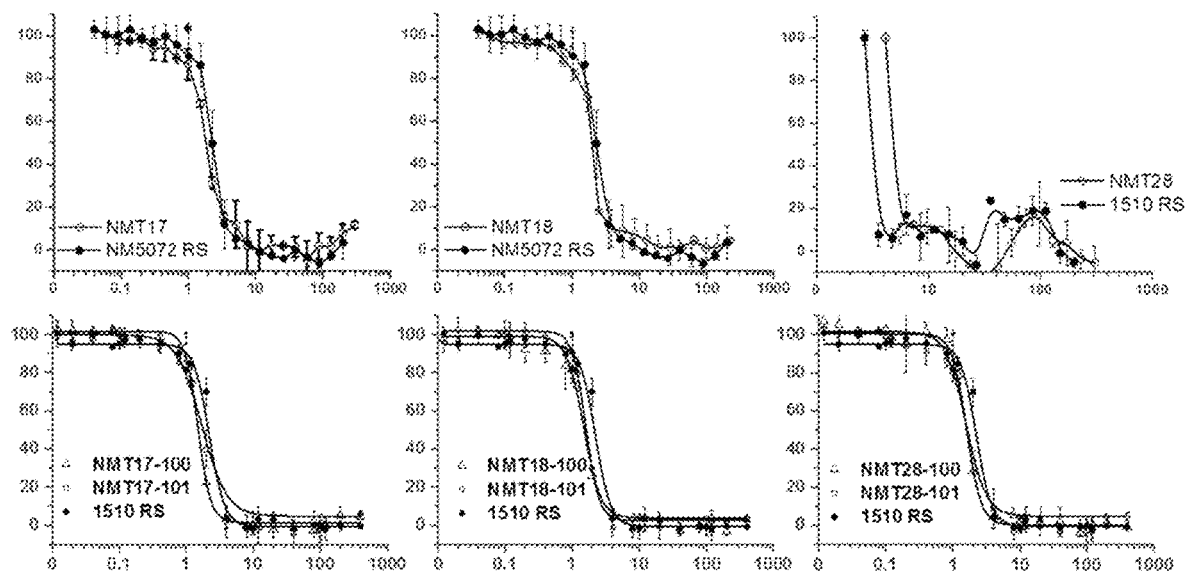
FIG. 41 illustrates plots showing binding Affinity Comparison of N297 and Xtend Fc regions—NMT17, NMT18, NMT28, NMT17-100, NMT17-101, NMT18-100, NMT18-101, NMT28-100, and NMT28-101 to Properdin.
Figure 42:
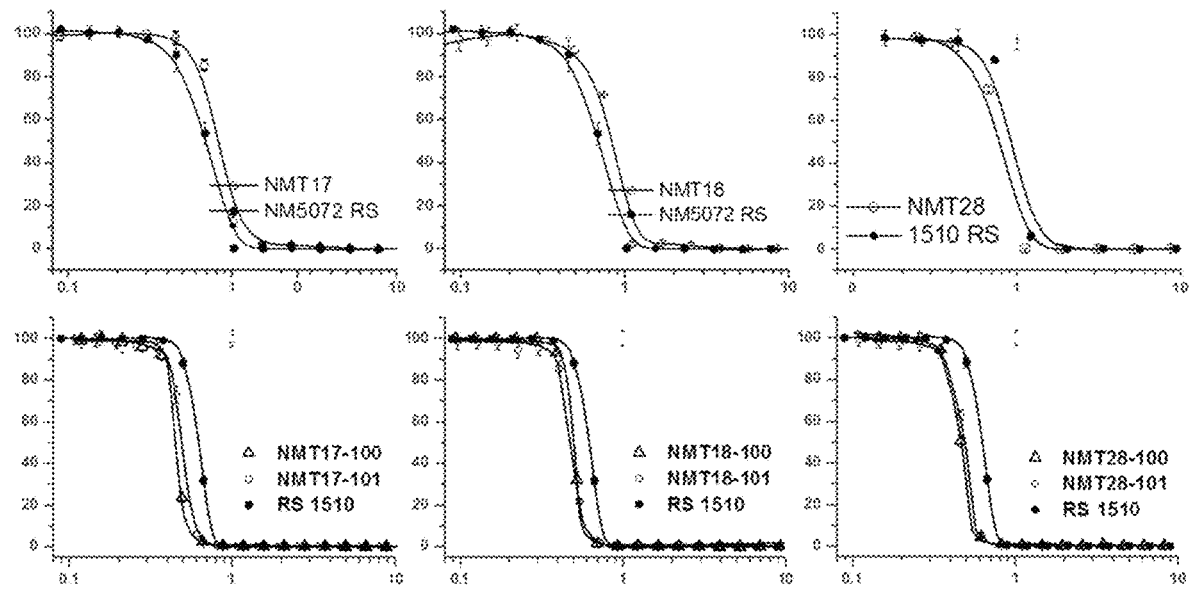
FIG. 42 illustrates plots showing inhibition of AP-Hemolysis Comparison of N297 and Xtend Fc regions—NMT17, NMT18, NMT28, NMT17-100, NMT17-101, NMT18-100, NMT18-101, NMT28-100, and NMT28-101.
Figure 43:
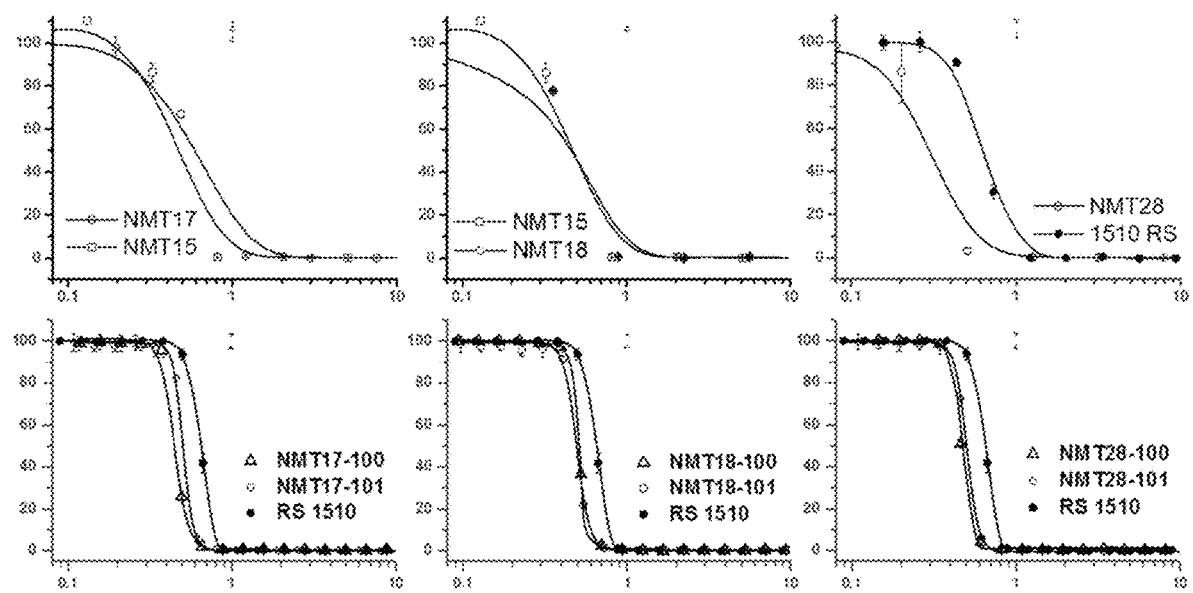
FIG. 43 illustrates plots showing inhibition of C3b Formation and Deposition—Comparison of N297 and Xtend Fc regions—NMT17, NMT18, NMT28, NMT17-100, NMT17-101, NMT18-100, NMT18-101, NMT28-100, and NMT28-101.

NMT17, NMT18, NMT28 with N297 and Xtend Fc Regions
Binding Potency and Functional Assays
Binding Affinity to Properdin FIG. 40 illustrates plots showing binding Affinity Comparison of N297 and Xtend Fc regions—NMT17, NMT18, NMT28, NMT17-100, NMT17-101, NMT18-100, NMT18-101, NMT28-100, and NMT28-101 to Properdin. Properdin binding affinity values of NMT17-100, NMT17-101, NMT18-100, NMT18-101, NMT28-100, and NMT28-101 were similar to NMT1510.
Inhibition of AP Hemolysis FIG. 41 illustrates plots showing inhibition of AP-Hemolysis Comparison of N297 and Xtend Fc regions—NMT17, NMT18, NMT28, NMT17-100, NMT17-101, NMT18-100, NMT18-101, NMT28-100, and NMT28-101. NMT17-100, NMT17-101, NMT18-100, NMT18-101, NMT28-100, and NMT28-101 were able to inhibit lysis at a similar concentration as NMT1510.
Inhibition of MAC Formation FIG. 42 illustrates plots showing inhibition of Mac Formation by Comparison of N297 and Xtend Fc regions—NMT17, NMT18, NMT28, NMT17-100, NMT17-101, NMT18-100, NMT18-101, NMT28-100, and NMT28-101. NMT17-100, NMT17-101, NMT18-100, NMT18-101, NMT28-100, and NMT28-101 were able to inhibit MAC formation and deposition at a similar concentration as NMT1510.
Inhibition of Properdin-C3b Binding FIG. 43 illustrates plots showing inhibition of C3b Formation and Deposition—Comparison of N297 and Xtend Fc regions—NMT17, NMT18, NMT28, NMT17-100, NMT17-101, NMT18-100, NMT18-101, NMT28-100, and NMT28-101. NMT17-100, NMT17-101, NMT18-100, NMT18-101, NMT28-100, and NMT28-101 were able to inhibit properdin binding to C3b and deposition C3b at a similar concentration as NMT1510.

Example 11

NMT29-NMT31 Binding Potency and Functional Assays
Binding Affinity to Properdin

Figure 44:
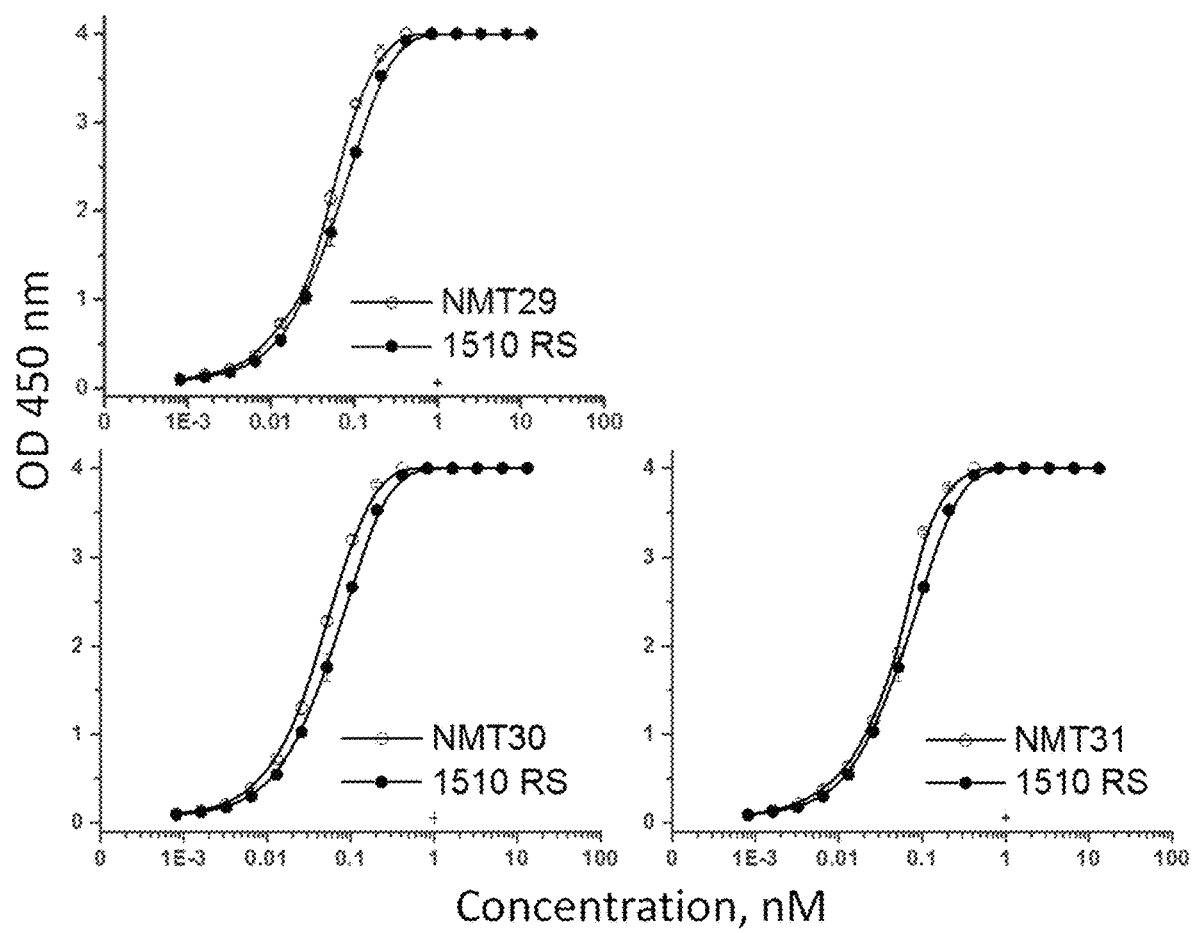
FIG. 44 illustrates plots showing binding Potency to Properdin—Comparison of N297 and Xtend Fc regions—NMT29, NMT30, NMT31.
Figure 45:
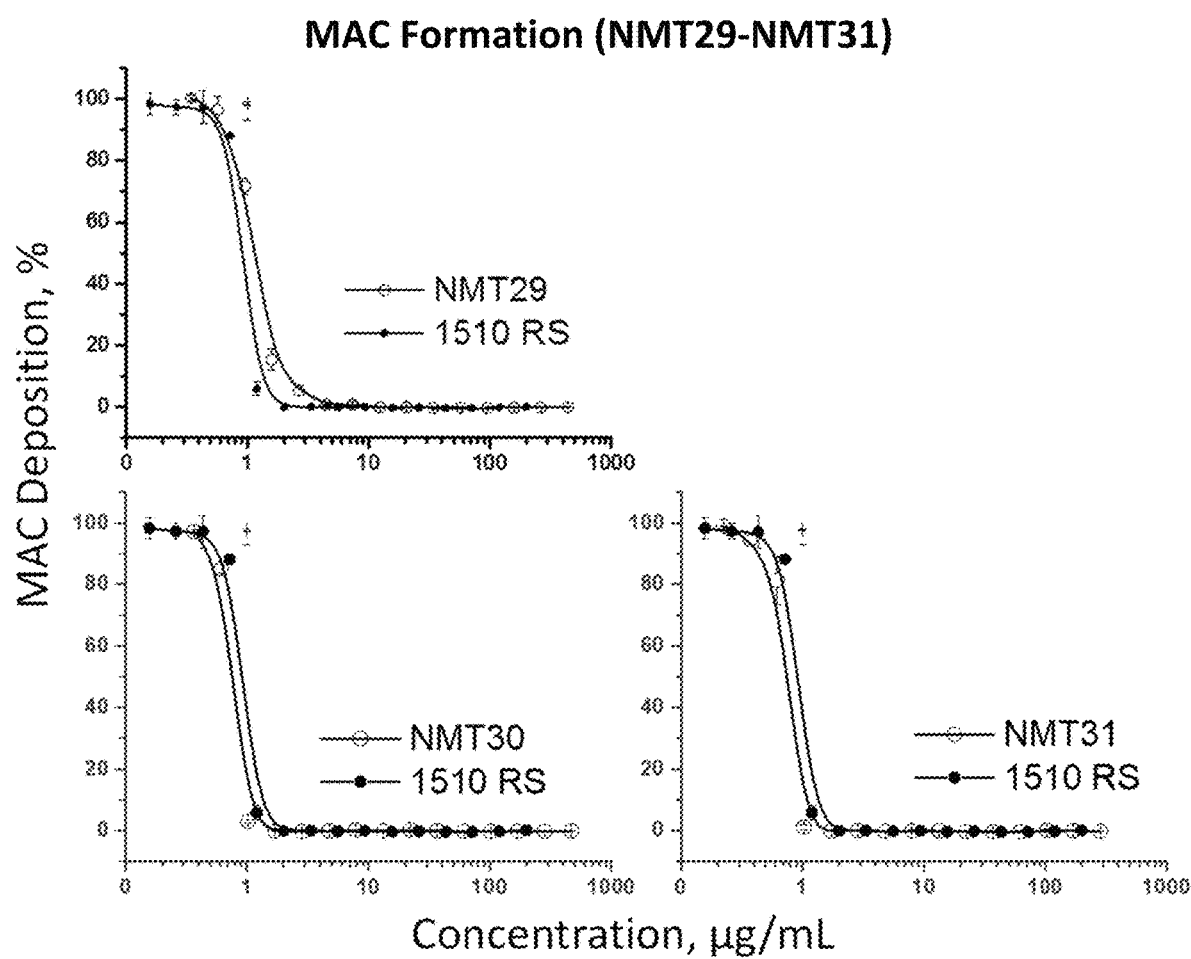
FIG. 45 illustrates plots showing formation of AP mediated MAC—Comparison of N297 and Xtend Fc regions—NMT29, NMT30, NMT31.
Figure 46:
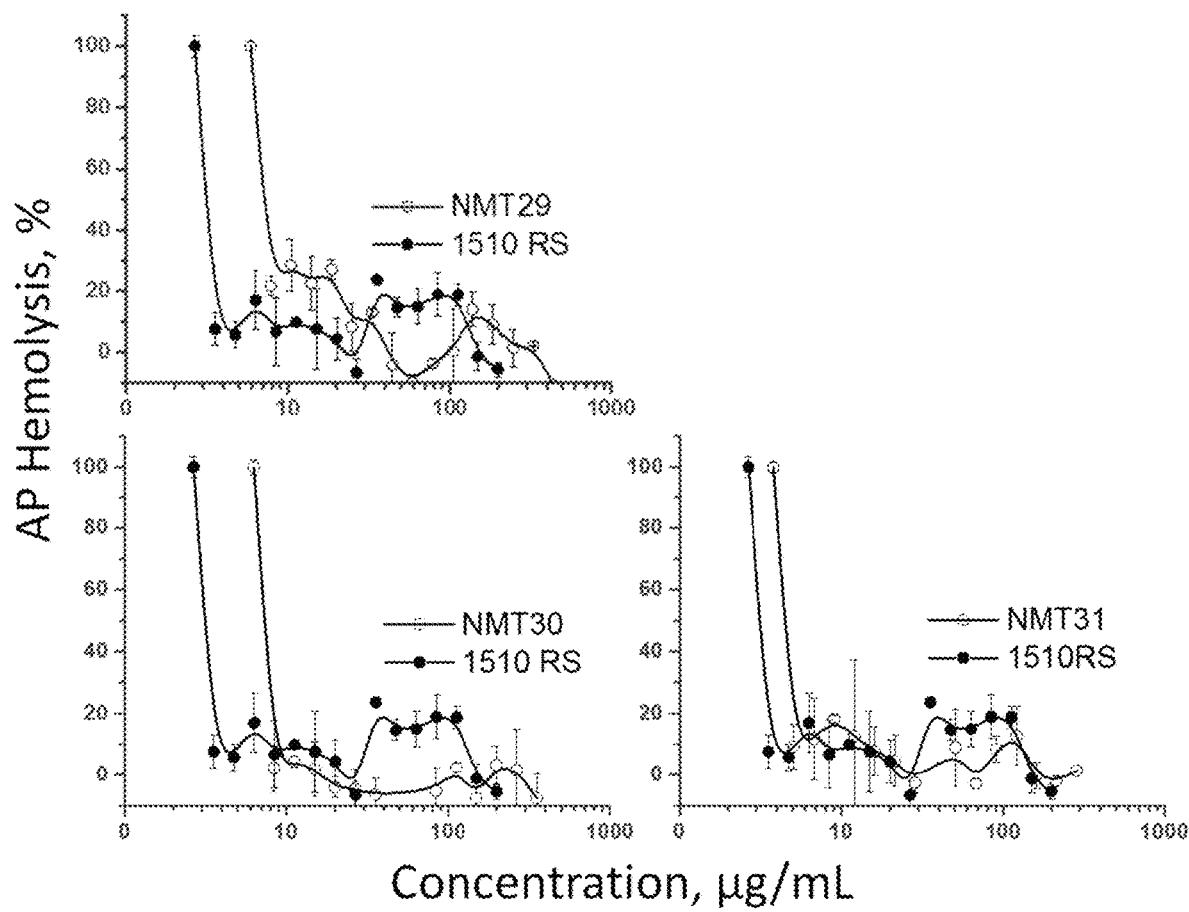
FIG. 46 illustrates plots showing inhibition of AP-mediated Hemolysis—Comparison of N297 and Xtend Fc regions—NMT29, NMT30, NMT31.
Figure 47:
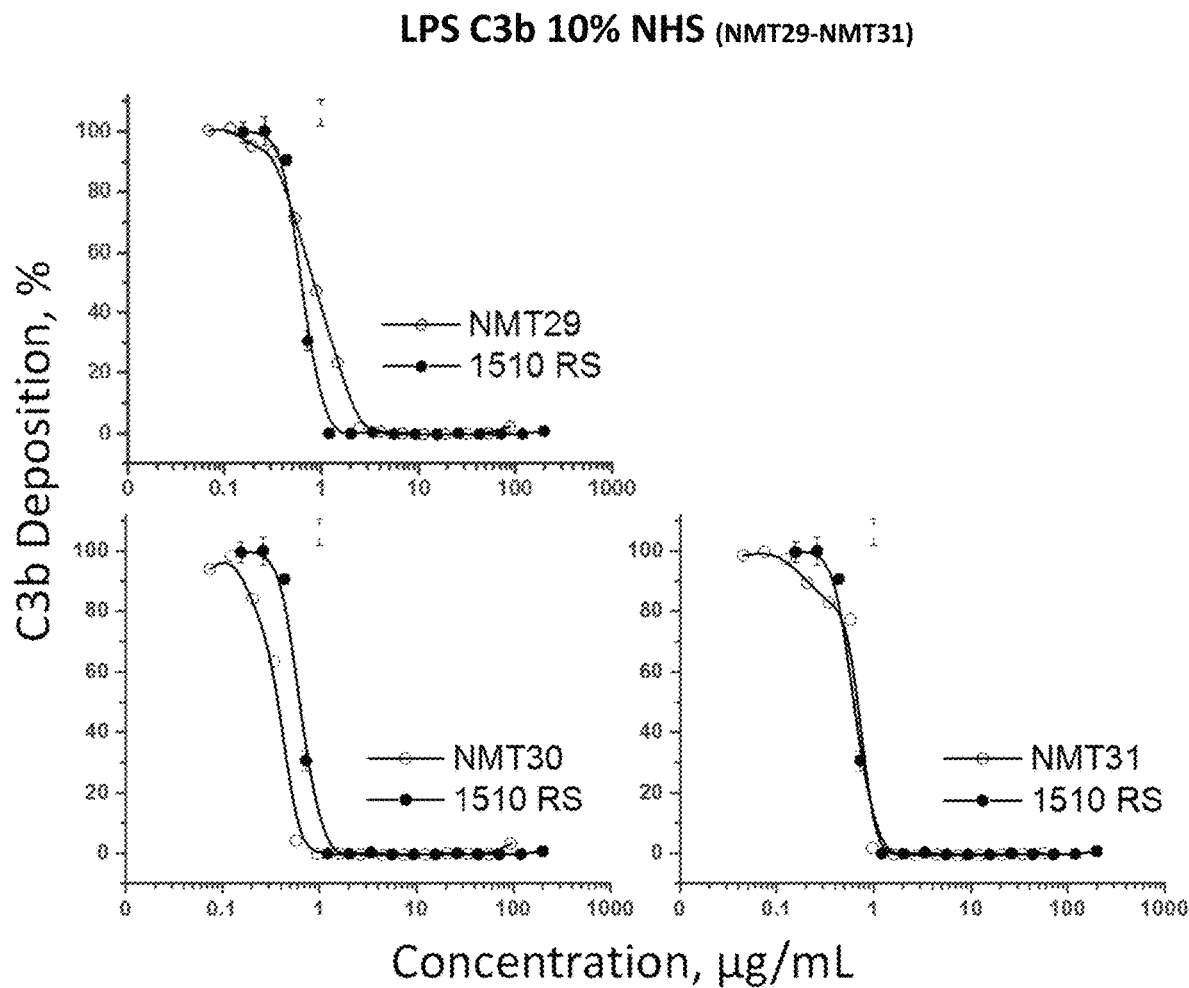
FIG. 47 illustrates plots showing inhibition of AP-mediated C3b Formation & Deposition—Comparison of N297 and Xtend Fc regions—NMT29, NMT30, NMT31.

FIG. 44 illustrates plots showing binding Potency to Properdin—Comparison of N297 and Xtend Fc regions—NMT29, NMT30, NMT31. The properdin binding affinity values of NMT29, NMT30, and NMT31 were similar to NMT1510.
Inhibition of MAC Formation FIG. 45 illustrates plots showing formation of AP mediated MAC—Comparison of N297 and Xtend Fc regions—NMT29, NMT30, NMT31. NMT29, NMT30, NMT31 were able to inhibit MAC formation and deposition at a similar concentration as NMT1510.
Inhibition of AP Hemolysis FIG. 46 illustrates plots showing inhibition of AP-mediated Hemolysis—Comparison of N297 and Xtend Fc regions—NMT29, NMT30, NMT31. NMT29, NMT30, NMT31 were able to inhibit lysis at a similar concentration as NMT1510.
Inhibition of Properdin-C3b Binding FIG. 47 illustrates plots showing inhibition of AP-mediated C3b Formation & Deposition—Comparison of N297 and Xtend Fc regions—NMT29, NMT30, NMT31. NMT29, NMT30, NMT3 1were able to inhibit properdin binding to C3b and deposition of C3b at a similar concentration as NMT1510.

Example 12

Figure 48:
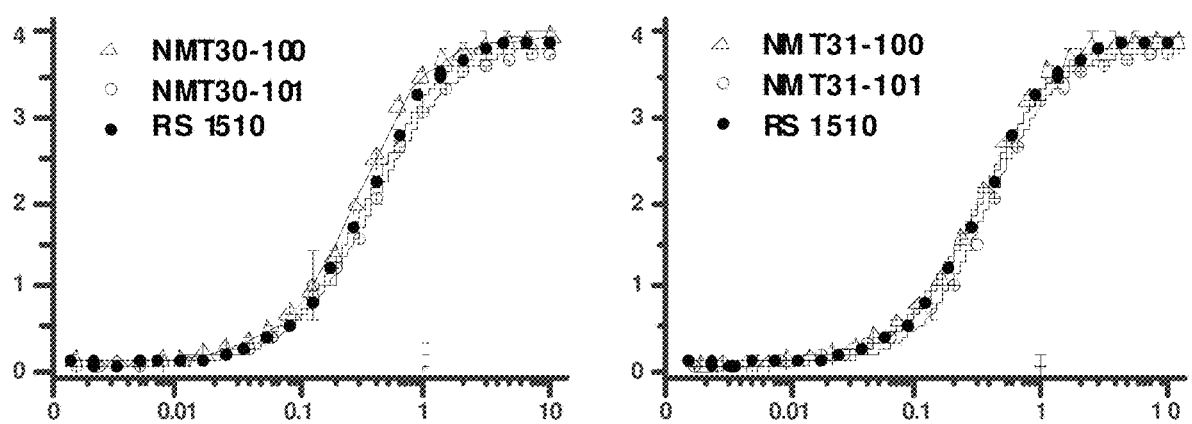
FIG. 48 illustrates plots showing binding Potency to Properdin—Comparison of N297 and Xtend Fc regions—NMT30-100, NMT30-101, NMT31-100, and NMT31-101.

NMT30 and NMT31 with Modified Fc regions Binding Potency and Functional Assays
Binding Affinity to Properdin FIG. 48 illustrates plots showing binding Potency to Properdin of NMT30-100, NMT30-101, NMT31-100, and NMT31-101. Properdin binding affinity values of NMT30-100, NMT30-101, NMT31-100, and NMT31-101 were similar to NMT1510.

Inhibition of AP Hemolysis

Figure 49:
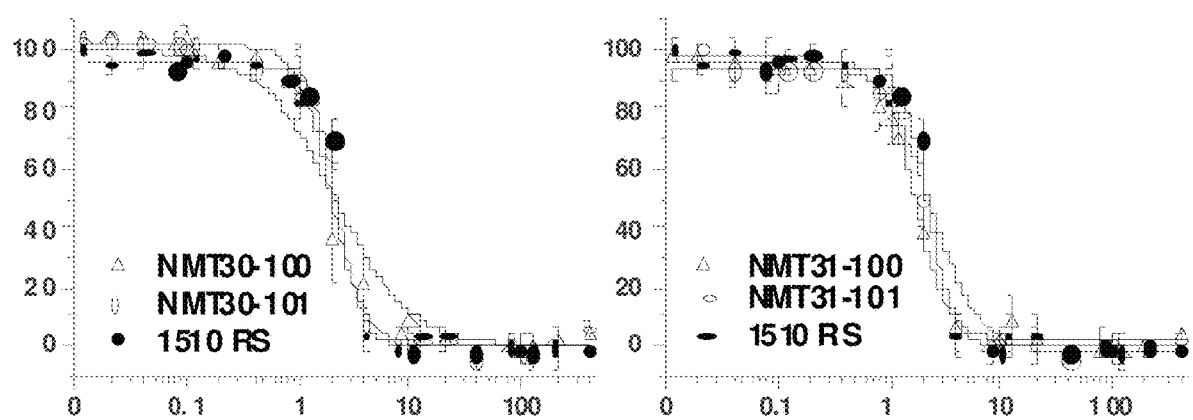
FIG. 49 illustrates plots showing inhibition of AP Hemolysis—Comparison of N297 and Xtend Fc regions—NMT30-100, NMT30-101, NMT31-100, and NMT31-101.

FIG. 49 illustrates plots showing inhibition of AP Hemolysis of NMT30-100, NMT30-101, NMT31-100, and NMT31-101. NMT30-100, NMT30-101, NMT31-100, and NMT31-101 were able to inhibit lysis at a similar concentration as NMT1510.

Inhibition of MAC Formation

Figure 50:
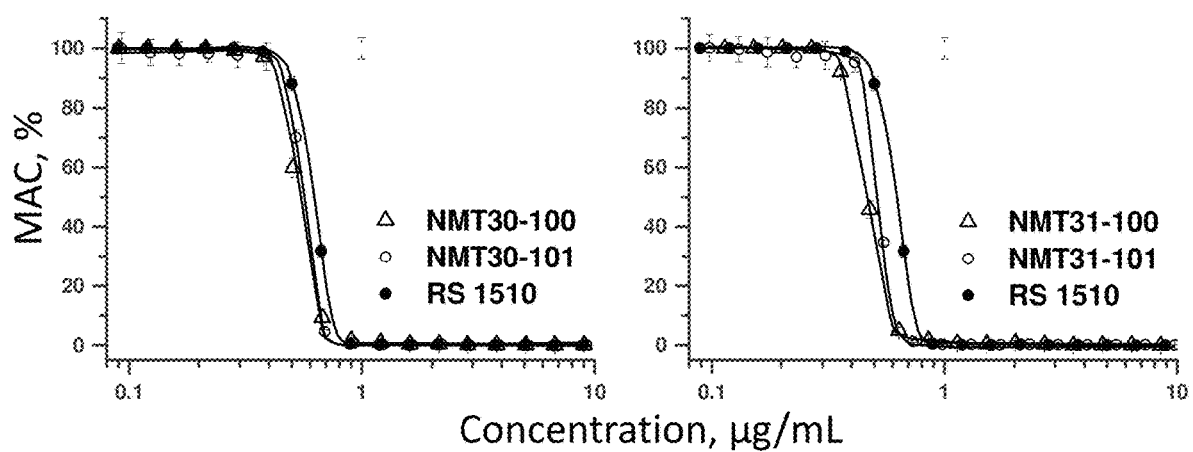
FIG. 50 illustrates plots showing inhibition of AP mediated MAC Formation—Comparison of N297 and Xtend Fc regions—NMT30-100, NMT30-101, NMT31-100, and NMT31-101.

FIG. 50 illustrates plots showing inhibition of AP mediated MAC Formation by NMT30-100, NMT30-101, NMT31-100, and NMT31-101. NMT30-100, NMT30-101, NMT31-100, and NMT31-101 were able to inhibit MAC formation and deposition at a similar concentration as NMT1510.

Inhibition of Properdin-C3b Binding

Figure 51:
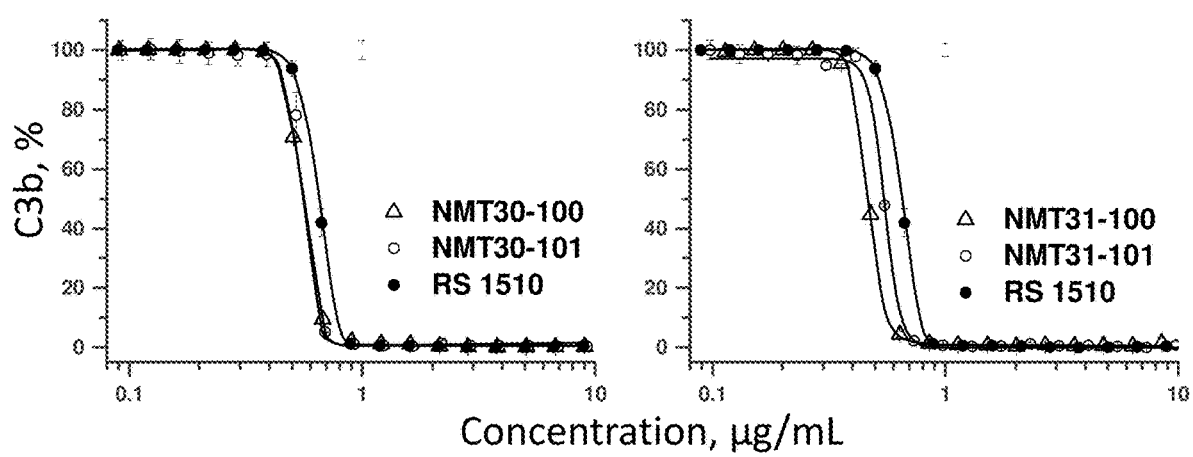
FIG. 51 illustrates plots showing inhibition of AP mediated C3b Formation and Deposition—Comparison of N297 and Xtend Fc regions—NMT30-100, NMT30-101, NMT31-100, and NMT31-101.

FIG. 51 illustrates plots showing inhibition of AP mediated C3b Formation and Deposition by NMT30-100, NMT30-101, NMT31-100, and NMT31-101. NMT30-100, NMT30-101, NMT31-100, and NMT31-101 were able to inhibit properdin binding to C3b and deposition C3b at a similar concentration as NMT1510.

Example 13

Figure 52:
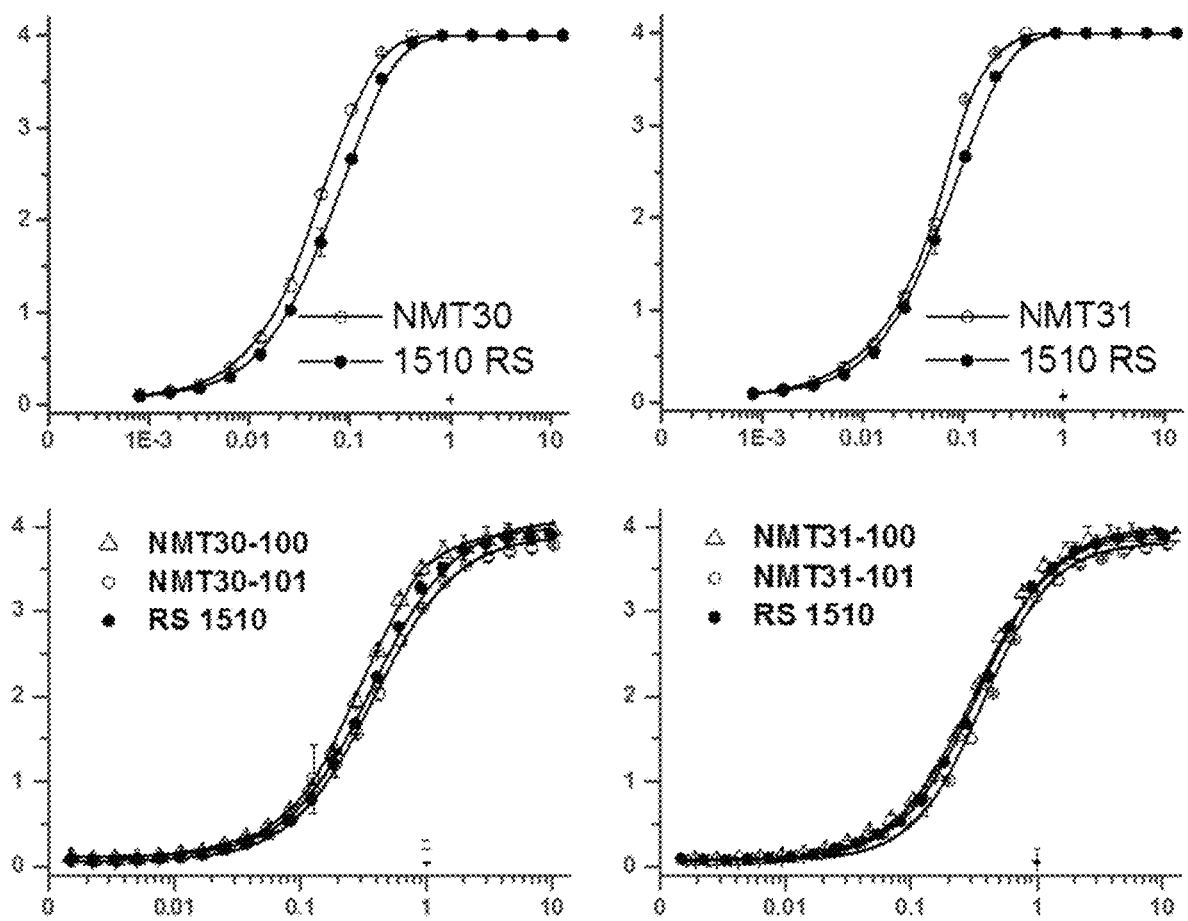
FIG. 52 illustrates plots showing potency Binding to Properdin—Comparison of N297 and Xtend Fc regions—NMT30, NMT31, NMT30-100, NMT30-101, NMT31-100, and NMT31-101.

NMT30 and NMT31 with N297 and Xtend Fc Regions
Binding Potency and Functional Assays
Binding Affinity to Properdin FIG. 52 illustrates plots showing potency Binding to Properdin—Comparison of N297 and Xtend Fc regions—NMT30, NMT31, NMT30-100, NMT30-101, NMT31-100, and NMT31-101. Properdin binding affinity values of NMT30-100, NMT30-101, NMT31-100, and NMT31-101 were similar to NMT1510.

Inhibition of AP Hemolysis

Figure 53:
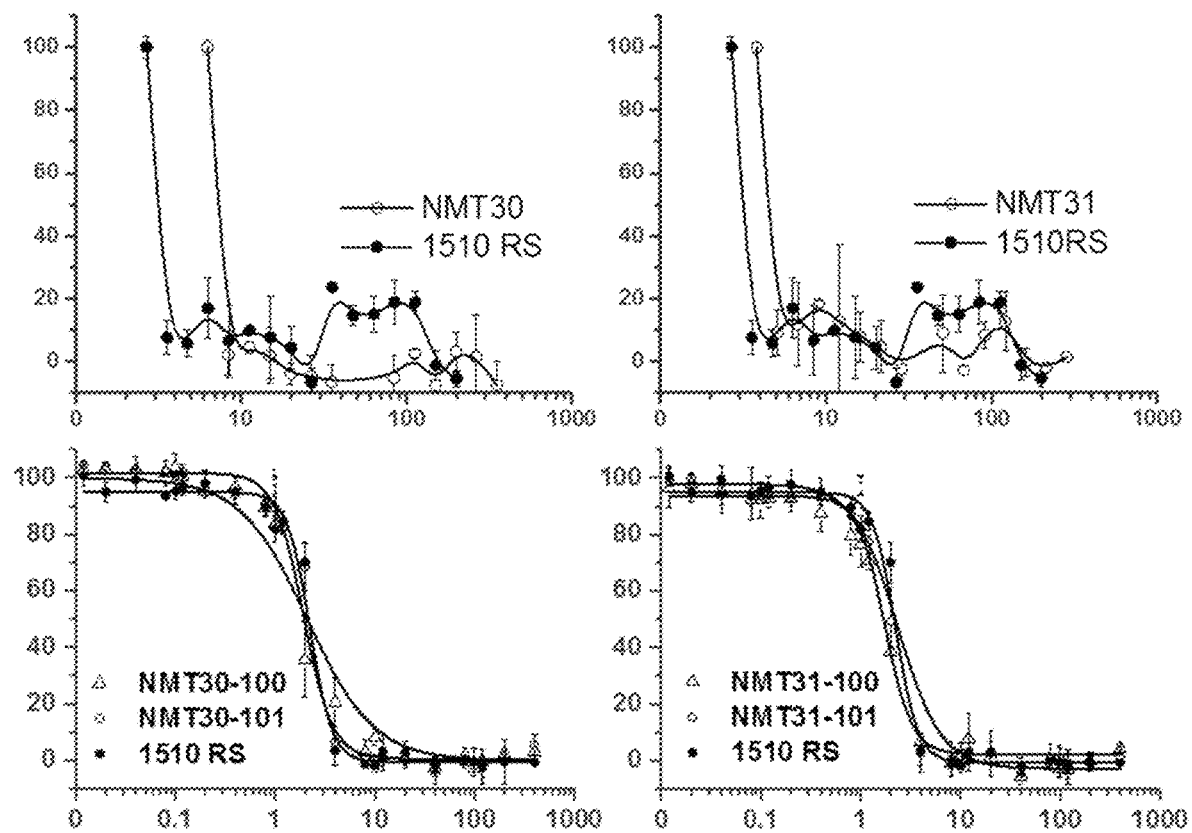
FIG. 53 illustrates plots showing inhibition of AP Hemolysis—Comparison of N297 and Xtend Fc regions—NMT30, NMT31, NMT30-100, NMT30-101, NMT31-100, and NMT31-101.

FIG. 53 illustrates plots showing inhibition of AP Hemolysis—Comparison of N297 and Xtend Fc regions—NMT30, NMT31, NMT30-100, NMT30-101, NMT31-100, and NMT31-101. NMT30-100, NMT30-101, NMT31-100, and NMT31-101 were able to inhibit lysis at a similar concentration as NMT1510.

Inhibition of MAC Formation

Figure 54:
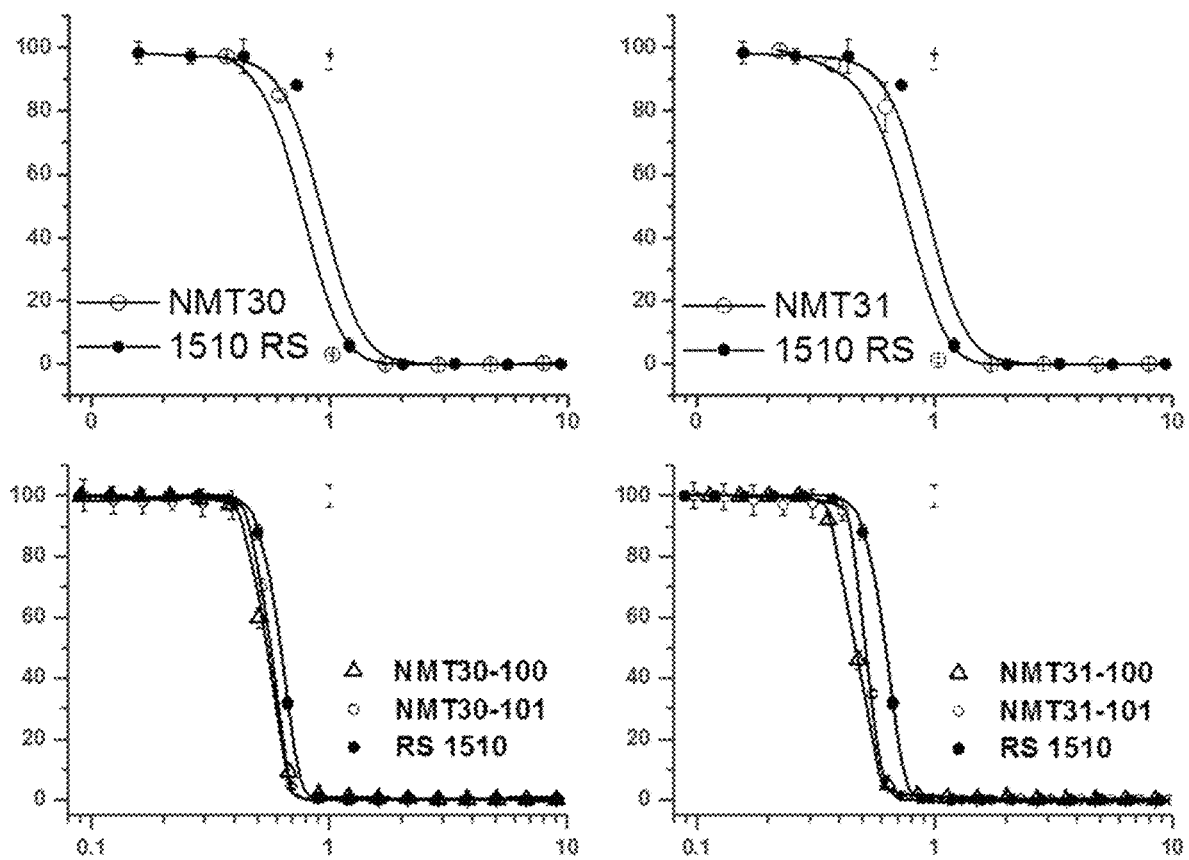
FIG. 54 illustrates plots showing inhibition of MAC Formation—Comparison of N297 and Xtend Fc regions—NMT30, NMT31, NMT30-100, NMT30-101, NMT31-100, and NMT31-101.

FIG. 54 illustrates plots showing inhibition of MAC Formation—Comparison of N297 and Xtend Fc regions—NMT30, NMT31, NMT30-100, NMT30-101, NMT31-100, and NMT31-101. NMT30-100, NMT30-101, NMT31-100, and NMT31-101 were able to inhibit MAC formation and deposition at a similar concentration as NMT1510.

Inhibition of Properdin-C3b Binding

Figure 55:
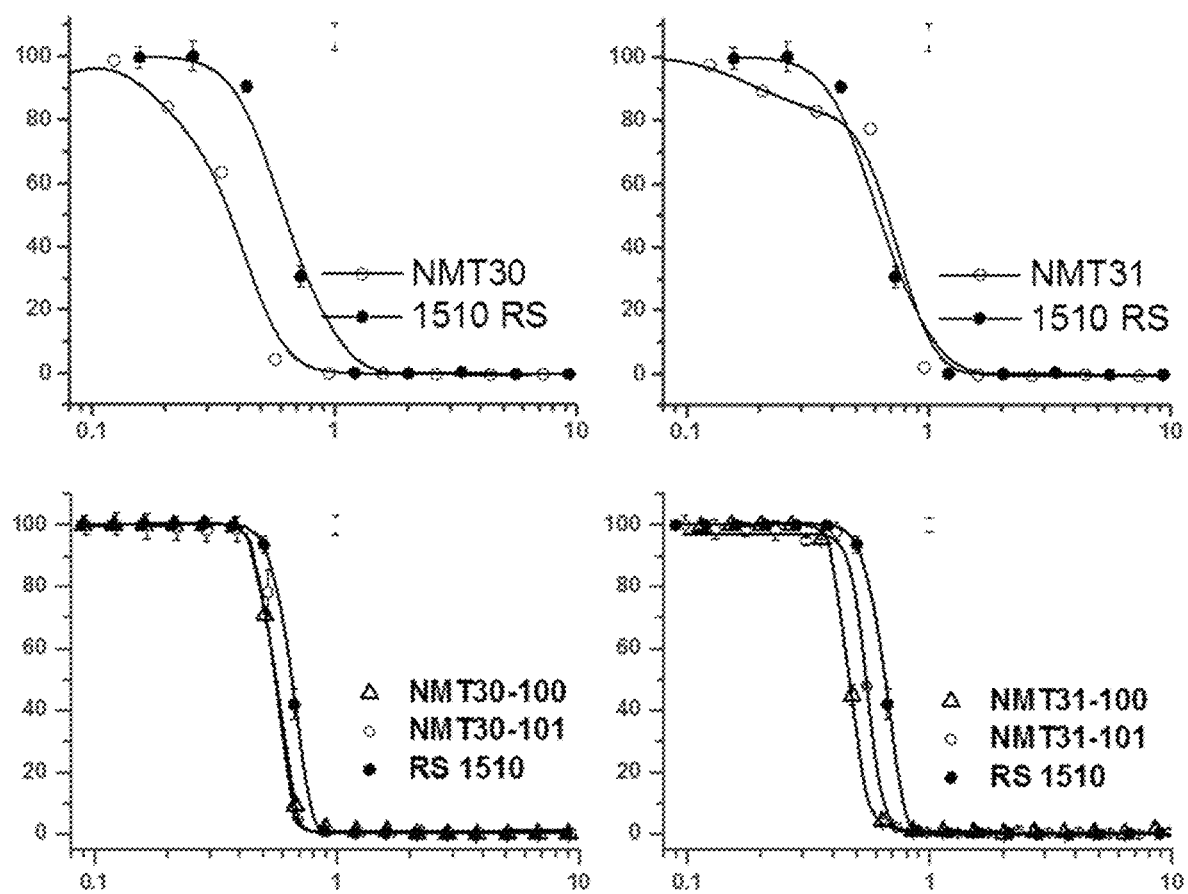
FIG. 55 illustrates plots showing inhibition of C3b Formation and Deposition—Comparison of N297 and Xtend Fc regions—NMT30, NMT31, NMT30-100, NMT30-101, NMT31-100, and NMT31-101.

FIG. 55 illustrates plots showing inhibition of C3b Formation and Deposition—Comparison of N297 and Xtend Fc regions—NMT30, NMT31, NMT30-100, NMT30-101, NMT31-100, and NMT31-101. NMT30-100, NMT30-101, NMT31-100, and NMT31-101 were able to inhibit properdin binding to C3b and deposition C3b at a similar concentration as NMT1510.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, the following is claimed:

1. An isolated antibody or antigen binding fragment thereof comprising a heavy chain variable region and light chain variable region selected from the group consisting of:
   (a) a heavy chain variable region that includes the 3 CDRs of SEQ ID NO: 3 and a light chain variable region that includes the 3 CDRs of SEQ ID NO: 26;
   (b) a heavy chain variable region that includes the 3 CDRs of SEQ ID NO: 4 and a light chain variable region that includes the 3 CDRs of SEQ ID NO: 27;
   (c) a heavy chain variable region that includes the 3 CDRs of SEQ ID NO: 6 and a light chain variable region that includes the 3 CDRs of SEQ ID NO: 29;
   (d) a heavy chain variable region that includes the 3 CDRs of SEQ ID NO: 7 and a light chain variable region that includes the 3 CDRs of SEQ ID NO: 30;
   (e) a heavy chain variable region that includes the 3 CDRs of SEQ ID NO: 8 and a light chain variable region that includes the 3 CDRs of SEQ ID NO: 31;
   (f) a heavy chain variable region that includes the 3 CDRs of SEQ ID NO: 9 and a light chain variable region that includes the 3 CDRs of SEQ ID NO: 32; and
   (g) a heavy chain variable region that includes the 3 CDRs of SEQ ID NO: 14 and a light chain variable region that includes the 3 CDRs of SEQ ID NO: 37, wherein the isolated antibody or antigen binding fragment thereof binds to human properdin.

2. The isolated antibody or antigen binding fragment of claim 1 comprising a heavy chain variable region and light chain variable region selected from the group consisting of:
(a) the heavy chain variable region of SEQ ID NO: 3 and the light chain variable region of SEQ ID NO: 26;
(b) the heavy chain variable region of SEQ ID NO: 4 and the light chain variable region of SEQ ID NO: 27;
(c) the heavy chain variable region of SEQ ID NO: 6 and the light chain variable region of SEQ ID NO: 29;
(d) the heavy chain variable region of SEQ ID NO: 7 and the light chain variable region of SEQ ID NO: 30;
(e) the heavy chain variable region of SEQ ID NO: 8 and the light chain variable region of SEQ ID NO: 31;
(f) the heavy chain variable region of SEQ ID NO: 9 and the light chain variable region of SEQ ID NO: 32; and
(g) the heavy chain variable region of SEQ ID NO: 14 and the light chain variable region of SEQ ID NO: 37.

3. The isolated antibody or antigen binding fragment thereof of claim 1, further comprising a constant chain region and wherein the antibody or antigen binding fragment including the constant chain region has enhanced in vivo half-live and/or reduced immunogenicity compared to the antibody or antigen binding fragment thereof without the constant chain region.

4. The isolated antibody or antigen binding fragment thereof of claim 3, wherein the constant chain region includes an amino acid sequence at least about 70%, at least about 80%, or at least about 90% identical to the amino acid sequence of SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, or SEQ ID NO: 139.

5. The isolated antibody or antigen binding fragment thereof of claim 1, wherein the antibody or antigen binding fragment thereof is humanized.

6. The isolated antibody or antigen binding fragment thereof of claim 1, wherein the antibody or antigen binding fragment thereof inhibits alternative complement pathway activation in a mammal without inhibiting classical complement pathway activation.

7. The isolated antibody or antigen binding fragment thereof of claim 1, inhibiting C3b and Mac complex (C5b-9) formation in vivo.

8. A method of treating a complement mediated disease or disorder in a subject in need thereof, comprising administering a therapeutically effective amount of the antibody or antigen binding fragment thereof of claim 1 to a subject in need thereof, wherein administration of the antibody or antigen binding fragment thereof inhibits C3b and Mac complex (C5b-9) formation.

* * * * *

SEQUENCE LISTING

```
<160> NUMBER OF SEQ ID NOS: 248

<210> SEQ ID NO 1
<211> LENGTH: 118
<212> TYPE: PRT
<213> ORGANISM: Artificial Sequence
<220> FEATURE:
<223> OTHER INFORMATION: Gen1_5072 Humanized Anti-P VH

<400> SEQUENCE: 1

Gln Val Gln Leu Val Gln Ser Ala Pro Glu Val Ala Lys Pro Gly Thr
1               5                   10                  15

Ser Val Lys Met Ser Cys Lys Ala Ser Gly Tyr Ile Phe Thr Asn Tyr
            20                  25                  30

Pro Ile His Trp Val Lys Gln Ala Pro Gly Gln Gly Leu Glu Trp Ile
        35                  40                  45

Gly Phe Ile Asp Pro Gly Gly Gly Tyr Asp Glu Pro Asp Glu Arg Phe
    50                  55                  60

Arg Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Ile Tyr Tyr Cys
                85                  90                  95

Ala Arg Arg Gly Gly Gly Tyr Tyr Leu Asp Tyr Trp Gly Gln Gly Thr
            100                 105                 110

Leu Val Thr Val Ser Ser
        115

<210> SEQ ID NO 2
```

```
<211> LENGTH: 118
<212> TYPE: PRT
<213> ORGANISM: Artificial Sequence
<220> FEATURE:
<223> OTHER INFORMATION: Gen1_5072 Humanized Anti-P VH

<400> SEQUENCE: 2

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Pro Ile His Trp Val Arg Gln Ala Pro Gly Gln Gly Leu Glu Trp Met
        35                  40                  45

Gly Phe Ile Asp Pro Gly Gly Gly Tyr Asp Glu Pro Asp Glu Arg Phe
    50                  55                  60

Arg Asp Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Gly Tyr Tyr Leu Asp Tyr Trp Gly Gln Gly Thr
            100                 105                 110

Thr Val Thr Val Ser Ser
        115

<210> SEQ ID NO 3
<211> LENGTH: 118
<212> TYPE: PRT
<213> ORGANISM: Artificial Sequence
<220> FEATURE:
<223> OTHER INFORMATION: Gen1_5072 Humanized Anti-P VH

<400> SEQUENCE: 3

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Pro Ile His Trp Val Arg Gln Ala Pro Gly Gln Gly Leu Glu Trp Met
        35                  40                  45

Gly Phe Ile Asp Pro Gly Gly Gly Tyr Asp Glu Pro Asp Glu Arg Phe
    50                  55                  60

Arg Asp Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Gly Tyr Tyr Leu Asp Tyr Trp Gly Gln Gly Thr
            100                 105                 110

Thr Val Thr Val Ser Ser
        115

<210> SEQ ID NO 4
<211> LENGTH: 118
<212> TYPE: PRT
<213> ORGANISM: Artificial Sequence
<220> FEATURE:
<223> OTHER INFORMATION: Gen1_5072 Humanized Anti-P VH

<400> SEQUENCE: 4

Glu Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Ile Phe Thr Asn Tyr
            20                  25                  30

Pro Ile His Trp Val Arg Gln Ala Pro Gly Gln Gly Leu Glu Trp Met
            35                  40                  45

Gly Phe Ile Asp Pro Gly Gly Gly Tyr Asp Glu Pro Asp Glu Arg Phe
        50                  55                  60

Arg Asp Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Gly Tyr Tyr Leu Asp Tyr Trp Gly Gln Gly Thr
            100                 105                 110

Thr Val Thr Val Ser Ser
            115

<210> SEQ ID NO 5
<211> LENGTH: 118
<212> TYPE: PRT
<213> ORGANISM: Artificial Sequence
<220> FEATURE:
<223> OTHER INFORMATION: Gen1_5072 Humanized Anti-P VH

<400> SEQUENCE: 5

Glu Val Gln Leu Val Gln Ser Gly Ala Glu Val Lys Lys Pro Gly Ala
1               5                   10                  15

Ser Val Lys Val Ser Cys Lys Ala Ser Gly His Ile Phe Thr Asn Tyr
            20                  25                  30

Pro Ile His Trp Val Arg Gln Ala Pro Gly Gln Gly Leu Glu Trp Met
            35                  40                  45

Gly Phe Ile Asp Pro Gly Gly Gly His Asp Glu Pro Asp Glu Arg Phe
        50                  55                  60

Arg Asp Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Gly Tyr Tyr Leu Asp Tyr Trp Gly Gln Gly Thr
            100                 105                 110

Thr Val Thr Val Ser Ser
            115

<210> SEQ ID NO 6
<211> LENGTH: 118
<212> TYPE: PRT
<213> ORGANISM: Artificial Sequence
<220> FEATURE:
<223> OTHER INFORMATION: Gen1_5072 Humanized Anti-P VH

<400> SEQUENCE: 6

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Pro Ile His Trp Val Arg Gln Ala Pro Gly Gln Gly Leu Glu Trp Met
            35                  40                  45

Gly Phe Ile Asp Pro Gly Gly Gly Tyr Asp Glu Pro Asp Glu Arg Phe
        50                  55                  60

Arg Asp Arg Val Thr Met Thr Ala Asp Thr Ser Thr Ser Thr Ala Tyr
65                  70                  75                  80
```

```
Met Glu Leu Ser Ser Leu Arg Ser Glu Asp Thr Ala Val Tyr Tyr Cys
            85                  90                  95

Ala Arg Arg Gly Gly Tyr Tyr Leu Asp Tyr Trp Gly Gln Gly Thr
            100                 105                 110

Thr Val Thr Val Ser Ser
            115

<210> SEQ ID NO 7
<211> LENGTH: 118
<212> TYPE: PRT
<213> ORGANISM: Artificial Sequence
<220> FEATURE:
<223> OTHER INFORMATION: Gen1_5072 Humanized Anti-P VH

<400> SEQUENCE: 7

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Pro Ile His Trp Val Arg Gln Ala Pro Gly Gln Gly Leu Glu Trp Met
            35                  40                  45

Gly Phe Ile Asp Pro Gly Gly Gly Tyr Asp Glu Tyr Ala Gln Lys Phe
    50                  55                  60

Gln Gly Arg Val Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Arg Gly Gly Tyr Tyr Leu Asp Tyr Trp Gly Gln Gly Thr
            100                 105                 110

Thr Leu Thr Val Ser Ser
            115

<210> SEQ ID NO 8
<211> LENGTH: 118
<212> TYPE: PRT
<213> ORGANISM: Artificial Sequence
<220> FEATURE:
<223> OTHER INFORMATION: Gen1_5072 Humanized Anti-P VH

<400> SEQUENCE: 8

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Pro Ile His Trp Val Arg Gln Ala Pro Gly Gln Gly Leu Glu Trp Met
            35                  40                  45

Gly Phe Ile Asp Pro Gly Gly Gly Tyr Asp Glu Ser Ala Gln Lys Phe
    50                  55                  60

Arg Gly Arg Val Thr Leu Thr Ala Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Arg Gly Gly Tyr Tyr Leu Asp Tyr Trp Gly Gln Gly Thr
            100                 105                 110

Thr Leu Thr Val Ser Ser
            115
```

<210> SEQ ID NO 9
<211> LENGTH: 118
<212> TYPE: PRT
<213> ORGANISM: Artificial Sequence
<220> FEATURE:
<223> OTHER INFORMATION: Gen2_5072 Humanized Anti-P VH

<400> SEQUENCE: 9

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Pro Ile His Trp Val Arg Gln Ala Pro Gly Lys Gly Leu Glu Trp Met
        35                  40                  45

Gly Phe Ile Asp Pro Gly Gly Gly His Asp Glu Tyr Ala Asp Ser Val
    50                  55                  60

Lys Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Gly Tyr Tyr Leu Asp Tyr Trp Gly Gln Gly Thr
            100                 105                 110

Leu Val Thr Val Ser Ser
        115

<210> SEQ ID NO 10
<211> LENGTH: 118
<212> TYPE: PRT
<213> ORGANISM: Artificial Sequence
<220> FEATURE:
<223> OTHER INFORMATION: Gen2_5072 Humanized Anti-P VH

<400> SEQUENCE: 10

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Pro Ile His Trp Val Arg Gln Ala Pro Gly Lys Gly Leu Glu Trp Met
        35                  40                  45

Gly Phe Ile Asp Pro Gly Gly Gly His Asp Glu Tyr Ala Asp Ser Val
    50                  55                  60

Lys Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Gly Tyr Tyr Leu Asp Tyr Trp Gly Gln Gly Thr
            100                 105                 110

Leu Val Thr Val Ser Ser
        115

<210> SEQ ID NO 11
<211> LENGTH: 118
<212> TYPE: PRT
<213> ORGANISM: Artificial Sequence
<220> FEATURE:
<223> OTHER INFORMATION: Gen2_5072 Humanized Anti-P VH

<400> SEQUENCE: 11

Glu Val Gln Leu Leu Glu Ser Gly Gly Gly Leu Val Gln Pro Gly Gly
1               5                   10                  15

```
Ser Leu Arg Leu Ser Cys Ala Ala Ser Gly Tyr Ile Phe Thr Asn Tyr
            20                  25                  30

Pro Ile His Trp Val Arg Gln Ala Pro Gly Lys Gly Leu Glu Trp Val
            35                  40                  45

Ser Phe Ile Asp Pro Gly Gly Tyr Asp Glu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Gly Tyr Tyr Leu Asp Tyr Trp Gly Gln Gly Thr
            100                 105                 110

Leu Val Thr Val Ser Ser
            115

<210> SEQ ID NO 12
<211> LENGTH: 118
<212> TYPE: PRT
<213> ORGANISM: Artificial Sequence
<220> FEATURE:
<223> OTHER INFORMATION: Gen2_5072 Humanized Anti-P VH

<400> SEQUENCE: 12

Glu Val Gln Leu Val Glu Ser Gly Gly Gly Leu Val Gln Pro Gly Arg
1               5                   10                  15

Ser Leu Arg Leu Ser Cys Ala Ala Ser Gly Tyr Ile Phe Thr Asn Tyr
            20                  25                  30

Pro Ile His Trp Val Arg Gln Ala Pro Gly Lys Gly Leu Glu Trp Val
            35                  40                  45

Ser Phe Ile Asp Pro Gly Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Arg Gly Gly Tyr Tyr Leu Asp Tyr Trp Gly Gln Gly Thr
            100                 105                 110

Leu Val Thr Val Ser Ser
            115

<210> SEQ ID NO 13
<211> LENGTH: 118
<212> TYPE: PRT
<213> ORGANISM: Artificial Sequence
<220> FEATURE:
<223> OTHER INFORMATION: Gen2_5072 Humanized Anti-P VH

<400> SEQUENCE: 13

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Pro Ile His Trp Val Arg Gln Ala Pro Gly Lys Gly Leu Glu Trp Met
            35                  40                  45

Gly Phe Ile Asp Pro Gly Gly Tyr Asp Glu Pro Asp Glu Arg Phe
    50                  55                  60

Arg Asp Arg Val Thr Met Thr Arg Asp Thr Ser Thr Ser Thr Val Tyr
```

```
                65                  70                  75                  80
Met Glu Leu Ser Ser Leu Arg Ser Glu Asp Thr Ala Val Tyr Tyr Cys
                    85                  90                  95

Ala Arg Arg Gly Gly Gly Tyr Tyr Leu Asp Tyr Trp Gly Gln Gly Thr
                100                 105                 110

Leu Val Thr Val Ser Ser
        115

<210> SEQ ID NO 14
<211> LENGTH: 118
<212> TYPE: PRT
<213> ORGANISM: Artificial Sequence
<220> FEATURE:
<223> OTHER INFORMATION: Gen2_5072 Humanized Anti-P VH

<400> SEQUENCE: 14

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
                20                  25                  30

Pro Ile His Trp Val Arg Gln Ala Pro Gly Gln Gly Leu Glu Trp Met
            35                  40                  45

Gly Phe Ile Asp Pro Gly Gly Tyr Asp Glu Pro Asp Glu Arg Phe
    50                  55                  60

Arg Asp Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                    85                  90                  95

Ala Arg Arg Gly Gly Gly Tyr Tyr Leu Asp Tyr Trp Gly Gln Gly Thr
                100                 105                 110

Leu Val Thr Val Ser Ser
        115

<210> SEQ ID NO 15
<211> LENGTH: 118
<212> TYPE: PRT
<213> ORGANISM: Artificial Sequence
<220> FEATURE:
<223> OTHER INFORMATION: h9401-H1 Humanized Anti-P VH

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
                20                  25                  30

Pro Ile His Trp Val Arg Gln Ala Pro Gly Gln Gly Leu Glu Trp Met
            35                  40                  45

Gly Phe Ile Asp Pro Gly Gly Tyr Asp Glu Pro Asp Glu Arg Phe
    50                  55                  60

Arg Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                    85                  90                  95

Ala Arg Arg Gly Gly Gly Tyr Tyr Leu Asp Tyr Trp Gly Gln Gly Thr
                100                 105                 110

Thr Val Thr Val Ser Ser
        115
```

```
<210> SEQ ID NO 16
<211> LENGTH: 118
<212> TYPE: PRT
<213> ORGANISM: Artificial Sequence
<220> FEATURE:
<223> OTHER INFORMATION: h9401-H2 Humanized Anti-P VH

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Pro Ile His Trp Val Arg Gln Ala Pro Gly Gln Gly Leu Glu Trp Met
        35                  40                  45

Gly Phe Ile Asp Pro Gly Gly Tyr Asp Glu Pro Asp Glu Arg Phe
    50                  55                  60

Arg Asp Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Gly Tyr Tyr Leu Asp Tyr Trp Gly Gln Gly Thr
            100                 105                 110

Thr Val Thr Val Ser Ser
        115

<210> SEQ ID NO 17
<211> LENGTH: 118
<212> TYPE: PRT
<213> ORGANISM: Artificial Sequence
<220> FEATURE:
<223> OTHER INFORMATION: h9401-H3 Humanized Anti-P VH

<400> SEQUENCE: 17

Gln Val Gln Leu Val Gln Ser Gly Ala Glu Val Lys Lys Pro Gly Ala
1               5                   10                  15

Ser Val Lys Met Ser Cys Lys Ala Ser Gly Tyr Ile Phe Thr Asn Tyr
            20                  25                  30

Pro Ile His Trp Val Arg Gln Ala Pro Gly Gln Gly Leu Glu Trp Met
        35                  40                  45

Gly Phe Ile Asp Pro Gly Gly Tyr Asp Glu Pro Asp Glu Arg Phe
    50                  55                  60

Arg Asp Arg Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Gly Tyr Tyr Leu Asp Tyr Trp Gly Gln Gly Thr
            100                 105                 110

Thr Leu Thr Val Ser Ser
        115

<210> SEQ ID NO 18
<211> LENGTH: 118
<212> TYPE: PRT
<213> ORGANISM: Artificial Sequence
<220> FEATURE:
<223> OTHER INFORMATION: h9401-H2b Humanized Anti-P VH

<400> SEQUENCE: 18

Gln Val Gln Leu Val Gln Ser Gly Ala Glu Val Lys Lys Pro Gly Ala
```

```
                1               5                   10                  15
Ser Val Lys Val Ser Cys Lys Ala Ser Gly Tyr Ile Phe Thr Asn Tyr
            20                  25                  30

Pro Ile His Trp Val Arg Gln Ala Pro Gly Gln Gly Leu Glu Trp Met
            35                  40                  45

Gly Phe Ile Asp Pro Gly Gly Gly Tyr Asp Glu Pro Asp Glu Arg Phe
        50                  55                  60

Arg Asp Arg Val Thr Met Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Gly Tyr Tyr Leu Asp Tyr Trp Gly Gln Gly Thr
                100                 105                 110

Thr Val Thr Val Ser Ser
            115
```

<210> SEQ ID NO 19
<211> LENGTH: 118
<212> TYPE: PRT
<213> ORGANISM: Artificial Sequence
<220> FEATURE:
<223> OTHER INFORMATION: h9401-H3b Humanized Anti-P VH

<400> SEQUENCE: 19

```
Gln Val Gln Leu Val Gln Ser Gly Ala Glu Val Lys Lys Pro Gly Ala
1               5                   10                  15

Ser Val Lys Met Ser Cys Lys Ala Ser Gly Tyr Ile Phe Thr Asn Tyr
            20                  25                  30

Pro Ile His Trp Val Arg Gln Ala Pro Gly Gln Gly Leu Glu Trp Met
            35                  40                  45

Gly Phe Ile Asp Pro Gly Gly Gly Tyr Asp Glu Pro Asp Glu Arg Phe
        50                  55                  60

Arg Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Gly Tyr Tyr Leu Asp Tyr Trp Gly Gln Gly Thr
                100                 105                 110

Thr Leu Thr Val Ser Ser
            115
```

<210> SEQ ID NO 20
<211> LENGTH: 118
<212> TYPE: PRT
<213> ORGANISM: Artificial Sequence
<220> FEATURE:
<223> OTHER INFORMATION: h9401-H2c Humanized Anti-P VH

<400> SEQUENCE: 20

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Pro Ile His Trp Val Arg Gln Ala Pro Gly Gln Gly Leu Glu Trp Met
            35                  40                  45

Gly Phe Ile Asp Pro Gly Gly Gly Tyr Asp Glu Tyr Ala Gln Lys Phe
        50                  55                  60
```

```
Gln Gly Arg Val Thr Met Thr Ala Asp Thr Ser Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Gly Gly Gly Tyr Tyr Leu Asp Tyr Trp Gly Gln Gly Thr
            100                 105                 110

Thr Val Thr Val Ser Ser
        115
```

<210> SEQ ID NO 21
<211> LENGTH: 118
<212> TYPE: PRT
<213> ORGANISM: Artificial Sequence
<220> FEATURE:
<223> OTHER INFORMATION: h9401-H3c Humanized Anti-P VH

<400> SEQUENCE: 21

```
Gln Val Gln Leu Val Gln Ser Gly Ala Glu Val Lys Lys Pro Gly Ala
1               5                   10                  15

Ser Val Lys Met Ser Cys Lys Ala Ser Gly Tyr Ile Phe Thr Asn Tyr
                20                  25                  30

Pro Ile His Trp Val Arg Gln Ala Pro Gly Gln Gly Leu Glu Trp Met
            35                  40                  45

Gly Phe Ile Asp Pro Gly Gly Gly Tyr Asp Glu Tyr Ala Gln Lys Phe
     50                  55                  60

Gln Gly Arg Ala Thr Leu Thr Ala Asp Thr Ser Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Gly Gly Gly Tyr Tyr Leu Asp Tyr Trp Gly Gln Gly Thr
            100                 105                 110

Thr Leu Thr Val Ser Ser
        115
```

<210> SEQ ID NO 22
<211> LENGTH: 118
<212> TYPE: PRT
<213> ORGANISM: Artificial Sequence
<220> FEATURE:
<223> OTHER INFORMATION: h9401-H2d Humanized Anti-P VH

<400> SEQUENCE: 22

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
                20                  25                  30

Pro Ile His Trp Val Arg Gln Ala Pro Gly Gln Gly Leu Glu Trp Met
            35                  40                  45

Gly Phe Ile Asp Pro Gly Gly Gly Tyr Asp Glu Tyr Ala Gln Lys Phe
     50                  55                  60

Gln Gly Arg Val Thr Met Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Gly Gly Gly Tyr Tyr Leu Asp Tyr Trp Gly Gln Gly Thr
            100                 105                 110

Thr Val Thr Val Ser Ser
        115
```

<210> SEQ ID NO 23
<211> LENGTH: 122
<212> TYPE: PRT
<213> ORGANISM: Artificial Sequence
<220> FEATURE:
<223> OTHER INFORMATION: h9401-H3d Humanized Anti-P VH

<400> SEQUENCE: 23

```
Gln Val Gln Leu Val Gln Ser Gly Ala Glu Val Lys Lys Pro Gly Ala
1               5                   10                  15

Ser Val Lys Met Ser Cys Lys Ala Ser Gly Tyr Ile Phe Thr Asn Tyr
            20                  25                  30

Pro Ile His Trp Val Arg Gln Ala Pro Gly Gln Gly Leu Glu Trp Met
        35                  40                  45

Gly Phe Ile Asp Pro Gly Gly Tyr Asp Tyr Ala Gln Lys Phe
    50                  55                  60

Gln Gly Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Tyr Tyr Leu Asp Tyr Trp Gly Gln Gly Thr
            100                 105                 110

Thr Leu Thr Val Ser Ser Ala Ser Thr Lys
        115                 120
```

<210> SEQ ID NO 24
<211> LENGTH: 107
<212> TYPE: PRT
<213> ORGANISM: Artificial Sequence
<220> FEATURE:
<223> OTHER INFORMATION: Gen1_5072 Humanized Anti-P VL

<400> SEQUENCE: 24

```
Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Asp Gly Thr Val Lys Leu Leu Ile
        35                  40                  45

Tyr Tyr Thr Ser Arg Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln His Gly Asn Thr Leu Pro Trp
                85                  90                  95

Thr Phe Gly Gln Gly Thr Lys Leu Glu Ile Lys
            100                 105
```

<210> SEQ ID NO 25
<211> LENGTH: 107
<212> TYPE: PRT
<213> ORGANISM: Artificial Sequence
<220> FEATURE:
<223> OTHER INFORMATION: Gen1_5072 Humanized Anti-P VL

<400> SEQUENCE: 25

```
Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Gly Asn Thr Leu Pro Trp
                85                  90                  95

Thr Phe Gly Gln Gly Thr Lys Leu Glu Ile Lys
            100                 105
```

<210> SEQ ID NO 26
<211> LENGTH: 107
<212> TYPE: PRT
<213> ORGANISM: Artificial Sequence
<220> FEATURE:
<223> OTHER INFORMATION: Gen1_5072 Humanized Anti-P VL

<400> SEQUENCE: 26

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Gly Ser Thr Leu Pro Trp
                85                  90                  95

Thr Phe Gly Gln Gly Thr Lys Leu Glu Ile Lys
            100                 105
```

<210> SEQ ID NO 27
<211> LENGTH: 107
<212> TYPE: PRT
<213> ORGANISM: Artificial Sequence
<220> FEATURE:
<223> OTHER INFORMATION: Gen1_5072 Humanized Anti-P VL

<400> SEQUENCE: 27

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Gly Gln Thr Leu Pro Trp
                85                  90                  95

Thr Phe Gly Gln Gly Thr Lys Leu Glu Ile Lys
            100                 105
```

<210> SEQ ID NO 28
<211> LENGTH: 107
<212> TYPE: PRT
<213> ORGANISM: Artificial Sequence
<220> FEATURE:
<223> OTHER INFORMATION: Gen1_5072 Humanized Anti-P VL

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Gly Gln Thr Leu Pro Trp
                85                  90                  95

Thr Phe Gly Gln Gly Thr Lys Leu Glu Ile Lys
            100                 105

<210> SEQ ID NO 29
<211> LENGTH: 107
<212> TYPE: PRT
<213> ORGANISM: Artificial Sequence
<220> FEATURE:
<223> OTHER INFORMATION: Gen1_5072 Humanized Anti-P VL

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Gly Ser Thr Leu Pro Tyr
                85                  90                  95

Thr Phe Gly Gln Gly Thr Lys Leu Glu Ile Lys
            100                 105

<210> SEQ ID NO 30
<211> LENGTH: 107
<212> TYPE: PRT
<213> ORGANISM: Artificial Sequence
<220> FEATURE:
<223> OTHER INFORMATION: Gen1_5072 Humanized Anti-P VL

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

```
Leu Asn Trp Tyr Gln Gln Lys Pro Gly Lys Ala Pro Lys Leu Leu Ile
         35                  40                  45

Tyr Tyr Thr Ser Arg Tyr His Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His Gly Gln Thr Leu Pro Trp
                 85                  90                  95

Thr Phe Gly Gln Gly Thr Lys Leu Glu Ile Lys
                100                 105
```

<210> SEQ ID NO 31
<211> LENGTH: 107
<212> TYPE: PRT
<213> ORGANISM: Artificial Sequence
<220> FEATURE:
<223> OTHER INFORMATION: Gen1_5072 Humanized Anti-P VL

<400> SEQUENCE: 31

```
Asp Ile Gln Met Thr Gln Ser Pro Ser Ser Leu Ser Ala Ser Val Gly
 1                5                  10                  15

Asp Arg Val Thr Ile Thr Cys Arg Ala Ser Gln Asp Ile Ser Phe Phe
             20                  25                  30

Leu Asn Trp Tyr Gln Gln Lys Pro Gly Lys Ala Pro Lys Leu Leu Ile
         35                  40                  45

Tyr Tyr Thr Ser Arg Tyr His Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His Gly Ser Thr Leu Pro Tyr
                 85                  90                  95

Thr Phe Gly Gln Gly Thr Lys Leu Glu Ile Lys
                100                 105
```

<210> SEQ ID NO 32
<211> LENGTH: 107
<212> TYPE: PRT
<213> ORGANISM: Artificial Sequence
<220> FEATURE:
<223> OTHER INFORMATION: Gen2_5072 Humanized Anti-P VL

<400> SEQUENCE: 32

```
Asp Ile Gln Met Thr Gln Ser Pro Ser Ser Leu Ser Ala Ser Val Gly
 1                5                  10                  15

Asp Arg Val Thr Ile Thr Cys Arg Ala Ser Gln Asp Ile Ser Phe Phe
             20                  25                  30

Leu Asn Trp Tyr Gln Gln Lys Pro Gly Lys Ala Pro Lys Leu Leu Ile
         35                  40                  45

Tyr Tyr Thr Ser Arg Tyr His Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His Gly Ser Thr Leu Pro Trp
                 85                  90                  95

Thr Phe Gly Gln Gly Thr Lys Val Glu Ile Lys
                100                 105
```

<210> SEQ ID NO 33

<211> LENGTH: 107
<212> TYPE: PRT
<213> ORGANISM: Artificial Sequence
<220> FEATURE:
<223> OTHER INFORMATION: Gen2_5072 Humanized Anti-P VL

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Gly Ala Ser Ser Tyr His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Gly Gln Thr Leu Pro Arg
                85                  90                  95

Thr Phe Gly Gln Gly Thr Lys Val Glu Ile Lys
            100                 105

<210> SEQ ID NO 34
<211> LENGTH: 107
<212> TYPE: PRT
<213> ORGANISM: Artificial Sequence
<220> FEATURE:
<223> OTHER INFORMATION: Gen2_5072 Humanized Anti-P VL

<400> SEQUENCE: 34

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Asp Ile Ser Phe Phe
            20                  25                  30

Leu Asn Trp Tyr Gln Gln Lys Pro Gly Gln Ala Pro Arg Leu Leu Ile
        35                  40                  45

Tyr Tyr Thr Ser Arg Tyr His Ser Gly Ile Pro Asp Arg Phe Ser Gly
50                  55                  60

Ser Gly Ser Gly Thr Asp Phe Thr Leu Thr Ile Ser Arg Leu Glu Pro
65                  70                  75                  80

Glu Asp Phe Ala Val Phe Tyr Cys Gln His Gly Ser Thr Leu Pro Arg
                85                  90                  95

Thr Phe Gly Gln Gly Thr Lys Val Glu Ile Lys
            100                 105

<210> SEQ ID NO 35
<211> LENGTH: 107
<212> TYPE: PRT
<213> ORGANISM: Artificial Sequence
<220> FEATURE:
<223> OTHER INFORMATION: Gen2_5072 Humanized Anti-P VL

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

```
Tyr Tyr Thr Ser Arg Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln His Gly Ser Thr Leu Pro Tyr
                85                  90                  95

Thr Phe Gly Gln Gly Thr Lys Val Glu Ile Lys
            100                 105
```

<210> SEQ ID NO 36
<211> LENGTH: 107
<212> TYPE: PRT
<213> ORGANISM: Artificial Sequence
<220> FEATURE:
<223> OTHER INFORMATION: Gen2_5072 Humanized Anti-P VL

<400> SEQUENCE: 36

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
                20                  25                  30

Leu Asn Trp Tyr Gln Gln Lys Pro Gly Lys Ala Pro Lys Leu Leu Ile
            35                  40                  45

Tyr Tyr Thr Ser Arg Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Gly Ser Thr Leu Pro Arg
                85                  90                  95

Thr Phe Gly Gln Gly Thr Lys Val Glu Ile Lys
            100                 105
```

<210> SEQ ID NO 37
<211> LENGTH: 107
<212> TYPE: PRT
<213> ORGANISM: Artificial Sequence
<220> FEATURE:
<223> OTHER INFORMATION: Gen2_5072 Humanized Anti-P VL

<400> SEQUENCE: 37

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
                20                  25                  30

Leu Asn Trp Tyr Gln Gln Lys Pro Gly Lys Ala Pro Lys Leu Leu Ile
            35                  40                  45

Tyr Tyr Thr Ser Arg Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Gly Gln Thr Leu Pro Trp
                85                  90                  95

Thr Phe Gly Gln Gly Thr Lys Val Glu Ile Lys
            100                 105
```

<210> SEQ ID NO 38
<211> LENGTH: 107
<212> TYPE: PRT
<213> ORGANISM: Artificial Sequence

```
<220> FEATURE:
<223> OTHER INFORMATION: h9401-L1 Humanized Anti-P VL

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Gly Asn Thr Leu Pro Trp
                85                  90                  95

Thr Phe Gly Gln Gly Thr Lys Leu Glu Ile Lys
            100                 105

<210> SEQ ID NO 39
<211> LENGTH: 107
<212> TYPE: PRT
<213> ORGANISM: Artificial Sequence
<220> FEATURE:
<223> OTHER INFORMATION: h9401-L2 Humanized Anti-P VL

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Val Lys Leu Leu Ile
        35                  40                  45

Tyr Tyr Thr Ser Arg Tyr His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Gly Asn Thr Leu Pro Trp
                85                  90                  95

Thr Phe Gly Gln Gly Thr Lys Leu Glu Ile Lys
            100                 105

<210> SEQ ID NO 40
<211> LENGTH: 120
<212> TYPE: PRT
<213> ORGANISM: Artificial Sequence
<220> FEATURE:
<223> OTHER INFORMATION: 3196 Humanized Anti-P VH

<400> SEQUENCE: 40

Glu Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Val Lys Ser Tyr Asn Pro Ala
50                  55                  60
```

```
Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Gly Asp Gly Tyr Tyr Ser Phe Asp Tyr Trp Gly Gln
            100                 105                 110

Gly Thr Thr Val Thr Val Ser Ser
            115                 120

<210> SEQ ID NO 41
<211> LENGTH: 120
<212> TYPE: PRT
<213> ORGANISM: Artificial Sequence
<220> FEATURE:
<223> OTHER INFORMATION: 3196 Humanized Anti-P VH

<400> SEQUENCE: 41

Glu Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Gly Val Gly Trp Ile Arg Gln Pro Pro Gly Lys Ala Leu Glu
            35                  40                  45

Trp Leu Ala His Ile Trp Trp Asp Asp Val Lys Ser Tyr Asn Pro Ala
        50                  55                  60

Leu Lys Ser Arg Leu Thr Ile Thr Lys Asp Thr Ser Lys Asn Gln Val
65                  70                  75                  80

Val Leu Thr Ile Thr Asn Val Asp Pro Val Asp Thr Ala Thr Tyr Tyr
                85                  90                  95

Cys Ala Arg Ile Gly Asp Gly Tyr Tyr Ser Phe Asp Tyr Trp Gly Gln
            100                 105                 110

Gly Thr Thr Leu Thr Val Ser Ser
            115                 120

<210> SEQ ID NO 42
<211> LENGTH: 120
<212> TYPE: PRT
<213> ORGANISM: Artificial Sequence
<220> FEATURE:
<223> OTHER INFORMATION: 3196 Humanized Anti-P VH

<400> SEQUENCE: 42

Glu Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Gly Val Gly Trp Ile Arg Gln Pro Pro Gly Lys Ala Leu Glu
            35                  40                  45

Trp Leu Ala His Ile Trp Trp Asp Asp Val Lys Ser Tyr Asn Pro Ala
        50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Gly Asp Gly Tyr Tyr Ser Phe Asp Tyr Trp Gly Gln
            100                 105                 110

Gly Thr Thr Val Thr Val Ser Ser
            115                 120
```

-continued

```
<210> SEQ ID NO 43
<211> LENGTH: 120
<212> TYPE: PRT
<213> ORGANISM: Artificial Sequence
<220> FEATURE:
<223> OTHER INFORMATION: h3196-H1 Humanized Anti-P VH

<400> SEQUENCE: 43
```

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Val Lys Ser Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Gly Asp Gly Tyr Tyr Ser Phe Asp Tyr Trp Gly Gln
            100                 105                 110

Gly Thr Thr Val Thr Val Ser Ser
        115                 120

```
<210> SEQ ID NO 44
<211> LENGTH: 120
<212> TYPE: PRT
<213> ORGANISM: Artificial Sequence
<220> FEATURE:
<223> OTHER INFORMATION: h3196-H2 Humanized Anti-P VH

<400> SEQUENCE: 44
```

Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Val Lys Ser Tyr Asn Pro Ala
    50                  55                  60

Leu Lys Ser Arg Leu Thr Ile Thr Lys Asp Thr Ser Lys Asn Gln Val
65                  70                  75                  80

Val Leu Thr Ile Thr Asn Val Asp Pro Val Asp Thr Ala Thr Tyr Tyr
                85                  90                  95

Cys Ala Arg Ile Gly Asp Gly Tyr Tyr Ser Phe Asp Tyr Trp Gly Gln
            100                 105                 110

Gly Thr Thr Leu Thr Val Ser Ser
        115                 120

```
<210> SEQ ID NO 45
<211> LENGTH: 107
<212> TYPE: PRT
<213> ORGANISM: Artificial Sequence
<220> FEATURE:
<223> OTHER INFORMATION: 3196 Humanized Anti-P VL

<400> SEQUENCE: 45
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Asp Ala
            20                  25                  30

Val Ala Trp Tyr Gln Gln Lys Pro Gly Lys Ala Pro Lys Leu Leu Ile
        35                  40                  45

Tyr Ser Pro Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Lys Leu Glu Ile Lys
            100                 105

<210> SEQ ID NO 46
<211> LENGTH: 107
<212> TYPE: PRT
<213> ORGANISM: Artificial Sequence
<220> FEATURE:
<223> OTHER INFORMATION: 3196 Humanized Anti-P VL

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Asp Ala
            20                  25                  30

Val Ala Trp Phe Gln Gln Lys Pro Gly Lys Ala Pro Lys Leu Leu Ile
        35                  40                  45

Tyr Ser Pro Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Lys Leu Glu Ile Lys
            100                 105

<210> SEQ ID NO 47
<211> LENGTH: 107
<212> TYPE: PRT
<213> ORGANISM: Artificial Sequence
<220> FEATURE:
<223> OTHER INFORMATION: 3196 Humanized Anti-P VL

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Asp Ala
            20                  25                  30

Val Ala Trp Phe Gln Gln Lys Pro Gly Lys Ala Pro Lys Leu Leu Ile
        35                  40                  45

Tyr Ser Pro Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Leu Ala Thr Tyr Tyr Cys Gln Gln His Tyr Ser Thr Pro Trp
                85                  90                  95

```
Thr Phe Gly Gln Gly Thr Lys Leu Glu Ile Lys
            100                 105

<210> SEQ ID NO 48
<211> LENGTH: 107
<212> TYPE: PRT
<213> ORGANISM: Artificial Sequence
<220> FEATURE:
<223> OTHER INFORMATION: h3196-L1 Humanized Anti-P VL

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Asp Ala
            20                  25                  30

Val Ala Trp Tyr Gln Gln Lys Pro Gly Lys Ala Pro Lys Leu Leu Ile
        35                  40                  45

Tyr Ser Pro Ser Tyr Arg Tyr Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Lys Leu Glu Ile Lys
            100                 105

<210> SEQ ID NO 49
<211> LENGTH: 107
<212> TYPE: PRT
<213> ORGANISM: Artificial Sequence
<220> FEATURE:
<223> OTHER INFORMATION: h3196-L2 Humanized Anti-P VL

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Asp Ala
            20                  25                  30

Val Ala Trp Phe Gln Gln Lys Pro Gly Lys Ala Pro Lys Leu Leu Ile
        35                  40                  45

Tyr Ser Pro Ser Tyr Arg Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Gln Gln His Tyr Ser Thr Pro Trp
                85                  90                  95

Thr Phe Gly Gln Gly Thr Lys Leu Glu Ile Lys
            100                 105

<210> SEQ ID NO 50
<211> LENGTH: 107
<212> TYPE: PRT
<213> ORGANISM: Artificial Sequence
<220> FEATURE:
<223> OTHER INFORMATION: h3196-L3 Humanized Anti-P VL

<400> SEQUENCE: 50

Asp Ile Gln Met Thr Gln Ser Pro Ser Ser Leu Ser Ala Ser Val Gly
1               5                   10                  15
```

-continued

```
Asp Arg Val Thr Ile Thr Cys Arg Ala Ser Gln Asp Val Ser Asp Ala
            20                  25                  30

Val Ala Trp Phe Gln Gln Lys Pro Gly Lys Ala Pro Lys Leu Leu Ile
        35                  40                  45

Tyr Ser Pro Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Leu Ala Thr Tyr Tyr Cys Gln Gln His Tyr Ser Thr Pro Trp
                85                  90                  95

Thr Phe Gly Gln Gly Thr Lys Leu Glu Ile Lys
            100                 105
```

<210> SEQ ID NO 51
<211> LENGTH: 125
<212> TYPE: PRT
<213> ORGANISM: Artificial Sequence
<220> FEATURE:
<223> OTHER INFORMATION: Humanized Anti-P VH

<400> SEQUENCE: 51

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Gly
            20                  25                  30

Tyr Trp Ile Phe Trp Val Arg Gln Ala Pro Gly Lys Gly Leu Glu Trp
        35                  40                  45

Val Ser Gly Ile Tyr Ser Gly Ser Ser Gly Thr Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Ser Val Asp Gly Ile Asp Ser Tyr Asp Ala Ala Phe
            100                 105                 110

Asn Leu Trp Gly Gln Gly Thr Leu Val Thr Val Ser Ser
        115                 120                 125
```

<210> SEQ ID NO 52
<211> LENGTH: 125
<212> TYPE: PRT
<213> ORGANISM: Artificial Sequence
<220> FEATURE:
<223> OTHER INFORMATION: Humanized Anti-P VH

<400> SEQUENCE: 52

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Gly
            20                  25                  30

Tyr Trp Ile Phe Trp Val Arg Gln Ala Pro Gly Lys Gly Leu Glu Leu
        35                  40                  45

Val Gly Gly Ile Tyr Ser Gly Ser Ser Gly Thr Thr Tyr Tyr Ala Asp
    50                  55                  60

Ser Val Lys Gly Arg Phe Thr Ile Ser Lys Asp Asn Ser Lys Asn Thr
65                  70                  75                  80

Val Tyr Leu Gln Met Asn Ser Leu Arg Ala Glu Asp Thr Ala Val Tyr
                85                  90                  95
```

```
Tyr Cys Ala Arg Ser Val Asp Gly Ile Asp Ser Tyr Asp Ala Ala Phe
            100                 105                 110

Asn Leu Trp Gly Gln Gly Thr Leu Val Thr Val Ser Ser
        115                 120                 125

<210> SEQ ID NO 53
<211> LENGTH: 125
<212> TYPE: PRT
<213> ORGANISM: Artificial Sequence
<220> FEATURE:
<223> OTHER INFORMATION: Humanized Anti-P VH

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Gly
            20                  25                  30

Tyr Trp Ile Phe Trp Val Arg Gln Ala Pro Gly Lys Gly Leu Glu Leu
        35                  40                  45

Val Gly Gly Ile Tyr Ser Gly Ser Ser Gly Thr Thr Tyr Tyr Ala Asp
    50                  55                  60

Trp Ala Lys Gly Arg Phe Thr Ile Ser Lys Asp Asn Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Ser Val Asp Gly Ile Asp Ser Tyr Asp Ala Ala Phe
            100                 105                 110

Asn Leu Trp Gly Gln Gly Thr Leu Val Thr Val Ser Ser
        115                 120                 125

<210> SEQ ID NO 54
<211> LENGTH: 125
<212> TYPE: PRT
<213> ORGANISM: Artificial Sequence
<220> FEATURE:
<223> OTHER INFORMATION: Humanized Anti-P VH

<400> SEQUENCE: 54

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Gly
            20                  25                  30

Tyr Trp Ile Phe Trp Val Arg Gln Ala Pro Gly Lys Gly Leu Glu Leu
        35                  40                  45

Val Gly Gly Ile Tyr Ser Gly Ser Ser Gly Thr Thr Tyr Tyr Ala Asp
    50                  55                  60

Ser Val Lys Gly Arg Phe Thr Ile Ser Lys Asp Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Ser Val Asp Gly Ile Asp Ser Tyr Asp Ala Ala Phe
            100                 105                 110

Asn Leu Trp Gly Gln Gly Thr Leu Val Thr Val Ser Ser
        115                 120                 125

<210> SEQ ID NO 55
<211> LENGTH: 125
<212> TYPE: PRT
```

<213> ORGANISM: Artificial Sequence
<220> FEATURE:
<223> OTHER INFORMATION: Humanized Anti-P VH

<400> SEQUENCE: 55

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Gly
            20                  25                  30

Tyr Trp Ile Phe Trp Val Arg Gln Ala Pro Gly Lys Gly Leu Glu Leu
        35                  40                  45

Val Gly Gly Ile Tyr Ser Gly Ser Ser Gly Thr Thr Tyr Tyr Ala Asp
    50                  55                  60

Trp Ala Lys Gly Arg Phe Thr Ile Ser Lys Asp Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Ser Val Asp Gly Ile Asp Ser Tyr Asp Ala Ala Phe
            100                 105                 110

Asn Leu Trp Gly Gln Gly Thr Leu Val Thr Val Ser Ser
        115                 120                 125

<210> SEQ ID NO 56
<211> LENGTH: 125
<212> TYPE: PRT
<213> ORGANISM: Artificial Sequence
<220> FEATURE:
<223> OTHER INFORMATION: Humanized Anti-P VH

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Ser
            20                  25                  30

Tyr Trp Ile Phe Trp Val Arg Gln Ala Pro Gly Lys Gly Leu Glu Trp
        35                  40                  45

Val Ser Gly Ile Tyr Ser Ser Gly Arg Met Tyr Tyr Ala Asp Ser
    50                  55                  60

Val Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Lys Ser Ala Asp Gly Ser Asp Ser Tyr Asp Ala Tyr Phe Thr
            100                 105                 110

Leu Trp Gly Gln Gly Thr Leu Val Thr Val Ser Ser
        115                 120                 125

<210> SEQ ID NO 57
<211> LENGTH: 125
<212> TYPE: PRT
<213> ORGANISM: Artificial Sequence
<220> FEATURE:
<223> OTHER INFORMATION: Humanized Anti-P VH

<400> SEQUENCE: 57

Glu Val Gln Leu Leu Glu Ser Gly Gly Gly Leu Val Gln Pro Gly Gly
1               5                   10                  15

Ser Leu Arg Ile Ser Cys Ala Ala Ser Gly Phe Ser Phe Ser Ser Ser
            20                  25                  30

Tyr Trp Ile Phe Trp Val Arg Gln Ala Pro Gly Lys Gly Leu Glu Leu
         35                  40                  45

Ile Gly Gly Ile Tyr Ser Ser Ser Gly Arg Met Tyr Tyr Ala Asp Ser
     50                  55                  60

Val Lys Gly Arg Phe Thr Ile Ser Lys Asp Asn Ser Lys Asn Thr Met
 65                  70                  75                  80

Tyr Leu Gln Met Asn Ser Leu Arg Ala Glu Asp Thr Ala Val Tyr Tyr
                 85                  90                  95

Cys Ala Arg Ser Ala Asp Gly Ser Asp Ser Tyr Asp Ala Tyr Phe Thr
                100                 105                 110

Leu Trp Gly Gln Gly Thr Leu Val Thr Val Ser Ser
        115                 120                 125

<210> SEQ ID NO 58
<211> LENGTH: 125
<212> TYPE: PRT
<213> ORGANISM: Artificial Sequence
<220> FEATURE:
<223> OTHER INFORMATION: Humanized Anti-P VH

<400> SEQUENCE: 58

Glu Val Gln Leu Leu Glu Ser Gly Gly Gly Leu Val Gln Pro Gly Gly
 1               5                  10                  15

Ser Leu Arg Ile Ser Cys Ala Ala Ser Gly Phe Ser Phe Ser Ser Ser
                 20                  25                  30

Tyr Trp Ile Phe Trp Val Arg Gln Ala Pro Gly Lys Gly Leu Glu Leu
         35                  40                  45

Ile Gly Gly Ile Tyr Ser Ser Ser Gly Arg Met Tyr Tyr Ala Asp Trp
     50                  55                  60

Ala Lys Gly Arg Phe Thr Ile Ser Lys Asp Asn Ser Lys Asn Thr Met
 65                  70                  75                  80

Tyr Leu Gln Met Asn Ser Leu Arg Ala Glu Asp Thr Ala Val Tyr Tyr
                 85                  90                  95

Cys Ala Arg Ser Ala Asp Gly Ser Asp Ser Tyr Asp Ala Tyr Phe Thr
                100                 105                 110

Leu Trp Gly Gln Gly Thr Leu Val Thr Val Ser Ser
        115                 120                 125

<210> SEQ ID NO 59
<211> LENGTH: 125
<212> TYPE: PRT
<213> ORGANISM: Artificial Sequence
<220> FEATURE:
<223> OTHER INFORMATION: Humanized Anti-P VH

<400> SEQUENCE: 59

Glu Val Gln Leu Leu Glu Ser Gly Gly Gly Leu Val Gln Pro Gly Gly
 1               5                  10                  15

Ser Leu Arg Ile Ser Cys Ala Ala Ser Gly Phe Ser Phe Ser Ser Ser
                 20                  25                  30

Tyr Trp Ile Phe Trp Val Arg Gln Ala Pro Gly Lys Gly Leu Glu Leu
         35                  40                  45

Ile Gly Gly Ile Tyr Ser Ser Ser Gly Arg Met Tyr Tyr Ala Asp Ser
     50                  55                  60

Val Lys Gly Arg Phe Thr Ile Ser Lys Asp Ser Ser Lys Asn Thr Met
 65                  70                  75                  80

Tyr Leu Gln Met Asn Ser Leu Arg Ala Glu Asp Thr Ala Val Tyr Tyr

```
                85                  90                  95

Cys Ala Arg Ser Ala Asp Gly Ser Asp Ser Tyr Asp Ala Tyr Phe Thr
            100                 105                 110

Leu Trp Gly Gln Gly Thr Leu Val Thr Val Ser Ser Ser
        115                 120                 125

<210> SEQ ID NO 60
<211> LENGTH: 125
<212> TYPE: PRT
<213> ORGANISM: Artificial Sequence
<220> FEATURE:
<223> OTHER INFORMATION: Humanized Anti-P VH

<400> SEQUENCE: 60

Glu Val Gln Leu Leu Glu Ser Gly Gly Gly Leu Val Gln Pro Gly Gly
1               5                   10                  15

Ser Leu Arg Ile Ser Cys Ala Ala Ser Gly Phe Ser Phe Ser Ser Ser
            20                  25                  30

Tyr Trp Ile Phe Trp Val Arg Gln Ala Pro Gly Lys Gly Leu Glu Leu
        35                  40                  45

Ile Gly Gly Ile Tyr Ser Ser Ser Gly Arg Met Tyr Tyr Ala Asp Trp
50                  55                  60

Ala Lys Gly Arg Phe Thr Ile Ser Lys Asp Ser Ser Lys Asn Thr Met
65                  70                  75                  80

Tyr Leu Gln Met Asn Ser Leu Arg Ala Glu Asp Thr Ala Val Tyr Tyr
                85                  90                  95

Cys Ala Arg Ser Ala Asp Gly Ser Asp Ser Tyr Asp Ala Tyr Phe Thr
            100                 105                 110

Leu Trp Gly Gln Gly Thr Leu Val Thr Val Ser Ser Ser
        115                 120                 125

<210> SEQ ID NO 61
<211> LENGTH: 110
<212> TYPE: PRT
<213> ORGANISM: Artificial Sequence
<220> FEATURE:
<223> OTHER INFORMATION: Humanized Anti-P VL

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Asp Asn Ile Tyr Ser Leu
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Asp Tyr Asn Tyr
                85                  90                  95

Leu Asp Val Ala Phe Gly Gly Gly Thr Lys Val Glu Ile Lys
            100                 105                 110

<210> SEQ ID NO 62
<211> LENGTH: 110
<212> TYPE: PRT
<213> ORGANISM: Artificial Sequence
<220> FEATURE:
```

<223> OTHER INFORMATION: Humanized Anti-P VL

<400> SEQUENCE: 62

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Asp Asn Ile Tyr Ser Leu
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Phe Ala Thr Tyr Tyr Cys Gln Gln His Tyr Asp Tyr Asn Tyr
                85                  90                  95

Leu Asp Val Ala Phe Gly Gly Gly Thr Lys Val Glu Ile Lys
            100                 105                 110
```

<210> SEQ ID NO 63
<211> LENGTH: 110
<212> TYPE: PRT
<213> ORGANISM: Artificial Sequence
<220> FEATURE:
<223> OTHER INFORMATION: Humanized Anti-P VL

<400> SEQUENCE: 63

```
Asp Tyr Gln Leu Thr Gln Ser Pro Ser Ser Leu Ser Ala Ser Val Gly
1               5                   10                  15

Asp Arg Val Thr Ile Thr Cys Arg Ala Ser Asp Asn Ile Tyr Ser Leu
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Phe Ala Thr Tyr Tyr Cys Gln Gln His Tyr Asp Tyr Asn Tyr
                85                  90                  95

Leu Asp Val Ala Phe Gly Gly Gly Thr Lys Val Glu Ile Lys
            100                 105                 110
```

<210> SEQ ID NO 64
<211> LENGTH: 110
<212> TYPE: PRT
<213> ORGANISM: Artificial Sequence
<220> FEATURE:
<223> OTHER INFORMATION: Humanized Anti-P VL

<400> SEQUENCE: 64

```
Asp Ile Gln Leu Thr Gln Ser Pro Ser Ser Leu Ser Ala Ser Val Gly
1               5                   10                  15

Asp Arg Val Thr Ile Thr Cys Arg Ala Ser Asp Asn Ile Tyr Ser Leu
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Val Gln Pro
```

```
                 65                  70                  75                  80
Glu Asp Ala Ala Thr Tyr Tyr Cys Gln Gln His Tyr Asp Tyr Asn Tyr
                         85                  90                  95

Leu Asp Val Ala Phe Gly Gly Gly Thr Lys Val Glu Ile Lys
                100                 105                 110

<210> SEQ ID NO 65
<211> LENGTH: 110
<212> TYPE: PRT
<213> ORGANISM: Artificial Sequence
<220> FEATURE:
<223> OTHER INFORMATION: Humanized Anti-P VL

<400> SEQUENCE: 65

Asp Tyr Gln Leu Thr Gln Ser Pro Ser Leu Ser Ala Ser Val Gly
1               5                   10                  15

Asp Arg Val Thr Ile Thr Cys Arg Ala Ser Asp Asn Ile Tyr Ser Leu
                20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Val Gln Pro
65                  70                  75                  80

Glu Asp Ala Ala Thr Tyr Tyr Cys Gln Gln His Tyr Asp Tyr Asn Tyr
                85                  90                  95

Leu Asp Val Ala Phe Gly Gly Gly Thr Lys Val Glu Ile Lys
                100                 105                 110

<210> SEQ ID NO 66
<211> LENGTH: 110
<212> TYPE: PRT
<213> ORGANISM: Artificial Sequence
<220> FEATURE:
<223> OTHER INFORMATION: Humanized Anti-P VL

<400> SEQUENCE: 66

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Tyr Ser Asn
                20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Trp Asp Tyr Asp Tyr
                85                  90                  95

Ile Asp Val Ala Phe Gly Gly Gly Thr Lys Val Glu Ile Lys
                100                 105                 110

<210> SEQ ID NO 67
<211> LENGTH: 110
<212> TYPE: PRT
<213> ORGANISM: Artificial Sequence
<220> FEATURE:
<223> OTHER INFORMATION: Humanized Anti-P VL

<400> SEQUENCE: 67
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Tyr Ser Asn
            20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Val Gln Pro
65                  70                  75                  80

Glu Asp Phe Ala Thr Tyr Tyr Cys Gln Gln His Trp Asp Tyr Asp Tyr
                85                  90                  95

Ile Asp Val Ala Phe Gly Gly Gly Thr Lys Val Glu Ile Lys
            100                 105                 110

<210> SEQ ID NO 68
<211> LENGTH: 110
<212> TYPE: PRT
<213> ORGANISM: Artificial Sequence
<220> FEATURE:
<223> OTHER INFORMATION: Humanized Anti-P VL

<400> SEQUENCE: 68

Asp Tyr Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Tyr Ser Asn
            20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Val Gln Pro
65                  70                  75                  80

Glu Asp Phe Ala Thr Tyr Tyr Cys Gln Gln His Trp Asp Tyr Asp Tyr
                85                  90                  95

Ile Asp Val Ala Phe Gly Gly Gly Thr Lys Val Glu Ile Lys
            100                 105                 110

<210> SEQ ID NO 69
<211> LENGTH: 110
<212> TYPE: PRT
<213> ORGANISM: Artificial Sequence
<220> FEATURE:
<223> OTHER INFORMATION: Humanized Anti-P VL

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Tyr Ser Asn
            20                  25                  30

Leu Ala Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Thr Asp Phe Thr Leu Thr Ile Ser Ser Val Gln Pro
65                  70                  75                  80

Glu Asp Ala Ala Thr Tyr Tyr Cys Gln Gln His Trp Asp Tyr Asp Tyr
```

```
              85                  90                  95

Ile Asp Val Ala Phe Gly Gly Gly Thr Lys Val Glu Ile Lys
            100                 105                 110

<210> SEQ ID NO 70
<211> LENGTH: 110
<212> TYPE: PRT
<213> ORGANISM: Artificial Sequence
<220> FEATURE:
<223> OTHER INFORMATION: Humanized Anti-P VL

<400> SEQUENCE: 70

Asp Tyr Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Tyr Ser Asn
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Ala Ala Thr Tyr Tyr Cys Gln Gln His Trp Asp Tyr Asp Tyr
                85                  90                  95

Ile Asp Val Ala Phe Gly Gly Gly Thr Lys Val Glu Ile Lys
            100                 105                 110

<210> SEQ ID NO 71
<211> LENGTH: 125
<212> TYPE: PRT
<213> ORGANISM: Artificial Sequence
<220> FEATURE:
<223> OTHER INFORMATION: Humanized Anti-ALB VH

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser Ala Ser Thr Lys
        115                 120                 125

<210> SEQ ID NO 72
<211> LENGTH: 116
<212> TYPE: PRT
<213> ORGANISM: Artificial Sequence
<220> FEATURE:
<223> OTHER INFORMATION: Humanized Anti-ALB VL

<400> SEQUENCE: 72
```

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65              70                  75                  80

Pro Glu Asp Phe Ala Thr Tyr Tyr Cys Gly Gly Tyr Ser Ser Ile
                85                  90                  95

Ser Asp Thr Thr Phe Gly Gly Gly Thr Lys Val Glu Ile Lys Arg Thr
            100                 105                 110

Val Ala Ala Pro
        115

<210> SEQ ID NO 73
<211> LENGTH: 119
<212> TYPE: PRT
<213> ORGANISM: Artificial Sequence
<220> FEATURE:
<223> OTHER INFORMATION: Humanized Lama Glama LVP058 Anti-P HC

<400> SEQUENCE: 73

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Ile Ser Ser Ile Ile
            20                  25                  30

His Met Ala Trp Tyr Arg Gln Ala Pro Gly Lys Gln Arg Glu Leu Val
        35                  40                  45

Ala Glu Ile Ser Arg Val Gly Thr Thr Val Tyr Ala Asp Ser Val Lys
    50                  55                  60

Gly Arg Phe Thr Ile Ser Arg Asp Asp Ala Lys Asn Thr Val Thr Leu
65              70                  75                  80

Gln Met Asn Ser Leu Lys Pro Glu Asp Thr Ala Val Tyr Tyr Cys Asn
                85                  90                  95

Ala Leu Gln Tyr Glu Lys His Gly Gly Ala Asp Tyr Trp Gly Gln Gly
            100                 105                 110

Thr Gln Val Thr Val Ser Ser
        115

<210> SEQ ID NO 74
<211> LENGTH: 119
<212> TYPE: PRT
<213> ORGANISM: Artificial Sequence
<220> FEATURE:
<223> OTHER INFORMATION: Humanized LVP058 Anti-P HC

<400> SEQUENCE: 74

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Ser Ser Ile Ile
            20                  25                  30

His Met Ala Trp Phe Arg Gln Ala Pro Gly Lys Glu Arg Glu Leu Val
        35                  40                  45

Ser Glu Ile Ser Arg Val Gly Thr Thr Val Tyr Ala Asp Ser Val Lys

```
                    50                  55                  60
Gly Arg Phe Thr Ile Ser Arg Asp Asn Ser Lys Asn Thr Leu Tyr Leu
 65                  70                  75                  80

Gln Met Asn Ser Leu Lys Pro Glu Asp Thr Ala Val Tyr Tyr Cys Asn
                 85                  90                  95

Ala Leu Gln Tyr Glu Lys His Gly Gly Ala Asp Tyr Trp Gly Gln Gly
            100                 105                 110

Thr Leu Val Thr Val Ser Ser
        115

<210> SEQ ID NO 75
<211> LENGTH: 119
<212> TYPE: PRT
<213> ORGANISM: Artificial Sequence
<220> FEATURE:
<223> OTHER INFORMATION: Humanized LVP058 Anti-P HC

<400> SEQUENCE: 75

Glu Val Gln Leu Val Glu Ser Gly Gly Gly Leu Val Gln Pro Gly Gly
  1               5                  10                  15

Ser Leu Arg Leu Ser Cys Ala Ala Ser Gly Arg Ile Ser Ser Ile Ile
             20                  25                  30

His Met Ala Trp Val Arg Gln Ala Pro Gly Lys Gln Arg Glu Leu Val
         35                  40                  45

Ser Glu Ile Ser Arg Val Gly Thr Thr Val Tyr Ala Asp Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Asn
                 85                  90                  95

Ala Leu Gln Tyr Glu Lys His Gly Gly Ala Asp Tyr Trp Gly Gln Gly
            100                 105                 110

Thr Leu Val Thr Val Ser Ser
        115

<210> SEQ ID NO 76
<211> LENGTH: 119
<212> TYPE: PRT
<213> ORGANISM: Artificial Sequence
<220> FEATURE:
<223> OTHER INFORMATION: Humanized Anti-Properdin Vhh

<400> SEQUENCE: 76

Glu Val Gln Leu Leu Glu Ser Gly Gly Gly Leu Val Gln Ala Gly Gly
  1               5                  10                  15

Ser Leu Arg Leu Ser Cys Ala Ala Ser Gly Arg Ile Ser Ser Ile Ile
             20                  25                  30

His Met Ala Trp Tyr Arg Gln Ala Pro Gly Lys Gln Arg Glu Leu Val
         35                  40                  45

Ser Glu Ile Ser Arg Val Gly Thr Thr Val Tyr Ala Asp Ser Val Lys
     50                  55                  60

Gly Arg Phe Thr Ile Ser Arg Asp Asp Ala Lys Asn Thr Val Thr Leu
 65                  70                  75                  80

Gln Met Asn Ser Leu Lys Pro Glu Asp Thr Ala Val Tyr Tyr Cys Asn
                 85                  90                  95

Ala Leu Gln Tyr Glu Ala His Gly Gly Ala Ser Tyr Trp Gly Gln Gly
            100                 105                 110
```

Thr Gln Val Thr Val Ser Ser
        115

<210> SEQ ID NO 77
<211> LENGTH: 119
<212> TYPE: PRT
<213> ORGANISM: Artificial Sequence
<220> FEATURE:
<223> OTHER INFORMATION: Humanized Vicugna pacos Anti-Properdin Vhh

<400> SEQUENCE: 77

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Ile Ser Ile Ile
            20                  25                  30

His Met Ala Trp Tyr Arg Gln Ala Pro Gly Lys Gln Arg Glu Leu Val
        35                  40                  45

Ala Glu Ile Ser Arg Ile Gly Thr Thr Val Tyr Ala Glu Ser Val Ala
    50                  55                  60

Gly Arg Phe Thr Ile Ser Arg Asp Asp Ala Lys Asn Thr Val Thr Leu
65                  70                  75                  80

Gln Met Asn Ser Leu Lys Pro Glu Asp Thr Ala Val Tyr Tyr Cys Asn
                85                  90                  95

Ala Leu Gln Tyr Glu Lys His Gly Gly Ala Ser Tyr Trp Gly Gln Gly
            100                 105                 110

Thr Gln Val Thr Val Ser Gly
        115

<210> SEQ ID NO 78
<211> LENGTH: 119
<212> TYPE: PRT
<213> ORGANISM: Artificial Sequence
<220> FEATURE:
<223> OTHER INFORMATION: Humanized Vicugna pacos Anti-Properdin Vhh

<400> SEQUENCE: 78

Gln Val Gln Val Val Glu Ser Gly Gly Gly Leu Arg Gln Thr Gly Gly
1               5                   10                  15

Ser Leu Arg Leu Ser Cys Thr Ala Ser Gly Arg Ile Phe Glu Val Asn
            20                  25                  30

Met Met Ala Trp Tyr Arg Gln Ala Pro Gly Lys Gln Arg Glu Leu Val
        35                  40                  45

Ala Glu Ile Ser Arg Val Gly Thr Thr Val Tyr Ala Asp Ser Val Lys
    50                  55                  60

Gly Arg Phe Thr Ile Ser Arg Asp Ser Ala Lys Asn Thr Val Thr Leu
65                  70                  75                  80

Gln Met Asn Ser Leu Lys Ser Glu Asp Thr Ala Val Tyr Tyr Cys Asn
                85                  90                  95

Ala Leu Gln Tyr Asp Arg Tyr Gly Gly Ala Glu Tyr Trp Gly Gln Gly
            100                 105                 110

Thr Gln Val Thr Val Ser Ser
        115

<210> SEQ ID NO 79
<211> LENGTH: 119
<212> TYPE: PRT
<213> ORGANISM: Artificial Sequence
<220> FEATURE:
<223> OTHER INFORMATION: Humanized Vicugna pacos Anti-Properdin Vhh

<400> SEQUENCE: 79

```
Gln Val Gln Leu Val Glu Ser Gly Gly Gly Leu Arg Gln Thr Gly Glu
1               5                   10                  15

Ser Leu Arg Leu Ser Cys Thr Ala Ser Gly Arg Ile Phe Glu Val Asn
            20                  25                  30

Met Met Ala Trp Tyr Arg Gln Ala Pro Gly Lys Gln Arg Glu Leu Val
        35                  40                  45

Ala Glu Ile Ser Arg Val Gly Thr Thr Thr Tyr Ala Asp Ser Val Lys
    50                  55                  60

Gly Arg Phe Thr Ile Ser Arg Asp Ser Ala Lys Asn Thr Val Thr Leu
65                  70                  75                  80

Gln Met Asn Ser Leu Lys Ser Glu Asp Thr Ala Val Tyr Tyr Cys Asn
                85                  90                  95

Ala Leu Gln Tyr Asp Arg Tyr Gly Gly Ala Glu Tyr Trp Gly Gln Gly
            100                 105                 110

Thr Gln Val Thr Val Ser Gly
        115
```

<210> SEQ ID NO 80
<211> LENGTH: 119
<212> TYPE: PRT
<213> ORGANISM: Artificial Sequence
<220> FEATURE:
<223> OTHER INFORMATION: Humanized Vicugna pacos Anti-P Vhh

<400> SEQUENCE: 80

```
Gln Val Gln Leu Ala Glu Ser Gly Gly Gly Leu Val Gln Ala Gly Asp
1               5                   10                  15

Ser Leu Lys Leu Ser Cys Thr Ala Ser Gly Arg Ile Phe Glu Val Asn
            20                  25                  30

Met Met Ala Trp Tyr Arg Gln Ala Pro Gly Lys Asp Arg Glu Leu Val
        35                  40                  45

Ala Glu Ile Ser Arg Val Gly Thr Thr Thr Tyr Ala Asp Ser Val Lys
    50                  55                  60

Gly Arg Phe Thr Ile Ser Arg Asp Ser Ala Lys Asn Thr Val Thr Leu
65                  70                  75                  80

Gln Met Asn Ser Leu Lys Ser Glu Asp Thr Ala Val Tyr Tyr Cys Asn
                85                  90                  95

Ala Leu Gln Tyr Ser Arg Tyr Gly Gly Ala Glu Tyr Trp Gly Gln Gly
            100                 105                 110

Thr Gln Val Thr Val Ser Gly
        115
```

<210> SEQ ID NO 81
<211> LENGTH: 129
<212> TYPE: PRT
<213> ORGANISM: Artificial Sequence
<220> FEATURE:
<223> OTHER INFORMATION: Humanized Camelidae Anti-P Fab - Vhh Domain

<400> SEQUENCE: 81

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Gly Thr Phe Ser Ser Tyr
            20                  25                  30

Ser Met Gly Trp Phe Arg Gln Ala Pro Gly Lys Glu Arg Glu Phe Val
        35                  40                  45
```

Ala Ala Ile Thr Trp Asn Gly Val Ser Thr Tyr Tyr Ala Asp Ser Val
            50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Thr Asp Thr Ala Val Tyr Tyr Cys
                85                  90                  95

Ala Ala Glu Ile Thr Thr Arg Tyr Ser Gly Phe Tyr Tyr Glu Asp
            100                 105                 110

Asn Lys Ser Tyr Asp Tyr Trp Gly Gln Gly Thr Gln Val Thr Val Ser
            115                 120                 125

Ser

<210> SEQ ID NO 82
<211> LENGTH: 129
<212> TYPE: PRT
<213> ORGANISM: Artificial Sequence
<220> FEATURE:
<223> OTHER INFORMATION: Humanized Lama glama Anti-P Fab - Vhh Domain

<400> SEQUENCE: 82

Gln Val Gln Leu Ile Glu Ser Gly Gly Gly Leu Val Gln Ala Gly Asp
 1               5                  10                  15

Ser Leu Arg Leu Ser Cys Ala Thr Ser Glu Gly Thr Phe Ser Arg Phe
                20                  25                  30

Ala Met Gly Trp Phe Arg Gln Ala Pro Gly Lys Glu Arg Glu Phe Val
            35                  40                  45

Ala Ala Ile Asn Trp Ser Gly Gly Ile Thr Tyr Tyr Ala Asp Ser Ile
            50                  55                  60

Ala Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Asp Tyr Tyr Cys
                85                  90                  95

Ala Ala Glu Thr Thr Thr Arg Tyr Ser Gly Tyr Tyr Tyr Glu Asp
            100                 105                 110

Asn Lys Ser Tyr Asp Tyr Trp Gly Gln Gly Thr Leu Val Thr Val Ser
            115                 120                 125

Gly

<210> SEQ ID NO 83
<211> LENGTH: 129
<212> TYPE: PRT
<213> ORGANISM: Artificial Sequence
<220> FEATURE:
<223> OTHER INFORMATION: Humanized Lama glama Anti-P Fab - Vhh Domain

<400> SEQUENCE: 83

Gln Val Gln Leu Val Glu Ser Gly Gly Gly Leu Val Gln Ala Gly Gly
 1               5                  10                  15

Ser Leu Arg Leu Ser Cys Ala Ser Gly Arg Thr Phe Ser Thr Leu
                20                  25                  30

Gly Met Gly Trp Phe Arg Gln Ala Pro Gly Lys Glu Arg Gln Phe Val
            35                  40                  45

Ala Ala Ile Asn Trp Ser Gly Ser Thr Tyr Tyr Ala Asn Ser Val
            50                  55                  60

Lys Gly Arg Phe Thr Ile Ser Arg Asp Asn Ala Gln Ser Thr Met Tyr
 65                  70                  75                  80

Leu Gln Met Asn Ser Leu Lys Pro Glu Asp Thr Ala Val Tyr Tyr Cys

```
                 85                  90                  95
Ala Ala Asp Leu Asp Ser Arg Tyr Ser Ala Tyr Tyr Tyr Ser Asp
            100                 105                 110

Glu Ser Gln Tyr Asp Tyr Trp Gly Gln Gly Thr Leu Val Thr Val Ser
        115                 120                 125

Gly

<210> SEQ ID NO 84
<211> LENGTH: 129
<212> TYPE: PRT
<213> ORGANISM: Artificial Sequence
<220> FEATURE:
<223> OTHER INFORMATION: Humanized Lama glama Anti-P Fab - Vhh Domain

<400> SEQUENCE: 84

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Pro Pro Gly Lys Glu Arg Glu Phe Val
        35                  40                  45

Ala Ala Ile Thr Trp Arg Gly Ala Ser Thr Tyr Tyr Ala Asp Pro Ile
    50                  55                  60

Lys Gly Arg Phe Thr Ile Ser Arg Asp Asn Ala Lys Asn Thr Val Tyr
65                  70                  75                  80

Leu Gln Met Ser Ser Leu Lys Pro Glu Asp Thr Ala Val Tyr Tyr Cys
                85                  90                  95

Ala Ala Glu Glu Pro Ser Tyr Tyr Ser Gly Ser Tyr Tyr Tyr Met Met
            100                 105                 110

Gly Glu Ser Tyr Ala Tyr Trp Gly Gln Gly Thr Leu Val Thr Val Ser
        115                 120                 125

Gly

<210> SEQ ID NO 85
<211> LENGTH: 129
<212> TYPE: PRT
<213> ORGANISM: Artificial Sequence
<220> FEATURE:
<223> OTHER INFORMATION: Humanized Lama glama Anti-P Fab - Vhh Domain

<400> SEQUENCE: 85

Gln Val His Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Pro Pro Gly Lys Glu Arg Gln Phe Val
        35                  40                  45

Ala Ala Ile Thr Trp Ser Gly Ser Ser Ile Tyr Tyr Ala Asp Ser Ile
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Glu Glu Thr Ser Ala Tyr Ser Gly Ser Tyr Tyr Tyr Met Met
            100                 105                 110

Gly Asp Ser Tyr Ser Tyr Trp Gly Gln Gly Thr Gln Val Thr Val Ser
        115                 120                 125
```

-continued

Gly

<210> SEQ ID NO 86
<211> LENGTH: 129
<212> TYPE: PRT
<213> ORGANISM: Artificial Sequence
<220> FEATURE:
<223> OTHER INFORMATION: Humanized Lama glama Anti-P Fab - Vhh Domain

<400> SEQUENCE: 86

```
Gln Val Gln Leu Val Glu Ser Gly Gly Gly Leu Val Gln Pro Gly Gly
1               5                   10                  15

Ser Leu Ser Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Trp Val
        35                  40                  45

Ala Ala Ile Thr Trp Ser Gly Ala Asn Ile Tyr Tyr Ala Asp Ser Ile
    50                  55                  60

Lys Gly Arg Phe Thr Leu Ser Arg Asp Asn Ala Glu Asn Thr Val Trp
65                  70                  75                  80

Leu Gln Leu Asn Ser Leu Lys Pro Glu Asp Thr Ala Val Tyr Tyr Cys
                85                  90                  95

Ala Ala Ala Glu Ser Gly Arg Tyr Ser Gly Arg Ala Tyr Tyr Ser Ala
            100                 105                 110

Pro Gly Val Tyr Leu Tyr Trp Gly Gln Gly Thr Leu Val Thr Val Ser
        115                 120                 125

Gly
```

<210> SEQ ID NO 87
<211> LENGTH: 129
<212> TYPE: PRT
<213> ORGANISM: Artificial Sequence
<220> FEATURE:
<223> OTHER INFORMATION: Humanized Lama glama Anti-P Fab - Vhh Domain

<400> SEQUENCE: 87

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Ala Met Ala Trp Phe Arg Gln Ala Pro Gly Lys Glu Arg Glu Phe Val
        35                  40                  45

Ala Ser Ile Ser Gly Ser Gly Asp Ser Arg Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Thr Asn Ser Pro Lys Pro Glu Asp Thr Ala Val Tyr Tyr Cys
                85                  90                  95

Ala Ala Val Leu Pro Thr Arg Tyr Ser Gly Phe Tyr Tyr Tyr Ser Asp
            100                 105                 110

Gly Thr Gln Tyr His Tyr Trp Gly Gln Gly Thr Gln Val Thr Val Ser
        115                 120                 125

Ser
```

<210> SEQ ID NO 88
<211> LENGTH: 129
<212> TYPE: PRT

<213> ORGANISM: Artificial Sequence
<220> FEATURE:
<223> OTHER INFORMATION: Humanized Lama glama Anti-P Fab - Vhh Domain

<400> SEQUENCE: 88

```
Gln Val Arg Leu Val Glu Ser Gly Gly Gly Leu Val Gln Ala Gly Asp
1               5                   10                  15
Ser Leu Arg Leu Ser Cys Ala Thr Ser Gly Arg Thr Leu Ser Ser Tyr
            20                  25                  30
Ala Met Gly Trp Phe Arg Gln Ala Pro Gly Lys Glu Arg Glu Phe Val
        35                  40                  45
Ala Ala Thr Thr Trp Arg Asp Thr Ser Thr Tyr Tyr Ala Asp Ser Val
    50                  55                  60
Lys Gly Arg Phe Thr Ile Ser Arg Asp Asn Ala Lys Asn Thr Val Tyr
65                  70                  75                  80
Leu Gln Thr Asn Ser Leu Lys Pro Glu Asp Thr Ala Ala Tyr Tyr Cys
                85                  90                  95
Ala Ala Glu Glu Pro Ser Lys Tyr Ser Gly Arg Ser Tyr Tyr Met Met
            100                 105                 110
Gly Ala Ser Tyr Asp Tyr Trp Gly Gln Gly Thr Gln Val Thr Val Ser
        115                 120                 125
Ser
```

<210> SEQ ID NO 89
<211> LENGTH: 129
<212> TYPE: PRT
<213> ORGANISM: Artificial Sequence
<220> FEATURE:
<223> OTHER INFORMATION: Humanized Lama glama Anti-P Fab - Vhh Domain

<400> SEQUENCE: 89

```
Gln Val Gln Leu Val Glu Ser Gly Gly Gly Leu Val Gln Pro Gly Gly
1               5                   10                  15
Ser Leu Arg Leu Ser Cys Ala Thr Ser Gly Gly Thr Phe Ser Ser Tyr
            20                  25                  30
Ala Met Gly Trp Phe Arg Gln Ala Pro Gly Lys Glu Arg Glu Phe Val
        35                  40                  45
Ala Ala Thr Thr Trp Gln Gly Ser Asn Arg Tyr Tyr Ala Glu Ser Val
    50                  55                  60
Ala Gly Arg Phe Thr Ile Ser Arg Asp Asn Ala Lys Ser Thr Val Trp
65                  70                  75                  80
Leu Gln Met Asn Ser Leu Lys Pro Glu Asp Thr Ala Val Tyr Tyr Cys
                85                  90                  95
Ala Ala Glu His Ser Thr Arg Tyr Ser Gly Phe Tyr Tyr Tyr Thr Arg
            100                 105                 110
Gly Glu Thr Tyr His Tyr Trp Gly Gln Gly Thr Gln Val Thr Val Ser
        115                 120                 125
Gly
```

<210> SEQ ID NO 90
<211> LENGTH: 129
<212> TYPE: PRT
<213> ORGANISM: Artificial Sequence
<220> FEATURE:
<223> OTHER INFORMATION: Humanized Lama glama Anti-P Fab - Vhh Domain

<400> SEQUENCE: 90

```
Gln Val Gln Leu Val Glu Ser Gly Gly Gly Leu Val Gln Pro Gly Gly
```

```
1               5                   10                  15
Ser Leu Arg Leu Ser Cys Ala Ala Ser Gly Phe Pro Leu Asn Ser Tyr
            20                  25                  30

Ala Ile Gly Trp Phe Arg Gln Ala Pro Gly Lys Glu Arg Glu Gly Val
            35                  40                  45

Ser Cys Ile Ser Val Ser Asp Ser Thr Tyr Tyr Thr Asp Ser Val
            50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Val Asp Ser Ala Pro Leu Tyr Gly Asp Tyr Val Cys Lys Pro Leu
                100                 105                 110

Glu Asn Glu Tyr Asp Phe Trp Gly Gln Gly Thr Gln Val Thr Val Ser
            115                 120                 125

Gly
```

```
<210> SEQ ID NO 91
<211> LENGTH: 129
<212> TYPE: PRT
<213> ORGANISM: Artificial Sequence
<220> FEATURE:
<223> OTHER INFORMATION: Humanized Lama glama Anti-P Fab - Vhh Domain

<400> SEQUENCE: 91

Gln Val Gln Leu Val Glu Ser Gly Gly Gly Leu Val Gln Ala Gly Asp
1               5                   10                  15

Ser Leu Arg Phe Ser Cys Ala Ala Ser Gly Phe Thr Phe Ser Ser Tyr
            20                  25                  30

Ala Met Gly Trp Phe Arg Gln Ala Pro Gly Lys Glu Arg Glu Phe Val
            35                  40                  45

Ala Ala Ile Thr Trp Ser Gly Val Ser Thr Tyr Tyr Ala Asp Ser Ile
            50                  55                  60

Ala Gly Arg Phe Thr Ile Ser Arg Asp Asn Ala Lys Asn Arg Val Tyr
65                  70                  75                  80

Leu Gln Met Asn Ser Leu Lys Pro Glu Asp Thr Ala Asp Tyr Ser Cys
                85                  90                  95

Ala Ala Asp Gly Ser Gly Arg Tyr Ser Gly Met Glu Tyr Tyr Asn Arg
                100                 105                 110

Asp Trp Val Tyr Asp Tyr Trp Gly Gln Gly Thr Gln Val Thr Val Ser
            115                 120                 125

Ser
```

```
<210> SEQ ID NO 92
<211> LENGTH: 128
<212> TYPE: PRT
<213> ORGANISM: Artificial Sequence
<220> FEATURE:
<223> OTHER INFORMATION: Humanized Lama glama Anti-P Fab - Vhh Domain

<400> SEQUENCE: 92

Gln Val Arg Leu Thr Glu Ser Gly Gly Gly Leu Val Gln Tyr Gly Thr
1               5                   10                  15

Asn Leu Thr Leu Thr Cys Val Ala Ser Gly Leu Ile Ser Thr Arg Asn
            20                  25                  30

Lys Met Gly Trp Phe Arg Arg Arg Ser Gly Gly Gln Arg Glu Phe Val
            35                  40                  45
```

Ala Ser Ser Thr Val Leu Ser Asp Val Ile Gln Asp Asp Ile Ala
    50                  55                  60

Glu Thr Val Lys Gly Arg Phe Ala Val Ala Arg Asn Asp Tyr Lys Asn
 65                  70                  75                  80

Ile Leu Tyr Leu Gln Met Thr Ala Val Lys Pro Glu Asp Thr Gly Phe
                     85                  90                  95

Tyr Trp Cys Ala Ser Gly Thr Ser Leu Phe Gly Ala Ser Arg Arg Glu
                100                 105                 110

Asp Asp Phe Asn Ala Trp Gly Val Gly Thr Gln Val Thr Val Ser Ala
                115                 120                 125

<210> SEQ ID NO 93
<211> LENGTH: 119
<212> TYPE: PRT
<213> ORGANISM: Artificial Sequence
<220> FEATURE:
<223> OTHER INFORMATION: Humanized Lama glama Fab - Vhh Domain

<400> SEQUENCE: 93

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Gly Ser Ala
                20                  25                  30

Asp Met Ser Trp Val Arg Gln Ala Pro Gly Lys Gly Pro Glu Trp Val
             35                  40                  45

Ser Ala Ile Asn Ser Asn Gly Gly Ser Thr Tyr Tyr Ala Ala Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Lys Pro Glu Asp Thr Ala Val Tyr Tyr Cys
                 85                  90                  95

Ala Gln Gly Asn Trp Tyr Thr Glu Glu Tyr His Tyr Trp Gly Gln Gly
                100                 105                 110

Thr Gln Val Thr Val Ser Gly
        115

<210> SEQ ID NO 94
<211> LENGTH: 122
<212> TYPE: PRT
<213> ORGANISM: Artificial Sequence
<220> FEATURE:
<223> OTHER INFORMATION: Humanized Vicugna pacos Fab HC Anti-Properdin

<400> SEQUENCE: 94

Gln Val Gln Leu Val Glu Ser Gly Gly Gly Leu Val Gln Ala Gly Gly
 1               5                  10                  15

Ser Leu Arg Leu Ser Cys Ala Ala Ser Gly Arg Thr Phe Ser Ser Tyr
                20                  25                  30

Ala Met Gly Trp Phe Arg Gln Ala Pro Gly Lys Glu Arg Glu Phe Val
             35                  40                  45

Ala Ala Ile Gly Trp Asn Gly Glu Gly Ile Tyr Tyr Ala Asp Ser Val
 50                  55                  60

Lys Gly Arg Phe Thr Ile Ser Arg Asp Asn Ala Lys Asn Thr Gly Tyr
 65                  70                  75                  80

Leu Gln Met Asn Ser Leu Lys Pro Glu Asp Thr Ala Val Tyr Tyr Cys
                 85                  90                  95

Ala Ala Asp Ser Glu Gly Val Val Pro Gly Phe Pro Ile Ala Tyr Trp

```
                    100                 105                 110
Gly Gln Gly Thr Gln Val Thr Val Ser Gly
            115                 120

<210> SEQ ID NO 95
<211> LENGTH: 122
<212> TYPE: PRT
<213> ORGANISM: Artificial Sequence
<220> FEATURE:
<223> OTHER INFORMATION: Humanized Lama glama Anti-P Fab - Vhh Domain

<400> SEQUENCE: 95

Glu Val Gln Leu Val Glu Ser Gly Gly Gly Leu Val Gln Pro Gly Gly
1               5                   10                  15

Ser Leu Arg Leu Ser Cys Ala Thr Ser Gly Arg Pro Phe Ser Ser Tyr
            20                  25                  30

Ala Met Gly Trp Phe Arg Gln Ala Pro Gly Lys Glu Arg Glu Ile Val
        35                  40                  45

Ala Gly Leu Ser Trp Ser Gly Gln Ile Tyr Tyr Ala Asp Ser Val
    50                  55                  60

Lys Gly Arg Phe Thr Ile Ser Arg Asp Asn Ala Lys Asn Thr Gly Asp
65                  70                  75                  80

Leu Gln Met Asn Ser Leu Lys Pro Glu Asp Thr Ala Val Tyr Tyr Cys
                85                  90                  95

Ala Ile Gly Pro Ala Leu Thr Thr Gly Pro Thr Ala Tyr Arg Tyr Trp
            100                 105                 110

Gly Gln Gly Thr Gln Val Thr Val Ser Ser
            115                 120

<210> SEQ ID NO 96
<211> LENGTH: 122
<212> TYPE: PRT
<213> ORGANISM: Artificial Sequence
<220> FEATURE:
<223> OTHER INFORMATION: Humanized Lama glama Anti-P Fab - Vhh Domain

<400> SEQUENCE: 96

Gln Val His Leu Val Glu Ser Gly Gly Gly Leu Val Gln Ala Gly Gly
1               5                   10                  15

Ser Leu Arg Leu Ser Cys Thr Ala Ser Gly Gly Thr Val Gly Asp Tyr
            20                  25                  30

Ala Val Gly Trp Phe Arg Gln Ala Pro Gly Lys Glu Arg Glu Leu Ile
        35                  40                  45

Gly Val Val Ser Arg Leu Gly Ala Arg Thr Gly Tyr Ala Asp Ser Val
    50                  55                  60

Leu Gly Arg Phe Thr Ile Ser Arg Asp Asp Val Lys Asn Thr Val Phe
65                  70                  75                  80

Leu Gln Met Asp Ser Val Lys Pro Glu Asp Thr Ala Val Tyr Tyr Cys
                85                  90                  95

Ala Ala Arg Arg Asp Tyr Ser Phe Glu Val Val Pro Tyr Asp Tyr Trp
            100                 105                 110

Gly Gln Gly Thr Gln Val Thr Val Ser Gly
            115                 120

<210> SEQ ID NO 97
<211> LENGTH: 124
<212> TYPE: PRT
<213> ORGANISM: Artificial Sequence
<220> FEATURE:
```

<223> OTHER INFORMATION: Humanized Lama glama Anti-P Fab - Vhh Domain

<400> SEQUENCE: 97

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Tyr
            20                  25                  30

Ser Met Gly Trp Phe Arg Gln His Gly Asn Glu Arg Glu Phe Val
        35                  40                  45

Ala Ala Ile Ser Trp Ser Gly Arg Ser Thr Tyr Tyr Ala Glu Ser Val
    50                  55                  60

Lys Gly Arg Phe Ala Ile Ser Arg Asp Asn Ala Asn Thr Thr Val Tyr
65                  70                  75                  80

Leu Gln Met Asn Ser Leu Lys Pro Glu Asp Ser Ala Val Tyr Tyr Cys
                85                  90                  95

Ala Ala Ser Thr Arg Gly Trp Tyr Gly Thr Gln Glu Ser Asp Tyr Asn
            100                 105                 110

Phe Trp Gly Gln Gly Thr Gln Val Thr Val Ser Gly
        115                 120
```

<210> SEQ ID NO 98
<211> LENGTH: 125
<212> TYPE: PRT
<213> ORGANISM: Artificial Sequence
<220> FEATURE:
<223> OTHER INFORMATION: Humanized Lama glama Anti-P Fab - Vhh Domain

<400> SEQUENCE: 98

```
Gln Val Gln Leu Ile Glu Ser Gly Gly Gly Leu Val Gln Ala Gly Gly
1               5                   10                  15

Ser Leu Arg Leu Ser Cys Thr Ala Ser Gly Arg Thr Phe Ser Asn Tyr
            20                  25                  30

Ala Met Gly Trp Phe Arg Gln Ala Pro Gly Lys Glu Arg Glu Phe Leu
        35                  40                  45

Ala Ala Ile Ser Arg Ser Gly Glu Ser Thr Gln Tyr Ala Thr Phe Val
    50                  55                  60

Lys Gly Arg Phe Ala Ile Ala Arg Asp Asn Ala Lys Asn Thr Val Ser
65                  70                  75                  80

Leu Gln Met Asn Ser Leu Lys Pro Glu Asp Thr Ala Val Tyr Phe Cys
                85                  90                  95

Ala Ala Lys Ile Ala Val Leu Val Ser Thr Thr Tyr Asn Ser Gln Tyr
            100                 105                 110

Glu Tyr Trp Gly Gln Gly Thr Leu Val Thr Val Ser Ser
        115                 120                 125
```

<210> SEQ ID NO 99
<211> LENGTH: 126
<212> TYPE: PRT
<213> ORGANISM: Artificial Sequence
<220> FEATURE:
<223> OTHER INFORMATION: Humanized Lama glama Anti-P Fab - Vhh Domain

<400> SEQUENCE: 99

```
Gln Val Gln Leu Ile Glu Ser Gly Gly Gly Leu Val Gln Glu Gly Ala
1               5                   10                  15

Ser Leu Arg Leu Ser Cys Ala Gly Ser Gly Pro Met Phe Ser Arg Leu
            20                  25                  30

Ala Val Gly Trp Phe Arg Gln Ala Pro Gly Lys Glu Arg Glu Phe Val
```

```
            35                  40                  45

Ala Val Ile Asn Trp Ser Gly Ser Ala Asp Phe Tyr Thr Asn Ser Val
         50                  55                  60

Lys Gly Arg Phe Thr Ile Ser Arg Asp Asn Ala Lys Asn Thr Val Tyr
 65                  70                  75                  80

Leu Glu Met Asn Thr Leu Lys Pro Glu Asp Ser Ala Val Tyr Tyr Cys
                 85                  90                  95

Ala Ala Asp Gln Asn Pro Leu Thr Leu Arg Thr Gly Val Arg Asp Val
            100                 105                 110

Gly Arg Gln Trp Gly Gln Gly Thr Glu Val Thr Val Ser Ser
            115                 120                 125

<210> SEQ ID NO 100
<211> LENGTH: 127
<212> TYPE: PRT
<213> ORGANISM: Artificial Sequence
<220> FEATURE:
<223> OTHER INFORMATION: Humanized Lama glama Anti-P Fab - Vhh Domain

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Asp Tyr Tyr
            20                  25                  30

Ala Ile Gly Trp Phe Arg Gln Ala Pro Gly Lys Glu Arg Glu Gly Val
            35                  40                  45

Ser Cys Ile Ser Arg Thr Asp Gly Ser Thr Tyr Tyr Ala Asp Ser Val
         50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Val Tyr Tyr Cys
                 85                  90                  95

Ala Val Asp Asp Ser Tyr Pro Thr Gly Gly Ile Ser Cys Leu Phe Gly
            100                 105                 110

His Phe Gly Ser Trp Gly Gln Gly Thr Gln Val Thr Val Ser Ser
            115                 120                 125

<210> SEQ ID NO 101
<211> LENGTH: 130
<212> TYPE: PRT
<213> ORGANISM: Artificial Sequence
<220> FEATURE:
<223> OTHER INFORMATION: Humanized Vicugna pacos Anti-P Fab - Vhh Domain

<400> SEQUENCE: 101

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Tyr
            20                  25                  30

Ala Met Gly Trp Phe Arg Gln Ala Pro Gly Lys Glu Arg Glu Phe Val
            35                  40                  45

Ala Ala Val Pro Trp Thr Tyr Gly Ser Lys Tyr Tyr Ala Asp Ser Val
         50                  55                  60

Lys Gly Arg Phe Thr Ile Ser Arg Asp Asp Ala Lys Asn Thr Val Tyr
 65                  70                  75                  80

Leu Gln Met Asn Asn Leu Lys Pro Glu Asp Thr Ala Val Tyr Tyr Cys
                 85                  90                  95
```

Ala Ala Asp Ser Ser Ala Gly Tyr Tyr Ser Gly Phe Asp Tyr Ser
            100                 105                 110

Ala Ala Thr Pro Tyr Asp Leu Trp Gly Gln Gly Thr Gln Val Thr Val
        115                 120                 125

Ser Gly
    130

<210> SEQ ID NO 102
<211> LENGTH: 116
<212> TYPE: PRT
<213> ORGANISM: Artificial Sequence
<220> FEATURE:
<223> OTHER INFORMATION: Humanized Lama glama Anti-P Fab - Vhh Domain

<400> SEQUENCE: 102

Gln Val Gln Met Val Glu Ser Gly Gly Gly Leu Val Gln Ala Gly Gly
1               5                   10                  15

Ser Leu Arg Leu Ser Cys Ala Ala Ser Gly Leu Thr Asn Arg Ile Arg
            20                  25                  30

Ile Met Gly Trp Tyr Arg Gln Ala Pro Gly Lys Leu Arg Glu Leu Val
        35                  40                  45

Ala Thr Ile Thr Asn Asp Gly Ser Thr His Tyr Ala Asp Ser Val Lys
    50                  55                  60

Gly Arg Phe Thr Ile Ser Thr Asp Asn Ala Lys Asn Thr Val Phe Leu
65                  70                  75                  80

Gln Met Asn Ser Leu Lys Pro Glu Asp Thr Ala Val Tyr Ile Cys Asn
                85                  90                  95

Val Gly Glu Asn Trp Gly Pro Ala Tyr Trp Gly Gln Gly Thr Gln Val
            100                 105                 110

Thr Val Ser Gly
        115

<210> SEQ ID NO 103
<211> LENGTH: 118
<212> TYPE: PRT
<213> ORGANISM: Artificial Sequence
<220> FEATURE:
<223> OTHER INFORMATION: Humanized Lama glama Anti-P Fab - Vhh Domain
<220> FEATURE:
<221> NAME/KEY: misc_feature
<222> LOCATION: (19)..(19)
<223> OTHER INFORMATION: Xaa can be any naturally occurring amino acid

<400> SEQUENCE: 103

Gln Val Gln Leu Val Glu Ser Gly Gly Gly Leu Val Gln Ala Gly Gly
1               5                   10                  15

Ser Leu Xaa Leu Ser Cys Ala Ala Ser Gly Ser Asp Arg Arg Ile Asn
            20                  25                  30

Gly Met Gly Trp Tyr Arg His Pro Pro Gly Lys Gln Arg Glu Leu Val
        35                  40                  45

Ala Ala Ile Thr Ser Gly Gly Thr Asn Tyr Ala Asp Ser Val Lys
    50                  55                  60

Gly Arg Phe Thr Ile Ser Thr Asn Asn Ala Asn Asn Met Met Tyr Leu
65                  70                  75                  80

Gln Met Asn Ser Leu Lys Pro Glu Asp Thr Ala Val Tyr Tyr Cys Ala
                85                  90                  95

Ile Asp Glu Phe Gly Thr Gly Trp Leu Asp Tyr Cys Gly Gln Gly Thr
            100                 105                 110

Gln Val Thr Val Ser Gly

-continued

```
        115

<210> SEQ ID NO 104
<211> LENGTH: 120
<212> TYPE: PRT
<213> ORGANISM: Artificial Sequence
<220> FEATURE:
<223> OTHER INFORMATION: Humanized Lama glama Anti-P Fab - Vhh Domain

<400> SEQUENCE: 104

Gln Val Leu Leu Glu Glu Ser Gly Gly Gly Leu Glu Arg Thr Gly Gly
1               5                   10                  15

Ser Leu Arg Leu Ser Cys Ala Ala Ser Gly Ser Ile Phe Ser Val Asn
            20                  25                  30

Ser Met Thr Trp Tyr Arg Gln Ala Pro Gly Lys Arg Arg Glu Phe Leu
        35                  40                  45

Gly Thr Ile Thr Glu Glu Gly Arg Thr Asn Tyr Ala Asp Ser Val Lys
    50                  55                  60

Gly Arg Phe Thr Ile Ser Arg Asp Asn Ala Lys Asn Thr Met Tyr Leu
65                  70                  75                  80

Gln Met Asn Ser Leu Lys Pro Glu Asp Thr Ala Val Tyr Tyr Cys Tyr
                85                  90                  95

Ala Asn Leu Ile Ser Ser Glu Asp Arg Thr Phe Gly Val Trp Gly Gln
            100                 105                 110

Gly Thr Gln Val Thr Val Ser Ser
        115                 120

<210> SEQ ID NO 105
<211> LENGTH: 121
<212> TYPE: PRT
<213> ORGANISM: Artificial Sequence
<220> FEATURE:
<223> OTHER INFORMATION: Humanized Lama glama Anti-P Fab - Vhh Domain

<400> SEQUENCE: 105

Gln Val His Met Val Glu Ser Gly Gly Gly Leu Val Gln Ala Gly Gly
1               5                   10                  15

Ser Leu Arg Phe Ser Cys Ala Ala Ser Gly Asn Ile Phe Thr Ile Ser
            20                  25                  30

Thr Leu Asp Trp Tyr Arg Gln Ala Pro Gly Glu Gln Arg Glu Leu Val
        35                  40                  45

Ala Thr Leu Thr Pro Asp Gly Ile Thr Asp Tyr Ala Gly Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ala Trp Arg Tyr Ser Asp Asp Tyr Arg Gly Arg Val Asp Tyr Trp Gly
            100                 105                 110

Gln Gly Thr Gln Val Thr Val Ser Gly
        115                 120

<210> SEQ ID NO 106
<211> LENGTH: 129
<212> TYPE: PRT
<213> ORGANISM: Artificial Sequence
<220> FEATURE:
<223> OTHER INFORMATION: Humanized Lama glama Anti-P Fab - Vhh Domain

<400> SEQUENCE: 106
```

```
Gln Val Gln Leu Met Glu Ser Gly Gly Gly Val Gln Ala Gly Gly
1               5                   10                  15

Ser Leu Arg Leu Ser Cys Ala Ala Ser Gly Ser Ile Phe Asp Ile Ser
            20                  25                  30

Ala Met Gly Trp Tyr Arg Gln Ala Pro Gly Lys Gln Arg Glu Leu Val
            35                  40                  45

Ala Asp Ile Thr Ser Ser Gly Ser Thr Gln Tyr Ala Asp Ser Val Lys
        50                  55                  60

Gly Arg Phe Thr Ile Ser Arg Asp Asn Ala Lys Asn Thr Val Tyr Leu
65                  70                  75                  80

Gln Met Asn Ser Leu Lys Pro Glu Asp Thr Ala Val Tyr Thr Cys Ala
                85                  90                  95

Ala Glu Ser Ile Arg Glu Ser Gln Asn Arg His Gln Leu Gly Tyr Met
            100                 105                 110

Gly Pro Leu Tyr Asp Tyr Trp Gly Gln Gly Thr Gln Val Thr Val Ser
            115                 120                 125

Gly
```

<210> SEQ ID NO 107
<211> LENGTH: 125
<212> TYPE: PRT
<213> ORGANISM: Artificial Sequence
<220> FEATURE:
<223> OTHER INFORMATION: Humanized Lama glama Anti-P Fab - Vhh Domain

<400> SEQUENCE: 107

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Asp Tyr Tyr Ala Ile
            20                  25                  30

Gly Trp Phe Arg Gln Ala Pro Gly Lys Glu Arg Glu Gly Val Ser Cys
        35                  40                  45

Met Ser Arg Thr Asp Gly Ser Thr Tyr Tyr Ala Asp Ser Val Lys Asp
    50                  55                  60

Arg Phe Thr Ile Ser Arg Asp Tyr Ala Lys Asn Thr Val Tyr Leu Gln
65                  70                  75                  80

Met Asn Ser Leu Lys Pro Glu Asp Thr Ala Val Tyr Tyr Cys Gly Leu
                85                  90                  95

Asp Arg Ser Tyr Pro Thr Gly Gly Ile Ser Cys Leu Phe Gly Asp Phe
            100                 105                 110

Gly Ser Trp Gly Gln Gly Thr Gln Val Thr Val Ser Gly
            115                 120                 125
```

<210> SEQ ID NO 108
<211> LENGTH: 123
<212> TYPE: PRT
<213> ORGANISM: Artificial Sequence
<220> FEATURE:
<223> OTHER INFORMATION: Humanized Anti-Albumin Fab-Vhh

<400> SEQUENCE: 108

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
            35                  40                  45
```

```
Ser Ala Ile Asn Trp Gln Lys Thr Ala Thr Tyr Ala Asp Ser Val Lys
        50                  55                  60

Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Tyr Cys Ala
                 85                  90                  95

Ala Val Phe Arg Val Val Ala Pro Lys Thr Gln Tyr Asp Tyr Asp Tyr
                100                 105                 110

Trp Gly Gln Gly Thr Leu Val Thr Val Ser Ser
            115                 120

<210> SEQ ID NO 109
<211> LENGTH: 115
<212> TYPE: PRT
<213> ORGANISM: Artificial Sequence
<220> FEATURE:
<223> OTHER INFORMATION: Humanized Anti-Albumin

<400> SEQUENCE: 109

Ala Val Gln Leu Val Glu Ser Gly Gly Gly Leu Val Gln Pro Gly Asn
 1               5                  10                  15

Ser Leu Arg Leu Ser Cys Ala Ala Ser Gly Phe Thr Phe Arg Ser Phe
                 20                  25                  30

Gly Met Ser Trp Val Arg Gln Ala Pro Gly Lys Glu Pro Glu Trp Val
             35                  40                  45

Ser Ser Ile Ser Gly Ser Gly Ser Asp Thr Leu Tyr Ala Asp Ser Val
         50                  55                  60

Lys Gly Arg Phe Thr Ile Ser Arg Asp Asn Ala Lys Thr Thr Leu Tyr
 65                  70                  75                  80

Leu Gln Met Asn Ser Leu Lys Pro Glu Asp Thr Ala Val Tyr Tyr Cys
                 85                  90                  95

Thr Ile Gly Gly Ser Leu Ser Arg Ser Ser Gln Gly Thr Gln Val Thr
                100                 105                 110

Val Ser Ser
        115

<210> SEQ ID NO 110
<211> LENGTH: 115
<212> TYPE: PRT
<213> ORGANISM: Artificial Sequence
<220> FEATURE:
<223> OTHER INFORMATION: Humanized Anti-Albumin

<400> SEQUENCE: 110

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Arg Ser Phe
                 20                  25                  30

Gly Met Ser Trp Val Arg Gln Ala Pro Gly Lys Glu Pro Glu Trp Val
             35                  40                  45

Ser Ser Ile Ser Gly Ser Gly Ser Asp Thr Leu Tyr Ala Asp Ser Val
         50                  55                  60

Lys Gly Arg Phe Thr Ile Ser Arg Asp Asn Ala Lys Thr Thr Leu Tyr
 65                  70                  75                  80

Leu Gln Met Asn Ser Leu Lys Pro Glu Asp Thr Ala Val Tyr Tyr Cys
                 85                  90                  95

Thr Ile Gly Gly Ser Leu Ser Arg Ser Ser Gln Gly Thr Gln Val Thr
```

Val Ser Ser
    115

<210> SEQ ID NO 111
<211> LENGTH: 115
<212> TYPE: PRT
<213> ORGANISM: Artificial Sequence
<220> FEATURE:
<223> OTHER INFORMATION: Humanized Anti-Albumin

<400> SEQUENCE: 111

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
    115

<210> SEQ ID NO 112
<211> LENGTH: 115
<212> TYPE: PRT
<213> ORGANISM: Artificial Sequence
<220> FEATURE:
<223> OTHER INFORMATION: Humanized Anti-Albumin

<400> SEQUENCE: 112

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
    115

<210> SEQ ID NO 113
<211> LENGTH: 115
<212> TYPE: PRT
<213> ORGANISM: Artificial Sequence
<220> FEATURE:

<223> OTHER INFORMATION: Humanized Anti-Albumin

<400> SEQUENCE: 113

```
Glu Val Gln Leu Val Glu Ser Gly Gly Gly Leu Val Gln Pro Gly Asn
1               5                   10                  15
Ser Leu Arg Leu Ser Cys Ala Ala Ser Gly Phe Thr Phe Arg Ser Phe
            20                  25                  30
Gly Met Ser Trp Val Arg Gln Ala Pro Gly Lys Gly Leu Glu Trp Val
        35                  40                  45
Ser Ser Ile Ser Gly Ser Gly Ser Asp Thr Leu Tyr Ala Asp Ser Val
    50                  55                  60
Lys Gly Arg Phe Thr Ile Ser Arg Asp Asn Ala Lys Thr Thr Leu Tyr
65                  70                  75                  80
Leu Gln Met Asn Ser Leu Lys Pro Glu Asp Thr Ala Val Tyr Tyr Cys
                85                  90                  95
Thr Ile Gly Gly Ser Leu Ser Arg Ser Ser Gln Gly Thr Leu Val Thr
            100                 105                 110
Val Ser Ser
        115
```

<210> SEQ ID NO 114
<211> LENGTH: 115
<212> TYPE: PRT
<213> ORGANISM: Artificial Sequence
<220> FEATURE:
<223> OTHER INFORMATION: Humanized Anti-Albumin

<400> SEQUENCE: 114

```
Glu Val Gln Leu Val Glu Ser Gly Gly Gly Leu Val Gln Pro Gly Asn
1               5                   10                  15
Ser Leu Arg Leu Ser Cys Ala Ala Ser Gly Phe Thr Phe Arg Ser Phe
            20                  25                  30
Gly Met Ser Trp Val Arg Gln Ala Pro Gly Lys Gly Leu Glu Trp Val
        35                  40                  45
Ser Ser Ile Ser Gly Ser Gly Ser Asp Thr Leu Tyr Ala Asp Ser Val
    50                  55                  60
Lys Gly Arg Phe Thr Ile Ser Arg Asp Asn Ala Lys Thr Thr Leu Tyr
65                  70                  75                  80
Leu Gln Met Asn Ser Leu Arg Pro Glu Asp Thr Ala Val Tyr Tyr Cys
                85                  90                  95
Thr Ile Gly Gly Ser Leu Ser Arg Ser Ser Gln Gly Thr Leu Val Thr
            100                 105                 110
Val Ser Ser
        115
```

<210> SEQ ID NO 115
<211> LENGTH: 115
<212> TYPE: PRT
<213> ORGANISM: Artificial Sequence
<220> FEATURE:
<223> OTHER INFORMATION: Humanized Anti-Albumin

<400> SEQUENCE: 115

```
Glu Val Gln Leu Val Glu Ser Gly Gly Gly Leu Val Gln Pro Gly Asn
1               5                   10                  15
Ser Leu Arg Leu Ser Cys Ala Ala Ser Gly Phe Thr Phe Ser Ser Phe
            20                  25                  30
Gly Met Ser Trp Val Arg Gln Ala Pro Gly Lys Gly Leu Glu Trp Val
```

```
                35                  40                  45

Ser Ser Ile Ser Gly Ser Gly Ser Asp Thr Leu Tyr Ala Asp Ser Val
 50                  55                  60

Lys Gly Arg Glu Thr Ile Ser Arg Asp Asn Ala Lys Thr Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
                100                 105                 110

Val Ser Ser
        115

<210> SEQ ID NO 116
<211> LENGTH: 115
<212> TYPE: PRT
<213> ORGANISM: Artificial Sequence
<220> FEATURE:
<223> OTHER INFORMATION: Humanized Anti-Albumin

<400> SEQUENCE: 116

Glu Val Gln Leu Val Glu Ser Gly Gly Gly Leu Val Gln Pro Gly Asn
 1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
                35                  40                  45

Ser Ser Ile Ser Gly Ser Gly Ser Asp Thr Leu Tyr Ala Asp Ser Val
 50                  55                  60

Lys Gly Arg Glu Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95

Thr Ile Gly Gly Ser Leu Ser Arg Ser Ser Gln Gly Thr Leu Val Thr
                100                 105                 110

Val Ser Ser
        115

<210> SEQ ID NO 117
<211> LENGTH: 115
<212> TYPE: PRT
<213> ORGANISM: Artificial Sequence
<220> FEATURE:
<223> OTHER INFORMATION: Humanized Anti-Albumin

<400> SEQUENCE: 117

Glu Val Gln Leu Val Glu Ser Gly Gly Gly Leu Val Gln Pro Gly Asn
 1               5                  10                  15

Ser Leu Arg Leu Ser Cys Ala Ala Ser Gly Phe Thr Phe Ser Ser Phe
                 20                  25                  30

Gly Met Ser Trp Val Arg Gln Ala Pro Gly Lys Gly Leu Glu Trp Val
                35                  40                  45

Ser Ser Ile Ser Gly Ser Gly Ser Asp Thr Leu Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Pro Glu Asp Thr Ala Val Tyr Tyr Cys
                 85                  90                  95
```

Thr Ile Gly Gly Ser Leu Ser Arg Ser Gly Gln Gly Thr Leu Val Thr
            100                 105                 110

Val Ser Ser
        115

<210> SEQ ID NO 118
<211> LENGTH: 115
<212> TYPE: PRT
<213> ORGANISM: Artificial Sequence
<220> FEATURE:
<223> OTHER INFORMATION: Humanized Anti-Albumin

<400> SEQUENCE: 118

Glu Val Gln Leu Val Glu Ser Gly Gly Gly Leu Val Gln Pro Gly Asn
1               5                   10                  15

Ser Leu Arg Leu Ser Cys Ala Ala Ser Gly Phe Thr Phe Ser Ser Phe
            20                  25                  30

Gly Met Ser Trp Val Arg Gln Ala Pro Gly Lys Gly Leu Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ala Lys Thr Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 119
<211> LENGTH: 115
<212> TYPE: PRT
<213> ORGANISM: Artificial Sequence
<220> FEATURE:
<223> OTHER INFORMATION: Humanized Anti-Albumin

<400> SEQUENCE: 119

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 120
<211> LENGTH: 115
<212> TYPE: PRT
<213> ORGANISM: Artificial Sequence

```
<220> FEATURE:
<223> OTHER INFORMATION: Humanized Anti-Albumin

<400> SEQUENCE: 120

Ala Trp Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 121
<211> LENGTH: 115
<212> TYPE: PRT
<213> ORGANISM: Artificial Sequence
<220> FEATURE:
<223> OTHER INFORMATION: Humanized Anti-Albumin

<400> SEQUENCE: 121

Ala Trp Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Gln Trp Thr
            100                 105                 110

Val Ser Ser
        115

<210> SEQ ID NO 122
<211> LENGTH: 115
<212> TYPE: PRT
<213> ORGANISM: Artificial Sequence
<220> FEATURE:
<223> OTHER INFORMATION: Humanized Anti-Albumin

<400> SEQUENCE: 122

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30
```

Gly Met Ser Trp Val Arg Gln Ala Pro Gly Lys Gly Pro Glu Trp Val
                35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser
        115

<210> SEQ ID NO 123
<211> LENGTH: 115
<212> TYPE: PRT
<213> ORGANISM: Artificial Sequence
<220> FEATURE:
<223> OTHER INFORMATION: Humanized Anti-Albumin

<400> SEQUENCE: 123

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
                20                  25                  30

Gly Met Ser Trp Val Arg Gln Ala Pro Gly Lys Gly Pro Glu Trp Val
                35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 124
<211> LENGTH: 115
<212> TYPE: PRT
<213> ORGANISM: Artificial Sequence
<220> FEATURE:
<223> OTHER INFORMATION: Humanized Anti-Albumin

<400> SEQUENCE: 124

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
                20                  25                  30

Gly Met Ser Trp Val Arg Gln Ala Pro Gly Lys Gly Pro Glu Trp Val
                35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Trp Thr
            100                 105                 110

Val Ser Ser
        115

<210> SEQ ID NO 125
<211> LENGTH: 115
<212> TYPE: PRT
<213> ORGANISM: Artificial Sequence
<220> FEATURE:
<223> OTHER INFORMATION: Humanized Anti-Albumin

<400> SEQUENCE: 125

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Trp Thr
            100                 105                 110

Val Ser Ser
        115

<210> SEQ ID NO 126
<211> LENGTH: 115
<212> TYPE: PRT
<213> ORGANISM: Artificial Sequence
<220> FEATURE:
<223> OTHER INFORMATION: Humanized Anti-Albumin

<400> SEQUENCE: 126

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 127
<211> LENGTH: 115
<212> TYPE: PRT

<213> ORGANISM: Artificial Sequence
<220> FEATURE:
<223> OTHER INFORMATION: Humanized Anti-Albumin

<400> SEQUENCE: 127

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Val Thr
            100                 105                 110

Val Ser Ser
        115

<210> SEQ ID NO 128
<211> LENGTH: 115
<212> TYPE: PRT
<213> ORGANISM: Artificial Sequence
<220> FEATURE:
<223> OTHER INFORMATION: Humanized Anti-Albumin

<400> SEQUENCE: 128

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Gly Pro Glu Trp Val
        35                  40                  45

Ser Ser Ile Ser Gly Ser Gly Ser Asp Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
                85                  90                  95

Thr Ile Gly Gly Ser Leu Ser Arg Ser Ser Gln Gly Thr Leu Trp Thr
            100                 105                 110

Val Ser Ser
        115

<210> SEQ ID NO 129
<211> LENGTH: 326
<212> TYPE: PRT
<213> ORGANISM: Artificial Sequence
<220> FEATURE:
<223> OTHER INFORMATION: Humanized IgG1 Fc

<400> SEQUENCE: 129

Gly Pro Ser Val Phe Pro Leu Ala Pro Ser Ser Lys Ser Thr Ser Gly
1               5                   10                  15

Gly Thr Ala Ala Leu Gly Cys Leu Val Lys Asp Tyr Phe Pro Glu Pro
            20                  25                  30

Val Thr Val Ser Trp Asn Ser Gly Ala Leu Thr Ser Gly Val His Thr
         35                  40                  45

Phe Pro Ala Val Leu Gln Ser Ser Gly Leu Tyr Ser Leu Ser Ser Val
 50                  55                  60

Val Thr Val Pro Ser Ser Leu Gly Thr Gln Thr Tyr Ile Cys Asn
 65                  70                  75                  80

Val Asn His Lys Pro Ser Asn Thr Lys Val Asp Lys Val Glu Pro
                 85                  90                  95

Lys Ser Cys Asp Lys Thr His Thr Cys Pro Pro Cys Pro Ala Pro Glu
                100                 105                 110

Leu Leu Gly Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Asp Glu Leu Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 130
<211> LENGTH: 326
<212> TYPE: PRT
<213> ORGANISM: Artificial Sequence
<220> FEATURE:
<223> OTHER INFORMATION: Humanized N297 Fc HC

<400> SEQUENCE: 130

Gly Pro Ser Val Phe Pro Leu Ala Pro Ser Ser Lys Ser Thr Ser Gly
1               5                   10                  15

Gly Thr Ala Ala Leu Gly Cys Leu Val Lys Asp Tyr Phe Pro Glu Pro
            20                  25                  30

Val Thr Val Ser Trp Asn Ser Gly Ala Leu Thr Ser Gly Val His Thr
        35                  40                  45

Phe Pro Ala Val Leu Gln Ser Ser Gly Leu Tyr Ser Leu Ser Ser Val
    50                  55                  60

Val Thr Val Pro Ser Ser Leu Gly Thr Gln Thr Tyr Ile Cys Asn
65                  70                  75                  80

Val Asn His Lys Pro Ser Asn Thr Lys Val Asp Lys Lys Val Glu Pro
            85                  90                  95

Lys Ser Cys Asp Lys Thr His Thr Cys Pro Pro Cys Pro Ala Pro Glu
            100                 105                 110

Leu Leu Gly Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Ala
            165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
            195                 200                 205

Ala Pro Ile Glu Lys Thr Ile Ser Lys Ala Lys Gly Gln Pro Arg Glu
            210                 215                 220

Pro Gln Val Tyr Thr Leu Pro Pro Ser Arg Asp Glu Leu Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 131
<211> LENGTH: 326
<212> TYPE: PRT
<213> ORGANISM: Artificial Sequence
<220> FEATURE:
<223> OTHER INFORMATION: Humanized N297 YTE Mutation Fc HC

<400> SEQUENCE: 131

Gly Pro Ser Val Phe Pro Leu Ala Pro Ser Ser Lys Ser Thr Ser Gly
1               5                   10                  15

Gly Thr Ala Ala Leu Gly Cys Leu Val Lys Asp Tyr Phe Pro Glu Pro
            20                  25                  30

Val Thr Val Ser Trp Asn Ser Gly Ala Leu Thr Ser Gly Val His Thr
            35                  40                  45

Phe Pro Ala Val Leu Gln Ser Ser Gly Leu Tyr Ser Leu Ser Ser Val
            50                  55                  60

Val Thr Val Pro Ser Ser Leu Gly Thr Gln Thr Tyr Ile Cys Asn
65                  70                  75                  80

Val Asn His Lys Pro Ser Asn Thr Lys Val Asp Lys Lys Val Glu Pro
            85                  90                  95

```
Lys Ser Cys Asp Lys Thr His Thr Cys Pro Pro Cys Pro Ala Pro Glu
                100                 105                 110

Leu Leu Gly Gly Pro Ser Val Phe Leu Phe Pro Pro Lys Pro Lys Asp
            115                 120                 125

Thr Leu Tyr Ile Thr Arg Glu Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Ala
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Asp Glu Leu Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 132
<211> LENGTH: 322
<212> TYPE: PRT
<213> ORGANISM: Artificial Sequence
<220> FEATURE:
<223> OTHER INFORMATION: Humanized Ultomiris Fc HC

<400> SEQUENCE: 132

Gly Pro Ser Val Phe Pro Leu Ala Pro Cys Ser Arg Ser Thr Ser Glu
1               5                   10                  15

Ser Thr Ala Ala Leu Gly Cys Leu Val Lys Asp Tyr Phe Pro Glu Pro
                20                  25                  30

Val Thr Val Ser Trp Asn Ser Gly Ala Leu Thr Ser Gly Val His Thr
            35                  40                  45

Phe Pro Ala Val Leu Gln Ser Ser Gly Leu Tyr Ser Leu Ser Ser Val
    50                  55                  60

Val Thr Val Pro Ser Ser Asn Phe Gly Thr Gln Thr Tyr Thr Cys Asn
65                  70                  75                  80

Val Asp His Lys Pro Ser Asn Thr Lys Val Asp Lys Thr Val Glu Arg
                85                  90                  95

Lys Cys Cys Val Glu Cys Pro Pro Cys Pro Ala Pro Val Ala Gly
            100                 105                 110

Pro Ser Val Phe Leu Phe Pro Pro Lys Pro Lys Asp Thr Leu Met Ile
        115                 120                 125
```

Ser Arg Thr Pro Glu Val Thr Cys Val Val Val Asp Val Ser Gln Glu
130             135             140

Asp Pro Glu Val Gln Phe Asn Trp Tyr Val Asp Gly Val Glu Val His
145             150             155             160

Asn Ala Lys Thr Lys Pro Arg Glu Glu Gln Phe Asn Ser Thr Tyr Arg
                165             170             175

Val Val Ser Val Leu Thr Val Leu His Gln Asp Trp Leu Asn Gly Lys
            180             185             190

Glu Tyr Lys Cys Lys Val Ser Asn Lys Gly Leu Pro Ser Ser Ile Glu
        195             200             205

Lys Thr Ile Ser Lys Ala Lys Gly Gln Pro Arg Glu Pro Gln Val Tyr
210             215             220

Thr Leu Pro Pro Ser Gln Glu Glu Met Thr Lys Asn Gln Val Ser Leu
225             230             235             240

Thr Cys Leu Val Lys Gly Phe Tyr Pro Ser Asp Ile Ala Val Glu Trp
                245             250             255

Glu Ser Asn Gly Gln Pro Glu Asn Asn Tyr Lys Thr Thr Pro Pro Val
            260             265             270

Leu Asp Ser Asp Gly Ser Phe Phe Leu Tyr Ser Arg Leu Thr Val Asp
        275             280             285

Lys Ser Arg Trp Gln Glu Gly Asn Val Phe Ser Cys Ser Val Leu His
290             295             300

Glu Ala Leu His Ser His Tyr Thr Gln Lys Ser Leu Ser Leu Ser Leu
305             310             315             320

Gly Lys

<210> SEQ ID NO 133
<211> LENGTH: 322
<212> TYPE: PRT
<213> ORGANISM: Artificial Sequence
<220> FEATURE:
<223> OTHER INFORMATION: Humanized Soliris Fc HC

<400> SEQUENCE: 133

Gly Pro Ser Val Phe Pro Leu Ala Pro Cys Ser Arg Ser Thr Ser Glu
1               5               10              15

Ser Thr Ala Ala Leu Gly Cys Leu Val Lys Asp Tyr Phe Pro Glu Pro
            20              25              30

Val Thr Val Ser Trp Asn Ser Gly Ala Leu Thr Ser Gly Val His Thr
        35              40              45

Phe Pro Ala Val Leu Gln Ser Ser Gly Leu Tyr Ser Leu Ser Ser Val
50              55              60

Val Thr Val Pro Ser Ser Asn Phe Gly Thr Gln Thr Tyr Thr Cys Asn
65              70              75              80

Val Asp His Lys Pro Ser Asn Thr Lys Val Asp Lys Thr Val Glu Arg
                85              90              95

Lys Cys Cys Val Glu Cys Pro Pro Cys Pro Ala Pro Pro Val Ala Gly
            100             105             110

Pro Ser Val Phe Leu Phe Pro Pro Lys Pro Lys Asp Thr Leu Met Ile
        115             120             125

Ser Arg Thr Pro Glu Val Thr Cys Val Val Val Asp Val Ser Gln Glu
130             135             140

Asp Pro Glu Val Gln Phe Asn Trp Tyr Val Asp Gly Val Glu Val His
145             150             155             160

Asn Ala Lys Thr Lys Pro Arg Glu Glu Gln Phe Asn Ser Thr Tyr Arg
            165                 170                 175

Val Val Ser Val Leu Thr Val Leu His Gln Asp Trp Leu Asn Gly Lys
        180                 185                 190

Glu Tyr Lys Cys Lys Val Ser Asn Lys Gly Leu Pro Ser Ser Ile Glu
        195                 200                 205

Lys Thr Ile Ser Lys Ala Lys Gly Gln Pro Arg Glu Pro Gln Val Tyr
210                 215                 220

Thr Leu Pro Pro Ser Gln Glu Glu Met Thr Lys Asn Gln Val Ser Leu
225                 230                 235                 240

Thr Cys Leu Val Lys Gly Phe Tyr Pro Ser Asp Ile Ala Val Glu Trp
            245                 250                 255

Glu Ser Asn Gly Gln Pro Glu Asn Asn Tyr Lys Thr Thr Pro Pro Val
        260                 265                 270

Leu Asp Ser Asp Gly Ser Phe Phe Leu Tyr Ser Arg Leu Thr Val Asp
        275                 280                 285

Lys Ser Arg Trp Gln Glu Gly Asn Val Phe Ser Cys Ser Val Met His
        290                 295                 300

Glu Ala Leu His Asn His Tyr Thr Gln Lys Ser Leu Ser Leu Ser Leu
305                 310                 315                 320

Gly Lys

<210> SEQ ID NO 134
<211> LENGTH: 232
<212> TYPE: PRT
<213> ORGANISM: Artificial Sequence
<220> FEATURE:
<223> OTHER INFORMATION: Humanized IgG1 Fc (No CH1)

<400> SEQUENCE: 134

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe

```
                195                 200                 205
Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 135
<211> LENGTH: 228
<212> TYPE: PRT
<213> ORGANISM: Artificial Sequence
<220> FEATURE:
<223> OTHER INFORMATION: Humanized IgG2 Fc (No CH1)

<400> SEQUENCE: 135

Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Met Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225

<210> SEQ ID NO 136
<211> LENGTH: 229
<212> TYPE: PRT
<213> ORGANISM: Artificial Sequence
<220> FEATURE:
<223> OTHER INFORMATION: Humanized IgG4 Fc (No CH1)

<400> SEQUENCE: 136

Glu Ser Lys Tyr Gly Pro Pro Cys Pro Ser Cys Pro Ala Pro Glu Phe
1               5                   10                  15

Leu Gly Gly Pro Ser Val Phe Leu Phe Pro Pro Lys Pro Lys Asp Thr
            20                  25                  30
```

```
Leu Met Ile Ser Arg Thr Pro Glu Val Thr Cys Val Val Asp Val
         35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
                100                 105                 110

Ser Ile Glu Lys Thr Ile Ser Lys Ala Lys Gly Gln Pro Arg Glu Pro
             115                 120                 125

Gln Val Tyr Thr Leu Pro Pro Ser Gln Glu Glu Met Thr Lys Asn Gln
         130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 137
<211> LENGTH: 229
<212> TYPE: PRT
<213> ORGANISM: Artificial Sequence
<220> FEATURE:
<223> OTHER INFORMATION: Humanized IgG4 Fc (No CH1)

<400> SEQUENCE: 137

Ala Glu Ser Lys Tyr Gly Pro Pro Cys Pro Cys Pro Ala Pro Glu
1               5                   10                  15

Ala Ala Gly Gly Pro Ser Val Phe Leu Phe Pro Pro Lys Pro Lys Asp
             20                  25                  30

Thr Leu Met Ile Ser Arg Thr Pro Glu Val Thr Cys Val Val Val Asp
             35                  40                  45

Val Ser Gln Glu Asp Pro Glu Val Gln Phe Asn Trp Tyr Val Asp Gly
 50                  55                  60

Val Glu Val His Asn Ala Lys Thr Lys Pro Arg Glu Glu Gln Phe Asn
 65                  70                  75                  80

Ser Thr Tyr Arg Val Val Ser Val Leu Thr Val Leu His Gln Asp Trp
                 85                  90                  95

Leu Asn Gly Lys Glu Tyr Lys Cys Lys Val Ser Asn Lys Gly Leu Pro
                100                 105                 110

Ser Ser Ile Glu Lys Thr Ile Ser Lys Ala Lys Gly Gln Pro Arg Glu
             115                 120                 125

Pro Gln Val Tyr Thr Leu Pro Pro Ser Gln Glu Glu Met Thr Lys Asn
         130                 135                 140

Gln Val Ser Leu Thr Cys Leu Val Lys Gly Phe Tyr Pro Ser Asp Ile
145                 150                 155                 160
```

Ala Val Glu Trp Glu Ser Asn Gly Gln Pro Glu Asn Asn Tyr Lys Thr
            165                 170                 175

Thr Pro Pro Val Leu Asp Ser Asp Gly Ser Phe Phe Leu Tyr Ser Arg
        180                 185                 190

Leu Thr Val Asp Lys Ser Arg Trp Gln Glu Gly Asn Val Phe Ser Cys
            195                 200                 205

Ser Val Met His Glu Ala Leu His Asn His Tyr Thr Gln Lys Ser Leu
        210                 215                 220

Ser Leu Ser Leu Gly
225

<210> SEQ ID NO 138
<211> LENGTH: 100
<212> TYPE: PRT
<213> ORGANISM: Artificial Sequence
<220> FEATURE:
<223> OTHER INFORMATION: Humanized Fc (CH1 Only)

<400> SEQUENCE: 138

Gly Pro Ser Val Phe Pro Leu Ala Pro Ser Ser Lys Ser Thr Ser Gly
1               5                   10                  15

Gly Thr Ala Ala Leu Gly Cys Leu Val Lys Asp Tyr Phe Pro Glu Pro
            20                  25                  30

Val Thr Val Ser Trp Asn Ser Gly Ala Leu Thr Ser Gly Val His Thr
        35                  40                  45

Phe Pro Ala Val Leu Gln Ser Ser Gly Leu Tyr Ser Leu Ser Ser Val
    50                  55                  60

Val Thr Val Pro Ser Ser Ser Leu Gly Thr Gln Thr Tyr Ile Cys Asn
65                  70                  75                  80

Val Asn His Lys Pro Ser Asn Thr Lys Val Asp Lys Lys Val Glu Pro
                85                  90                  95

Lys Ser Cys Asp
            100

<210> SEQ ID NO 139
<211> LENGTH: 101
<212> TYPE: PRT
<213> ORGANISM: Artificial Sequence
<220> FEATURE:
<223> OTHER INFORMATION: Humanized Fc LC

<400> SEQUENCE: 139

Ser Val Phe Ile Phe Pro Pro Ser Asp Glu Gln Leu Lys Ser Gly Thr
1               5                   10                  15

Ala Ser Val Val Cys Leu Leu Asn Asn Phe Tyr Pro Arg Glu Ala Lys
            20                  25                  30

Val Gln Trp Lys Val Asp Asn Ala Leu Gln Ser Gly Asn Ser Gln Glu
        35                  40                  45

Ser Val Thr Glu Gln Asp Ser Lys Asp Ser Thr Tyr Ser Leu Ser Ser
    50                  55                  60

Thr Leu Thr Leu Ser Lys Ala Asp Tyr Glu Lys His Lys Val Tyr Ala
65                  70                  75                  80

Cys Glu Val Thr His Gln Gly Leu Ser Ser Pro Val Thr Lys Ser Phe
                85                  90                  95

Asn Arg Gly Glu Cys
            100

<210> SEQ ID NO 140

```
<211> LENGTH: 5
<212> TYPE: PRT
<213> ORGANISM: Artificial Sequence
<220> FEATURE:
<223> OTHER INFORMATION: Humanized Linker

<400> SEQUENCE: 140

Gly Gly Gly Gly Ser
1               5

<210> SEQ ID NO 141
<211> LENGTH: 5
<212> TYPE: PRT
<213> ORGANISM: Artificial Sequence
<220> FEATURE:
<223> OTHER INFORMATION: Humanized Linker

<400> SEQUENCE: 141

Gly Gly Gly Ser Gly
1               5

<210> SEQ ID NO 142
<211> LENGTH: 4
<212> TYPE: PRT
<213> ORGANISM: Artificial Sequence
<220> FEATURE:
<223> OTHER INFORMATION: Humanized Linker

<400> SEQUENCE: 142

Ser Gly Gly Gly
1

<210> SEQ ID NO 143
<211> LENGTH: 15
<212> TYPE: PRT
<213> ORGANISM: Artificial Sequence
<220> FEATURE:
<223> OTHER INFORMATION: Humanized Linker

<400> SEQUENCE: 143

Gly Gly Gly Gly Ser Gly Gly Gly Ser Gly Gly Gly Gly Ser
1               5                   10                  15

<210> SEQ ID NO 144
<211> LENGTH: 14
<212> TYPE: PRT
<213> ORGANISM: Artificial Sequence
<220> FEATURE:
<223> OTHER INFORMATION: Humanized Linker

<400> SEQUENCE: 144

Gly Gly Gly Gly Asp Gly Gly Gly Gly Asp Gly Gly Gly Gly
1               5                   10

<210> SEQ ID NO 145
<211> LENGTH: 14
<212> TYPE: PRT
<213> ORGANISM: Artificial Sequence
<220> FEATURE:
<223> OTHER INFORMATION: Humanized Linker

<400> SEQUENCE: 145

Gly Gly Gly Gly Glu Gly Gly Gly Glu Gly Gly Gly Gly
1               5                   10

<210> SEQ ID NO 146
<211> LENGTH: 4
```

```
<212> TYPE: PRT
<213> ORGANISM: Artificial Sequence
<220> FEATURE:
<223> OTHER INFORMATION: Humanized Linker

<400> SEQUENCE: 146

Gly Gly Gly Glu
1

<210> SEQ ID NO 147
<211> LENGTH: 4
<212> TYPE: PRT
<213> ORGANISM: Artificial Sequence
<220> FEATURE:
<223> OTHER INFORMATION: Humanized Linker

<400> SEQUENCE: 147

Gly Gly Gly Asp
1

<210> SEQ ID NO 148
<211> LENGTH: 5
<212> TYPE: PRT
<213> ORGANISM: Artificial Sequence
<220> FEATURE:
<223> OTHER INFORMATION: Humanized Linker

<400> SEQUENCE: 148

Gly Gly Gly Gly Ala
1               5

<210> SEQ ID NO 149
<211> LENGTH: 15
<212> TYPE: PRT
<213> ORGANISM: Artificial Sequence
<220> FEATURE:
<223> OTHER INFORMATION: Humanized Linker

<400> SEQUENCE: 149

Gly Gly Gly Gly Ala Gly Gly Gly Ala Gly Gly Gly Ser
1               5                   10                  15

<210> SEQ ID NO 150
<211> LENGTH: 125
<212> TYPE: PRT
<213> ORGANISM: Artificial Sequence
<220> FEATURE:
<223> OTHER INFORMATION: Humanized Anti-TNF VH

<400> SEQUENCE: 150

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110
```

```
Gln Gly Thr Leu Val Thr Val Ser Ser Ala Ser Thr Lys
        115                 120                 125

<210> SEQ ID NO 151
<211> LENGTH: 113
<212> TYPE: PRT
<213> ORGANISM: Artificial Sequence
<220> FEATURE:
<223> OTHER INFORMATION: Humanized Anti-TNF VL

<400> SEQUENCE: 151

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro

<210> SEQ ID NO 152
<211> LENGTH: 127
<212> TYPE: PRT
<213> ORGANISM: Artificial Sequence
<220> FEATURE:
<223> OTHER INFORMATION: Humanized Anti-VEGF VH

<400> SEQUENCE: 152

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys
        115                 120                 125

<210> SEQ ID NO 153
<211> LENGTH: 113
<212> TYPE: PRT
<213> ORGANISM: Artificial Sequence
<220> FEATURE:
<223> OTHER INFORMATION: Humanized Anti-VEGF VL
```

-continued

```
<400> SEQUENCE: 153

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro

<210> SEQ ID NO 154
<211> LENGTH: 254
<212> TYPE: PRT
<213> ORGANISM: Artificial Sequence
<220> FEATURE:
<223> OTHER INFORMATION: Humanized Camelid Anti-Alb & Anti-P mAb

<400> SEQUENCE: 154

Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
        35                  40                  45

Ser Ala Ile Asn Trp Gln Lys Thr Ala Thr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Tyr Asp Tyr
            100                 105                 110

Trp Gly Gln Gly Thr Leu Val Thr Val Ser Ser Gly Gly Ser Gly
        115                 120                 125

Gly Gly Ser Gly Gly Ser Glu Val Gln Leu Val Glu Ser Gly Gly
    130                 135                 140

Gly Leu Val Gln Pro Gly Gly Ser Leu Arg Leu Ser Cys Ala Ala Ser
145                 150                 155                 160

Gly Arg Ile Ser Ser Ile Ile His Met Ala Trp Val Arg Gln Ala Pro
                165                 170                 175

Gly Lys Gln Arg Glu Leu Val Ser Glu Ile Ser Arg Val Gly Thr Thr
            180                 185                 190

Val Tyr Ala Asp Ser Val Lys Gly Arg Phe Thr Ile Ser Arg Asp Asn
        195                 200                 205

Ser Lys Asn Thr Leu Tyr Leu Gln Met Asn Ser Leu Arg Ala Glu Asp
    210                 215                 220

Thr Ala Val Tyr Tyr Cys Asn Ala Leu Gln Tyr Glu Lys His Gly Gly
225                 230                 235                 240
```

```
Ala Asp Tyr Trp Gly Gln Gly Thr Leu Val Thr Val Ser Ser
             245                 250
```

<210> SEQ ID NO 155
<211> LENGTH: 246
<212> TYPE: PRT
<213> ORGANISM: Artificial Sequence
<220> FEATURE:
<223> OTHER INFORMATION: Humanized Camelid Anti-Alb & Anti-P mAb

<400> SEQUENCE: 155

```
Glu Val Gln Leu Val Glu Ser Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Glu Pro Glu Trp Val
            35                  40                  45

Ser Ser Ile Ser Gly Ser Gly Ser Asp Thr Leu Tyr Ala Asp Ser Val
        50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
                85                  90                  95

Thr Ile Gly Gly Ser Leu Ser Arg Ser Ser Gln Gly Thr Gln Val Thr
            100                 105                 110

Val Ser Ser Gly Gly Gly Ser Gly Gly Gly Ser Gly Gly Gly Ser Glu
            115                 120                 125

Val Gln Leu Val Glu Ser Gly Gly Gly Leu Val Gln Pro Gly Gly Ser
        130                 135                 140

Leu Arg Leu Ser Cys Ala Ala Ser Gly Arg Ile Ser Ser Ile Ile His
145                 150                 155                 160

Met Ala Trp Val Arg Gln Ala Pro Gly Lys Gln Arg Glu Leu Val Ser
                165                 170                 175

Glu Ile Ser Arg Val Gly Thr Thr Val Tyr Ala Asp Ser Val Lys Gly
            180                 185                 190

Arg Phe Thr Ile Ser Arg Asp Asn Ser Lys Asn Thr Leu Tyr Leu Gln
        195                 200                 205

Met Asn Ser Leu Arg Ala Glu Asp Thr Ala Val Tyr Tyr Cys Asn Ala
    210                 215                 220

Leu Gln Tyr Glu Lys His Gly Gly Ala Asp Tyr Trp Gly Gln Gly Thr
225                 230                 235                 240

Leu Val Thr Val Ser Ser
            245
```

<210> SEQ ID NO 156
<211> LENGTH: 222
<212> TYPE: PRT
<213> ORGANISM: Artificial Sequence
<220> FEATURE:
<223> OTHER INFORMATION: Humanized Anti-P HC

<400> SEQUENCE: 156

```
Gln Val Gln Leu Val Gln Ser Ala Pro Glu Val Ala Lys Pro Gly Thr
1               5                   10                  15

Ser Val Lys Met Ser Cys Lys Ala Ser Gly Tyr Ile Phe Thr Asn Tyr
            20                  25                  30

Pro Ile His Trp Val Lys Gln Ala Pro Gly Gln Gly Leu Glu Trp Ile
```

```
            35                  40                  45
Gly Phe Ile Asp Pro Gly Gly Tyr Asp Glu Pro Asp Glu Arg Phe
 50                  55                  60

Arg Asp Arg Ala Thr Leu Thr Ala Asp Lys Ser Thr Ser Thr Ala Tyr
 65                  70                  75                  80

Met Glu Leu Ser Ser Leu Arg Ser Glu Asp Thr Ala Ile Tyr Tyr Cys
                 85                  90                  95

Ala Arg Arg Gly Gly Tyr Tyr Leu Asp Tyr Trp Gly Gln Gly Thr
             100                 105                 110

Leu Val Thr Val Ser Ser Ala Ser Thr Lys Gly Pro Ser Val Phe Pro
         115                 120                 125

Leu Ala Pro Ser Ser Lys Ser Thr Ser Gly Gly Thr Ala Ala Leu Gly
     130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp
    210                 215                 220

<210> SEQ ID NO 157
<211> LENGTH: 214
<212> TYPE: PRT
<213> ORGANISM: Artificial Sequence
<220> FEATURE:
<223> OTHER INFORMATION: Humanized Anti-P LC

<400> SEQUENCE: 157

Asp Ile Gln Met Thr Gln Ser Pro Ser Ser Leu Ser Ala Ser Leu Gly
  1               5                  10                  15

Asp Arg Val Thr Ile Thr Cys Arg Ala Ser Gln Asp Ile Ser Phe Phe
             20                  25                  30

Leu Asn Trp Tyr Gln Gln Lys Pro Asp Gly Thr Val Lys Leu Leu Ile
         35                  40                  45

Tyr Tyr Thr Ser Arg Tyr His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln His Gly Asn Thr Leu Pro Trp
                 85                  90                  95

Thr Phe Gly Gln Gly Thr Lys Leu Glu Ile Lys Arg Thr Val Ala Ala
             100                 105                 110

Pro Ser Val Phe Ile Phe Pro Pro Ser Asp Glu Gln Leu Lys Ser Gly
         115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
                    180                 185                 190
Ala Cys Glu Val Thr His Gln Gly Leu Ser Ser Pro Val Thr Lys Ser
                195                 200                 205

Phe Asn Arg Gly Glu Cys
        210

<210> SEQ ID NO 158
<211> LENGTH: 360
<212> TYPE: PRT
<213> ORGANISM: Artificial Sequence
<220> FEATURE:
<223> OTHER INFORMATION: Humanized Anti-Alb & Anti-P - HC

<400> SEQUENCE: 158

Gln Val Gln Leu Val Gln Ser Ala Pro Glu Val Ala Lys Pro Gly Thr
1               5                   10                  15

Ser Val Lys Met Ser Cys Lys Ala Ser Gly Tyr Ile Phe Thr Asn Tyr
                20                  25                  30

Pro Ile His Trp Val Lys Gln Ala Pro Gly Gln Gly Leu Glu Trp Ile
            35                  40                  45

Gly Phe Ile Asp Pro Gly Gly Gly Tyr Asp Glu Pro Asp Glu Arg Phe
    50                  55                  60

Arg Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Ile Tyr Tyr Cys
                85                  90                  95

Ala Arg Arg Gly Gly Gly Tyr Tyr Leu Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Gly Gly
    210                 215                 220

Gly Gly Ser Gly Gly Gly Gly Ser Gly Gly Gly Gly Ser Glu Val Gln
225                 230                 235                 240

Leu Val Glu Ser Gly Gly Gly Leu Val Lys Pro Gly Gly Ser Leu Arg
                245                 250                 255

Leu Ser Cys Ala Ala Ser Gly Arg Pro Val Ser Asn Tyr Ala Ala Ala
            260                 265                 270

Trp Phe Arg Gln Ala Pro Gly Lys Glu Arg Glu Phe Val Ser Ala Ile
        275                 280                 285

Asn Trp Gln Lys Thr Ala Thr Tyr Ala Asp Ser Val Lys Gly Arg Phe
    290                 295                 300

Thr Ile Ser Arg Asp Asn Ala Lys Asn Ser Leu Tyr Leu Gln Met Asn
305                 310                 315                 320

Ser Leu Arg Ala Glu Asp Thr Ala Val Tyr Tyr Cys Ala Ala Val Phe
```

```
                   325                 330                 335
Arg Val Val Ala Pro Lys Thr Gln Tyr Asp Tyr Asp Tyr Trp Gly Gln
                340                 345                 350

Gly Thr Leu Val Thr Val Ser Ser
            355                 360

<210> SEQ ID NO 159
<211> LENGTH: 214
<212> TYPE: PRT
<213> ORGANISM: Artificial Sequence
<220> FEATURE:
<223> OTHER INFORMATION: Humanized Anti-P LC

<400> SEQUENCE: 159

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Ile Ser Phe Phe
                20                  25                  30

Leu Asn Trp Tyr Gln Gln Lys Pro Asp Gly Thr Val Lys Leu Leu Ile
            35                  40                  45

Tyr Tyr Thr Ser Arg Tyr His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln His Gly Asn Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 160
<211> LENGTH: 352
<212> TYPE: PRT
<213> ORGANISM: Artificial Sequence
<220> FEATURE:
<223> OTHER INFORMATION: Humanized Anti-Alb & Anti-P - HC

<400> SEQUENCE: 160

Gln Val Gln Leu Val Gln Ser Ala Pro Glu Val Ala Lys Pro Gly Thr
1               5                   10                  15

Ser Val Lys Met Ser Cys Lys Ala Ser Gly Tyr Ile Phe Thr Asn Tyr
                20                  25                  30

Pro Ile His Trp Val Lys Gln Ala Pro Gly Gln Gly Leu Glu Trp Ile
            35                  40                  45
```

Gly Phe Ile Asp Pro Gly Gly Gly Tyr Asp Glu Pro Asp Glu Arg Phe
            50                  55                  60

Arg Asp Arg Ala Thr Leu Thr Ala Asp Lys Ser Thr Ser Thr Ala Tyr
65                  70                  75                  80

Met Glu Leu Ser Ser Leu Arg Ser Glu Asp Thr Ala Ile Tyr Tyr Cys
                85                  90                  95

Ala Arg Arg Gly Gly Tyr Tyr Leu Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Gly Gly
210                 215                 220

Gly Gly Ser Gly Gly Gly Ser Gly Gly Gly Ser Glu Val Gln
225                 230                 235                 240

Leu Val Glu Ser Gly Gly Gly Leu Val Gln Pro Gly Gly Ser Leu Arg
            245                 250                 255

Leu Ser Cys Ala Ala Ser Gly Phe Thr Phe Arg Ser Phe Gly Met Ser
            260                 265                 270

Trp Val Arg Gln Ala Pro Gly Lys Glu Pro Glu Trp Val Ser Ser Ile
            275                 280                 285

Ser Gly Ser Gly Ser Asp Thr Leu Tyr Ala Asp Ser Val Lys Gly Arg
            290                 295                 300

Phe Thr Ile Ser Arg Asp Asn Ala Lys Thr Thr Leu Tyr Leu Gln Met
305                 310                 315                 320

Asn Ser Leu Lys Pro Glu Asp Thr Ala Val Tyr Tyr Cys Thr Ile Gly
                325                 330                 335

Gly Ser Leu Ser Arg Ser Ser Gln Gly Thr Gln Val Thr Val Ser Ser
            340                 345                 350

<210> SEQ ID NO 161
<211> LENGTH: 214
<212> TYPE: PRT
<213> ORGANISM: Artificial Sequence
<220> FEATURE:
<223> OTHER INFORMATION: Humanized Anti-P LC

<400> SEQUENCE: 161

Asp Ile Gln Met Thr Gln Ser Pro Ser Ser Leu Ser Ala Ser Leu Gly
1               5                   10                  15

Asp Arg Val Thr Ile Thr Cys Arg Ala Ser Gln Asp Ile Ser Phe Phe
                20                  25                  30

Leu Asn Trp Tyr Gln Gln Lys Pro Asp Gly Thr Val Lys Leu Leu Ile
            35                  40                  45

Tyr Tyr Thr Ser Arg Tyr His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln His Gly Asn Thr Leu Pro Trp
            85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 162
<211> LENGTH: 363
<212> TYPE: PRT
<213> ORGANISM: Artificial Sequence
<220> FEATURE:
<223> OTHER INFORMATION: Humanized Camelid Anti-P Full IgG4 HC

<400> SEQUENCE: 162

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Ser Ser Ile Ile
            20                  25                  30

His Met Ala Trp Phe Arg Gln Ala Pro Gly Lys Glu Arg Glu Leu Val
            35                  40                  45

Ser Glu Ile Ser Arg Val Gly Thr Thr Val Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Lys Pro Glu Asp Thr Ala Val Tyr Tyr Cys Asn
            85                  90                  95

Ala Leu Gln Tyr Glu Lys His Gly Gly Ala Asp Tyr Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Ala Glu Ser Lys Tyr Gly Pro Pro Cys Pro
            130                 135                 140

Pro Cys Pro Ala Pro Glu Ala Ala Gly Gly Pro Ser Val Phe Leu Phe
145                 150                 155                 160

Pro Pro Lys Pro Lys Asp Thr Leu Met Ile Ser Arg Thr Pro Glu Val
            165                 170                 175

Thr Cys Val Val Val Asp Val Ser Gln Glu Asp Pro Glu Val Gln Phe
            180                 185                 190

Asn Trp Tyr Val Asp Gly Val Glu Val His Asn Ala Lys Thr Lys Pro
            195                 200                 205

```
Arg Glu Glu Gln Phe Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Gly Leu Pro Ser Ser Ile Glu Lys Thr Ile Ser Lys Ala
                245                 250                 255

Lys Gly Gln Pro Arg Glu Pro Gln Val Tyr Thr Leu Pro Pro Ser Gln
                    260                 265                 270

Glu Glu Met Thr Lys Asn Gln Val Ser Leu Thr Cys Leu Val Lys Gly
                275                 280                 285

Phe Tyr Pro Ser Asp Ile Ala Val Glu Trp Glu Ser Asn Gly Gln Pro
290                 295                 300

Glu Asn Asn Tyr Lys Thr Thr Pro Pro Val Leu Asp Ser Asp Gly Ser
305                 310                 315                 320

Phe Phe Leu Tyr Ser Arg Leu Thr Val Asp Lys Ser Arg Trp Gln Glu
                325                 330                 335

Gly Asn Val Phe Ser Cys Ser Val Met His Glu Ala Leu His Asn His
                340                 345                 350

Tyr Thr Gln Lys Ser Leu Ser Leu Ser Leu Gly
                355                 360

<210> SEQ ID NO 163
<211> LENGTH: 367
<212> TYPE: PRT
<213> ORGANISM: Artificial Sequence
<220> FEATURE:
<223> OTHER INFORMATION: Humanized Anti-Alb Full IgG4 HC

<400> SEQUENCE: 163

Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
        35                  40                  45

Ser Ala Ile Asn Trp Gln Lys Thr Ala Thr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Asp Tyr Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Ser Ala Glu Ser Lys Tyr Gly
    130                 135                 140

Pro Pro Cys Pro Pro Cys Pro Ala Pro Glu Ala Ala Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Asp Val Ser Gln Glu Asp Pro
            180                 185                 190

Glu Val Gln Phe Asn Trp Tyr Val Asp Gly Val Glu Val His Asn Ala
        195                 200                 205
```

```
Lys Thr Lys Pro Arg Glu Glu Gln Phe Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Gly Leu Pro Ser Ser Ile Glu Lys Thr
                245                 250                 255

Ile Ser Lys Ala Lys Gly Gln Pro Arg Glu Pro Gln Val Tyr Thr Leu
                260                 265                 270

Pro Pro Ser Gln Glu Glu Met Thr Lys Asn Gln Val Ser Leu Thr Cys
            275                 280                 285

Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Arg Leu Thr Val Asp Lys Ser
                325                 330                 335

Arg Trp Gln Glu Gly Asn Val Phe Ser Cys Ser Val Met His Glu Ala
            340                 345                 350

Leu His Asn His Tyr Thr Gln Lys Ser Leu Ser Leu Ser Leu Gly
    355                 360                 365

<210> SEQ ID NO 164
<211> LENGTH: 366
<212> TYPE: PRT
<213> ORGANISM: Artificial Sequence
<220> FEATURE:
<223> OTHER INFORMATION: Humanized Camelid Anti-P Full IgG1 HC

<400> SEQUENCE: 164

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Ser Ser Ile Ile
            20                  25                  30

His Met Ala Trp Phe Arg Gln Ala Pro Gly Lys Glu Arg Glu Leu Val
        35                  40                  45

Ser Glu Ile Ser Arg Val Gly Thr Thr Val Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Lys Pro Glu Asp Thr Ala Val Tyr Tyr Cys Asn
            85                  90                  95

Ala Leu Gln Tyr Glu Lys His Gly Gly Ala Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Glu Pro Lys Ser Cys Asp Lys Thr His Thr
130                 135                 140

Cys Pro Pro Cys Pro Ala Pro Glu Leu Leu Gly Gly Pro Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
        195                 200                 205
```

```
Lys Pro Arg Glu Glu Gln Tyr Asn Ser Thr Tyr Arg Val Val Ser Val
    210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Pro Ile Glu Lys Thr Ile Ser
                245                 250                 255

Lys Ala Lys Gly Gln Pro Arg Glu Pro Gln Val Tyr Thr Leu Pro Pro
            260                 265                 270

Ser Arg Asp Glu Leu Thr Lys Asn Gln Val Ser Leu Thr Cys Leu Val
        275                 280                 285

Lys Gly Phe Tyr Pro Ser Asp Ile Ala Val Glu Trp Glu Ser Asn Gly
    290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly Lys
        355                 360                 365

<210> SEQ ID NO 165
<211> LENGTH: 370
<212> TYPE: PRT
<213> ORGANISM: Artificial Sequence
<220> FEATURE:
<223> OTHER INFORMATION: Humanized Anti-Alb Full IgG1 HC

<400> SEQUENCE: 165

Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
        35                  40                  45

Ser Ala Ile Asn Trp Gln Lys Thr Ala Thr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Asp Tyr Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Glu Pro Lys Ser Cys Asp
    130                 135                 140

Lys Thr His Thr Cys Pro Pro Cys Pro Ala Pro Glu Leu Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser His Glu
            180                 185                 190

Asp Pro Glu Val Lys Phe Asn Trp Tyr Val Asp Gly Val Glu Val His
        195                 200                 205
```

-continued

```
Asn Ala Lys Thr Lys Pro Arg Glu Glu Gln Tyr Asn Ser Thr Tyr Arg
    210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Ala Leu Pro Ala Pro Ile Glu
                245                 250                 255

Lys Thr Ile Ser Lys Ala Lys Gly Gln Pro Arg Glu Pro Gln Val Tyr
            260                 265                 270

Thr Leu Pro Pro Ser Arg Asp Glu Leu Thr Lys Asn Gln Val Ser Leu
        275                 280                 285

Thr Cys Leu Val Lys Gly Phe Tyr Pro Ser Asp Ile Ala Val Glu Trp
290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Lys Leu Thr Val Asp
                325                 330                 335

Lys Ser Arg Trp Gln Gln Gly Asn Val Phe Ser Cys Ser Val Met His
            340                 345                 350

Glu Ala Leu His Asn His Tyr Thr Gln Lys Ser Leu Ser Leu Ser Pro
        355                 360                 365

Gly Lys
    370

<210> SEQ ID NO 166
<211> LENGTH: 448
<212> TYPE: PRT
<213> ORGANISM: Artificial Sequence
<220> FEATURE:
<223> OTHER INFORMATION: Humanized Anti-P Full IgG1 HC

<400> SEQUENCE: 166

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Pro Ile His Trp Val Arg Gln Ala Pro Gly Gln Gly Leu Glu Trp Met
        35                  40                  45

Gly Phe Ile Asp Pro Gly Gly Gly Tyr Asp Glu Pro Asp Glu Arg Phe
    50                  55                  60

Arg Asp Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Tyr Tyr Leu Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190
```

Asn Phe Gly Thr Gln Thr Tyr Thr Cys Asn Val Asp His Lys Pro Ser
            195                 200                 205

Asn Thr Lys Val Asp Lys Thr Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 167
<211> LENGTH: 214
<212> TYPE: PRT
<213> ORGANISM: Artificial Sequence
<220> FEATURE:
<223> OTHER INFORMATION: Humanized Anti-P Full LC

<400> SEQUENCE: 167

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Gly Asn Thr Leu Pro Trp
            85                  90                  95

Thr Phe Gly Gln Gly Thr Lys Leu Glu Ile Lys Arg Thr Val Ala Ala
            100                 105                 110

-continued

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 168
<211> LENGTH: 451
<212> TYPE: PRT
<213> ORGANISM: Artificial Sequence
<220> FEATURE:
<223> OTHER INFORMATION: Humanized Anti-Alb Full IgG1 HC

<400> SEQUENCE: 168

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
            85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Asn Phe Gly Thr Gln Thr Tyr Thr Cys Asn Val Asp His
            195                 200                 205

Lys Pro Ser Asn Thr Lys Val Asp Lys Thr Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

```
Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 169
<211> LENGTH: 217
<212> TYPE: PRT
<213> ORGANISM: Artificial Sequence
<220> FEATURE:
<223> OTHER INFORMATION: Humanized Anti-Alb Full LC

<400> SEQUENCE: 169

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
            35                  40                  45

Ile Tyr Glu Ala Ser Lys Leu Thr Ser Gly Val Pro Ser Arg Phe Ser
50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Tyr Ser Ser Ile
                85                  90                  95

Ser Asp Thr Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
            130                 135                 140

Arg Glu Ala Lys Val Gln Trp Lys Val Asp Asn Ala Leu Gln Ser Gly
145                 150                 155                 160
```

-continued

```
Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 170
<211> LENGTH: 455
<212> TYPE: PRT
<213> ORGANISM: Artificial Sequence
<220> FEATURE:
<223> OTHER INFORMATION: Humanized Anti-P Full IgG1 HC

<400> SEQUENCE: 170

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Gly
            20                  25                  30

Tyr Trp Ile Phe Trp Val Arg Gln Ala Pro Gly Lys Gly Leu Glu Leu
        35                  40                  45

Val Gly Gly Ile Tyr Ser Gly Ser Ser Gly Thr Thr Tyr Tyr Ala Asp
    50                  55                  60

Ser Val Lys Gly Arg Phe Thr Ile Ser Lys Asp Asn Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Ser Val Asp Gly Ile Asp Ser Tyr Asp Ala Ala Phe
            100                 105                 110

Asn Leu Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Tyr Ile Thr Arg Glu Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300
```

```
Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 171
<211> LENGTH: 217
<212> TYPE: PRT
<213> ORGANISM: Artificial Sequence
<220> FEATURE:
<223> OTHER INFORMATION: Humanized Anti-P Full LC

<400> SEQUENCE: 171

Asp Ile Gln Leu Thr Gln Ser Pro Ser Ser Leu Ser Ala Ser Val Gly
1               5                   10                  15

Asp Arg Val Thr Ile Thr Cys Arg Ala Ser Asp Asn Ile Tyr Ser Leu
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
50                  55                  60

Ser Gly Ser Gly Thr Asp Phe Thr Leu Thr Ile Ser Ser Val Gln Pro
65                  70                  75                  80

Glu Asp Phe Ala Thr Tyr Tyr Cys Gln Gln His Tyr Asp Tyr Asn Tyr
                85                  90                  95

Leu Asp Val Ala Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205
```

```
Thr Lys Ser Phe Asn Arg Gly Glu Cys
    210                 215

<210> SEQ ID NO 172
<211> LENGTH: 451
<212> TYPE: PRT
<213> ORGANISM: Artificial Sequence
<220> FEATURE:
<223> OTHER INFORMATION: Humanized Anti-Alb Full IgG1 HC

<400> SEQUENCE: 172

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Tyr
                245                 250                 255

Ile Thr Arg Glu Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350
```

-continued

```
Tyr Thr Leu Pro Pro Ser Arg Asp Glu Leu Thr Lys Asn Gln Val Ser
            355                 360                 365
Leu Thr Cys Leu Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys
    450

<210> SEQ ID NO 173
<211> LENGTH: 217
<212> TYPE: PRT
<213> ORGANISM: Artificial Sequence
<220> FEATURE:
<223> OTHER INFORMATION: Humanized Anti-Alb Full LC

<400> SEQUENCE: 173

Asp Ile Gln Met Thr Gln Ser Pro Ser Ser Val Ser Ala Ser Val Gly
1               5                   10                  15
Asp Arg Val Thr Ile Thr Cys Gln Ser Ser Pro Ser Val Trp Ser Asn
            20                  25                  30
Phe Leu Ser Trp Tyr Gln Gln Lys Pro Gly Lys Ala Pro Lys Leu Leu
        35                  40                  45
Ile Tyr Glu Ala Ser Lys Leu Thr Ser Gly Val Pro Ser Arg Phe Ser
    50                  55                  60
Gly Ser Gly Ser Gly Thr Asp Phe Thr Leu Thr Ile Ser Ser Leu Gln
65                  70                  75                  80
Pro Glu Asp Phe Ala Thr Tyr Tyr Cys Gly Gly Tyr Ser Ser Ile
                85                  90                  95
Ser Asp Thr Thr Phe Gly Gly Gly Thr Lys Val Glu Ile Lys Arg Thr
            100                 105                 110
Val Ala Ala Pro Ser Val Phe Ile Phe Pro Pro Ser Asp Glu Gln Leu
        115                 120                 125
Lys Ser Gly Thr Ala Ser Val Val Cys Leu Leu Asn Asn Phe Tyr Pro
    130                 135                 140
Arg Glu Ala Lys Val Gln Trp Lys Val Asp Asn Ala Leu Gln Ser Gly
145                 150                 155                 160
Asn Ser Gln Glu Ser Val Thr Glu Gln Asp Ser Lys Asp Ser Thr Tyr
                165                 170                 175
Ser Leu Ser Ser Thr Leu Thr Leu Ser Lys Ala Asp Tyr Glu Lys His
            180                 185                 190
Lys Val Tyr Ala Cys Glu Val Thr His Gln Gly Leu Ser Ser Pro Val
        195                 200                 205
Thr Lys Ser Phe Asn Arg Gly Glu Cys
    210                 215

<210> SEQ ID NO 174
<211> LENGTH: 448
<212> TYPE: PRT
<213> ORGANISM: Artificial Sequence
<220> FEATURE:
```

<223> OTHER INFORMATION: Humanized Anti-P Full HC (IgG1)

<400> SEQUENCE: 174

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Pro Ile His Trp Val Arg Gln Ala Pro Gly Gln Gly Leu Glu Trp Met
        35                  40                  45

Gly Phe Ile Asp Pro Gly Gly Gly Tyr Asp Glu Pro Asp Glu Arg Phe
    50                  55                  60

Arg Asp Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Gly Tyr Tyr Leu Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400
```

```
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
            435                 440                 445
```

<210> SEQ ID NO 175
<211> LENGTH: 214
<212> TYPE: PRT
<213> ORGANISM: Artificial Sequence
<220> FEATURE:
<223> OTHER INFORMATION: Humanized Anti-P Full LC

<400> SEQUENCE: 175

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Ser Phe Phe
            20                  25                  30
Leu Asn Trp Tyr Gln Gln Lys Pro Gly Lys Ala Pro Lys Leu Leu Ile
        35                  40                  45
Tyr Tyr Thr Ser Arg Tyr His Ser Gly Val Pro Ser Arg Phe Ser Gly
50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln His Gly Asn Thr Leu Pro Trp
                85                  90                  95
Thr Phe Gly Gln Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 176
<211> LENGTH: 451
<212> TYPE: PRT
<213> ORGANISM: Artificial Sequence
<220> FEATURE:
<223> OTHER INFORMATION: Humanized Anti-TNF Full HC (IgG1)

<400> SEQUENCE: 176

```
Glu Val Gln Leu Val Glu Ser Gly Gly Gly Leu Val Gln Pro Gly Arg
1               5                   10                  15
Ser Leu Arg Leu Ser Cys Ala Ala Ser Gly Phe Thr Phe Asp Asp Tyr
            20                  25                  30
Ala Met His Trp Val Arg Gln Ala Pro Gly Lys Gly Leu Glu Trp Val
        35                  40                  45
```

```
Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 177
<211> LENGTH: 214
<212> TYPE: PRT
<213> ORGANISM: Artificial Sequence
<220> FEATURE:
<223> OTHER INFORMATION: Humanized Anti-TNF Full LC

<400> SEQUENCE: 177

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 178
<211> LENGTH: 448
<212> TYPE: PRT
<213> ORGANISM: Artificial Sequence
<220> FEATURE:
<223> OTHER INFORMATION: Humanized Anti-P Full HC

<400> SEQUENCE: 178

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Pro Ile His Trp Val Arg Gln Ala Pro Gly Gln Gly Leu Glu Trp Met
        35                  40                  45

Gly Phe Ile Asp Pro Gly Gly Gly Tyr Asp Glu Pro Asp Glu Arg Phe
    50                  55                  60

Arg Asp Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

Ala Arg Arg Gly Gly Gly Tyr Tyr Leu Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Ala Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 179
<211> LENGTH: 214
<212> TYPE: PRT
<213> ORGANISM: Artificial Sequence
<220> FEATURE:
<223> OTHER INFORMATION: Humanized Anti-P Full LC

<400> SEQUENCE: 179

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His Gly Asn Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 180
<211> LENGTH: 453
<212> TYPE: PRT
<213> ORGANISM: Artificial Sequence
<220> FEATURE:
<223> OTHER INFORMATION: Humanized Anti-VEGF Full HC

<400> SEQUENCE: 180

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
 50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
        130                 135                 140

Thr Ala Ala Leu Gly Cys Leu Val Lys Asp Tyr Phe Pro Glu Pro Val
145                 150                 155                 160

```
Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Ala Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 181
<211> LENGTH: 214
<212> TYPE: PRT
<213> ORGANISM: Artificial Sequence
<220> FEATURE:
<223> OTHER INFORMATION: Humanized Anti-VEGF Full LC

<400> SEQUENCE: 181

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 182
<211> LENGTH: 460
<212> TYPE: PRT
<213> ORGANISM: Artificial Sequence
<220> FEATURE:
<223> OTHER INFORMATION: Humanized Camelid Anti-P w/ IgG1 N297A Fc

<400> SEQUENCE: 182

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Arg Ile Ser Ser Ile Ile
            20                  25                  30

His Met Ala Trp Val Arg Gln Ala Pro Gly Lys Gln Arg Glu Leu Val
        35                  40                  45

Ser Glu Ile Ser Arg Val Gly Thr Thr Val Tyr Ala Asp Ser Val Lys
    50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Asn
                 85                  90                  95

Ala Leu Gln Tyr Glu Lys His Gly Gly Ala Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Ser Gly Pro Ser Val Phe Pro Leu Ala Pro Ser
    130                 135                 140

Ser Lys Ser Thr Ser Gly Gly Thr Ala Ala Leu Gly Cys Leu Val Lys
145                 150                 155                 160

Asp Tyr Phe Pro Glu Pro Val Thr Val Ser Trp Asn Ser Gly Ala Leu
                165                 170                 175

Thr Ser Gly Val His Thr Phe Pro Ala Val Leu Gln Ser Ser Gly Leu
            180                 185                 190

Tyr Ser Leu Ser Ser Val Val Thr Val Pro Ser Ser Ser Leu Gly Thr
        195                 200                 205
```

Gln Thr Tyr Ile Cys Asn Val Asn His Lys Pro Ser Asn Thr Lys Val
            210                 215                 220

Asp Lys Lys Val Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
            245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
            275                 280                 285

Asn Trp Tyr Val Asp Gly Val Glu Val His Asn Ala Lys Thr Lys Pro
            290                 295                 300

Arg Glu Glu Gln Tyr Ala Ser Thr Tyr Arg Val Val Ser Val Leu Thr
305                 310                 315                 320

Val Leu His Gln Asp Trp Leu Asn Gly Lys Glu Tyr Lys Cys Lys Val
            325                 330                 335

Ser Asn Lys Ala Leu Pro Ala Pro Ile Glu Lys Thr Ile Ser Lys Ala
            340                 345                 350

Lys Gly Gln Pro Arg Glu Pro Gln Val Tyr Thr Leu Pro Pro Ser Arg
            355                 360                 365

Asp Glu Leu Thr Lys Asn Gln Val Ser Leu Thr Cys Leu Val Lys Gly
            370                 375                 380

Phe Tyr Pro Ser Asp Ile Ala Val Glu Trp Glu Ser Asn Gly Gln Pro
385                 390                 395                 400

Glu Asn Asn Tyr Lys Thr Thr Pro Pro Val Leu Asp Ser Asp Gly Ser
            405                 410                 415

Phe Phe Leu Tyr Ser Lys Leu Thr Val Asp Lys Ser Arg Trp Gln Gln
            420                 425                 430

Gly Asn Val Phe Ser Cys Ser Val Met His Glu Ala Leu His Asn His
            435                 440                 445

Tyr Thr Gln Lys Ser Leu Ser Leu Ser Pro Gly Lys
            450                 455                 460

<210> SEQ ID NO 183
<211> LENGTH: 464
<212> TYPE: PRT
<213> ORGANISM: Artificial Sequence
<220> FEATURE:
<223> OTHER INFORMATION: Humanized Camelid Anti-Alb w/ IgG1 N297A Fc

<400> SEQUENCE: 183

Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
            35                  40                  45

Ser Ala Ile Asn Trp Gln Lys Thr Ala Thr Tyr Ala Asp Ser Val Lys
        50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Asp Tyr Asp Tyr
            100                 105                 110

Trp Gly Gln Gly Thr Leu Val Thr Val Ser Ser Gly Gly Gly Ser
            115                 120                 125

Gly Gly Gly Gly Ser Gly Gly Gly Ser Gly Pro Ser Val Phe Pro
        130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Lys Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Lys Phe Asn Trp Tyr Val Asp Gly Val Glu Val His Asn Ala
    290                 295                 300

Lys Thr Lys Pro Arg Glu Gln Tyr Ala Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

Pro Pro Ser Arg Asp Glu Leu Thr Lys Asn Gln Val Ser Leu Thr Cys
    370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Val Leu Asp
                405                 410                 415

Ser Asp Gly Ser Phe Phe Leu Tyr Ser Lys Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 184
<211> LENGTH: 244
<212> TYPE: PRT
<213> ORGANISM: Artificial Sequence
<220> FEATURE:
<223> OTHER INFORMATION: Humanized Anti-P Full HC (IgG1 YTE Fc)

<400> SEQUENCE: 184

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Pro Ile His Trp Val Arg Gln Ala Pro Gly Gln Gly Leu Glu Trp Met
            35                  40                  45

Gly Phe Ile Asp Pro Gly Gly Tyr Asp Glu Pro Asp Glu Arg Phe
 50                  55                  60

Arg Asp Arg Val Thr Met Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Arg Gly Gly Tyr Tyr Leu Asp Tyr Trp Gly Gln Gly Thr
            100                 105                 110

Thr Val Thr Val Ser Ser Ala Ser Thr Lys Glu Val Gln Leu Val Gln
            115                 120                 125

Ser Gly Ala Glu Val Lys Lys Pro Gly Ala Ser Val Lys Val Ser Cys
130                 135                 140

Lys Ala Ser Gly Tyr Ile Phe Thr Asn Tyr Pro Ile His Trp Val Arg
145                 150                 155                 160

Gln Ala Pro Gly Gln Gly Leu Glu Trp Met Gly Phe Ile Asp Pro Gly
            165                 170                 175

Gly Gly Tyr Asp Glu Pro Asp Glu Arg Phe Arg Asp Arg Val Thr Met
            180                 185                 190

Thr Ala Asp Thr Ser Thr Ser Thr Ala Tyr Met Glu Leu Ser Ser Leu
            195                 200                 205

Arg Ser Glu Asp Thr Ala Val Tyr Tyr Cys Ala Arg Arg Gly Gly Gly
210                 215                 220

Tyr Tyr Leu Asp Tyr Trp Gly Gln Gly Thr Thr Val Thr Val Ser Ser
225                 230                 235                 240

Ala Ser Thr Lys

<210> SEQ ID NO 185
<211> LENGTH: 214
<212> TYPE: PRT
<213> ORGANISM: Artificial Sequence
<220> FEATURE:
<223> OTHER INFORMATION: Humanized Anti-P Full LC

<400> SEQUENCE: 185

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
            35                  40                  45

Tyr Tyr Thr Ser Arg Tyr His Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Gly Asn Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

```
Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 186
<211> LENGTH: 456
<212> TYPE: PRT
<213> ORGANISM: Artificial Sequence
<220> FEATURE:
<223> OTHER INFORMATION: Humanized Camelid Anti-Alb Full HC (IgG1 YTE
      Fc)

<400> SEQUENCE: 186

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser Phe
            20                  25                  30

Gly Met Ser Trp Val Arg Gln Ala Pro Gly Lys Glu Pro Glu Trp Val
        35                  40                  45

Ser Ser Ile Ser Gly Ser Gly Ser Asp Thr Leu Tyr Ala Asp Ser Val
50                  55                  60

Lys Gly Arg Phe Thr Ile Ser Arg Asp Asn Ala Lys Thr Thr Leu Tyr
65                  70                  75                  80

Leu Gln Met Asn Ser Leu Lys Pro Glu Asp Thr Ala Val Tyr Tyr Cys
            85                  90                  95

Thr Ile Gly Gly Ser Leu Ser Arg Ser Ser Gln Gly Thr Gln Val Thr
        100                 105                 110

Val Ser Ser Gly Gly Gly Gly Ser Gly Gly Gly Gly Ser Gly Gly Gly
    115                 120                 125

Gly Ser Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Tyr Ile Thr Arg Glu Pro Glu Val Thr Cys Val Val
            260                 265                 270
```

```
Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 187
<211> LENGTH: 448
<212> TYPE: PRT
<213> ORGANISM: Artificial Sequence
<220> FEATURE:
<223> OTHER INFORMATION: Humanized Anti-P Full HC (IgG1 N297A Fc)

<400> SEQUENCE: 187

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Pro Ile His Trp Val Arg Gln Ala Pro Gly Gln Gly Leu Glu Trp Met
        35                  40                  45

Gly Phe Ile Asp Pro Gly Gly Gly Tyr Asp Glu Pro Asp Glu Arg Phe
    50                  55                  60

Arg Asp Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Gly Tyr Tyr Leu Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Ala Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 188
<211> LENGTH: 214
<212> TYPE: PRT
<213> ORGANISM: Artificial Sequence
<220> FEATURE:
<223> OTHER INFORMATION: Humanized Anti-P Full LC

<400> SEQUENCE: 188

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Gly Asn Thr Leu Pro Trp
            85                  90                  95
```

```
Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 189
<211> LENGTH: 451
<212> TYPE: PRT
<213> ORGANISM: Artificial Sequence
<220> FEATURE:
<223> OTHER INFORMATION: Humanized Anti-Alb Full HC (IgG1 N297A Fc)

<400> SEQUENCE: 189

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240
```

```
Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Ala Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 190
<211> LENGTH: 217
<212> TYPE: PRT
<213> ORGANISM: Artificial Sequence
<220> FEATURE:
<223> OTHER INFORMATION: Humanized Anti-Alb Full LC

<400> SEQUENCE: 190

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Tyr Ser Ser Ile
                85                  90                  95

Ser Asp Thr Thr Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140
```

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 191
<211> LENGTH: 363
<212> TYPE: PRT
<213> ORGANISM: Artificial Sequence
<220> FEATURE:
<223> OTHER INFORMATION: Humanized Camelid Anti-P IgG4 Fc (CH2/CH3 Only)

<400> SEQUENCE: 191

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ile Ser Ser Ile Ile
            20                  25                  30

His Met Ala Trp Val Arg Gln Ala Pro Gly Lys Gln Arg Glu Leu Val
        35                  40                  45

Ser Glu Ile Ser Arg Val Gly Thr Thr Val Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Asn
                85                  90                  95

Ala Leu Gln Tyr Glu Lys His Gly Gly Ala Asp Tyr Trp Gly Gln Gly
            100                 105                 110

Thr Leu Val Thr Val Ser Ser Gly Gly Gly Ser Gly Gly Gly Gly
        115                 120                 125

Ser Gly Gly Gly Gly Ser Ala Glu Ser Lys Tyr Gly Pro Pro Cys Pro
    130                 135                 140

Pro Cys Pro Ala Pro Glu Ala Ala Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser Gln Glu Asp Pro Glu Val Gln Phe
            180                 185                 190

Asn Trp Tyr Val Asp Gly Val Glu Val His Asn Ala Lys Thr Lys Pro
        195                 200                 205

Arg Glu Glu Gln Phe Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Gly Leu Pro Ser Ser Ile Glu Lys Thr Ile Ser Lys Ala
                245                 250                 255

Lys Gly Gln Pro Arg Glu Pro Gln Val Tyr Thr Leu Pro Pro Ser Gln
            260                 265                 270

Glu Glu Met Thr Lys Asn Gln Val Ser Leu Thr Cys Leu Val Lys Gly
        275                 280                 285

```
Phe Tyr Pro Ser Asp Ile Ala Val Glu Trp Glu Ser Asn Gly Gln Pro
    290                 295                 300

Glu Asn Asn Tyr Lys Thr Thr Pro Val Leu Asp Ser Asp Gly Ser
305                 310                 315                 320

Phe Phe Leu Tyr Ser Arg Leu Thr Val Asp Lys Ser Arg Trp Gln Glu
                325                 330                 335

Gly Asn Val Phe Ser Cys Ser Val Met His Glu Ala Leu His Asn His
            340                 345                 350

Tyr Thr Gln Lys Ser Leu Ser Leu Ser Leu Gly
            355                 360
```

<210> SEQ ID NO 192
<211> LENGTH: 367
<212> TYPE: PRT
<213> ORGANISM: Artificial Sequence
<220> FEATURE:
<223> OTHER INFORMATION: Humanized Camelid Anti-Alb IgG4 Fc (CH2/CH3 Only)

<400> SEQUENCE: 192

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Arg Pro Val Ser Asn Tyr
            20                  25                  30

Ala Ala Ala Trp Phe Arg Gln Ala Pro Gly Lys Glu Arg Glu Phe Val
            35                  40                  45

Ser Ala Ile Asn Trp Gln Lys Thr Ala Thr Tyr Ala Asp Ser Val Lys
50                  55                  60

Gly Arg Phe Thr Ile Ser Arg Asp Asn Ala Lys Asn Ser Leu Tyr Leu
65              70                  75                  80

Gln Met Asn Ser Leu Arg Ala Glu Asp Thr Ala Val Tyr Tyr Cys Ala
                85                  90                  95

Ala Val Phe Arg Val Val Ala Pro Lys Thr Gln Tyr Asp Tyr Asp Tyr
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Ala Glu Ser Lys Tyr Gly
    130                 135                 140

Pro Pro Cys Pro Pro Cys Pro Ala Pro Glu Ala Ala Gly Gly Pro Ser
145                 150                 155                 160

Val Phe Leu Phe Pro Pro Lys Pro Lys Asp Thr Leu Met Ile Ser Arg
                165                 170                 175

Thr Pro Glu Val Thr Cys Val Val Val Asp Val Ser Gln Glu Asp Pro
            180                 185                 190

Glu Val Gln Phe Asn Trp Tyr Val Asp Gly Val Glu Val His Asn Ala
        195                 200                 205

Lys Thr Lys Pro Arg Glu Glu Gln Phe Asn Ser Thr Tyr Arg Val Val
    210                 215                 220

Ser Val Leu Thr Val Leu His Gln Asp Trp Leu Asn Gly Lys Glu Tyr
225                 230                 235                 240

Lys Cys Lys Val Ser Asn Lys Gly Leu Pro Ser Ser Ile Glu Lys Thr
                245                 250                 255

Ile Ser Lys Ala Lys Gly Gln Pro Arg Glu Pro Gln Val Tyr Thr Leu
            260                 265                 270

Pro Pro Ser Gln Glu Glu Met Thr Lys Asn Gln Val Ser Leu Thr Cys
```

```
                    275                 280                 285
Leu Val Lys Gly Phe Tyr Pro Ser Asp Ile Ala Val Glu Trp Glu Ser
    290                 295                 300

Asn Gly Gln Pro Glu Asn Asn Tyr Lys Thr Thr Pro Pro Val Leu Asp
305                 310                 315                 320

Ser Asp Gly Ser Phe Phe Leu Tyr Ser Arg Leu Thr Val Asp Lys Ser
                325                 330                 335

Arg Trp Gln Glu Gly Asn Val Phe Ser Cys Ser Val Met His Glu Ala
                340                 345                 350

Leu His Asn His Tyr Thr Gln Lys Ser Leu Ser Leu Ser Leu Gly
                355                 360                 365

<210> SEQ ID NO 193
<211> LENGTH: 244
<212> TYPE: PRT
<213> ORGANISM: Artificial Sequence
<220> FEATURE:
<223> OTHER INFORMATION: Humanized Anti-P Full HC (IgG1 YTE Fc)

<400> SEQUENCE: 193

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
                20                  25                  30

Pro Ile His Trp Val Arg Gln Ala Pro Gly Gln Gly Leu Glu Trp Met
            35                  40                  45

Gly Phe Ile Asp Pro Gly Gly Tyr Asp Glu Pro Asp Glu Arg Phe
    50                  55                  60

Arg Asp Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Tyr Tyr Leu Asp Tyr Trp Gly Gln Gly Thr
                100                 105                 110

Thr Val Thr Val Ser Ser Ala Ser Thr Lys Glu Val Gln Leu Val Gln
            115                 120                 125

Ser Gly Ala Glu Val Lys Lys Pro Gly Ala Ser Val Lys Val Ser Cys
        130                 135                 140

Lys Ala Ser Gly Tyr Ile Phe Thr Asn Tyr Pro Ile His Trp Val Arg
145                 150                 155                 160

Gln Ala Pro Gly Gln Gly Leu Glu Trp Met Gly Phe Ile Asp Pro Gly
                165                 170                 175

Gly Gly Tyr Asp Glu Pro Asp Glu Arg Phe Arg Asp Arg Val Thr Met
                180                 185                 190

Thr Ala Asp Thr Ser Thr Ser Thr Ala Tyr Met Glu Leu Ser Ser Leu
            195                 200                 205

Arg Ser Glu Asp Thr Ala Val Tyr Tyr Cys Ala Arg Arg Gly Gly Gly
        210                 215                 220

Tyr Tyr Leu Asp Tyr Trp Gly Gln Gly Thr Thr Val Thr Val Ser Ser
225                 230                 235                 240

Ala Ser Thr Lys

<210> SEQ ID NO 194
<211> LENGTH: 214
<212> TYPE: PRT
<213> ORGANISM: Artificial Sequence
```

```
<220> FEATURE:
<223> OTHER INFORMATION: Humanized Anti-P Full LC

<400> SEQUENCE: 194

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Gly Asn Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 195
<211> LENGTH: 451
<212> TYPE: PRT
<213> ORGANISM: Artificial Sequence
<220> FEATURE:
<223> OTHER INFORMATION: Humanized Anti-TNF Full HC (IgG1 YTE Fc)

<400> SEQUENCE: 195

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser Ala Ser Thr Lys Gly Pro Ser
```

```
            115                 120                 125
Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Tyr
                245                 250                 255

Ile Thr Arg Glu Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 196
<211> LENGTH: 214
<212> TYPE: PRT
<213> ORGANISM: Artificial Sequence
<220> FEATURE:
<223> OTHER INFORMATION: Humanized Anti-TNF Full LC

<400> SEQUENCE: 196

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
```

```
                20                  25                  30
Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 197
<211> LENGTH: 244
<212> TYPE: PRT
<213> ORGANISM: Artificial Sequence
<220> FEATURE:
<223> OTHER INFORMATION: Humanized Anti-P Full HC (IgG1 YTE Fc)

<400> SEQUENCE: 197

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Ile Phe Thr Asn Tyr
            20                  25                  30

Pro Ile His Trp Val Arg Gln Ala Pro Gly Gln Gly Leu Glu Trp Met
            35                  40                  45

Gly Phe Ile Asp Pro Gly Gly Tyr Asp Glu Pro Asp Glu Arg Phe
 50                  55                  60

Arg Asp Arg Val Thr Met Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Arg Gly Gly Tyr Tyr Leu Asp Tyr Trp Gly Gln Gly Thr
            100                 105                 110

Thr Val Thr Val Ser Ser Ala Ser Thr Lys Glu Val Gln Leu Val Gln
            115                 120                 125

Ser Gly Ala Glu Val Lys Lys Pro Gly Ala Ser Val Lys Val Ser Cys
        130                 135                 140

Lys Ala Ser Gly Tyr Ile Phe Thr Asn Tyr Pro Ile His Trp Val Arg
145                 150                 155                 160

Gln Ala Pro Gly Gln Gly Leu Glu Trp Met Gly Phe Ile Asp Pro Gly
```

```
                165                 170                 175

Gly Gly Tyr Asp Glu Pro Asp Glu Arg Phe Arg Asp Arg Val Thr Met
            180                 185                 190

Thr Ala Asp Thr Ser Thr Ser Thr Ala Tyr Met Glu Leu Ser Ser Leu
            195                 200                 205

Arg Ser Glu Asp Thr Ala Val Tyr Tyr Cys Ala Arg Arg Gly Gly Gly
        210                 215                 220

Tyr Tyr Leu Asp Tyr Trp Gly Gln Gly Thr Thr Val Thr Val Ser Ser
225                 230                 235                 240

Ala Ser Thr Lys

<210> SEQ ID NO 198
<211> LENGTH: 214
<212> TYPE: PRT
<213> ORGANISM: Artificial Sequence
<220> FEATURE:
<223> OTHER INFORMATION: Humanized Anti-P Full LC

<400> SEQUENCE: 198

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Tyr Thr Ser Arg Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Gly Asn Thr Leu Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 199
<211> LENGTH: 453
<212> TYPE: PRT
<213> ORGANISM: Artificial Sequence
<220> FEATURE:
<223> OTHER INFORMATION: Humanized Anti-VEGF Full HC (IgG1 YTE Fc)

<400> SEQUENCE: 199

Glu Val Gln Leu Val Glu Ser Gly Gly Gly Leu Val Gln Pro Gly Gly
```

```
 1               5                   10                  15
Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
            35                  40                  45

Gly Trp Ile Asn Thr Tyr Thr Gly Glu Pro Thr Tyr Ala Ala Asp Phe
 50                  55                  60

Lys Arg Arg Phe Thr Phe Ser Leu Asp Thr Ser Lys Ser Thr Ala Tyr
 65                  70                  75                  80

Leu Gln Met Asn Ser Leu Arg Ala Glu Asp Thr Ala Val Tyr Tyr Cys
            85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Tyr Ile Thr Arg Glu Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430
```

```
Val Met His Glu Ala Leu His Asn His Tyr Thr Gln Lys Ser Leu Ser
        435                 440                 445

Leu Ser Pro Gly Lys
    450

<210> SEQ ID NO 200
<211> LENGTH: 214
<212> TYPE: PRT
<213> ORGANISM: Artificial Sequence
<220> FEATURE:
<223> OTHER INFORMATION: Humanized Anti-VEGF Full LC

<400> SEQUENCE: 200

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 201
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Asn, Gln, Ser, Ala, or Asp
<220> FEATURE:
<221> NAME/KEY: MOD_RES
<222> LOCATION: (6)..(6)
<223> OTHER INFORMATION: Xaa is Asn, Gln, Ser, Ala, or Asp

<400> SEQUENCE: 201

Gly Tyr Ile Phe Thr Xaa Tyr Pro Ile His
1               5                   10
```

```
<210> SEQ ID NO 202
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Asp, Glu, Ser, or Ala
<220> FEATURE:
<221> NAME/KEY: MOD_RES
<222> LOCATION: (8)..(8)
<223> OTHER INFORMATION: Xaa is His or Tyr
<220> FEATURE:
<221> NAME/KEY: MOD_RES
<222> LOCATION: (11)..(11)
<223> OTHER INFORMATION: Xaa is Pro, Ser, or Tyr
<220> FEATURE:
<221> NAME/KEY: MOD_RES
<222> LOCATION: (12)..(12)
<223> OTHER INFORMATION: Xaa is Ala or Asp
<220> FEATURE:
<221> NAME/KEY: MOD_RES
<222> LOCATION: (13)..(13)
<223> OTHER INFORMATION: Xaa is Asp, Glu, or Gln
<220> FEATURE:
<221> NAME/KEY: MOD_RES
<222> LOCATION: (14)..(14)
<223> OTHER INFORMATION: Xaa is Lys, Arg, or Ser
<220> FEATURE:
<221> NAME/KEY: MOD_RES
<222> LOCATION: (15)..(15)
<223> OTHER INFORMATION: Xaa is Phe or Val
<220> FEATURE:
<221> NAME/KEY: MOD_RES
<222> LOCATION: (16)..(16)
<223> OTHER INFORMATION: Xaa is Glu, Lys, Gln, or Arg
<220> FEATURE:
<221> NAME/KEY: MOD_RES
<222> LOCATION: (17)..(17)
<223> OTHER INFORMATION: Xaa is Asp or Gly

<400> SEQUENCE: 202

Phe Ile Xaa Pro Gly Gly Gly Xaa Asp Glu Xaa Xaa Xaa Xaa Xaa Xaa
1               5                   10                  15

Xaa

<210> SEQ ID NO 203
<211> LENGTH: 9
<212> TYPE: PRT
<213> ORGANISM: Artificial Sequence
<220> FEATURE:
<223> OTHER INFORMATION: Synthetic Construct

<400> SEQUENCE: 203

Arg Gly Gly Gly Tyr Tyr Leu Asp Tyr
1               5

<210> SEQ ID NO 204
<211> LENGTH: 118
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (31)..(31)
<223> OTHER INFORMATION: Xaa is Asn, Gln, Ser, Ala, or Asp
<220> FEATURE:
<221> NAME/KEY: MOD_RES
<222> LOCATION: (52)..(52)
```

```
<223> OTHER INFORMATION: Xaa is Asp, Glu, Ser, or Ala
<220> FEATURE:
<221> NAME/KEY: MOD_RES
<222> LOCATION: (57)..(57)
<223> OTHER INFORMATION: Xaa is His or Tyr
<220> FEATURE:
<221> NAME/KEY: MOD_RES
<222> LOCATION: (60)..(60)
<223> OTHER INFORMATION: Xaa is Pro, Ser, or Tyr
<220> FEATURE:
<221> NAME/KEY: MOD_RES
<222> LOCATION: (61)..(61)
<223> OTHER INFORMATION: Xaa is Ala or Asp
<220> FEATURE:
<221> NAME/KEY: MOD_RES
<222> LOCATION: (62)..(62)
<223> OTHER INFORMATION: Xaa is Asp, Glu, or Gln
<220> FEATURE:
<221> NAME/KEY: MOD_RES
<222> LOCATION: (63)..(63)
<223> OTHER INFORMATION: Xaa is Lys, Arg, or Ser
<220> FEATURE:
<221> NAME/KEY: MOD_RES
<222> LOCATION: (64)..(64)
<223> OTHER INFORMATION: Xaa is Phe or Val
<220> FEATURE:
<221> NAME/KEY: MOD_RES
<222> LOCATION: (65)..(65)
<223> OTHER INFORMATION: Xaa is Glu, Lys, Gln, or Arg
<220> FEATURE:
<221> NAME/KEY: MOD_RES
<222> LOCATION: (66)..(66)
<223> OTHER INFORMATION: Xaa is Asp or Gly

<400> SEQUENCE: 204

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Xaa Tyr
            20                  25                  30

Pro Ile His Trp Val Arg Gln Ala Pro Gly Gln Gly Leu Glu Trp Met
        35                  40                  45

Gly Phe Ile Xaa Pro Gly Gly Gly Xaa Asp Glu Xaa Xaa Xaa Xaa Xaa
    50                  55                  60

Xaa Xaa Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Gly Tyr Tyr Leu Asp Tyr Trp Gly Gln Gly Thr
            100                 105                 110

Thr Val Thr Val Ser Ser
        115

<210> SEQ ID NO 205
<211> LENGTH: 118
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (31)..(31)
<223> OTHER INFORMATION: Xaa is Asn, Gln, Ser, Ala, or Asp
<220> FEATURE:
<221> NAME/KEY: MOD_RES
<222> LOCATION: (52)..(52)
<223> OTHER INFORMATION: Xaa is Asp, Glu, Ser, or Ala
<220> FEATURE:
<221> NAME/KEY: MOD_RES
<222> LOCATION: (57)..(57)
<223> OTHER INFORMATION: Xaa is His or Tyr
```

```
<220> FEATURE:
<221> NAME/KEY: MOD_RES
<222> LOCATION: (60)..(60)
<223> OTHER INFORMATION: Xaa is Pro, Ser, or Tyr
<220> FEATURE:
<221> NAME/KEY: MOD_RES
<222> LOCATION: (61)..(61)
<223> OTHER INFORMATION: Xaa is Ala or Asp
<220> FEATURE:
<221> NAME/KEY: MOD_RES
<222> LOCATION: (62)..(62)
<223> OTHER INFORMATION: Xaa is Asp, Arg, or Gln
<220> FEATURE:
<221> NAME/KEY: MOD_RES
<222> LOCATION: (63)..(63)
<223> OTHER INFORMATION: Xaa is Lys, Arg, or Ser
<220> FEATURE:
<221> NAME/KEY: MOD_RES
<222> LOCATION: (64)..(64)
<223> OTHER INFORMATION: Xaa is Phe or Val
<220> FEATURE:
<221> NAME/KEY: MOD_RES
<222> LOCATION: (65)..(65)
<223> OTHER INFORMATION: Xaa is Glu, Lys, Gln, or Arg
<220> FEATURE:
<221> NAME/KEY: MOD_RES
<222> LOCATION: (66)..(66)
<223> OTHER INFORMATION: Xaa is Asp or Gly

<400> SEQUENCE: 205

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Xaa Tyr
            20                  25                  30

Pro Ile His Trp Val Arg Gln Ala Pro Gly Gln Gly Leu Glu Trp Met
        35                  40                  45

Gly Phe Ile Xaa Pro Gly Gly Gly Xaa Asp Glu Xaa Xaa Xaa Xaa Xaa
    50                  55                  60

Xaa Xaa Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Gly Gly Gly Tyr Tyr Leu Asp Tyr Trp Gly Gln Gly Thr
            100                 105                 110

Thr Val Thr Val Ser Ser
        115

<210> SEQ ID NO 206
<211> LENGTH: 11
<212> TYPE: PRT
<213> ORGANISM: Artificial Sequence
<220> FEATURE:
<223> OTHER INFORMATION: Synthetic Construct

<400> SEQUENCE: 206

Arg Ala Ser Gln Asp Ile Ser Phe Phe Leu Asn
1               5                   10

<210> SEQ ID NO 207
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Gly or Tyr
```

```
<220> FEATURE:
<221> NAME/KEY: MOD_RES
<222> LOCATION: (2)..(2)
<223> OTHER INFORMATION: Xaa is Ala or Thr
<220> FEATURE:
<221> NAME/KEY: MOD_RES
<222> LOCATION: (4)..(4)
<223> OTHER INFORMATION: Xaa is Arg or Ser

<400> SEQUENCE: 207

Xaa Xaa Ser Xaa Tyr His Ser
1               5

<210> SEQ ID NO 208
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Ala, Asp, Asn, Gln, or Ser
<220> FEATURE:
<221> NAME/KEY: MOD_RES
<222> LOCATION: (8)..(8)
<223> OTHER INFORMATION: Xaa is Phe, His, Arg, Trp, or Tyr

<400> SEQUENCE: 208

Gln His Gly Xaa Thr Leu Pro Xaa Thr
1               5

<210> SEQ ID NO 209
<211> LENGTH: 107
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (50)..(50)
<223> OTHER INFORMATION: Xaa is Gly or Tyr
<220> FEATURE:
<221> NAME/KEY: MOD_RES
<222> LOCATION: (51)..(51)
<223> OTHER INFORMATION: Xaa is Ala or Thr
<220> FEATURE:
<221> NAME/KEY: MOD_RES
<222> LOCATION: (53)..(53)
<223> OTHER INFORMATION: Xaa is Arg or Ser
<220> FEATURE:
<221> NAME/KEY: MOD_RES
<222> LOCATION: (92)..(92)
<223> OTHER INFORMATION: Xaa is Ala, Asp, Asn, Gln, or Ser
<220> FEATURE:
<221> NAME/KEY: MOD_RES
<222> LOCATION: (96)..(96)
<223> OTHER INFORMATION: Xaa is Phe, His, Arg, Trp, or Tyr

<400> SEQUENCE: 209

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Xaa Xaa Ser Xaa Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln His Gly Xaa Thr Leu Pro Xaa
                85                  90                  95

Thr Phe Gly Gln Gly Thr Lys Leu Glu Ile Lys
            100                 105

<210> SEQ ID NO 210
<211> LENGTH: 107
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (50)..(50)
<223> OTHER INFORMATION: Xaa is Gly or Tyr
<220> FEATURE:
<221> NAME/KEY: MOD_RES
<222> LOCATION: (51)..(51)
<223> OTHER INFORMATION: Xaa is Ala or Thr
<220> FEATURE:
<221> NAME/KEY: MOD_RES
<222> LOCATION: (53)..(53)
<223> OTHER INFORMATION: Xaa is Arg or Ser
<220> FEATURE:
<221> NAME/KEY: MOD_RES
<222> LOCATION: (91)..(91)
<223> OTHER INFORMATION: Xaa is Ala, Asp, Asn, Gln, or Ser
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: MOD_RES
<222> LOCATION: (95)..(95)
<223> OTHER INFORMATION: Xaa is Phe, His, Arg, Trp, or Tyr
<220> FEATURE:
<221> NAME/KEY: misc_feature
<222> LOCATION: (96)..(96)
<223> OTHER INFORMATION: Xaa can be any naturally occurring amino acid

<400> SEQUENCE: 210

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
            20                  25                  30

Leu Asn Trp Tyr Gln Gln Lys Pro Gly Lys Ala Pro Lys Leu Leu Ile
        35                  40                  45

Tyr Xaa Xaa Ser Xaa Tyr His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Gly Xaa Thr Leu Pro Xaa
                85                  90                  95

Thr Phe Gly Gln Gly Thr Lys Leu Glu Ile Lys
            100                 105

<210> SEQ ID NO 211
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Xaa is Ile, Lys, Met, or Val

<400> SEQUENCE: 211
```

```
Gly Phe Ser Leu Ser Thr Ser Gly Xaa Gly Val Gly
1               5                   10

<210> SEQ ID NO 212
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Phe, His, Trp, or Tyr
<220> FEATURE:
<221> NAME/KEY: MOD_RES
<222> LOCATION: (4)..(4)
<223> OTHER INFORMATION: Xaa is Phe, His, Trp, or Tyr
<220> FEATURE:
<221> NAME/KEY: MOD_RES
<222> LOCATION: (11)..(11)
<223> OTHER INFORMATION: Xaa is Ala, Asn, Gln, or Ser

<400> SEQUENCE: 212

His Ile Xaa Xaa Asp Asp Val Lys Ser Tyr Xaa Pro Ala Leu Lys Ser
1               5                   10                  15

<210> SEQ ID NO 213
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Ala, Asn, Glu, or Ser

<400> SEQUENCE: 213

Ile Gly Xaa Gly Tyr Tyr Ser Phe Asp Tyr
1               5                   10

<210> SEQ ID NO 214
<211> LENGTH: 120
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (34)..(34)
<223> OTHER INFORMATION: Xaa is Ile, Lys, Met, or Val
<220> FEATURE:
<221> NAME/KEY: MOD_RES
<222> LOCATION: (54)..(54)
<223> OTHER INFORMATION: Xaa is Phe, His, Trp, or Tyr
<220> FEATURE:
<221> NAME/KEY: MOD_RES
<222> LOCATION: (55)..(55)
<223> OTHER INFORMATION: Xaa is Phe, His, Trp, or Tyr
<220> FEATURE:
<221> NAME/KEY: MOD_RES
<222> LOCATION: (62)..(62)
<223> OTHER INFORMATION: Xaa is Ala, Asn, Gln, or Ser
<220> FEATURE:
<221> NAME/KEY: MOD_RES
<222> LOCATION: (102)..(102)
<223> OTHER INFORMATION: Xaa is Ala, Asp, Glu, or Ser

<400> SEQUENCE: 214

Glu Val Thr Leu Lys Glu Ser Gly Pro Thr Leu Val Lys Pro Thr Gln
1               5                   10                  15
```

```
Thr Leu Thr Leu Thr Cys Thr Phe Ser Gly Phe Ser Leu Ser Thr Ser
            20                  25                  30

Gly Xaa Gly Val Gly Trp Ile Arg Gln Pro Pro Gly Lys Ala Leu Glu
        35                  40                  45

Trp Leu Ala His Ile Xaa Xaa Asp Asp Val Lys Ser Tyr Xaa Pro Ala
 50                  55                  60

Leu Lys Ser Arg Leu Thr Ile Thr Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Ile Gly Xaa Gly Tyr Tyr Ser Phe Asp Tyr Trp Gly Gln
                100                 105                 110

Gly Thr Thr Val Thr Val Ser Ser
            115                 120
```

<210> SEQ ID NO 215
<211> LENGTH: 120
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (34)..(34)
<223> OTHER INFORMATION: Xaa is Ile, Lys, Met, or Val
<220> FEATURE:
<221> NAME/KEY: MOD_RES
<222> LOCATION: (54)..(54)
<223> OTHER INFORMATION: Xaa is Phe, His, Trp, or Tyr
<220> FEATURE:
<221> NAME/KEY: MOD_RES
<222> LOCATION: (55)..(55)
<223> OTHER INFORMATION: Xaa is Phe, His, Trp, or Tyr
<220> FEATURE:
<221> NAME/KEY: MOD_RES
<222> LOCATION: (62)..(62)
<223> OTHER INFORMATION: Xaa is Ala, Asn, Gln, or Ser
<220> FEATURE:
<221> NAME/KEY: MOD_RES
<222> LOCATION: (102)..(102)
<223> OTHER INFORMATION: Xaa is Ala, Asp, Glu, or Ser

<400> SEQUENCE: 215

```
Gln Val Thr Leu Lys Glu Ser Gly Pro Thr Leu Val Lys Pro Thr Gln
 1               5                  10                  15

Thr Leu Thr Leu Thr Cys Thr Phe Ser Gly Phe Ser Leu Ser Thr Ser
            20                  25                  30

Gly Xaa Gly Val Gly Trp Ile Arg Gln Pro Pro Gly Lys Ala Leu Glu
        35                  40                  45

Trp Leu Ala His Ile Xaa Xaa Asp Asp Val Lys Ser Tyr Xaa Pro Ala
 50                  55                  60

Leu Lys Ser Arg Leu Thr Ile Thr Lys Asp Thr Ser Lys Asn Gln Val
 65                  70                  75                  80

Val Leu Thr Ile Thr Asn Val Asp Pro Val Asp Thr Ala Thr Tyr Tyr
                 85                  90                  95

Cys Ala Arg Ile Gly Xaa Gly Tyr Tyr Ser Phe Asp Tyr Trp Gly Gln
                100                 105                 110

Gly Thr Thr Leu Thr Val Ser Ser
            115                 120
```

<210> SEQ ID NO 216
<211> LENGTH: 11
<212> TYPE: PRT

<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa can be any naturally occurring amino acid

<400> SEQUENCE: 216

Xaa Ala Ser Gln Asp Val Ser Asp Ala Val Ala
1               5                   10

<210> SEQ ID NO 217
<211> LENGTH: 7
<212> TYPE: PRT
<213> ORGANISM: Artificial Sequence
<220> FEATURE:
<223> OTHER INFORMATION: Synthetic Construct

<400> SEQUENCE: 217

Ser Pro Ser Tyr Arg Tyr Thr
1               5

<210> SEQ ID NO 218
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (8)..(8)
<223> OTHER INFORMATION: Xaa is Phe, His, Trp, or Tyr

<400> SEQUENCE: 218

Gln Gln His Tyr Ser Thr Pro Xaa Thr Phe
1               5                   10

<210> SEQ ID NO 219
<211> LENGTH: 107
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (24)..(24)
<223> OTHER INFORMATION: Xaa is Lys or Arg
<220> FEATURE:
<221> NAME/KEY: MOD_RES
<222> LOCATION: (96)..(96)
<223> OTHER INFORMATION: Xaa is Phe, His, Trp, or Tyr

<400> SEQUENCE: 219

Asp Ile Gln Met Thr Gln Ser Pro Ser Ser Leu Ser Ala Ser Val Gly
1               5                   10                  15

Asp Arg Val Thr Ile Thr Cys Xaa Ala Ser Gln Asp Val Ser Asp Ala
            20                  25                  30

Val Ala Trp Tyr Gln Gln Lys Pro Gly Lys Ala Pro Lys Leu Leu Ile
        35                  40                  45

Tyr Ser Pro Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Xaa
                85                  90                  95

Thr Phe Gly Gln Gly Thr Lys Leu Glu Ile Lys
            100                 105

<210> SEQ ID NO 220
<211> LENGTH: 107
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (24)..(24)
<223> OTHER INFORMATION: Xaa is Lys or Arg
<220> FEATURE:
<221> NAME/KEY: MOD_RES
<222> LOCATION: (96)..(96)
<223> OTHER INFORMATION: Xaa is Phe, His, Trp, or Tyr

<400> SEQUENCE: 220

Asp Ile Gln Met Thr Gln Ser Pro Ser Ser Leu Ser Ala Ser Val Gly
1               5                   10                  15

Asp Arg Val Thr Ile Thr Cys Xaa Ala Ser Gln Asp Val Ser Asp Ala
            20                  25                  30

Val Ala Trp Phe Gln Gln Lys Pro Gly Lys Ala Pro Lys Leu Leu Ile
        35                  40                  45

Tyr Ser Pro Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Leu Ala Thr Tyr Tyr Cys Gln Gln His Tyr Ser Thr Pro Xaa
                85                  90                  95

Thr Phe Gly Gln Gly Thr Lys Leu Glu Ile Lys
            100                 105

<210> SEQ ID NO 221
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Xaa is Phe, His, Trp, or Tyr
<220> FEATURE:
<221> NAME/KEY: MOD_RES
<222> LOCATION: (9)..(9)
<223> OTHER INFORMATION: Xaa is Phe, His, Trp, or Tyr

<400> SEQUENCE: 221

Gly Phe Ser Phe Ser Ser Gly Tyr Xaa Ile Phe
1               5                   10

<210> SEQ ID NO 222
<211> LENGTH: 11
<212> TYPE: PRT
<213> ORGANISM: Artificial Sequence
<220> FEATURE:
<223> OTHER INFORMATION: Synthetic Construct

<400> SEQUENCE: 222

Gly Ile Tyr Ser Gly Ser Ser Gly Thr Thr Tyr
1               5                   10

<210> SEQ ID NO 223
<211> LENGTH: 13

```
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Ala, Asp, Glu, or Ser
<220> FEATURE:
<221> NAME/KEY: MOD_RES
<222> LOCATION: (5)..(5)
<223> OTHER INFORMATION: Xaa is Ala, Asp, Glu, or Ser
<220> FEATURE:
<221> NAME/KEY: MOD_RES
<222> LOCATION: (8)..(8)
<223> OTHER INFORMATION: Xaa is Ala, Asp, Glu, or Ser
<220> FEATURE:
<221> NAME/KEY: MOD_RES
<222> LOCATION: (12)..(12)
<223> OTHER INFORMATION: Xaa is Ala, Asn, Gln, or Ser

<400> SEQUENCE: 223

Val Xaa Gly Ile Xaa Ser Tyr Xaa Ala Ala Phe Xaa Leu
1               5                   10

<210> SEQ ID NO 224
<211> LENGTH: 125
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (34)..(34)
<223> OTHER INFORMATION: Xaa is Phe, His, Trp, or Tyr
<220> FEATURE:
<221> NAME/KEY: MOD_RES
<222> LOCATION: (103)..(103)
<223> OTHER INFORMATION: Xaa is Ala, Asp, Glu, or Ser
<220> FEATURE:
<221> NAME/KEY: MOD_RES
<222> LOCATION: (106)..(106)
<223> OTHER INFORMATION: Xaa is Ala, Asp, Glu, or Ser
<220> FEATURE:
<221> NAME/KEY: MOD_RES
<222> LOCATION: (109)..(109)
<223> OTHER INFORMATION: Xaa is Ala, Asp, Glu, or Ser
<220> FEATURE:
<221> NAME/KEY: MOD_RES
<222> LOCATION: (113)..(113)
<223> OTHER INFORMATION: Xaa is Ala, Asn, Gln, or Ser

<400> SEQUENCE: 224

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Gly
                20                  25                  30

Tyr Xaa Ile Phe Trp Val Arg Gln Ala Pro Gly Lys Gly Leu Glu Trp
            35                  40                  45

Val Ser Gly Ile Tyr Ser Gly Ser Ser Gly Thr Thr Tyr Tyr Ala Asp
        50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Ser Val Xaa Gly Ile Xaa Ser Tyr Xaa Ala Ala Phe
            100                 105                 110

Xaa Leu Trp Gly Gln Gly Thr Leu Val Thr Val Ser Ser
            115                 120                 125
```

```
<210> SEQ ID NO 225
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Xaa is Phe, His, Trp, or Tyr

<400> SEQUENCE: 225

Gly Phe Ser Phe Ser Ser Ser Tyr Xaa Ile Phe
1               5                   10

<210> SEQ ID NO 226
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (9)..(9)
<223> OTHER INFORMATION: Xaa is Ile, Lys, Leu, or Met

<400> SEQUENCE: 226

Gly Ile Tyr Ser Ser Ser Gly Arg Xaa Tyr
1               5                   10

<210> SEQ ID NO 227
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (3)..(3)
<223> OTHER INFORMATION: Xaa is Ala, Asp, Glu, or Ser
<220> FEATURE:
<221> NAME/KEY: MOD_RES
<222> LOCATION: (6)..(6)
<223> OTHER INFORMATION: Xaa is Ala, Asp, Glu, or Ser
<220> FEATURE:
<221> NAME/KEY: MOD_RES
<222> LOCATION: (9)..(9)
<223> OTHER INFORMATION: Xaa is Ala, Asp, Glu, or Ser

<400> SEQUENCE: 227

Ser Ala Xaa Gly Ser Xaa Ser Tyr Xaa Ala Tyr Phe Thr Leu
1               5                   10

<210> SEQ ID NO 228
<211> LENGTH: 124
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (34)..(34)
<223> OTHER INFORMATION: Xaa is Phe, His, Trp, or Tyr
<220> FEATURE:
<221> NAME/KEY: MOD_RES
<222> LOCATION: (59)..(59)
<223> OTHER INFORMATION: Xaa is Phe, His, Trp, or Tyr
<220> FEATURE:
<221> NAME/KEY: misc_feature
<222> LOCATION: (102)..(102)
<223> OTHER INFORMATION: Xaa can be any naturally occurring amino acid
```

```
<220> FEATURE:
<221> NAME/KEY: misc_feature
<222> LOCATION: (105)..(105)
<223> OTHER INFORMATION: Xaa can be any naturally occurring amino acid
<220> FEATURE:
<221> NAME/KEY: misc_feature
<222> LOCATION: (108)..(108)
<223> OTHER INFORMATION: Xaa can be any naturally occurring amino acid
<220> FEATURE:
<221> NAME/KEY: MOD_RES
<222> LOCATION: (112)..(112)
<223> OTHER INFORMATION: Xaa is Ala, Asp, Glu, or Ser
<220> FEATURE:
<221> NAME/KEY: MOD_RES
<222> LOCATION: (115)..(115)
<223> OTHER INFORMATION: Xaa is Ala, Asp, Glu, or Ser
<220> FEATURE:
<221> NAME/KEY: MOD_RES
<222> LOCATION: (118)..(118)
<223> OTHER INFORMATION: Xaa is Ala, Asp, Glu, or Ser

<400> SEQUENCE: 228

Glu Val Gln Leu Leu Glu Ser Gly Gly Gly Leu Val Gln Pro Gly Gly
1               5                   10                  15

Ser Leu Arg Ile Ser Cys Ala Ala Ser Gly Phe Ser Phe Ser Ser Ser
            20                  25                  30

Tyr Xaa Ile Phe Trp Val Arg Gln Ala Pro Gly Lys Gly Leu Glu Leu
        35                  40                  45

Ile Gly Gly Ile Tyr Ser Ser Ser Gly Arg Xaa Tyr Tyr Ala Asp Ser
50                  55                  60

Val Lys Gly Arg Phe Thr Ile Ser Lys Asp Asn Ser Lys Asn Thr Met
65                  70                  75                  80

Tyr Leu Gln Met Asn Ser Leu Arg Ala Glu Asp Thr Ala Val Tyr Tyr
                85                  90                  95

Cys Ala Arg Ser Ala Xaa Gly Ser Xaa Ser Tyr Xaa Ala Tyr Phe Thr
            100                 105                 110

Leu Trp Gly Gln Gly Thr Leu Val Thr Val Ser Ser
        115                 120

<210> SEQ ID NO 229
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Gln or Arg
<220> FEATURE:
<221> NAME/KEY: MOD_RES
<222> LOCATION: (5)..(5)
<223> OTHER INFORMATION: Xaa is Ala, Asn, Gln, or Ser

<400> SEQUENCE: 229

Xaa Ala Ser Asp Xaa Ile Tyr Ser Leu Leu Ala
1               5                   10

<210> SEQ ID NO 230
<211> LENGTH: 7
<212> TYPE: PRT
<213> ORGANISM: Artificial Sequence
<220> FEATURE:
<223> OTHER INFORMATION: Synthetic Construct

<400> SEQUENCE: 230

Arg Ala Ser Thr Leu Ala Ser
```

```
1               5
```

<210> SEQ ID NO 231
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (7)..(7)
<223> OTHER INFORMATION: Xaa is Ala, Asn, Gln, or Ser

<400> SEQUENCE: 231

```
Gln Gln His Tyr Asp Tyr Xaa Tyr Leu Asp Val Ala
1               5                   10
```

<210> SEQ ID NO 232
<211> LENGTH: 110
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (24)..(24)
<223> OTHER INFORMATION: Xaa is Gln or Arg
<220> FEATURE:
<221> NAME/KEY: MOD_RES
<222> LOCATION: (28)..(28)
<223> OTHER INFORMATION: Xaa is Ala, Asn, Gln, or Ser
<220> FEATURE:
<221> NAME/KEY: MOD_RES
<222> LOCATION: (95)..(95)
<223> OTHER INFORMATION: Xaa is Ala, Asn, Gln, or Ser

<400> SEQUENCE: 232

```
Asp Ile Gln Met Thr Gln Ser Pro Ser Ser Leu Ser Ala Ser Val Gly
1               5                   10                  15

Asp Arg Val Thr Ile Thr Cys Xaa Ala Ser Asp Xaa Ile Tyr Ser Leu
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Asp Tyr Xaa Tyr
                85                  90                  95

Leu Asp Val Ala Phe Gly Gly Gly Thr Lys Val Glu Ile Lys
            100                 105                 110
```

<210> SEQ ID NO 233
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (1)..(1)
<223> OTHER INFORMATION: Xaa is Gln or Arg
<220> FEATURE:
<221> NAME/KEY: MOD_RES
<222> LOCATION: (5)..(5)
<223> OTHER INFORMATION: Xaa is Ala, Asn, Gln, or Ser
<220> FEATURE:
<221> NAME/KEY: MOD_RES

```
<222> LOCATION: (9)..(9)
<223> OTHER INFORMATION: Xaa is Ala, Asn, Gln, or Ser

<400> SEQUENCE: 233

Xaa Ala Ser Asp Xaa Ile Tyr Ser Xaa Leu Ala
1               5                   10

<210> SEQ ID NO 234
<211> LENGTH: 7
<212> TYPE: PRT
<213> ORGANISM: Artificial Sequence
<220> FEATURE:
<223> OTHER INFORMATION: Synthetic Construct

<400> SEQUENCE: 234

Arg Ala Ser Thr Leu Ala Ser
1               5

<210> SEQ ID NO 235
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (4)..(4)
<223> OTHER INFORMATION: Xaa is Phe, His, Trp, or Tyr

<400> SEQUENCE: 235

Gln Gln His Xaa Asp Tyr Asp Tyr Ile Asp Val
1               5                   10

<210> SEQ ID NO 236
<211> LENGTH: 110
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (24)..(24)
<223> OTHER INFORMATION: Xaa is Gln or Arg
<220> FEATURE:
<221> NAME/KEY: MOD_RES
<222> LOCATION: (28)..(28)
<223> OTHER INFORMATION: Xaa is Ala, Asn, Gln, or Ser
<220> FEATURE:
<221> NAME/KEY: MOD_RES
<222> LOCATION: (32)..(32)
<223> OTHER INFORMATION: Xaa is Ala, Asn, Gln, or Ser
<220> FEATURE:
<221> NAME/KEY: MOD_RES
<222> LOCATION: (92)..(92)
<223> OTHER INFORMATION: Xaa is Phe, His, Trp, or Tyr

<400> SEQUENCE: 236

Asp Tyr Gln Met Thr Gln Ser Pro Ser Ser Leu Ser Ala Ser Val Gly
1               5                   10                  15

Asp Arg Val Thr Ile Thr Cys Xaa Ala Ser Asp Xaa Ile Tyr Ser Xaa
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Val Gln Pro
65                  70                  75                  80
```

```
Glu Asp Phe Ala Thr Tyr Tyr Cys Gln Gln His Xaa Asp Tyr Asp Tyr
                85                  90                  95

Ile Asp Val Ala Phe Gly Gly Gly Thr Lys Val Glu Ile Lys
            100                 105                 110

<210> SEQ ID NO 237
<211> LENGTH: 10
<212> TYPE: PRT
<213> ORGANISM: Artificial Sequence
<220> FEATURE:
<223> OTHER INFORMATION: Synthetic Construct

<400> SEQUENCE: 237

Gly Arg Ile Ser Ser Ile Ile His Met Ala
1               5                   10

<210> SEQ ID NO 238
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Ile or Val
<220> FEATURE:
<221> NAME/KEY: MOD_RES
<222> LOCATION: (6)..(6)
<223> OTHER INFORMATION: Xaa is Ile or Val
<220> FEATURE:
<221> NAME/KEY: MOD_RES
<222> LOCATION: (9)..(9)
<223> OTHER INFORMATION: Xaa is Ala, Asp, Glu, or Ser
<220> FEATURE:
<221> NAME/KEY: MOD_RES
<222> LOCATION: (11)..(11)
<223> OTHER INFORMATION: Xaa is Ile or Val
<220> FEATURE:
<221> NAME/KEY: MOD_RES
<222> LOCATION: (12)..(12)
<223> OTHER INFORMATION: Xaa is Ala or Lys

<400> SEQUENCE: 238

Arg Xaa Gly Thr Thr Xaa Tyr Ala Xaa Ser Xaa Xaa Gly
1               5                   10

<210> SEQ ID NO 239
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: Xaa is Ala or Lys
<220> FEATURE:
<221> NAME/KEY: MOD_RES
<222> LOCATION: (10)..(10)
<223> OTHER INFORMATION: Xaa is Ala, Asp, Glu, or Ser

<400> SEQUENCE: 239

Leu Gln Tyr Glu Xaa His Gly Gly Ala Xaa Tyr
1               5                   10

<210> SEQ ID NO 240
<211> LENGTH: 119
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: MOD_RES
<222> LOCATION: (54)..(54)
<223> OTHER INFORMATION: Xaa is Ile or Val
<220> FEATURE:
<221> NAME/KEY: MOD_RES
<222> LOCATION: (58)..(58)
<223> OTHER INFORMATION: Xaa is Ile or Val
<220> FEATURE:
<221> NAME/KEY: MOD_RES
<222> LOCATION: (61)..(61)
<223> OTHER INFORMATION: Xaa is Ala, Asp, Glu, or Ser
<220> FEATURE:
<221> NAME/KEY: MOD_RES
<222> LOCATION: (63)..(63)
<223> OTHER INFORMATION: Xaa is Ile or Val
<220> FEATURE:
<221> NAME/KEY: MOD_RES
<222> LOCATION: (64)..(64)
<223> OTHER INFORMATION: Xaa is Ala or Lys
<220> FEATURE:
<221> NAME/KEY: MOD_RES
<222> LOCATION: (102)..(102)
<223> OTHER INFORMATION: Xaa is Ala or Lys
<220> FEATURE:
<221> NAME/KEY: MOD_RES
<222> LOCATION: (107)..(107)
<223> OTHER INFORMATION: Xaa is Ala, Asp, Glu, or Ser

<400> SEQUENCE: 240

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Ser Ser Ile Ile
            20                  25                  30

His Met Ala Trp Phe Arg Gln Ala Pro Gly Lys Glu Arg Glu Leu Val
        35                  40                  45

Ser Glu Ile Ser Arg Xaa Gly Thr Thr Xaa Tyr Ala Xaa Ser Xaa Xaa
    50                  55                  60

Gly Arg Phe Thr Ile Ser Arg Asp Asn Ser Lys Asn Thr Leu Tyr Leu
65                  70                  75                  80

Gln Met Asn Ser Leu Lys Pro Glu Asp Thr Ala Val Tyr Tyr Cys Asn
                85                  90                  95

Ala Leu Gln Tyr Glu Xaa His Gly Gly Ala Xaa Tyr Trp Gly Gln Gly
            100                 105                 110

Thr Leu Val Thr Val Ser Ser
            115

<210> SEQ ID NO 241
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (6)..(6)
<223> OTHER INFORMATION: Xaa is Ile or Val
<220> FEATURE:
<221> NAME/KEY: MOD_RES
<222> LOCATION: (7)..(7)
<223> OTHER INFORMATION: Xaa is Ala, Asp, Asn, Gln, or Ser

<400> SEQUENCE: 241

Gly Arg Ile Phe Glu Xaa Xaa Met Met Ala
1               5                   10

<210> SEQ ID NO 242
```

```
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (2)..(2)
<223> OTHER INFORMATION: Xaa is Ile or Val
<220> FEATURE:
<221> NAME/KEY: MOD_RES
<222> LOCATION: (9)..(9)
<223> OTHER INFORMATION: Xaa is Ala, Asp, Glu, or Ser
<220> FEATURE:
<221> NAME/KEY: MOD_RES
<222> LOCATION: (11)..(11)
<223> OTHER INFORMATION: Xaa is Ile or Val
<220> FEATURE:
<221> NAME/KEY: MOD_RES
<222> LOCATION: (12)..(12)
<223> OTHER INFORMATION: Xaa is Ala or Lys

<400> SEQUENCE: 242

Arg Xaa Gly Thr Thr Thr Tyr Ala Xaa Ser Xaa Xaa Gly
1               5                   10

<210> SEQ ID NO 243
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (5)..(5)
<223> OTHER INFORMATION: Xaa is Ala or Lys
<220> FEATURE:
<221> NAME/KEY: MOD_RES
<222> LOCATION: (10)..(10)
<223> OTHER INFORMATION: Xaa is Ala, Asp, Glu, or Ser

<400> SEQUENCE: 243

Leu Gln Tyr Glu Xaa His Gly Gly Ala Xaa Tyr
1               5                   10

<210> SEQ ID NO 244
<211> LENGTH: 119
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (31)..(31)
<223> OTHER INFORMATION: Xaa is Ile or Val
<220> FEATURE:
<221> NAME/KEY: MOD_RES
<222> LOCATION: (32)..(32)
<223> OTHER INFORMATION: Xaa is Ala, Asp, Asn, Gln, or Ser
<220> FEATURE:
<221> NAME/KEY: MOD_RES
<222> LOCATION: (54)..(54)
<223> OTHER INFORMATION: Xaa is Ile or Val
<220> FEATURE:
<221> NAME/KEY: MOD_RES
<222> LOCATION: (61)..(61)
<223> OTHER INFORMATION: Xaa is Ala, Asp, Glu, or Ser
<220> FEATURE:
<221> NAME/KEY: MOD_RES
<222> LOCATION: (63)..(63)
<223> OTHER INFORMATION: Xaa is Ile or Val
<220> FEATURE:
<221> NAME/KEY: MOD_RES
<222> LOCATION: (64)..(64)
<223> OTHER INFORMATION: Xaa is Ala or Lys
```

```
<220> FEATURE:
<221> NAME/KEY: MOD_RES
<222> LOCATION: (102)..(102)
<223> OTHER INFORMATION: Xaa is Ala or Lys
<220> FEATURE:
<221> NAME/KEY: MOD_RES
<222> LOCATION: (107)..(107)
<223> OTHER INFORMATION: Xaa is Ala, Asp, Glu, or Ser

<400> SEQUENCE: 244
```

Gln Val Gln Leu Ala Glu Ser Gly Gly Gly Leu Val Gln Ala Gly Asp
1               5                   10                  15

Ser Leu Lys Leu Ser Cys Thr Ala Ser Gly Arg Ile Phe Glu Xaa Xaa
                20                  25                  30

Met Met Ala Trp Tyr Arg Gln Ala Pro Gly Lys Asp Arg Glu Leu Val
            35                  40                  45

Ala Glu Ile Ser Arg Xaa Gly Thr Thr Thr Tyr Ala Xaa Ser Xaa Xaa
        50                  55                  60

Gly Arg Phe Thr Ile Ser Arg Asp Ser Ala Lys Asn Thr Val Thr Leu
65                  70                  75                  80

Gln Met Asn Ser Leu Lys Ser Glu Asp Thr Ala Val Tyr Tyr Cys Asn
                85                  90                  95

Ala Leu Gln Tyr Glu Xaa His Gly Gly Ala Xaa Tyr Trp Gly Gln Gly
            100                 105                 110

Thr Gln Val Thr Val Ser Gly
        115

```
<210> SEQ ID NO 245
<211> LENGTH: 4
<212> TYPE: PRT
<213> ORGANISM: Artificial Sequence
<220> FEATURE:
<223> OTHER INFORMATION: Synthetic Construct

<400> SEQUENCE: 245
```

Ala Ser Thr Lys
1

```
<210> SEQ ID NO 246
<211> LENGTH: 6
<212> TYPE: PRT
<213> ORGANISM: Artificial Sequence
<220> FEATURE:
<223> OTHER INFORMATION: Synthetic Construct

<400> SEQUENCE: 246
```

Arg Thr Val Ala Ala Pro
1               5

```
<210> SEQ ID NO 247
<211> LENGTH: 120
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (31)..(31)
<223> OTHER INFORMATION: Xaa is Gln, Ser, Ala, or Asp
<220> FEATURE:
<221> NAME/KEY: MOD_RES
<222> LOCATION: (53)..(53)
<223> OTHER INFORMATION: Xaa is Glu, Ser, or Ala

<400> SEQUENCE: 247
```

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Xaa Asn
                20                  25                  30

Tyr Pro Ile His Trp Val Arg Gln Ala Pro Gly Gln Gly Leu Glu Trp
            35                  40                  45

Met Gly Phe Ile Xaa Asp Pro Gly Gly Gly Tyr Asp Glu Pro Asp Glu
    50              55                  60

Arg Phe Arg Asp Arg Val Thr Met Thr Ala Asp Thr Ser Thr Ser Thr
65              70                  75                  80

Ala Tyr Met Glu Leu Ser Ser Leu Arg Ser Glu Asp Thr Ala Val Tyr
                85                  90                  95

Tyr Cys Ala Arg Arg Gly Gly Gly Tyr Tyr Leu Asp Tyr Trp Gly Gln
                100                 105                 110

Gly Thr Thr Val Thr Val Ser Ser
            115                 120

<210> SEQ ID NO 248
<211> LENGTH: 109
<212> TYPE: PRT
<213> ORGANISM: Artificial Sequence
<220> FEATURE:
<223> OTHER INFORMATION: Synthetic Construct
<220> FEATURE:
<221> NAME/KEY: MOD_RES
<222> LOCATION: (92)..(92)
<223> OTHER INFORMATION: Xaa is Gln, Ser, Ala, or Asp
<220> FEATURE:
<221> NAME/KEY: MOD_RES
<222> LOCATION: (96)..(96)
<223> OTHER INFORMATION: Xaa is His, Tyr, or Phe

<400> SEQUENCE: 248

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Phe Phe
                20                  25                  30

Leu Asn Trp Tyr Gln Gln Lys Pro Gly Lys Ala Pro Lys Leu Leu Ile
            35                  40                  45

Tyr Tyr Thr Ser Arg Tyr His Ser Gly Val Pro Ser Arg Phe Ser Gly
    50              55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln His Gly Xaa Asn Thr Leu Xaa
                85                  90                  95

Pro Trp Thr Phe Gly Gln Gly Thr Lys Leu Glu Ile Lys
                100                 105
```